US009499608B2

(12) United States Patent
Chen et al.

(10) Patent No.: US 9,499,608 B2
(45) Date of Patent: Nov. 22, 2016

(54) BISPECIFIC MONOCLONAL ANTIBODY THERAPEUTICS AGAINST WEST NILE VIRUS WITH IMPROVED CNS PENETRATION

(75) Inventors: Qiang Chen, Scottsdale, AZ (US); Huafang Lai, Scottsdale, AZ (US); Junyun He, Scottsdale, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 179 days.

(21) Appl. No.: 14/124,173

(22) PCT Filed: Jun. 6, 2012

(86) PCT No.: PCT/US2012/041121

§ 371 (c)(1), (2), (4) Date: Dec. 5, 2013

(87) PCT Pub. No.: WO2013/006244

PCT Pub. Date: Jan. 10, 2013

(65) Prior Publication Data

US 2014/0112927 A1 Apr. 24, 2014

Related U.S. Application Data

(60) Provisional application No. 61/494,612, filed on Jun. 8, 2011.

(51) Int. Cl.

| | |
|---|---|
| ***C07K 16/46*** | (2006.01) |
| ***C07K 16/10*** | (2006.01) |
| ***C07K 16/28*** | (2006.01) |
| *C07K 19/00* | (2006.01) |
| *A61K 39/00* | (2006.01) |

(52) U.S. Cl.

CPC .......... *C07K 16/10* (2013.01); *C07K 16/1081* (2013.01); *C07K 16/2869* (2013.01); *C07K 16/2881* (2013.01); *C07K 16/46* (2013.01); *A61K 2039/505* (2013.01); *C07K 19/00* (2013.01); *C07K 2317/13* (2013.01); *C07K 2317/24* (2013.01); *C07K 2317/31* (2013.01); *C07K 2317/41* (2013.01); *C07K 2317/622* (2013.01); *C07K 2317/64* (2013.01); *C07K 2317/66* (2013.01); *C07K 2317/734* (2013.01); *C07K 2317/76* (2013.01); *C07K 2317/90* (2013.01); *C07K 2317/92* (2013.01)

(58) Field of Classification Search

CPC ................................................ C07K 2317/622

See application file for complete search history.

(56) References Cited

U.S. PATENT DOCUMENTS

| | | | |
|---|---|---|---|
| 2002/0076406 | A1 | 6/2002 | Leung |
| 2004/0001825 | A1 | 1/2004 | Govindan et al. |
| 2006/0057149 | A1 | 3/2006 | Johnson et al. |
| 2008/0170994 | A1 | 7/2008 | Pardridge et al. |
| 2009/0130123 | A1 | 5/2009 | Fikrig et al. |
| 2010/0331192 | A1 | 12/2010 | Zha et al. |

FOREIGN PATENT DOCUMENTS

WO WO2009120922 A2 10/2009

OTHER PUBLICATIONS

Rudikoff et al. Proc. Natl. Acad. Sci. USA 1982 vol. 79: p. 1979.*

Hubalek et al., (1999). "West Nile fever—a reemerging mosquito-borne viral disease in Europe." Emerg. Inf. Dis. 5(5): 643-650.

Petersen et al., (2001). "The mannan-binding lectin pathway of complement activation: biology and disease association." Mol. Immunol. 38: 133-149.

Bode et al., (2006). "West Nile virus disease: a descriptive study of 228 patients hospitalized in a 4-county region of Colorado in 2003." Clin. Infect. Dis. 42(9): 1234-1240.

Glass et al., (2006). "CCR5 deficiency increases risk of symptomatic West Nile virus infection." J. Exp. Med. 203: 35-40.

Diamond et al., (2006). "A genetic basis for human susceptibility to West Nile virus." Trends Microbial. 14(7): 287-289.

Lim et al., (2009). "Genetic variation in OAS 1 is a risk factor for initial infection with West Nile virus in man." PLoS Pathog. 5(2): 1-12.

Lim et al., (2008). "Genetic deficiency of chemokine receptor CCR5 is a strong risk factor for symptomatic West Nile virus infection: a meta-analysis of 4 cohorts in the US epidemic." J. Infect. Dis. 197(2): 262-265.

Diamond, (2009). "Progress on the development of therapeutics against West Nile virus." Antiviral Res. 83(3): 214-227.

Furuta et al., (2009). "T-705 (favipiravir) and related compounds: Novel broad spectrum inhibitors of RNA viral infections." Antiviral Res. 82: 95-102.

Morrey et al., (2008). "Efficacy of orally administered T-705 pyrazine analog on lethal West Nile virus infection in rodents." Antiviral Res. 80(3): 377-379.

Pierson et al., (2007). "The stoichiometry of antibody-mediated neutralization and enhancement of West Nile virus infection." Cell Host Microbe. 1: 135-145.

Thompson et al., (2009). "A therapeutic antibody against west nile virus neutralizes infection by blocking fusion within endosomes." PLoS Pathog. 5(5): 1-10.

Morrey et al., (2006). "Humanized monoclonal antibody against West Nile virus envelope protein administered after neuronal infection protects against lethal encephalitis in hamsters." J. Infect. Dis. 194(9): 1300-1308.

(Continued)

*Primary Examiner* — Bao Li

(74) *Attorney, Agent, or Firm* — Viksnins Harris & Padys PLLP

(57) ABSTRACT

The plant-based production of a therapeutic antibody against West Nile Virus is disclosed.

16 Claims, 16 Drawing Sheets

(56) References Cited

OTHER PUBLICATIONS

Morrey et al., (2008). "West Nile virus-induced acute flaccid paralysis is prevented by monoclonal antibody treatment when administered after infection of spinal cord neurons." J. Neurovirol. 14(2): 152-163.
Samuel et al., (2007). "Axonal transport mediates West Nile virus entry into the central nervous system and induces acute flaccid paralysis." Proc. Natl. Acad. Sci. 104(43): 17140-17145.
Chen, (2008). "Expression and purification of pharmaceutical proteins in plants." Biol. Eng. 1(4): 291-321.
Vitale et al., (2005). "Recombinant pharmaceuticals from plants: the plant endomembrane system as bioreactor." Mol. Interv. 5(4): 216-225.
Gomord et al., (2004). "Production and glycosylation of plant-made pharmaceuticals: the antibodies as a challenge." Plant Biotechnol. J. 2: 83-100.
McLean et al., (2007). "A Human AntiPseudomonas aeruginosa Serotype 06ad Immunoglobulin GI Expressed in Transgenic Tobacco Is Capable of Recruiting Immune System Effector FunctionIin vitro." Antimicrob. Agents Chemother. 51(9): 3322-3328.
McCormick et al., (2008). "Plant-produced idiotype vaccines for the treatment of non-Hodgkin's lymphoma: Safety and immunogenicity in a phase I clinical study." Proc. Natl. Acad. Sci. USA. 105(29): 10131-10136.
Villalobos et al., (2006). "Gene Designer: a synthetic biology tool for constructing artificial DNA segments." BMC Bioinformatics 7: 285.
Oliphant et al., (2007). "Induction of epitope-specific neutralizing antibodies against West Nile virus." J. Viral. 81(21): 11828-11839.
Mehlhop et al., (2009). "Complement protein C1q reduces the stoichiometric threshold for antibody-mediated neutralization of West Nile virus." Cell Host Microbe. 6(4): 381-391.
Ko et al., (2003). "Function and glycosylation of plant-derived antiviral monoclonal antibody." Proc. Natl. Acad. Sci. USA. 100(13): 8013-8018.
Ko et al., (2005). "Plant biopharming of monoclonal antibodies." Virus Research 111: 93-100.
Raju, (2008). "Terminal sugars of Fc glycans influence antibody effector functions of IgGs." Curr. Opin. Immunol. 20(4): 471-478.
Wang et al., (2006). "Structural and functional characterization of glycosylation in an immunoglobulin G1 to Cryptococcus neoformans glucuronoxylomannan." Mol. Immunol. 43(7): 987-998.
Qun et al., (2008). "Development of a simple and rapid method for producing nonfucosylated oligomannose containing antibodies with increased effector function." Biotechnology and Bioengineering 99(3): 652-665.
Chargelegue et al., (2000). "A murine monoclonal antibody produced in transgenic plants with plantspecific glycans is not immunogenic in mice." Transgenic Research 9: 187-194.
Jin et al., (2008). "A plant derived human monoclonal antibody induces an anti-carbohydrate immune response in rabbits." Glycobiology 18(3): 235-241.
Zeitlin et al., (1998). "A humanized monoclonal antibody produced in transgenic plants for immunoprotection of the vagina against genital herpes." Nat. Biotech. 16(13): 1361-1364.
Ma et al., (1998). "Characterization of a recombinant plant monoclonal secretory antibody and preventive immunotherapy in humans." Nat. Med. 4(5): 601-606.
Shields et al., (2002). "Lack of fucose on human IgG1 N-linked oligosaccharide improves binding to human Fcgamma RIII and antibody-dependent cellular toxicity." J. Biol. Chem. 277(30): 26733-26740.
Huang et al., (2009). "A DNA replicon system for rapid high-level production of virus-like particles in plants." Biotechnology and Bioengineering 103(4): 706-714.
Pierson et al., (2005). "An infectious West Nile Virus that expresses a GFP reporter gene." Virology 334: 28-40.
Diamond et al., (2003). "Innate and adaptive immune responses determine protection against disseminated infection by West Nile Encephalitis virus." Viral Immunology 16(3): 259-278.
Weintraub et al., (2005). "Clinical trial of a plant-derived antibody on recolonization of mutans streptococci." Caries Research 39: 241-250.
Diamond, (2009). "Mechanisms of Evasion of the Type I Interferon Antiviral Response by Flaviviruses." Interferon Cytokine Res. 29(9): 521-530.
Melnick et al., (1951). "Isolation from human sera in Egypt of a virus apparently identical to West Nile virus." Proc. Soc. Exp. Biol. Med. 77: 661-665.
Eldadah et al., (1967). "Pathogenesis of West Nile Virus encepahlitis in mice and rats. II. Virus multiplication, evolution of immunofluorescence, and development of histological lesions in the brain." Am J Epidemiol 86(3): 776-790.
Zhang et al., (1992). "Preparation and characterization of the monoclonal antibodies against Japanese encephalitis virus." Acta Virologica 36: 533-540.
Giritch et al., (2006). "Rapid high-yield expression of full-size IgG antibodies in plants coinfected with noncompeting viral vectors." PNAS 103(40): 14701-14706.
Lai et al., (2010). "Monoclonal antibody produced in plants efficiently treats West Nile virus infection in mice." Proceedings of the National Academy of Sciences 107(6): 2419-2424.
Oliphant et al., (2005). "Development of a humanized monoclonal antibody with therapeutic potential against West Nile virus." Nature Medicine 11(5): 522-530.
Morrey et al., (2007). Defining limits of treatment with humanized neutralizing monoclonal antibody for West Nile virus neurological infection in a hamster model. Antimicrobial Agents and Chemotherapy 51(7): 2396-2402.
Kaneko et al., (2006). "Anti-Inflammatory Activity of Immunoglobulin G Resulting from Fc Sialylation." Science 313: 670-673.
Nimmerjahn et al., (2008). "Fcgamma receptors as regulators of immune responses." Nat. Rev. Immunol. 8: 34-47.
Royston, (2005). "Glycosylation of Recombinant Antibody Therapeutics." Biotechnology Progress 21: 11-16.
Schahs et al., (2007). "Production of a monoclonal antibody in plants with a humanized N-glycosylation pattern." Plant Biotechnology Journal 5: 657-663.
Strasser et al., (2008). "Generation of glyco-engineered Nicotiana benthamiana for the production of monoclonal antibodies with a homogeneous human-like N-glycan structure." Plant Biotechnology Journal 6: 392-402.
Cox et al., (2006). "Glycan optimization of a human monoclonal antibody in the aquatic plant Lemna minor." Nature Biotechnology 24: 1591-1597.
Castilho et al., (2010). "In Planta Protein Sialylation through Over-expression of the Respective Mammalian Pathway." Journal of Biological Chemistry 285(21): 15923-15930.
Strasser et al., (2009). "Improved Virus Neutralization by Plant-produced Anti-HIV Antibodies with a Homogeneous Î²1,4-Galactosylated N-Glycan Profile." Journal of Biological Chemistry 284: 20479-20485.
Hudson et al., (2003). "Engineered antibodies." Nat. Med. 9: 129-134.
Boado et al., (2007). "Humanization of anti-human insulin receptor antibody for drug targeting across the human blood-brain barrier." Biotechnology and Bioengineering 96(2): 381-391.
McGrath et al., (1997). "Bifunctional fusion between nerve growth factor and a transferrin receptor antibody." Journal of Neuroscience Research 47: 123-133.
Boado et al., (2009). "Engineering and expression of a chimeric transferrin receptor monoclonal antibody for blood-brain barrier delivery in the mouse." Biotechnology and Bioengineering 102(4): 1251-1258.
Zhang et al., (2005). "Delivery of beta-galactosidase to mouse brain via the blood-brain barrier transferrin receptor." J. Pharmacol. Exp. Ther. 313(3): 1075-1081.

(56) References Cited

OTHER PUBLICATIONS

Huang et al., (2010). "High-level rapid production of full-size monoclonal antibodies in plants by a single-vector DNA replicon system." Biotechnology and Bioengineering 106: 9-17.
Marillonnet et al. (2004). "In planta engineering of viral RNA replicons: efficient assembly by recombination of DNA modules delivered by Agrobacterium." Proc. Natl. Acad. Sci. 101(18): 6852-6857.
Hudson et al., (1999). "High avidity scFv multimer; diabodies and triabodies." Journal of Immunological Methods 231: 177-189.
Nuttall et al., (2002). "ER-resident chaperone interactions with recombinant antibodies in transgenic plants." Eur. J. Biochem. 269: 6042-6051.
Wang et al., (2007). "Mining a yeast library for brain endothelial cell-binding antibodies." Nat. Meth. 4(2): 143-145.
Santi et al., (2008). "An efficient plant viral expression system generating orally immunogenic Norwalk virus-like particles." Vaccine 26(15): 1846-1854.
Santi et al., (2006). "Virus-like particles production in green plants." Methods 40: 66-76.
Weiner et al., (2006). "Immunology and immunotherapy of Alzheimer's disease." Nat. Rev. Immunol. 6: 404-416.
Lue et al., (2002). "Modeling Alzheimer's disease immune therapy mechanisms: Interactions of human postmortem microglia with antibody-opsonized amyloid beta peptide." Journal of Neuroscience Research 70: 599-610.
Pierson et al., (2006). "A rapid and quantitative assay for measuring antibody-mediated neutralization of West Nile virus infection." Virology 346: 53-65.
Stanley et al., (1986). "Monoclonal antibody cure and prophylaxis of lethal Sindbis virus encephalitis in mice." J. Virol. 58: 107-115.
Mehlhop et al., (2005). "Complement activation is required for the induction of a protective antibody response against West Nile virus infection." J. Virol. 79(12): 7466-7477.
Mehlhop et al., (2007). "Complement protein C1q inhibits antibody-dependent enhancement of flavivirus infection In Vitro and In Vivo in an IgG subclass-specific manner." Cell host & microbe 2(6): 417-426.
Kurane et al., (1984). "Lysis of dengue virus-infected cells by natural cell-mediated cytotoxicity and antibody-dependent cell-mediated cytotoxicity." J. Virol. 52: 223-230.
Meguro et al., (1979). "Antibody-dependent cell-mediated cytotoxicity against cells infected with respiratory syncytial virus: characterization of in vitro and in vivo properties." J. Immunol. 122(6): 2521-2526.
Chung et al., (2007). "Antibody recognition of cell surface-associated NS1 triggers Fc-gamma receptor-mediated phagocytosis and clearance of West Nile Virus-infected cells." J. Virol. 81(17): 9551-9555.
Laoprasopwattana et al., (2007). "Antibody-dependent cellular cytotoxicity mediated by plasma obtained before secondary dengue virus infections: potential involvement in early control of viral replication." J. Infect. Dis. 195: 1108-1116.
Brown et al., (2007). "Tight junction protein expression and barrier properties of immortalized mouse brain microvessel endothelial cells." Brain Research 1130: 17-30.
Coisne et al., (2005). "Mouse syngenic in vitro blood-brain barrier model: a new tool to examine inflammatory events in cerebral endothelium." Lab Invest 85(6): 734-746.
Stamatovic et al., (2003). "Potential role of MCP-1 in endothelial cell tight junction 'opening': signaling via Rho and Rho kinase." Journal of Cell Science 116: 4615-4628.
Pardridge et al., (1990). "Comparison of in vitro and in vivo models of drug transcytosis through the blood-brain barrier." J. Pharmacol. Exp. Ther. 253(2): 884-891.
Nakagawa et al., (2009). "A new blood-brain barrier model using primary rat brain endothelial cells, pericytes and astrocytes." Neurochemistry International 54: 253-263.
Wu et al., (2007). "Simultaneous targeting of multiple disease mediators by a dual-variable-domain immunoglobulin." Nat. Biotech. 25: 1290-1297.
Natsume et al., (2006). "Fucose Removal from Complex-Type Oligosaccharide Enhances the Antibody-Dependent Cellular Cytotoxicity of Single-Gene-Encoded Bispecific Antibody Comprising of Two Single-Chain Antibodies Linked to the Antibody Constant Region." J. Biochem. 140: 359-368.
Lee et al., (2000). "Targeting Rat Anti-Mouse Transferrin Receptor Monoclonal Antibodies through Blood-Brain Barrier in Mouse." Journal of Pharmacology and Experimental Therapeutics 292(3): 1048-1052.
Li et al., (1999). "Genetically engineered brain drug delivery vectors: cloning, expression and in vivo application of an anti-transferrin receptor single chain antibody-streptavidin fusion gene and protein." Protein Eng. 12(9): 787-796.
Ebel et al., (2001). "Partial genetic characterization of West Nile Virus strains, New York State, 2000." Emerg. Inf. Dis. 7(4): 650-653.
Diamond et al., (2003). "B cells and antibody play critical roles in the immediate defense of disseminated infection by West Nile encephalitis virus." J. Virol. 77(4): 2578-2586.
Lanciotti et al., (2000). "Rapid detection of west nile virus from human clinical specimens, field-collected mosquitoes, and avian samples by a TaqMan reverse transcriptase-PCR assay." J. Clin. Microbiol. 38(11): 4066-4071.
Diamond et al., (2000). "Modulation of dengue virus infection in human cells by alpha, beta, and gamma interferons." J. Virol. 74(11): 4957-4966.
Wang et al., (2004). "Toll-like receptor 3 mediates West Nile virus entry into the brain causing lethal encephalitis." Nat. Med. 10(12): 1366-1373.
Engle et al., (2003). "Antibody prophylaxis and therapy against West Nile Virus infection in wild type and immunodeficient mice." J. Virol. 77(24): 12941-12949.
Chung et al., (2006). "Antibodies against West Nile virus non-structural (NS)-1 protein prevent lethal infection through Fc gamma receptor-dependent and independent mechanisms." J. Virol. 80(3): 1340-1351.

* cited by examiner

| WNV antigen | Antibody | Ka (1/Ms) | Kd (1/s) | KD (M) |
| --- | --- | --- | --- | --- |
| E Protein | mHu-E16 | $1.1e^{5}$ | $4.9e^{-3}$ | $4.5e^{-8}$ |
| | pHu-E16 | $1.2e^{5}$ | $5.3e^{-3}$ | $4.6e^{-8}$ |
| E protein DIII | mHu-E16 | $2.2e^{5}$ | $6.9e^{-3}$ | $3.2e^{-8}$ |
| | pHu-E16 | $2.1e^{5}$ | $8.6e^{-3}$ | $4.1e^{-8}$ |

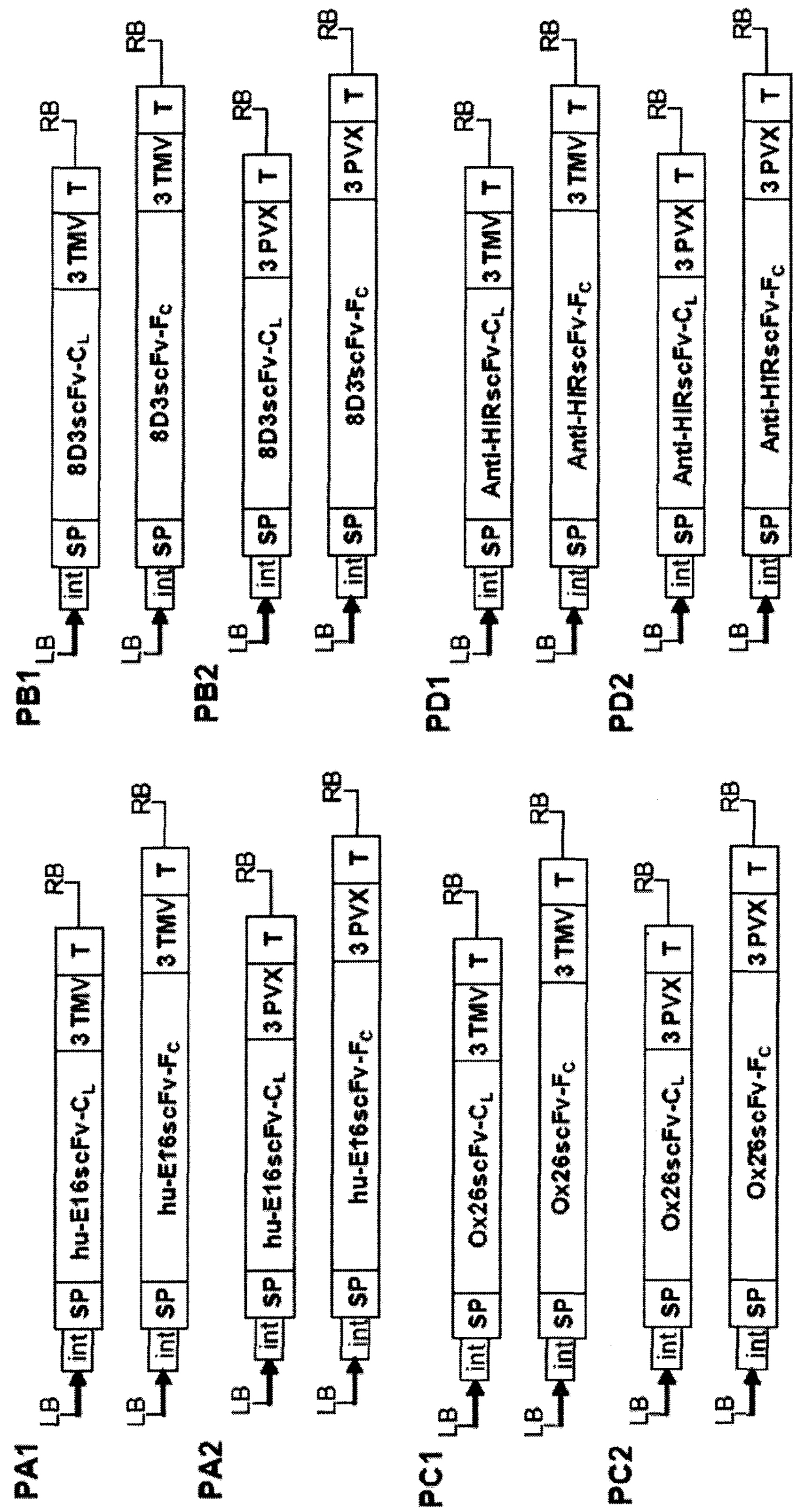
FIGURE 7A
PA1
LB int SP hu-E16scFv-C_L 3 TMV T RB
LB int SP hu-E16scFv-F_C 3 TMV T RB
PA2
LB int SP hu-E16scFv-C_L 3 PVX T RB
LB int SP hu-E16scFv-F_C 3 PVX T RB
PC1
LB int SP Ox26scFv-C_L 3 TMV T RB
LB int SP Ox26scFv-F_C 3 TMV T RB
PC2
LB int SP Ox26scFv-C_L 3 PVX T RB
LB int SP Ox26scFv-F_C 3 PVX T RB
PB1
LB int SP 8D3scFv-C_L 3 TMV T RB
LB int SP 8D3scFv-F_C 3 TMV T RB
PB2
LB int SP 8D3scFv-C_L 3 PVX T RB
LB int SP 8D3scFv-F_C 3 PVX T RB
PD1
LB int SP Anti-HIRscFv-C_L 3 TMV T RB
LB int SP Anti-HIRscFv-F_C 3 TMV T RB
PD2
LB int SP Anti-HIRscFv-C_L 3 PVX T RB
LB int SP Anti-HIRscFv-F_C 3 PVX T RB A
B
C
D
E
F
G
H
I
4°C
37°C
Control Bif-E16 Var 1
EC50 = 15 ng/ml
Bif-E16 Var 2
EC50 = 10 ng/ml
Bif-E16 Var 3
EC50 = 9 ng/ml
Bif-E16 Var 4
EC50 = 17 ng/ml
Bif-E16 Var5
EC50 = 5 ng/ml
Bif-E16 Var 6
EC50 = 17 ng/ml
Bif-E16 Var 7
EC50 = 13 ng/ml
Percent infection
Log10 ng/ml Antibody

SEQUENCE LISTING

<160> NUMBER OF SEQ ID NOS: 86

<210> SEQ ID NO 1
<211> LENGTH: 650
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt               650
```

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser
        115


<210> SEQ ID NO 4
<211> LENGTH: 1615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt gggcactcag    660

acctacatct gcaatgtgaa tcacaaaccc agcaacacca aggttgacaa gaaagttgag    720

cccaagtctt gtgacaagac tcatacgtgt ccaccgtgcc cagcacctga acttcttgga    780

ggaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

aacagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cctctagagt cgacctgcag   1440

ggtctcagct tggtcgtatc actggaacaa caaccgctga ggctgttgtc actctaccac   1500

caccataact acgtctacat aaccgacgcc taccccagtt tcatagtatt ttctggtttg   1560

attgtatgaa taatataaat aaaaaaaaaa aaaaaaaaaa aaaactagtg agctc        1615


<210> SEQ ID NO 5
<211> LENGTH: 468
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 5

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
```

```
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 6
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

atgggatggt cttgtatcat ccttttcttg gttgcaacag ctactggtgt tcattctgat      60

atcgttatga cacaatctcc agattctttg gctgtttctc ttggagagag ggctactatc     120

aattgcaagg cttctcaaga tgtttctact gctgttgctt ggtaccaaca gaaacctgga     180

cagccaccaa aacttcttat ctcttgggca tctactaggc acactggagt tccagataga     240

ttttctggat ctggatctgg aacagatttc actcttacta tctcatctct tcaagctgag     300

gatgttgcag tttattactg tcagcaacat tatacaactc cacttacttt cggacaagga     360

actaagttgg agatcaaaag aactgttgct gcaccatctg ttttcatctt ccctccatct     420

gatgagcagt tgaaatctgg aactgcttct gttgtgtgcc ttcttaataa cttctatcct     480

agagaggcta aagttcagtg gaaggtggat aacgcacttc aatctggtaa ctctcaagag     540

tctgttacag agcaagattc taaggactca acttactctc tttcatctac acttactttg     600

tcaaaagcag attacgagaa acacaaagtt tacgcatgcg aagttactca tcaaggactt     660

tcttcaccag ttacaaagtc tttcaataga ggagagtgtt aa                        702


<210> SEQ ID NO 7
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Lys Ala Ser Gln Asp Val
        35                  40                  45

Ser Thr Ala Val Ala Trp Tyr Gln Gln Lys Pro Gly Gln Pro Pro Lys
    50                  55                  60

Leu Leu Ile Ser Trp Ala Ser Thr Arg His Thr Gly Val Pro Asp Arg
65                  70                  75                  80

Phe Ser Gly Ser Gly Ser Gly Thr Asp Phe Thr Leu Thr Ile Ser Ser
```

```
                85                  90                  95

Leu Gln Ala Glu Asp Val Ala Val Tyr Tyr Cys Gln Gln His Tyr Thr
            100                 105                 110

Thr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 8
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asn Glu Lys Leu Lys Ala Arg Val Thr Met Thr Ala Asp Thr Ser Thr
1               5                   10                  15

Ser Thr Ala Tyr Met Glu Leu Arg Ser Leu Arg Ser Asp Asp Thr Ala
            20                  25                  30

Val Tyr Tyr Cys Ala Arg Ser Ala Ser Tyr Gly Asp Tyr Ala Asp Tyr
        35                  40                  45

Trp Gly Gln Gly Thr Thr Val Thr Val Ser Ser Ala Ser Thr Lys Gly
    50                  55                  60

Pro Ser Val Phe Pro Leu Ala Pro Ser Ser Lys Ser Thr Ser Gly Gly
65                  70                  75                  80

Thr Ala Ala Leu Gly Cys Leu Val Lys Asp Tyr Phe Pro Glu Pro Val
                85                  90                  95

Thr Val Ser Trp Asn Ser Gly Ala Leu Thr Ser Gly Val His Thr Phe
            100                 105                 110

Pro Ala Val Leu Gln Ser Ser Gly Leu Tyr Ser Leu Ser Ser Val Val
        115                 120                 125

Thr Val Pro Ser Ser Ser Leu Gly Thr Gln Thr Tyr Ile Cys Asn Val
    130                 135                 140

Asn His Lys Pro Ser Asn Thr Lys Val Asp Lys Arg Val
145                 150                 155


<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Glu Pro Lys Ser Cys Asp Lys Thr His Thr Cys Pro Pro Cys Pro
1               5                   10                  15


<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

Lys Asp Glu Leu
1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ser Glu Lys Asp Glu Leu
1 5

<210> SEQ ID NO 14
<211> LENGTH: 6446
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
cccggggatc ctctagagtc gacctgcaga agcttactag agcgtggtgc gcacgatagc 60
gcatagtgtt tttctctcca cttgaatcga agagatagac ttacggtgta aatccgtagg 120
ggtggcgtaa accaaattac gcaatgtttt gggttccatt taaatcgaaa ccccttattt 180
cctggatcac ctgttaacgc acgtttgacg tgtattacag tgggaataag taaaagtgag 240
aggttcgaat cctccctaac cccgggtagg ggcccagcgg ccgctctagc tagagtcaag 300
cagatcgttc aaacatttgg caataaagtt tcttaagatt gaatcctgtt gccggtcttg 360
cgatgattat catataattt ctgttgaatt acgttaagca tgtaataatt aacatgtaat 420
gcatgacgtt atttatgaga tgggttttta tgattagagt cccgcaatta tacatttaat 480
acgcgataga aaacaaaata tagcgcgcaa actaggataa attatcgcgc gcggtgtcat 540
ctatgttact agatcgacca gcttagatca gattgtcgtt tcccgccttc agtttaaact 600
atcagtgttt gacaggatat attggcgggt aaacctaaga gaaaagagcg tttattagaa 660
taatcggata tttaaaaggg cgtgaaaagg tttatccgtt cgtccatttg tatgtgccaa 720
ccacagggtt ccccagatca gtaaagcgct ggctgctgaa cccccagccg gaactgaccc 780
cacaaggccc tagcgtttgc aatgcaccag gtcatcattg acccaggcgt gttccaccag 840
gccgctgcct cgcaactctt cgcaggcttc gccgacctgc tcgcgccact tcttcacgcg 900
ggtggaatcc gatccgcaca tgaggcggaa ggtttccagc ttgagcgggt acggctcccg 960
gtgcgagctg aaatagtcga acatccgtcg ggccgtcggc gacagcttgc ggtacttctc 1020
ccatatgaat ttcgtgtagt ggtcgccagc aaacagcacg acgatttcct cgtcgatcag 1080
gacctggcaa cgggacgttt tcttgccacg gtccaggacg cggaagcggt gcagcagcga 1140
caccgattcc aggtgcccaa cgcggtcgga cgtgaagccc atcgccgtcg cctgtaggcg 1200
cgacaggcat tcctcggcct tcgtgtaata ccggccattg atcgaccagc ccaggtcctg 1260
gcaaagctcg tagaacgtga aggtgatcgg ctcgccgata ggggtgcgct tcgcgtactc 1320
caacacctgc tgccacacca gttcgtcatc gtcggcccgc agctcgacgc cggtgtaggt 1380
gatcttcacg tccttgttga cgtggaaaat gaccttgttt tgcagcgcct cgcgcgggat 1440
tttcttgttg cgcgtggtga acagggcaga gcgggccgtg tcgtttggca tcgctcgcat 1500

```
cgtgtccggc cacggcgcaa tatcgaacaa ggaaagctgc atttccttga tctgctgctt   1560
cgtgtgtttc agcaacgcgg cctgcttggc ctcgctgacc tgttttgcca ggtcctcgcc   1620
ggcggttttt cgcttcttgg tcgtcatagt tcctcgcgtg tcgatggtca tcgacttcgc   1680
caaacctgcc gcctcctgtt cgagacgacg cgaacgctcc acggcggccg atggcgcggg   1740
cagggcaggg ggagccagtt gcacgctgtc gcgctcgatc ttggccgtag cttgctggac   1800
catcgagccg acggactgga aggtttcgcg gggcgcacgc atgacggtgc ggcttgcgat   1860
ggtttcggca tcctcggcgg aaaaccccgc gtcgatcagt tcttgcctgt atgccttccg   1920
gtcaaacgtc cgattcattc accctccttg cgggattgcc ccgactcacg ccggggcaat   1980
gtgcccttat tcctgatttg acccgcctgg tgccttggtg tccagataat ccaccttatc   2040
ggcaatgaag tcggtcccgt agaccgtctg gccgtccttc tcgtacttgg tattccgaat   2100
cttgccctgc acgaatacca gcgacccctt gcccaaatac ttgccgtggg cctcggcctg   2160
agagccaaaa cacttgatgc ggaagaagtc ggtgcgctcc tgcttgtcgc cggcatcgtt   2220
gcgccacatc taggatctgc caggaaccgt aaaaaggccg cgttgctggc gtttttccat   2280
aggctccgcc cccctgacga gcatcacaaa aatcgacgct caagtcagag gtggcgaaac   2340
ccgacaggac tataaagata ccaggcgttt ccccctggaa gctccctcgt gcgctctcct   2400
gttccgaccc tgccgcttac cggatacctg tccgcctttc tcccttcggg aagcgtggcg   2460
ctttctcata gctcacgctg taggtatctc agttcggtgt aggtcgttcg ctccaagctg   2520
ggctgtgtgc acgaaccccc cgttcagccc gaccgctgcg ccttatccgg taactatcgt   2580
cttgagtcca acccggtaag acacgactta tcgccactgg cagcagccac tggtaacagg   2640
attagcagag cgaggtatgt aggcggtgct acagagttct tgaagtggtg gcctaactac   2700
ggctacacta gaagaacagt atttggtatc tgcgctctgc tgaagccagt taccttcgga   2760
aaaagagttg gtagctcttg atccggcaaa caaaccaccg ctggtagcgg tggttttttt   2820
gtttgcaagc agcagattac gcgcagaaaa aaaggatctc aagaagatcc tttgatcttt   2880
tctacggggt ctgacgctca gtggaacgaa aactcacgtt aagggatttt ggtcatgaga   2940
ttatcaaaaa ggatcttcac ctagatcctt ttaaattaaa aatgaagttt taaatcaatc   3000
taaagtatat atgagtaaac ttggtctgac agttaccaat gcttaatcag tgaggcacct   3060
atctcagcga tctgtctatt tcgttcatcc atagttgcct gactccccgt cgtgtagata   3120
actacgatac gggagggctt accatctggc cccagtgctg caatgatacc gcgagaccca   3180
cgctcaccgg ctccagattt atcagcaata aaccagccag ccggaagggc cgagcgcaga   3240
agtggtcctg caactttatc cgcctccatc cagtctatta attgttgccg ggaagctaga   3300
gtaagtagtt cgccagttaa tagtttgcgc aacgttgttg ccattgctac aggcatcgtg   3360
gtgtcacgct cgtcgtttgg tatggcttca ttcagctccg gttcccaacg atcaaggcga   3420
gttacatgat cccccatgtt gtgcaaaaaa gcggttagct ccttcggtcc tccgatcgtt   3480
gtcagaagta agttggccgc agtgttatca ctcatggtta tggcagcact gcataattct   3540
cttactgtca tgccatccgt aagatgcttt tctgtgactg gtgagtactc aaccaagtca   3600
ttctgagaat agtgtatgcg gcgaccgagt tgctcttgcc cggcgtcaat acgggataat   3660
accgcgccac atagcagaac tttaaaagtg ctcatcattg gaaaacgttc ttcggggcga   3720
aaactctcaa ggatcttacc gctgttgaga tccagttcga tgtaacccac tcgtgcaccc   3780
aactgatctt cagcatcttt tactttcacc agcgtttctg ggtgagcaaa aacaggaagg   3840
caaaatgccg caaaaaaggg aataagggcg acacggaaat gttgaatact catactcttc   3900
```

```
cttttcaat attattgaag catttatcag ggttattgtc tcatgagcgg atacatattt   3960
gaatgtattt agaaaaataa acaaataggg gttccgcgca cgaattggcc agcgctgcca   4020
tttttggggt gaggccgttc gcggccgagg ggcgcagccc ctggggggat gggaggcccg   4080
cgttagcggg ccgggagggt tcgagaaggg ggggcacccc ccttcggcgt gcgcggtcac   4140
gcgcacaggg cgcagccctg gttaaaaaca aggtttataa atattggttt aaaagcaggt   4200
taaaagacag gttagcggtg gccgaaaaac gggcggaaac ccttgcaaat gctggatttt   4260
ctgcctgtgg acagcccctc aaatgtcaat aggtgcgccc ctcatctgtc agcactctgc   4320
ccctcaagtg tcaaggatcg cgcccctcat ctgtcagtag tcgcgcccct caagtgtcaa   4380
taccgcaggg cacttatccc caggcttgtc cacatcatct gtgggaaact cgcgtaaaat   4440
caggcgtttt cgccgatttg cgaggctggc cagctccacg tcgccggccg aaatcgagcc   4500
tgcccctcat ctgtcaacgc cgcgccgggt gagtcggccc ctcaagtgtc aacgtccgcc   4560
cctcatctgt cagtgagggc caagttttcc gcgaggtatc cacaacgccg gcggccgcgg   4620
tgtctcgcac acggcttcga cggcgtttct ggcgcgtttg cagggccata gacggccgcc   4680
agcccagcgg cgagggcaac cagcccggtg agcgtcgcaa aggagatcct gatctgactg   4740
atgggctgcc tgtatcgagt ggtgattttg tgccgagctg ccggtcgggg agctgttggc   4800
tggctggtgg caggatatat tgtggtgtaa acaaattgac gcttagacaa cttaataaca   4860
cattgcggac gtttttaatg tactggggtg gatgcaggtc gatctagtaa catagatgac   4920
accgcgcgcg ataatttatc ctagtttgcg cgctatattt tgttttctat cgcgtattaa   4980
atgtataatt gcgggactct aatcataaaa acccatctca taaataacgt catgcattac   5040
atgttaatta ttacatgctt aacgtaattc aacagaaatt atatgataat catcgcaaga   5100
ccggcaacag gattcaatct taagaaactt tattgccaaa tgtttgaacg atctgcttga   5160
ctctagatcc agagtcccgc tcagaagaac tcgtcaagaa ggcgatagaa ggcgatgcgc   5220
tgcgaatcgg gagcggcgat accgtaaagc acgaggaagc ggtcagccca ttcgccgcca   5280
agctcttcag caatatcacg ggtagccaac gctatgtcct gatagcggtc cgccacaccc   5340
agccggccac agtcgatgaa tccagaaaag cggccatttt ccaccatgat attcggcaag   5400
caggcatcgc catgagtcac gacgagatcc tcgccgtcgg gcatacgcgc cttgagcctg   5460
gcgaacagtt cggctggcgc gagcccctga tgctcttcgt ccagatcatc ctgatcgaca   5520
agaccggctt ccatccgagt acgtgctcgc tcgatgcgat gtttcgcttg gtggtcgaat   5580
gggcaggtag ccggatcaag cgtatgcagc cgccgcattg catcagccat gatggatact   5640
ttctcggcag gagcaaggtg agatgacagg agatcctgcc ccggcacttc gcccaatagc   5700
agccagtccc ttcccgcttc agtgacaacg tcgagcacag ctgcgcaagg aacgcccgtc   5760
gtggccagcc acgatagccg cgctgcctcg tcctggagtt cattcagggc accggacagg   5820
tcggtcttga caaaaagaac cgggcgcccc tgcgctgaca gccggaacac ggcggcatca   5880
gagcagccga ttgtctgttg tgcccagtca tagccgaata gcctctccac ccaagcggcc   5940
ggagaacctg cgtgcaatcc atcttgttca atcatgcgaa acgatccaga tccggtgcag   6000
attatttgga ttgagagtga atatgagact ctaattggat accgagggga atttatggaa   6060
cgtcagtgga gcatttttga caagaaatat ttgctagctg atagtgacct taggcgactt   6120
ttgaacgcgc aataatggtt tctgacgtat gtgcttagct cattaaactc cagaaacccg   6180
cggctgagtg gctccttcaa cgttgcggtt ctgtcagttc caaacgtaaa acggcttgtc   6240
```

```
ccgcgtcatc ggcgggggtc ataacgtgac tcccttaatt ctccgctcat ggtacctcga   6300

agccgcggtg cgggtgccag ggcgtgccct tgggctcccc gggcgcgtac tccacctcac   6360

ccatctttta ttacatgttt gaacttcaac aatttatgac tttttgttct tattgttgca   6420

ggtaccatgg cagaattcgt ggagct                                        6446
```

```
<210> SEQ ID NO 15
<211> LENGTH: 6489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

agcttgaaga ctaggcgtgg tgcgcacgat agcgcatagt gtttttctct ccacttgaat     60

cgaagagata gacttacggt gtaaatccgt aggggtggcg taaaccaaat tacgcaatgt    120

tttgggttcc atttaaatcg aaacccctta tttcctggat cacctgttaa cgcacgtttg    180

acgtgtatta cagtgggaat aagtaaaagt gagaggttcg aatcctccct aaccccgggt    240

aggggcccag cggccgctct agctagagtc aagcagatcg ttcaaacatt tggcaataaa    300

gtttcttaag attgaatcct gttgccggtc ttgcgatgat tatcatataa tttctgttga    360

attacgttaa gcatgtaata attaacatgt aatgcatgac gttatttatg agatgggttt    420

ttatgattag agtcccgcaa ttatacattt aatacgcgat agaaaacaaa atatagcgcg    480

caaactagga taaattatcg cgcgcggtgt catctatgtt actagatcga ccagtcctat    540

ggtagtcttc agcttagatc agattgtcgt ttcccgcctt cagtttaaac tatcagtgtt    600

tgacaggata tattggcggg taaacctaag agaaaagagc gtttattaga ataatcggat    660

atttaaaagg gcgtgaaaag gtttatccgt tcgtccattt gtatgtgcat gccaaccaca    720

gggttcccca gatcagtaaa gcgctggctg ctgaaccccc agccggaact gaccccacaa    780

ggccctagcg tttgcaatgc accaggtcat cattgaccca ggcgtgttcc accaggccgc    840

tgcctcgcaa ctcttcgcag gcttcgccga cctgctcgcg ccacttcttc acgcgggtgg    900

aatccgatcc gcacatgagg cggaaggttt ccagcttgag cgggtacggc tcccggtgcg    960

agctgaaata gtcgaacatc cgtcgggccg tcggcgacag cttgcggtac ttctcccata   1020

tgaatttcgt gtagtggtcg ccagcaaaca gcacgacgat ttcctcgtcg atcaggacct   1080

ggcaacggga cgttttcttg ccacggtcca ggacgcggaa gcggtgcagc agcgacaccg   1140

attccaggtg cccaacgcgg tcggacgtga agcccatcgc cgtcgcctgt aggcgcgaca   1200

ggcattcctc ggccttcgtg taataccggc cattgatcga ccagcccagg tcctggcaaa   1260

gctcgtagaa cgtgaaggtg atcggctcgc cgataggggt gcgcttcgcg tactccaaca   1320

cctgctgcca caccagttcg tcatcgtcgg cccgcagctc gacgccggtg taggtgatct   1380

tcacgtcctt gttgacgtgg aaaatgacct tgttttgcag cgcctcgcgc gggattttct   1440

tgttgcgcgt ggtgaacagg gcagagcggg ccgtgtcgtt tggcatcgct cgcatcgtgt   1500

ccggccacgg cgcaatatcg aacaaggaaa gctgcatttc cttgatctgc tgcttcgtgt   1560

gtttcagcaa cgcggcctgc ttggcctcgc tgacctgttt tgccaggtcc tcgccggcgg   1620

tttttcgctt cttggtcgtc atagttcctc gcgtgtcgat ggtcatcgac ttcgccaaac   1680

ctgccgcctc ctgttcgaga cgacgcgaac gctccacggc ggccgatggc gcgggcaggg   1740

caggggggagc cagttgcacg ctgtcgcgct cgatcttggc cgtagcttgc tggaccatcg   1800
```

```
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgagggggcgc agcccctggg gggatgggag gcccgcgtta   4080
gcgggccggg agggttcgag aagggggggc acccccccttc ggcgtgcgcg gtcacgcgca   4140
cagggcgcag ccctggttaa aaacaaggtt tataaatatt ggtttaaaag caggttaaaa   4200
```

```
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cgagctcccg gggatcctct agagtcgacc tgcagaagct ggcagctagg   6480
atgggtctc                                                           6489
```

<210> SEQ ID NO 16
<211> LENGTH: 5015
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattctgc 960
agatatccag cacagtggcg gccgctcgag tctagagggc ccgtttaaac ccgctgatca 1020
gcctcgactg tgccttctag ttgccagcca tctgttgttt gcccctcccc cgtgccttcc 1080
ttgaccctgg aaggtgccac tcccactgtc ctttcctaat aaaatgagga aattgcatcg 1140
cattgtctga gtaggtgtca ttctattctg gggggtgggg tggggcagga cagcaagggg 1200
gaggattggg aagacaatag caggcatgct ggggatgcgg tgggctctat ggcttctgag 1260
gcggaaagaa ccagctgggg ctctaggggg tatccccacg cgccctgtag cggcgcatta 1320
agcgcggcgg gtgtggtggt tacgcgcagc gtgaccgcta cacttgccag cgccctagcg 1380
cccgctcctt tcgctttctt cccttccttt ctcgccacgt tcgccggctt tccccgtcaa 1440
gctctaaatc ggggcatccc tttagggttc cgatttagtg ctttacggca cctcgacccc 1500
aaaaaacttg attagggtga tggttcacgt agtgggccat cgccctgata gacggttttt 1560
cgccctttga cgttggagtc cacgttcttt aatagtggac tcttgttcca aactggaaca 1620
acactcaacc ctatctcggt ctattctttt gatttataag ggattttggg gatttcggcc 1680
tattggttaa aaaatgagct gatttaacaa aaatttaacg cgaattaatt ctgtggaatg 1740
tgtgtcagtt agggtgtgga aagtccccag gctccccagg caggcagaag tatgcaaagc 1800
atgcatctca attagtcagc aaccaggtgt ggaaagtccc caggctcccc agcaggcaga 1860
agtatgcaaa gcatgcatct caattagtca gcaaccatag tcccgcccct aactccgccc 1920
atcccgcccc taactccgcc cagttccgcc cattctccgc cccatggctg actaattttt 1980
tttatttatg cagaggccga ggccgcctct gcctctgagc tattccagaa gtagtgagga 2040

```
ggctttttttg gaggcctagg cttttgcaaa aagctcccgg gagcttgtat atccattttc   2100
ggatctgatc agcacgtgtt gacaattaat catcggcata gtatatcggc atagtataat   2160
acgacaaggt gaggaactaa accatggcca agttgaccag tgccgttccg gtgctcaccg   2220
cgcgcgacgt cgccggagcg gtcgagttct ggaccgaccg gctcgggttc tcccgggact   2280
tcgtggagga cgacttcgcc ggtgtggtcc gggacgacgt gaccctgttc atcagcgcgg   2340
tccaggacca ggtggtgccg gacaacaccc tggcctgggt gtgggtgcgc ggcctggacg   2400
agctgtacgc cgagtggtcg gaggtcgtgt ccacgaactt ccgggacgcc tccgggccgg   2460
ccatgaccga gatcggcgag cagccgtggg ggcgggagtt cgccctgcgc gacccggccg   2520
gcaactgcgt gcacttcgtg gccgaggagc aggactgaca cgtgctacga gatttcgatt   2580
ccaccgccgc cttctatgaa aggttgggct tcggaatcgt tttccgggac gccggctgga   2640
tgatcctcca gcgcggggat ctcatgctgg agttcttcgc ccaccccaac ttgtttattg   2700
cagcttataa tggttacaaa taaagcaata gcatcacaaa tttcacaaat aaagcatttt   2760
tttcactgca ttctagttgt ggtttgtcca aactcatcaa tgtatcttat catgtctgta   2820
taccgtcgac ctctagctag agcttggcgt aatcatggtc atagctgttt cctgtgtgaa   2880
attgttatcc gctcacaatt ccacacaaca tacgagccgg aagcataaag tgtaaagcct   2940
ggggtgccta atgagtgagc taactcacat taattgcgtt gcgctcactg cccgctttcc   3000
agtcgggaaa cctgtcgtgc cagctgcatt aatgaatcgg ccaacgcgcg gggagaggcg   3060
gtttgcgtat tgggcgctct tccgcttcct cgctcactga ctcgctgcgc tcggtcgttc   3120
ggctgcggcg agcggtatca gctcactcaa aggcggtaat acggttatcc acagaatcag   3180
gggataacgc aggaaagaac atgtgagcaa aaggccagca aaaggccagg aaccgtaaaa   3240
aggccgcgtt gctggcgttt ttccataggc tccgcccccc tgacgagcat cacaaaaatc   3300
gacgctcaag tcagaggtgg cgaaacccga caggactata aagataccag gcgtttcccc   3360
ctggaagctc cctcgtgcgc tctcctgttc cgaccctgcc gcttaccgga tacctgtccg   3420
cctttctccc ttcgggaagc gtggcgcttt ctcaatgctc acgctgtagg tatctcagtt   3480
cggtgtaggt cgttcgctcc aagctgggct gtgtgcacga accccccgtt cagcccgacc   3540
gctgcgcctt atccggtaac tatcgtcttg agtccaaccc ggtaagacac gacttatcgc   3600
cactggcagc agccactggt aacaggatta gcagagcgag gtatgtaggc ggtgctacag   3660
agttcttgaa gtggtggcct aactacggct acactagaag gacagtattt ggtatctgcg   3720
ctctgctgaa gccagttacc ttcggaaaaa gagttggtag ctcttgatcc ggcaaacaaa   3780
ccaccgctgg tagcggtggt ttttttgttt gcaagcagca gattacgcgc agaaaaaaag   3840
gatctcaaga agatcctttg atcttttcta cggggtctga cgctcagtgg aacgaaaact   3900
cacgttaagg gattttggtc atgagattat caaaaaggat cttcacctag atccttttaa   3960
attaaaaatg aagttttaaa tcaatctaaa gtatatatga gtaaacttgg tctgacagtt   4020
accaatgctt aatcagtgag gcacctatct cagcgatctg tctatttcgt tcatccatag   4080
ttgcctgact ccccgtcgtg tagataacta cgatacggga gggcttacca tctggcccca   4140
gtgctgcaat gataccgcga gacccacgct caccggctcc agatttatca gcaataaacc   4200
agccagccgg aagggccgag cgcagaagtg gtcctgcaac tttatccgcc tccatccagt   4260
ctattaattg ttgccgggaa gctagagtaa gtagttcgcc agttaatagt ttgcgcaacg   4320
ttgttgccat tgctacaggc atcgtggtgt cacgctcgtc gtttggtatg gcttcattca   4380
gctccggttc ccaacgatca aggcgagtta catgatcccc catgttgtgc aaaaaagcgg   4440
```

```
ttagctcctt cggtcctccg atcgttgtca gaagtaagtt ggccgcagtg ttatcactca   4500
tggttatggc agcactgcat aattctctta ctgtcatgcc atccgtaaga tgcttttctg   4560
tgactggtga gtactcaacc aagtcattct gagaatagtg tatgcggcga ccgagttgct   4620
cttgcccggc gtcaatacgg gataataccg cgccacatag cagaacttta aaagtgctca   4680
tcattggaaa acgttcttcg gggcgaaaac tctcaaggat cttaccgctg ttgagatcca   4740
gttcgatgta acccactcgt gcacccaact gatcttcagc atcttttact ttcaccagcg   4800
tttctgggtg agcaaaaaca ggaaggcaaa atgccgcaaa aaagggaata agggcgacac   4860
ggaaatgttg aatactcata ctcttccttt ttcaatatta ttgaagcatt tatcagggtt   4920
attgtctcat gagcggatac atatttgaat gtatttagaa aaataaacaa ataggggttc   4980
cgcgcacatt tccccgaaaa gtgccacctg acgtc                              5015
```

<210> SEQ ID NO 17
<211> LENGTH: 5597
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg gggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
```

```
gctctaaatc gggggctccc tttagggttc cgatttagtg ctttacggca cctcgacccc   1500
aaaaaacttg attagggtga tggttcacgt agtgggccat cgccctgata gacggttttt   1560
cgccctttga cgttggagtc cacgttcttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga aagtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca gcacgtgatg aaaaagcctg aactcaccgc gacgtctgtc gagaagtttc   2160
tgatcgaaaa gttcgacagc gtctccgacc tgatgcagct ctcggagggc gaagaatctc   2220
gtgctttcag cttcgatgta ggagggcgtg gatatgtcct gcgggtaaat agctgcgccg   2280
atggtttcta caaagatcgt tatgtttatc ggcactttgc atcggccgcg ctcccgattc   2340
cggaagtgct tgacattggg gaattcagcg agagcctgac ctattgcatc tcccgccgtg   2400
cacagggtgt cacgttgcaa gacctgcctg aaaccgaact gcccgctgtt ctgcagccgg   2460
tcgcggaggc catggatgcg atcgctgcgg ccgatcttag ccagacgagc gggttcggcc   2520
cattcggacc gcaaggaatc ggtcaataca ctacatggcg tgatttcata tgcgcgattg   2580
ctgatcccca tgtgtatcac tggcaaactg tgatggacga caccgtcagt gcgtccgtcg   2640
cgcaggctct cgatgagctg atgctttggg ccgaggactg ccccgaagtc cggcacctcg   2700
tgcacgcgga tttcggctcc aacaatgtcc tgacggacaa tggccgcata acagcggtca   2760
ttgactggag cgaggcgatg ttcggggatt cccaatacga ggtcgccaac atcttcttct   2820
ggaggccgtg gttggcttgt atggagcagc agacgcgcta cttcgagcgg aggcatccgg   2880
agcttgcagg atcgccgcgg ctccgggcgt atatgctccg cattggtctt gaccaactct   2940
atcagagctt ggttgacggc aatttcgatg atgcagcttg ggcgcagggt cgatgcgacg   3000
caatcgtccg atccggagcc gggactgtcg ggcgtacaca aatcgcccgc agaagcgcgg   3060
ccgtctggac cgatggctgt gtagaagtac tcgccgatag tggaaaccga cgccccagca   3120
ctcgtccgag ggcaaaggaa tagcacgtgc tacgagattt cgattccacc gccgccttct   3180
atgaaaggtt gggcttcgga atcgttttcc gggacgccgg ctggatgatc ctccagcgcg   3240
gggatctcat gctggagttc ttcgcccacc ccaacttgtt tattgcagct tataatggtt   3300
acaaataaag caatagcatc acaaatttca caaataaagc atttttttca ctgcattcta   3360
gttgtggttt gtccaaactc atcaatgtat cttatcatgt ctgtataccg tcgacctcta   3420
gctagagctt ggcgtaatca tggtcatagc tgtttcctgt gtgaaattgt tatccgctca   3480
caattccaca caacatacga gccggaagca taaagtgtaa agcctggggt gcctaatgag   3540
tgagctaact cacattaatt gcgttgcgct cactgcccgc tttccagtcg ggaaacctgt   3600
cgtgccagct gcattaatga atcggccaac gcgcggggag aggcggtttg cgtattgggc   3660
gctcttccgc ttcctcgctc actgactcgc tgcgctcggt cgttcggctg cggcgagcgg   3720
tatcagctca ctcaaaggcg gtaatacggt tatccacaga atcaggggat aacgcaggaa   3780
```

```
agaacatgtg agcaaaaggc cagcaaaagg ccaggaaccg taaaaaggcc gcgttgctgg   3840

cgtttttcca taggctccgc ccccctgacg agcatcacaa aaatcgacgc tcaagtcaga   3900

ggtggcgaaa cccgacagga ctataaagat accaggcgtt tccccctgga agctccctcg   3960

tgcgctctcc tgttccgacc ctgccgctta ccggatacct gtccgccttt ctcccttcgg   4020

gaagcgtggc gctttctcat agctcacgct gtaggtatct cagttcggtg taggtcgttc   4080

gctccaagct gggctgtgtg cacgaacccc ccgttcagcc cgaccgctgc gccttatccg   4140

gtaactatcg tcttgagtcc aacccggtaa gacacgactt atcgccactg gcagcagcca   4200

ctggtaacag gattagcaga gcgaggtatg taggcggtgc tacagagttc ttgaagtggt   4260

ggcctaacta cggctacact agaagaacag tatttggtat ctgcgctctg ctgaagccag   4320

ttaccttcgg aaaaagagtt ggtagctctt gatccggcaa acaaaccacc gctggtagcg   4380

gtttttttgt ttgcaagcag cagattacgc gcagaaaaaa aggatctcaa gaagatcctt   4440

tgatcttttc tacggggtct gacgctcagt ggaacgaaaa ctcacgttaa gggattttgg   4500

tcatgagatt atcaaaaagg atcttcacct agatcctttt aaattaaaaa tgaagtttta   4560

aatcaatcta aagtatatat gagtaaactt ggtctgacag ttaccaatgc ttaatcagtg   4620

aggcacctat ctcagcgatc tgtctatttc gttcatccat agttgcctga ctccccgtcg   4680

tgtagataac tacgatacgg gagggcttac catctggccc cagtgctgca atgataccgc   4740

gagacccacg ctcaccggct ccagatttat cagcaataaa ccagccagcc ggaagggccg   4800

agcgcagaag tggtcctgca actttatccg cctccatcca gtctattaat tgttgccggg   4860

aagctagagt aagtagttcg ccagttaata gtttgcgcaa cgttgttgcc attgctacag   4920

gcatcgtggt gtcacgctcg tcgtttggta tggcttcatt cagctccggt tcccaacgat   4980

caaggcgagt tacatgatcc cccatgttgt gcaaaaaagc ggttagctcc ttcggtcctc   5040

cgatcgttgt cagaagtaag ttggccgcag tgttatcact catggttatg gcagcactgc   5100

ataattctct tactgtcatg ccatccgtaa gatgcttttc tgtgactggt gagtactcaa   5160

ccaagtcatt ctgagaatag tgtatgcggc gaccgagttg ctcttgcccg gcgtcaatac   5220

gggataatac cgcgccacat agcagaactt taaaagtgct catcattgga aaacgttctt   5280

cggggcgaaa actctcaagg atcttaccgc tgttgagatc cagttcgatg taacccactc   5340

gtgcacccaa ctgatcttca gcatctttta ctttcaccag cgtttctggg tgagcaaaaa   5400

caggaaggca aaatgccgca aaaaagggaa taagggcgac acggaaatgt tgaatactca   5460

tactcttcct ttttcaatat tattgaagca tttatcaggg ttattgtctc atgagcggat   5520

acatatttga atgtatttag aaaaataaac aaataggggt tccgcgcaca tttccccgaa   5580

aagtgccacc tgacgtc                                                  5597
```

<210> SEQ ID NO 18
<211> LENGTH: 804
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180
```

```
caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctggttcaa cttcaggagg aggatcaggt ggtggttcag gaggtggagg atcttctgat    480

atcgttatga cacaatctcc agattctttg gctgtttctc ttggagagag ggctactatc    540

aattgcaagg cttctcaaga tgtttctact gctgttgctt ggtaccaaca gaaacctgga    600

cagccaccaa aacttcttat ctcttgggca tctactaggc acactggagt tccagataga    660

ttttctggat ctggatctgg aacagatttc actcttacta tctcatctct tcaagctgag    720

gatgttgcag tttattactg tcagcaacat tatacaactc cacttacttt cggacaagga    780

actaagttgg agatcaaagc tagc                                           804
```

<210> SEQ ID NO 19
<211> LENGTH: 1797
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctggttcaa cttcaggagg aggatcaggt ggtggttcag gaggtggagg atcttctgat    480

atcgttatga cacaatctcc agattctttg gctgtttctc ttggagagag ggctactatc    540

aattgcaagg cttctcaaga tgtttctact gctgttgctt ggtaccaaca gaaacctgga    600

cagccaccaa aacttcttat ctcttgggca tctactaggc acactggagt tccagataga    660

ttttctggat ctggatctgg aacagatttc actcttacta tctcatctct tcaagctgag    720

gatgttgcag tttattactg tcagcaacat tatacaactc cacttacttt cggacaagga    780

actaagttgg agatcaaagc tagcaccaag ggaccttctg tttttccact tgctccttct    840

tctaagtcta cttctggtgg aactgctgct ttgggttgtt tggtgaaaga ttactttcct    900

gagccagtga ccgtttcttg gaactcaggt gctcttacat ctggtgttca tactttccca    960

gctgttcttc aatcttcagg actttactca ctttcttctg ttgttaccgt tccttcttca   1020

agcttgggca ctcagaccta catctgcaat gtgaatcaca aacccagcaa caccaaggtt   1080

gacaagaaag ttgagcccaa gtcttgtgac aagactcata cgtgtccacc gtgcccagca   1140

cctgaacttc ttggaggacc gtcagtcttc ttgtttcctc caaagcctaa ggataccttg   1200

atgatctcca ggactcctga agtcacatgt gtagttgtgg atgtgagcca tgaagatcct   1260

gaggtgaagt tcaactggta tgtggatggt gtggaagtgc acaatgccaa gacaaagccg   1320

agagaggaac agtacaacag cacgtacagg gttgtctcag ttctcactgt tctccatcaa   1380
```

gattggttga atggcaaaga gtacaagtgc aaggtctcca acaaagccct cccagccccc 1440
attgagaaga ccatttccaa agcgaaaggg caaccccgtg aaccacaagt gtacacactt 1500
cctccatctc gcgatgaact gaccaagaac caggtcagct tgacttgcct ggtgaaaggc 1560
ttctatccct ctgacatagc tgtagagtgg gagagcaatg ggcaaccgga gaacaactac 1620
aagactacac ctcccgttct cgattctgac ggctccttct tcctctacag caagctcaca 1680
gtggacaaga gcaggtggca acaagggaat gtcttctcat gctccgtgat gcatgaggct 1740
cttcacaatc actacacaca gaagagtctc tccttgtctc cgggtaaatg aggatcc 1797

<210> SEQ ID NO 20
<211> LENGTH: 8218
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
tctagagtcg acctgcagaa gcttactaga gcgtggtgcg cacgatagcg catagtgttt 60
ttctctccac ttgaatcgaa gagatagact tacggtgtaa atccgtaggg gtggcgtaaa 120
ccaaattacg caatgttttg ggttccattt aaatcgaaac cccttatttc ctggatcacc 180
tgttaacgca cgtttgacgt gtattacagt gggaataagt aaaagtgaga ggttcgaatc 240
ctccctaacc ccgggtaggg gcccagcggc cgctctagct agagtcaagc agatcgttca 300
aacatttggc aataaagttt cttaagattg aatcctgttg ccggtcttgc gatgattatc 360
atataatttc tgttgaatta cgttaagcat gtaataatta acatgtaatg catgacgtta 420
tttatgagat gggtttttat gattagagtc ccgcaattat acatttaata cgcgatagaa 480
aacaaaatat agcgcgcaaa ctaggataaa ttatcgcgcg cggtgtcatc tatgttacta 540
gatcgaccag cttagatcag attgtcgttt cccgccttca gtttaaacta tcagtgtttg 600
acaggatata ttggcgggta aacctaagag aaaagagcgt ttattagaat aatcggatat 660
ttaaaagggc gtgaaaaggt ttatccgttc gtccatttgt atgtgccaac cacagggttc 720
cccagatcag taaagcgctg gctgctgaac cccagccgg aactgacccc acaaggccct 780
agcgtttgca atgcaccagg tcatcattga cccaggcgtg ttccaccagg ccgctgcctc 840
gcaactcttc gcaggcttcg ccgacctgct cgcgccactt cttcacgcgg gtggaatccg 900
atccgcacat gaggcggaag gtttccagct tgagcgggta cggctcccgg tgcgagctga 960
aatagtcgaa catccgtcgg gccgtcggcg acagcttgcg gtacttctcc catatgaatt 1020
tcgtgtagtg gtcgccagca aacagcacga cgatttcctc gtcgatcagg acctggcaac 1080
gggacgtttt cttgccacgg tccaggacgc ggaagcggtg cagcagcgac accgattcca 1140
ggtgcccaac gcggtcggac gtgaagccca tcgccgtcgc ctgtaggcgc gacaggcatt 1200
cctcggcctt cgtgtaatac cggccattga tcgaccagcc caggtcctgg caaagctcgt 1260
agaacgtgaa ggtgatcggc tcgccgatag gggtgcgctt cgcgtactcc aacacctgct 1320
gccacaccag ttcgtcatcg tcggcccgca gctcgacgcc ggtgtaggtg atcttcacgt 1380
ccttgttgac gtggaaaatg accttgtttt gcagcgcctc gcgcgggatt ttcttgttgc 1440
gcgtggtgaa cagggcagag cgggccgtgt cgtttggcat cgctcgcatc gtgtccggcc 1500
acggcgcaat atcgaacaag gaaagctgca tttccttgat ctgctgcttc gtgtgtttca 1560
gcaacgcggc ctgcttggcc tcgctgacct gttttgccag gtcctcgccg gcggtttttc 1620

```
gcttcttggt cgtcatagtt cctcgcgtgt cgatggtcat cgacttcgcc aaacctgccg   1680

cctcctgttc gagacgacgc gaacgctcca cggcggccga tggcgcgggc agggcagggg   1740

gagccagttg cacgctgtcg cgctcgatct tggccgtagc ttgctggacc atcgagccga   1800

cggactggaa ggtttcgcgg ggcgcacgca tgacggtgcg gcttgcgatg gtttcggcat   1860

cctcggcgga aaccccgcg tcgatcagtt cttgcctgta tgccttccgg tcaaacgtcc    1920

gattcattca ccctccttgc gggattgccc cgactcacgc cggggcaatg tgcccttatt   1980

cctgatttga cccgcctggt gccttggtgt ccagataatc caccttatcg gcaatgaagt   2040

cggtcccgta gaccgtctgg ccgtccttct cgtacttggt attccgaatc ttgccctgca   2100

cgaataccag cgaccccttg cccaaatact tgccgtgggc ctcggcctga gagccaaaac   2160

acttgatgcg gaagaagtcg gtgcgctcct gcttgtcgcc ggcatcgttg cgccacatct   2220

aggatctgcc aggaaccgta aaaaggccgc gttgctggcg tttttccata ggctccgccc   2280

ccctgacgag catcacaaaa atcgacgctc aagtcagagg tggcgaaacc cgacaggact   2340

ataaagatac caggcgtttc cccctggaag ctccctcgtg cgctctcctg ttccgaccct   2400

gccgcttacc ggatacctgt ccgcctttct cccttcggga agcgtggcgc tttctcatag   2460

ctcacgctgt aggtatctca gttcggtgta ggtcgttcgc tccaagctgg gctgtgtgca   2520

cgaacccccc gttcagcccg accgctgcgc cttatccggt aactatcgtc ttgagtccaa   2580

cccggtaaga cacgacttat cgccactggc agcagccact ggtaacagga ttagcagagc   2640

gaggtatgta ggcggtgcta cagagttctt gaagtggtgg cctaactacg gctacactag   2700

aagaacagta tttggtatct gcgctctgct gaagccagtt accttcggaa aaagagttgg   2760

tagctcttga tccggcaaac aaaccaccgc tggtagcggt ggtttttttg tttgcaagca   2820

gcagattacg cgcagaaaaa aaggatctca agaagatcct ttgatctttt ctacggggtc   2880

tgacgctcag tggaacgaaa actcacgtta agggattttg gtcatgagat tatcaaaaag   2940

gatcttcacc tagatccttt taaattaaaa atgaagtttt aaatcaatct aaagtatata   3000

tgagtaaact tggtctgaca gttaccaatg cttaatcagt gaggcaccta tctcagcgat   3060

ctgtctattt cgttcatcca tagttgcctg actccccgtc gtgtagataa ctacgatacg   3120

ggagggctta ccatctggcc ccagtgctgc aatgataccg cgagacccac gctcaccggc   3180

tccagattta tcagcaataa accagccagc cggaagggcc gagcgcagaa gtggtcctgc   3240

aactttatcc gcctccatcc agtctattaa ttgttgccgg gaagctagag taagtagttc   3300

gccagttaat agtttgcgca acgttgttgc cattgctaca ggcatcgtgg tgtcacgctc   3360

gtcgtttggt atggcttcat tcagctccgg ttcccaacga tcaaggcgag ttacatgatc   3420

ccccatgttg tgcaaaaaag cggttagctc cttcggtcct ccgatcgttg tcagaagtaa   3480

gttggccgca gtgttatcac tcatggttat ggcagcactg cataattctc ttactgtcat   3540

gccatccgta agatgctttt ctgtgactgg tgagtactca accaagtcat tctgagaata   3600

gtgtatgcgg cgaccgagtt gctcttgccc ggcgtcaata cgggataata ccgcgccaca   3660

tagcagaact ttaaaagtgc tcatcattgg aaaacgttct tcggggcgaa aactctcaag   3720

gatcttaccg ctgttgagat ccagttcgat gtaacccact cgtgcaccca actgatcttc   3780

agcatctttt actttcacca gcgtttctgg gtgagcaaaa acaggaaggc aaaatgccgc   3840

aaaaaaggga ataagggcga cacggaaatg ttgaatactc atactcttcc tttttcaata   3900

ttattgaagc atttatcagg gttattgtct catgagcgga tacatatttg aatgtattta   3960

gaaaaataaa caaatagggg ttccgcgcac gaattggcca gcgctgccat tttggggtg    4020
```

```
aggccgttcg cggccgaggg gcgcagcccc tggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
```

```
tacatgtttg aacttcaaca atttatgact ttttgttctt attgttgcag gtaccatggc   6420

agaattcaca atgggatggt cttgtatcat ccttttcttg gttgcaacag ctactggtgt   6480

tcattctcaa gttcaattgg tgcagtcagg tgctgaggtg aagaaaccag gtgcttcagt   6540

taaggtttct tgtaaggctt ctggttacac attcacagat tattggattg aatgggtgag   6600

acaagctcct ggtcagggtc ttgagtggat gggagatatt ctttgtggaa ctggaagaac   6660

tagatacaac gagaaactta aggctagagt tactatgact gctgatacct ctacatctac   6720

tgcttacatg gaacttagat ctttgagatc agatgacact gctgtgtact attgtgctag   6780

gtcagcttct tatggagact acgctgacta ttggggacaa ggtactactg ttactgtgtc   6840

ttctggttca acttcaggag gaggatcagg tggtggttca ggaggtggag gatcttctga   6900

tatcgttatg acacaatctc cagattcttt ggctgtttct cttggagaga gggctactat   6960

caattgcaag gcttctcaag atgtttctac tgctgttgct tggtaccaac agaaacctgg   7020

acagccacca aaacttctta tctcttgggc atctactagg cacactggag ttccagatag   7080

attttctgga tctggatctg gaacagattt cactcttact atctcatctc ttcaagctga   7140

ggatgttgca gtttattact gtcagcaaca ttatacaact ccacttactt tcggacaagg   7200

aactaagttg gagatcaaag ctagcaccaa gggaccttct gtttttccac ttgctccttc   7260

ttctaagtct acttctggtg gaactgctgc tttgggttgt ttggtgaaag attactttcc   7320

tgagccagtg accgtttctt ggaactcagg tgctcttaca tctggtgttc atactttccc   7380

agctgttctt caatcttcag gactttactc actttcttct gttgttaccg ttccttcttc   7440

aagcttgggc actcagacct acatctgcaa tgtgaatcac aaacccagca acaccaaggt   7500

tgacaagaaa gttgagccca agtcttgtga caagactcat acgtgtccac cgtgcccagc   7560

acctgaactt cttggaggac cgtcagtctt cttgtttcct ccaaagccta aggatacctt   7620

gatgatctcc aggactcctg aagtcacatg tgtagttgtg gatgtgagcc atgaagatcc   7680

tgaggtgaag ttcaactggt atgtggatgg tgtggaagtg cacaatgcca agacaaagcc   7740

gagagaggaa cagtacaaca gcacgtacag ggttgtctca gttctcactg ttctccatca   7800

agattggttg aatggcaaag agtacaagtg caaggtctcc aacaaagccc tcccagcccc   7860

cattgagaag accatttcca aagcgaaagg gcaaccccgt gaaccacaag tgtacacact   7920

tcctccatct cgcgatgaac tgaccaagaa ccaggtcagc ttgacttgcc tggtgaaagg   7980

cttctatccc tctgacatag ctgtagagtg ggagagcaat gggcaaccgg agaacaacta   8040

caagactaca cctcccgttc tcgattctga cggctccttc ttcctctaca gcaagctcac   8100

agtggacaag agcaggtggc aacaagggaa tgtcttctca tgctccgtga tgcatgaggc   8160

tcttcacaat cactacacac agaagagtct ctccttgtct ccgggtaaat gaggatcc     8218
```

```
<210> SEQ ID NO 21
<211> LENGTH: 8264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

agcttgaaga ctaggcgtgg tgcgcacgat agcgcatagt gtttttctct ccacttgaat     60

cgaagagata gacttacggt gtaaatccgt aggggtggcg taaaccaaat tacgcaatgt    120

tttgggttcc atttaaatcg aaacccctta tttcctggat cacctgttaa cgcacgtttg    180
```

```
acgtgtatta cagtgggaat aagtaaaagt gagaggttcg aatcctccct aaccccgggt    240
aggggcccag cggccgctct agctagagtc aagcagatcg ttcaaacatt tggcaataaa    300
gtttcttaag attgaatcct gttgccggtc ttgcgatgat tatcatataa tttctgttga    360
attacgttaa gcatgtaata attaacatgt aatgcatgac gttatttatg agatgggttt    420
ttatgattag agtcccgcaa ttatacattt aatacgcgat agaaaacaaa atatagcgcg    480
caaactagga taaattatcg cgcgcggtgt catctatgtt actagatcga ccagtcctat    540
ggtagtcttc agcttagatc agattgtcgt ttcccgcctt cagtttaaac tatcagtgtt    600
tgacaggata tattggcggg taaacctaag agaaaagagc gtttattaga ataatcggat    660
atttaaaagg gcgtgaaaag gtttatccgt tcgtccattt gtatgtgcat gccaaccaca    720
gggttcccca gatcagtaaa gcgctggctg ctgaaccccc agccggaact gaccccacaa    780
ggccctagcg tttgcaatgc accaggtcat cattgaccca ggcgtgttcc accaggccgc    840
tgcctcgcaa ctcttcgcag gcttcgccga cctgctcgcg ccacttcttc acgcgggtgg    900
aatccgatcc gcacatgagg cggaaggttt ccagcttgag cgggtacggc tcccggtgcg    960
agctgaaata gtcgaacatc cgtcgggccg tcggcgacag cttgcggtac ttctcccata   1020
tgaatttcgt gtagtggtcg ccagcaaaca gcacgacgat ttcctcgtcg atcaggacct   1080
ggcaacggga cgttttcttg ccacggtcca ggacgcggaa gcggtgcagc agcgacaccg   1140
attccaggtg cccaacgcgg tcggacgtga agcccatcgc cgtcgcctgt aggcgcgaca   1200
ggcattcctc ggccttcgtg taataccggc cattgatcga ccagcccagg tcctggcaaa   1260
gctcgtagaa cgtgaaggtg atcggctcgc cgatagggt gcgcttcgcg tactccaaca    1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggattttct   1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
```

```
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg gggatgggag gcccgcgtta   4080
gcgggccggg agggttcgag aagggggggc acccccccttc ggcgtgcgcg gtcacgcgca   4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
```

```
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cacaatggga tggtcttgta tcatcctttt cttggttgca acagctactg   6480
gtgttcattc tcaagttcaa ttggtgcagt caggtgctga ggtgaagaaa ccaggtgctt   6540
cagttaaggt ttcttgtaag gcttctggtt acacattcac agattattgg attgaatggg   6600
tgagacaagc tcctggtcag ggtcttgagt ggatgggaga tattctttgt ggaactggaa   6660
gaactagata caacgagaaa cttaaggcta gagttactat gactgctgat acctctacat   6720
ctactgctta catggaactt agatctttga gatcagatga cactgctgtg tactattgtg   6780
ctaggtcagc ttcttatgga gactacgctg actattgggg acaaggtact actgttactg   6840
tgtcttctgg ttcaacttca ggaggaggat caggtggtgg ttcaggaggt ggaggatctt   6900
ctgatatcgt tatgacacaa tctccagatt ctttggctgt ttctcttgga gagagggcta   6960
ctatcaattg caaggcttct caagatgttt ctactgctgt tgcttggtac caacagaaac   7020
ctggacagcc accaaaactt cttatctctt gggcatctac taggcacact ggagttccag   7080
atagattttc tggatctgga tctggaacag atttcactct tactatctca tctcttcaag   7140
ctgaggatgt tgcagtttat tactgtcagc aacattatac aactccactt actttcggac   7200
aaggaactaa gttggagatc aaagctagca ccaagggacc ttctgttttt ccacttgctc   7260
cttcttctaa gtctacttct ggtggaactg ctgctttggg ttgtttggtg aaagattact   7320
```

```
ttcctgagcc agtgaccgtt tcttggaact caggtgctct tacatctggt gttcatactt   7380

tcccagctgt tcttcaatct tcaggacttt actcactttc ttctgttgtt accgttcctt   7440

cttcaagctt gggcactcag acctacatct gcaatgtgaa tcacaaaccc agcaacacca   7500

aggttgacaa gaaagttgag cccaagtctt gtgacaagac tcatacgtgt ccaccgtgcc   7560

cagcacctga acttcttgga ggaccgtcag tcttcttgtt tcctccaaag cctaaggata   7620

ccttgatgat ctccaggact cctgaagtca catgtgtagt tgtggatgtg agccatgaag   7680

atcctgaggt gaagttcaac tggtatgtgg atggtgtgga agtgcacaat gccaagacaa   7740

agccgagaga ggaacagtac aacagcacgt acagggttgt ctcagttctc actgttctcc   7800

atcaagattg gttgaatggc aaagagtaca agtgcaaggt ctccaacaaa gccctcccag   7860

cccccattga gaagaccatt tccaaagcga aagggcaacc ccgtgaacca caagtgtaca   7920

cacttcctcc atctcgcgat gaactgacca agaaccaggt cagcttgact tgcctggtga   7980

aaggcttcta tccctctgac atagctgtag agtgggagag caatgggcaa ccggagaaca   8040

actacaagac tacacctccc gttctcgatt ctgacggctc cttcttcctc tacagcaagc   8100

tcacagtgga caagagcagg tggcaacaag ggaatgtctt ctcatgctcc gtgatgcatg   8160

aggctcttca caatcactac acacagaaga gtctctcctt gtctccgggt aaatgaggat   8220

cctctagagt cgacctgcag aagctggcag ctaggatggg tctc                  8264
```

```
<210> SEQ ID NO 22
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
```

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctggttcaa cttcaggagg aggatcaggt ggtggttcag gaggtggagg atcttctgat    480

atcgttatga cacaatctcc agattctttg gctgtttctc ttggagagag ggctactatc    540

aattgcaagg cttctcaaga tgtttctact gctgttgctt ggtaccaaca gaaacctgga    600

cagccaccaa aacttcttat ctcttgggca tctactaggc acactggagt tccagataga    660

ttttctggat ctggatctgg aacagatttc actcttacta tctcatctct tcaagctgag    720

gatgttgcag tttattactg tcagcaacat tatacaactc cacttacttt cggacaagga    780

actaagttgg agatcaaagc tagcagaact gttgctgcac catctgtttt catcttccct    840

ccatctgatg agcagttgaa atctggaact gcttctgttg tgtgccttct taataacttc    900

tatcctagag aggctaaagt tcagtggaag gtggataacg cacttcaatc tggtaactct    960

caagagtctg ttacagagca agattctaag gactcaactt actctctttc atctacactt   1020

actttgtcaa aagcagatta cgagaaacac aaagtttacg catgcgaagt tactcatcaa   1080
```

ggactttctt caccagttac aaagtctttc aatagaggag agtgttaagg atcc 1134

<210> SEQ ID NO 23
<211> LENGTH: 7555
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
tctagagtcg acctgcagaa gcttactaga gcgtggtgcg cacgatagcg catagtgttt 60
ttctctccac ttgaatcgaa gagatagact tacggtgtaa atccgtaggg gtggcgtaaa 120
ccaaattacg caatgttttg ggttccattt aaatcgaaac cccttatttc ctggatcacc 180
tgttaacgca cgtttgacgt gtattacagt gggaataagt aaaagtgaga ggttcgaatc 240
ctccctaacc ccgggtaggg gcccagcggc cgctctagct agagtcaagc agatcgttca 300
aacatttggc aataaagttt cttaagattg aatcctgttg ccggtcttgc gatgattatc 360
atataatttc tgttgaatta cgttaagcat gtaataatta acatgtaatg catgacgtta 420
tttatgagat gggtttttat gattagagtc ccgcaattat acatttaata cgcgatagaa 480
aacaaaatat agcgcgcaaa ctaggataaa ttatcgcgcg cggtgtcatc tatgttacta 540
gatcgaccag cttagatcag attgtcgttt cccgccttca gtttaaacta tcagtgtttg 600
acaggatata ttggcgggta aacctaagag aaaagagcgt ttattagaat aatcggatat 660
ttaaaagggc gtgaaaaggt ttatccgttc gtccatttgt atgtgccaac cacagggttc 720
cccagatcag taaagcgctg gctgctgaac ccccagccgg aactgacccc acaaggccct 780
agcgtttgca atgcaccagg tcatcattga cccaggcgtg ttccaccagg ccgctgcctc 840
gcaactcttc gcaggcttcg ccgacctgct cgcgccactt cttcacgcgg gtggaatccg 900
atccgcacat gaggcggaag gtttccagct tgagcgggta cggctcccgg tgcgagctga 960
aatagtcgaa catccgtcgg gccgtcggcg acagcttgcg gtacttctcc catatgaatt 1020
tcgtgtagtg gtcgccagca aacagcacga cgatttcctc gtcgatcagg acctggcaac 1080
gggacgtttt cttgccacgg tccaggacgc ggaagcggtg cagcagcgac accgattcca 1140
ggtgcccaac gcggtcggac gtgaagccca tcgccgtcgc ctgtaggcgc gacaggcatt 1200
cctcggcctt cgtgtaatac cggccattga tcgaccagcc caggtcctgg caaagctcgt 1260
agaacgtgaa ggtgatcggc tcgccgatag gggtgcgctt cgcgtactcc aacacctgct 1320
gccacaccag ttcgtcatcg tcggcccgca gctcgacgcc ggtgtaggtg atcttcacgt 1380
ccttgttgac gtggaaaatg accttgtttt gcagcgcctc gcgcgggatt ttcttgttgc 1440
gcgtggtgaa cagggcagag cgggccgtgt cgtttggcat cgctcgcatc gtgtccggcc 1500
acggcgcaat atcgaacaag gaaagctgca tttccttgat ctgctgcttc gtgtgtttca 1560
gcaacgcggc ctgcttggcc tcgctgacct gttttgccag gtcctcgccg gcggtttttc 1620
gcttcttggt cgtcatagtt cctcgcgtgt cgatggtcat cgacttcgcc aaacctgccg 1680
cctcctgttc gagacgacgc gaacgctcca cggcggccga tggcgcgggc agggcagggg 1740
gagccagttg cacgctgtcg cgctcgatct tggccgtagc ttgctggacc atcgagccga 1800
cggactggaa ggtttcgcgg ggcgcacgca tgacggtgcg gcttgcgatg gtttcggcat 1860
cctcggcgga aaaccccgcg tcgatcagtt cttgcctgta tgccttccgg tcaaacgtcc 1920
gattcattca ccctccttgc gggattgccc cgactcacgc cggggcaatg tgcccttatt 1980

```
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg   4020
aggccgttcg cggccgaggg gcgcagcccc tgggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
```

```
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact ttttgttctt attgttgcag gtaccatggc   6420
agaattcaca atgggatggt cttgtatcat ccttttcttg gttgcaacag ctactggtgt   6480
tcattctcaa gttcaattgg tgcagtcagg tgctgaggtg aagaaaccag gtgcttcagt   6540
taaggtttct tgtaaggctt ctggttacac attcacagat tattggattg aatgggtgag   6600
acaagctcct ggtcagggtc ttgagtggat gggagatatt ctttgtggaa ctggaagaac   6660
tagatacaac gagaaactta aggctagagt tactatgact gctgatacct ctacatctac   6720
```

```
tgcttacatg gaacttagat ctttgagatc agatgacact gctgtgtact attgtgctag   6780

gtcagcttct tatggagact acgctgacta ttggggacaa ggtactactg ttactgtgtc   6840

ttctggttca acttcaggag gaggatcagg tggtggttca ggaggtggag gatcttctga   6900

tatcgttatg acacaatctc cagattcttt ggctgtttct cttggagaga gggctactat   6960

caattgcaag gcttctcaag atgtttctac tgctgttgct tggtaccaac agaaacctgg   7020

acagccacca aaacttctta tctcttgggc atctactagg cacactggag ttccagatag   7080

attttctgga tctggatctg gaacagattt cactcttact atctcatctc ttcaagctga   7140

ggatgttgca gtttattact gtcagcaaca ttatacaact ccacttactt tcggacaagg   7200

aactaagttg gagatcaaag ctagcagaac tgttgctgca ccatctgttt tcatcttccc   7260

tccatctgat gagcagttga aatctggaac tgcttctgtt gtgtgccttc ttaataactt   7320

ctatcctaga gaggctaaag ttcagtggaa ggtggataac gcacttcaat ctggtaactc   7380

tcaagagtct gttacagagc aagattctaa ggactcaact tactctcttt catctacact   7440

tactttgtca aaagcagatt acgagaaaca caaagtttac gcatgcgaag ttactcatca   7500

aggactttct tcaccagtta caaagtcttt caatagagga gagtgttaag gatcc        7555
```

```
<210> SEQ ID NO 24
<211> LENGTH: 7601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
```

```
agcttgaaga ctaggcgtgg tgcgcacgat agcgcatagt gtttttctct ccacttgaat     60

cgaagagata gacttacggt gtaaatccgt aggggtggcg taaaccaaat tacgcaatgt    120

tttgggttcc atttaaatcg aaacccctta tttcctggat cacctgttaa cgcacgtttg    180

acgtgtatta cagtgggaat aagtaaaagt gagaggttcg aatcctccct aaccccgggt    240

aggggcccag cggccgctct agctagagtc aagcagatcg ttcaaacatt tggcaataaa    300

gtttcttaag attgaatcct gttgccggtc ttgcgatgat tatcatataa tttctgttga    360

attacgttaa gcatgtaata attaacatgt aatgcatgac gttatttatg agatgggttt    420

ttatgattag agtcccgcaa ttatacattt aatacgcgat agaaaacaaa atatagcgcg    480

caaactagga taaattatcg cgcgcggtgt catctatgtt actagatcga ccagtcctat    540

ggtagtcttc agcttagatc agattgtcgt ttcccgcctt cagtttaaac tatcagtgtt    600

tgacaggata tattggcggg taaacctaag agaaaagagc gtttattaga ataatcggat    660

atttaaaagg gcgtgaaaag gtttatccgt tcgtccattt gtatgtgcat gccaaccaca    720

gggttcccca gatcagtaaa gcgctggctg ctgaaccccc agccggaact gaccccacaa    780

ggccctagcg tttgcaatgc accaggtcat cattgaccca ggcgtgttcc accaggccgc    840

tgcctcgcaa ctcttcgcag gcttcgccga cctgctcgcg ccacttcttc acgcgggtgg    900

aatccgatcc gcacatgagg cggaaggttt ccagcttgag cgggtacggc tcccggtgcg    960

agctgaaata gtcgaacatc cgtcgggccg tcggcgacag cttgcggtac ttctcccata   1020

tgaatttcgt gtagtggtcg ccagcaaaca gcacgacgat ttcctcgtcg atcaggacct   1080

ggcaacggga cgttttcttg ccacggtcca ggacgcggaa gcggtgcagc agcgacaccg   1140

attccaggtg cccaacgcgg tcggacgtga agcccatcgc cgtcgcctgt aggcgcgaca   1200
```

-continued

```
ggcattcctc ggccttcgtg taataccggc cattgatcga ccagcccagg tcctggcaaa   1260
gctcgtagaa cgtgaaggtg atcggctcgc cgataggggt gcgcttcgcg tactccaaca   1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggattttct   1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
```

```
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg gggatgggag gcccgcgtta   4080
gcgggccggg agggttcgag aagggggggc accccccttc ggcgtgcgcg gtcacgcgca   4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
```

```
acctgcgtgc aatccatctt gttcaatcat gcgaaacgat ccagatccgg tgcagattat   6000

ttggattgag agtgaatatg agactctaat tggataccga ggggaattta tggaacgtca   6060

gtggagcatt tttgacaaga aatatttgct agctgatagt gaccttaggc gacttttgaa   6120

cgcgcaataa tggtttctga cgtatgtgct tagctcatta aactccagaa acccgcggct   6180

gagtggctcc ttcaacgttg cggttctgtc agttccaaac gtaaaacggc ttgtcccgcg   6240

tcatcggcgg gggtcataac gtgactccct taattctccg ctcatggtac ctcgaagccg   6300

cggtgcgggt gccagggcgt gcccttgggc tccccgggcg cgtactccac ctcacccatc   6360

ttttattaca tgtttgaact tcaacaattt atgacttttt gttcttattg ttgcaggtag   6420

agaccgaatt cacaatggga tggtcttgta tcatcctttt cttggttgca acagctactg   6480

gtgttcattc tcaagttcaa ttggtgcagt caggtgctga ggtgaagaaa ccaggtgctt   6540

cagttaaggt ttcttgtaag gcttctggtt acacattcac agattattgg attgaatggg   6600

tgagacaagc tcctggtcag ggtcttgagt ggatgggaga tattctttgt ggaactggaa   6660

gaactagata caacgagaaa cttaaggcta gagttactat gactgctgat acctctacat   6720

ctactgctta catggaactt agatctttga gatcagatga cactgctgtg tactattgtg   6780

ctaggtcagc ttcttatgga gactacgctg actattgggg acaaggtact actgttactg   6840

tgtcttctgg ttcaacttca ggaggaggat caggtggtgg ttcaggaggt ggaggatctt   6900

ctgatatcgt tatgacacaa tctccagatt ctttggctgt ttctcttgga gagagggcta   6960

ctatcaattg caaggcttct caagatgttt ctactgctgt tgcttggtac caacagaaac   7020

ctggacagcc accaaaactt cttatctctt gggcatctac taggcacact ggagttccag   7080

atagattttc tggatctgga tctggaacag atttcactct tactatctca tctcttcaag   7140

ctgaggatgt tgcagtttat tactgtcagc aacattatac aactccactt actttcggac   7200

aaggaactaa gttggagatc aaagctagca gaactgttgc tgcaccatct gttttcatct   7260

tccctccatc tgatgagcag ttgaaatctg gaactgcttc tgttgtgtgc cttcttaata   7320

acttctatcc tagagaggct aaagttcagt ggaaggtgga taacgcactt caatctggta   7380

actctcaaga gtctgttaca gagcaagatt ctaaggactc aacttactct ctttcatcta   7440

cacttacttt gtcaaaagca gattacgaga aacacaaagt ttacgcatgc gaagttactc   7500

atcaaggact ttcttcacca gttacaaagt ctttcaatag aggagagtgt taaggatcct   7560

ctagagtcga cctgcagaag ctggcagcta ggatgggtct c                       7601
```

```
<210> SEQ ID NO 25
<211> LENGTH: 880
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

ggatccgcca ccatgggatg gagctgtatc atcctcttct tggtagcaac agctacaggt     60

aaggggctca cagtagcagg cttgaggtct ggacatatat atgggtgaca atgacatcca    120

ctttgccttt ctctccacag gtgtccactc ccaggttcag ctggtgcagt ctggagctga    180

ggtgaagaag cctggggcct cagtgaaggt ctcctgcaag gcttctggtt acacctttac    240

cgactactgg attgagtggg tgcgacaggc ccctggacaa gggcttgagt ggatgggaga    300

tattttatgt ggaactggta gaactagata caatgagaag ttaaaggcca gagtcaccat    360
```

```
gaccgcagac acatccacga gcacagccta catggagctg aggagcctga gatctgacga    420

cacggccgtg tattactgtg cgagatcggc gtcatatggt gattacgctg actactgggg    480

gcaagggacc acggtcaccg tctcctcagg tggtggtggt tctggtggtg gtggttctgg    540

cggcggcggc tccgacatcg tgatgaccca atctccagac tctttggctg tgtctctagg    600

ggagagggcc accatcaact gcaaggccag tcaggacgtc tctactgctg tagcctggta    660

ccaacagaaa ccaggacagc cacccaaact cctcatctct tgggcatcca cccggcacac    720

tggggtccca gacaggttta gtggcagtgg gtctgggaca gacttcaccc tcaccatcag    780

cagcctgcag gctgaggatg tggcagttta ttactgtcag caacattata ccactcccct    840

cacgttcgga caagggacca agcttgagat caaagctagc                          880
```

```
<210> SEQ ID NO 26
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
```

```
ggatccgcca ccatgggatg gagctgtatc atcctcttct tggtagcaac agctacaggt     60

aaggggctca cagtagcagg cttgaggtct ggacatatat atgggtgaca atgacatcca    120

ctttgccttt ctctccacag gtgtccactc ccaggttcag ctggtgcagt ctggagctga    180

ggtgaagaag cctggggcct cagtgaaggt ctcctgcaag gcttctggtt acacctttac    240

cgactactgg attgagtggg tgcgacaggc ccctggacaa gggcttgagt ggatgggaga    300

tattttatgt ggaactggta gaactagata caatgagaag ttaaaggcca gagtcaccat    360

gaccgcagac acatccacga gcacagccta catggagctg aggagcctga gatctgacga    420

cacggccgtg tattactgtg cgagatcggc gtcatatggt gattacgctg actactgggg    480

gcaagggacc acggtcaccg tctcctcagg tggtggtggt tctggtggtg gtggttctgg    540

cggcggcggc tccgacatcg tgatgaccca atctccagac tctttggctg tgtctctagg    600

ggagagggcc accatcaact gcaaggccag tcaggacgtc tctactgctg tagcctggta    660

ccaacagaaa ccaggacagc cacccaaact cctcatctct tgggcatcca cccggcacac    720

tggggtccca gacaggttta gtggcagtgg gtctgggaca gacttcaccc tcaccatcag    780

cagcctgcag gctgaggatg tggcagttta ttactgtcag caacattata ccactcccct    840

cacgttcgga caagggacca agcttgagat caaagctagc accaagggcc catcggtctt    900

cccoctggca ccctcctcca agagcacctc tgggggcaca gcggccctgg gctgcctggt    960

caaggactac ttccccgaac cggtgacggt gtcgtggaac tcaggcgccc tgaccagcgg   1020

cgtgcacacc ttcccggctg tcctacagtc ctcaggactc tactccctca gcagcgtggt   1080

gaccgtgccc tccagcagct tgggcaccca gacctacatc tgcaacgtga atcacaagcc   1140

cagcaacacc aaggtggaca agagagttga gcccaaatct tgtgacaaaa ctcacacatg   1200

cccaccgtgc ccagcacctg aactcctggg gggaccgtca gtcttcctct tccccccaaa   1260

acccaaggac accctcatga tctcccggac ccctgaggtc acatgcgtgg tggtggacgt   1320

gagccacgaa gaccctgagg tcaagttcaa ctggtacgtg gacggcgtgg aggtgcataa   1380

tgccaagaca aagccgcggg aggagcagta caacagcacg taccgtgtgg tcagcgtcct   1440

caccgtcctg caccaggact ggctgaatgg caaggagtac aagtgcaagg tctccaacaa   1500
```

agccctccca gcccccatcg agaaaaccat ctccaaagcc aaagggcagc cccgagaacc 1560
acaggtgtac accctgcccc catcccggga tgagctgacc aagaaccagg tcagcctgac 1620
ctgcctggtc aaaggcttct atcccagcga catcgccgtg gagtgggaga gcaatgggca 1680
gccggagaac aactacaaga ccacgcctcc cgtgctggac tccgacggct ccttcttcct 1740
ctacagcaag ctcaccgtgg acaagagcag gtggcagcag gggaacgtct tctcatgctc 1800
cgtgatgcat gaggctctgc acaaccacta cacgcagaag agcctctccc tgtctccggg 1860
taaatgagcg gccgc 1875

<210> SEQ ID NO 27
<211> LENGTH: 6833
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccgccacc atgggatgga gctgtatcat 960
cctcttcttg gtagcaacag ctacaggtaa ggggctcaca gtagcaggct tgaggtctgg 1020
acatatatat gggtgacaat gacatccact ttgcctttct ctccacaggt gtccactccc 1080
aggttcagct ggtgcagtct ggagctgagg tgaagaagcc tggggcctca gtgaaggtct 1140
cctgcaaggc ttctggttac acctttaccg actactggat tgagtgggtg cgacaggccc 1200
ctggacaagg gcttgagtgg atgggagata ttttatgtgg aactggtaga actagataca 1260
atgagaagtt aaaggccaga gtcaccatga ccgcagacac atccacgagc acagcctaca 1320
tggagctgag gagcctgaga tctgacgaca cggccgtgta ttactgtgcg agatcggcgt 1380
catatggtga ttacgctgac tactgggggc aagggaccac ggtcaccgtc tcctcaggtg 1440
gtggtggttc tggtggtggt ggttctggcg gcggcggctc cgacatcgtg atgacccaat 1500
ctccagactc tttggctgtg tctctagggg agagggccac catcaactgc aaggccagtc 1560
aggacgtctc tactgctgta gcctggtacc aacagaaacc aggacagcca cccaaactcc 1620

```
tcatctcttg ggcatccacc cggcacactg ggtcccaga caggtttagt ggcagtgggt   1680
ctgggacaga cttcaccctc accatcagca gcctgcaggc tgaggatgtg gcagtttatt   1740
actgtcagca acattatacc actcccctca cgttcggaca agggaccaag cttgagatca   1800
aagctagcac caagggccca tcggtcttcc ccctggcacc ctcctccaag agcacctctg   1860
ggggcacagc ggccctgggc tgcctggtca aggactactt ccccgaaccg gtgacggtgt   1920
cgtggaactc aggcgccctg accagcggcg tgcacacctt cccggctgtc ctacagtcct   1980
caggactcta ctccctcagc agcgtggtga ccgtgccctc cagcagcttg ggcacccaga   2040
cctacatctg caacgtgaat cacaagccca gcaacaccaa ggtggacaag agagttgagc   2100
ccaaatcttg tgacaaaact cacacatgcc caccgtgccc agcacctgaa ctcctggggg   2160
gaccgtcagt cttcctcttc cccccaaaac ccaaggacac cctcatgatc tcccggaccc   2220
ctgaggtcac atgcgtggtg gtggacgtga gccacgaaga ccctgaggtc aagttcaact   2280
ggtacgtgga cggcgtggag gtgcataatg ccaagacaaa gccgcgggag gagcagtaca   2340
acagcacgta ccgtgtggtc agcgtcctca ccgtcctgca ccaggactgg ctgaatggca   2400
aggagtacaa gtgcaaggtc tccaacaaag ccctcccagc ccccatcgag aaaaccatct   2460
ccaaagccaa agggcagccc cgagaaccac aggtgtacac cctgccccca tcccgggatg   2520
agctgaccaa gaaccaggtc agcctgacct gcctggtcaa aggcttctat cccagcgaca   2580
tcgccgtgga gtgggagagc aatgggcagc cggagaacaa ctacaagacc acgcctcccg   2640
tgctggactc cgacggctcc ttcttcctct acagcaagct caccgtggac aagagcaggt   2700
ggcagcaggg gaacgtcttc tcatgctccg tgatgcatga ggctctgcac aaccactaca   2760
cgcagaagag cctctccctg tctccgggta aatgagcggc cgctcgagtc tagagggccc   2820
gtttaaaccc gctgatcagc ctcgactgtg ccttctagtt gccagccatc tgttgtttgc   2880
ccctcccccg tgccttcctt gaccctggaa ggtgccactc ccactgtcct ttcctaataa   2940
aatgaggaaa ttgcatcgca ttgtctgagt aggtgtcatt ctattctggg gggtggggtg   3000
gggcaggaca gcaaggggga ggattgggaa gacaatagca ggcatgctgg ggatgcggtg   3060
ggctctatgg cttctgaggc ggaaagaacc agctggggct ctagggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
ccctgataga cggtttttcg ccctttgacg ttggagtcca cgttctttaa tagtggactc   3420
ttgttccaaa ctggaacaac actcaaccct atctcggtct attcttttga tttataaggg   3480
attttgggga tttcggccta ttggttaaaa aatgagctga tttaacaaaa atttaacgcg   3540
aattaattct gtggaatgtg tgtcagttag ggtgtggaaa gtccccaggc tccccaggca   3600
ggcagaagta tgcaaagcat gcatctcaat tagtcagcaa ccaggtgtgg aaagtcccca   3660
ggctccccag caggcagaag tatgcaaagc atgcatctca attagtcagc aaccatagtc   3720
ccgcccctaa ctccgcccat cccgccccta actccgccca gttccgccca ttctccgccc   3780
catggctgac taattttttt tatttatgca gaggccgagg ccgcctctgc ctctgagcta   3840
ttccagaagt agtgaggagg cttttttgga ggcctaggct tttgcaaaaa gctcccggga   3900
gcttgtatat ccattttcgg atctgatcag cacgtgttga caattaatca tcggcatagt   3960
```

```
atatcggcat agtataatac gacaaggtga ggaactaaac catggccaag ttgaccagtg   4020
ccgttccggt gctcaccgcg cgcgacgtcg ccggagcggt cgagttctgg accgaccggc   4080
tcgggttctc ccgggacttc gtggaggacg acttcgccgg tgtggtccgg gacgacgtga   4140
ccctgttcat cagcgcggtc caggaccagg tggtgccgga caacaccctg gcctgggtgt   4200
gggtgcgcgg cctggacgag ctgtacgccg agtggtcgga ggtcgtgtcc acgaacttcc   4260
gggacgcctc cgggccggcc atgaccgaga tcggcgagca gccgtggggg cgggagttcg   4320
ccctgcgcga cccggccggc aactgcgtgc acttcgtggc cgaggagcag gactgacacg   4380
tgctacgaga tttcgattcc accgccgcct tctatgaaag gttgggcttc ggaatcgttt   4440
tccgggacgc cggctggatg atcctccagc gcggggatct catgctggag ttcttcgccc   4500
accccaactt gtttattgca gcttataatg gttacaaata aagcaatagc atcacaaatt   4560
tcacaaataa agcatttttt tcactgcatt ctagttgtgg tttgtccaaa ctcatcaatg   4620
tatcttatca tgtctgtata ccgtcgacct ctagctagag cttggcgtaa tcatggtcat   4680
agctgtttcc tgtgtgaaat tgttatccgc tcacaattcc acacaacata cgagccggaa   4740
gcataaagtg taaagcctgg ggtgcctaat gagtgagcta actcacatta attgcgttgc   4800
gctcactgcc cgctttccag tcgggaaacc tgtcgtgcca gctgcattaa tgaatcggcc   4860
aacgcgcggg gagaggcggt ttgcgtattg ggcgctcttc cgcttcctcg ctcactgact   4920
cgctgcgctc ggtcgttcgg ctgcggcgag cggtatcagc tcactcaaag gcggtaatac   4980
ggttatccac agaatcaggg gataacgcag gaaagaacat gtgagcaaaa ggccagcaaa   5040
aggccaggaa ccgtaaaaag gccgcgttgc tggcgttttt ccataggctc cgcccccctg   5100
acgagcatca caaaaatcga cgctcaagtc agaggtggcg aaacccgaca ggactataaa   5160
gataccaggc gtttccccct ggaagctccc tcgtgcgctc tcctgttccg accctgccgc   5220
ttaccggata cctgtccgcc tttctccctt cgggaagcgt ggcgctttct caatgctcac   5280
gctgtaggta tctcagttcg gtgtaggtcg ttcgctccaa gctgggctgt gtgcacgaac   5340
cccccgttca gcccgaccgc tgcgccttat ccggtaacta tcgtcttgag tccaacccgg   5400
taagacacga cttatcgcca ctggcagcag ccactggtaa caggattagc agagcgaggt   5460
atgtaggcgg tgctacagag ttcttgaagt ggtggcctaa ctacggctac actagaagga   5520
cagtatttgg tatctgcgct ctgctgaagc cagttacctt cggaaaaaga gttggtagct   5580
cttgatccgg caaacaaacc accgctggta gcggtggttt ttttgtttgc aagcagcaga   5640
ttacgcgcag aaaaaaagga tctcaagaag atcctttgat cttttctacg gggtctgacg   5700
ctcagtggaa cgaaaactca cgttaaggga ttttggtcat gagattatca aaaaggatct   5760
tcacctagat ccttttaaat taaaaatgaa gttttaaatc aatctaaagt atatatgagt   5820
aaacttggtc tgacagttac caatgcttaa tcagtgaggc acctatctca gcgatctgtc   5880
tatttcgttc atccatagtt gcctgactcc ccgtcgtgta gataactacg atacgggagg   5940
gcttaccatc tggccccagt gctgcaatga taccgcgaga cccacgctca ccggctccag   6000
atttatcagc aataaaccag ccagccggaa gggccgagcg cagaagtggt cctgcaactt   6060
tatccgcctc catccagtct attaattgtt gccgggaagc tagagtaagt agttcgccag   6120
ttaatagttt gcgcaacgtt gttgccattg ctacaggcat cgtggtgtca cgctcgtcgt   6180
ttggtatggc ttcattcagc tccggttccc aacgatcaag gcgagttaca tgatccccca   6240
tgttgtgcaa aaaagcggtt agctccttcg gtcctccgat cgttgtcaga agtaagttgg   6300
ccgcagtgtt atcactcatg gttatggcag cactgcataa ttctcttact gtcatgccat   6360
```

```
ccgtaagatg cttttctgtg actggtgagt actcaaccaa gtcattctga gaatagtgta   6420

tgcggcgacc gagttgctct tgcccggcgt caatacggga taataccgcg ccacatagca   6480

gaactttaaa agtgctcatc attggaaaac gttcttcggg gcgaaaactc tcaaggatct   6540

taccgctgtt gagatccagt tcgatgtaac ccactcgtgc acccaactga tcttcagcat   6600

cttttacttt caccagcgtt tctgggtgag caaaaacagg aaggcaaaat gccgcaaaaa   6660

agggaataag ggcgacacgg aaatgttgaa tactcatact cttccttttt caatattatt   6720

gaagcattta tcagggttat tgtctcatga gcggatacat atttgaatgt atttagaaaa   6780

ataaacaaat aggggttccg cgcacatttc cccgaaaagt gccacctgac gtc          6833
```

<210> SEQ ID NO 28
<211> LENGTH: 7415
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccgccacc atgggatgga gctgtatcat    960

cctcttcttg gtagcaacag ctacaggtaa ggggctcaca gtagcaggct tgaggtctgg   1020

acatatatat gggtgacaat gacatccact ttgcctttct ctccacaggt gtccactccc   1080

aggttcagct ggtgcagtct ggagctgagg tgaagaagcc tggggcctca gtgaaggtct   1140

cctgcaaggc ttctggttac acctttaccg actactggat tgagtgggtg cgacaggccc   1200

ctggacaagg gcttgagtgg atgggagata ttttatgtgg aactggtaga actagataca   1260

atgagaagtt aaaggccaga gtcaccatga ccgcagacac atccacgagc acagcctaca   1320

tggagctgag gagcctgaga tctgacgaca cggccgtgta ttactgtgcg agatcggcgt   1380

catatggtga ttacgctgac tactgggggc aagggaccac ggtcaccgtc tcctcaggtg   1440

gtggtggttc tggtggtggt ggttctggcg gcggcggctc cgacatcgtg atgacccaat   1500

ctccagactc tttggctgtg tctctagggg agagggccac catcaactgc aaggccagtc   1560
```

```
aggacgtctc tactgctgta gcctggtacc aacagaaacc aggacagcca cccaaactcc   1620
tcatctcttg ggcatccacc cggcacactg ggtcccaga caggtttagt ggcagtgggt   1680
ctgggacaga cttcaccctc accatcagca gcctgcaggc tgaggatgtg gcagtttatt   1740
actgtcagca acattatacc actcccctca cgttcggaca agggaccaag cttgagatca   1800
aagctagcac caagggccca tcggtcttcc ccctggcacc ctcctccaag agcacctctg   1860
ggggcacagc ggccctgggc tgcctggtca aggactactt ccccgaaccg gtgacggtgt   1920
cgtggaactc aggcgccctg accagcggcg tgcacacctt cccggctgtc ctacagtcct   1980
caggactcta ctccctcagc agcgtggtga ccgtgccctc cagcagcttg ggcacccaga   2040
cctacatctg caacgtgaat cacaagccca gcaacaccaa ggtggacaag agagttgagc   2100
ccaaatcttg tgacaaaact cacacatgcc caccgtgccc agcacctgaa ctcctggggg   2160
gaccgtcagt cttcctcttc cccccaaaac ccaaggacac cctcatgatc tcccggaccc   2220
ctgaggtcac atgcgtggtg gtggacgtga gccacgaaga ccctgaggtc aagttcaact   2280
ggtacgtgga cggcgtggag gtgcataatg ccaagacaaa gccgcgggag gagcagtaca   2340
acagcacgta ccgtgtggtc agcgtcctca ccgtcctgca ccaggactgg ctgaatggca   2400
aggagtacaa gtgcaaggtc tccaacaaag ccctcccagc ccccatcgag aaaaccatct   2460
ccaaagccaa agggcagccc cgagaaccac aggtgtacac cctgccccca tcccgggatg   2520
agctgaccaa gaaccaggtc agcctgacct gcctggtcaa aggcttctat cccagcgaca   2580
tcgccgtgga gtgggagagc aatgggcagc cggagaacaa ctacaagacc acgcctcccg   2640
tgctggactc cgacggctcc ttcttcctct acagcaagct caccgtggac aagagcaggt   2700
ggcagcaggg gaacgtcttc tcatgctccg tgatgcatga ggctctgcac aaccactaca   2760
cgcagaagag cctctccctg tctccgggta aatgagcggc cgctcgagtc tagagggccc   2820
gtttaaaccc gctgatcagc ctcgactgtg ccttctagtt gccagccatc tgttgtttgc   2880
ccctcccccg tgccttcctt gaccctggaa ggtgccactc ccactgtcct ttcctaataa   2940
aatgaggaaa ttgcatcgca ttgtctgagt aggtgtcatt ctattctggg gggtggggtg   3000
gggcaggaca gcaaggggga ggattgggaa gacaatagca ggcatgctgg ggatgcggtg   3060
ggctctatgg cttctgaggc ggaaagaacc agctggggct ctagggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg gggctccctt tagggttccg atttagtgct   3300
ttacggcacc tcgaccccaa aaaacttgat tagggtgatg gttcacgtag tgggccatcg   3360
ccctgataga cggtttttcg ccctttgacg ttggagtcca cgttctttaa tagtggactc   3420
ttgttccaaa ctggaacaac actcaaccct atctcggtct attcttttga tttataaggg   3480
attttgccga tttcggccta ttggttaaaa aatgagctga tttaacaaaa atttaacgcg   3540
aattaattct gtggaatgtg tgtcagttag ggtgtggaaa gtccccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgcccctaac tccgcccatc ccgcccctaa ctccgcccag ttccgcccat tctccgcccc   3780
atggctgact aattttttt atttatgcag aggccgaggc cgcctctgcc tctgagctat   3840
tccagaagta gtgaggaggc ttttttggag gcctaggctt ttgcaaaaag ctcccgggag   3900
```

```
cttgtatatc cattttcgga tctgatcagc acgtgatgaa aaagcctgaa ctcaccgcga   3960
cgtctgtcga gaagtttctg atcgaaaagt tcgacagcgt ctccgacctg atgcagctct   4020
cggagggcga agaatctcgt gctttcagct tcgatgtagg agggcgtgga tatgtcctgc   4080
gggtaaatag ctgcgccgat ggtttctaca aagatcgtta tgtttatcgg cactttgcat   4140
cggccgcgct cccgattccg gaagtgcttg acattgggga attcagcgag agcctgacct   4200
attgcatctc ccgccgtgca cagggtgtca cgttgcaaga cctgcctgaa accgaactgc   4260
ccgctgttct gcagccggtc gcggaggcca tggatgcgat cgctgcggcc gatcttagcc   4320
agacgagcgg gttcggccca ttcggaccgc aaggaatcgg tcaatacact acatggcgtg   4380
atttcatatg cgcgattgct gatccccatg tgtatcactg gcaaactgtg atggacgaca   4440
ccgtcagtgc gtccgtcgcg caggctctcg atgagctgat gctttgggcc gaggactgcc   4500
ccgaagtccg gcacctcgtg cacgcggatt tcggctccaa caatgtcctg acggacaatg   4560
gccgcataac agcggtcatt gactggagcg aggcgatgtt cggggattcc caatacgagg   4620
tcgccaacat cttcttctgg aggccgtggt tggcttgtat ggagcagcag acgcgctact   4680
tcgagcggag gcatccggag cttgcaggat cgccgcggct ccgggcgtat atgctccgca   4740
ttggtcttga ccaactctat cagagcttgg ttgacggcaa tttcgatgat gcagcttggg   4800
cgcagggtcg atgcgacgca atcgtccgat ccggagccgg gactgtcggg cgtacacaaa   4860
tcgcccgcag aagcgcggcc gtctggaccg atggctgtgt agaagtactc gccgatagtg   4920
gaaaccgacg ccccagcact cgtccgaggg caaaggaata gcacgtgcta cgagatttcg   4980
attccaccgc cgccttctat gaaaggttgg gcttcggaat cgttttccgg gacgccggct   5040
ggatgatcct ccagcgcggg gatctcatgc tggagttctt cgcccacccc aacttgttta   5100
ttgcagctta taatggttac aaataaagca atagcatcac aaatttcaca aataaagcat   5160
tttttcact gcattctagt tgtggtttgt ccaaactcat caatgtatct tatcatgtct   5220
gtataccgtc gacctctagc tagagcttgg cgtaatcatg gtcatagctg tttcctgtgt   5280
gaaattgtta tccgctcaca attccacaca acatacgagc cggaagcata aagtgtaaag   5340
cctggggtgc ctaatgagtg agctaactca cattaattgc gttgcgctca ctgcccgctt   5400
tccagtcggg aaacctgtcg tgccagctgc attaatgaat cggccaacgc gcggggagag   5460
gcggtttgcg tattgggcgc tcttccgctt cctcgctcac tgactcgctg cgctcggtcg   5520
ttcggctgcg gcgagcggta tcagctcact caaaggcggt aatacggtta tccacagaat   5580
caggggataa cgcaggaaag aacatgtgag caaaaggcca gcaaaaggcc aggaaccgta   5640
aaaaggccgc gttgctggcg tttttccata ggctccgccc ccctgacgag catcacaaaa   5700
atcgacgctc aagtcagagg tggcgaaacc cgacaggact ataaagatac caggcgtttc   5760
cccctggaag ctccctcgtg cgctctcctg ttccgaccct gccgcttacc ggatacctgt   5820
ccgcctttct cccttcggga agcgtggcgc tttctcatag ctcacgctgt aggtatctca   5880
gttcggtgta ggtcgttcgc tccaagctgg gctgtgtgca cgaacccccc gttcagcccg   5940
accgctgcgc cttatccggt aactatcgtc ttgagtccaa cccggtaaga cacgacttat   6000
cgccactggc agcagccact ggtaacagga ttagcagagc gaggtatgta ggcggtgcta   6060
cagagttctt gaagtggtgg cctaactacg gctacactag aagaacagta tttggtatct   6120
gcgctctgct gaagccagtt accttcggaa aaagagttgg tagctcttga tccggcaaac   6180
aaaccaccgc tggtagcggt ttttttgttt gcaagcagca gattacgcgc agaaaaaaag   6240
gatctcaaga agatcctttg atcttttcta cggggtctga cgctcagtgg aacgaaaact   6300
```

```
cacgttaagg gattttggtc atgagattat caaaaaggat cttcacctag atccttttaa   6360

attaaaaatg aagttttaaa tcaatctaaa gtatatatga gtaaacttgg tctgacagtt   6420

accaatgctt aatcagtgag gcacctatct cagcgatctg tctatttcgt tcatccatag   6480

ttgcctgact ccccgtcgtg tagataacta cgatacggga gggcttacca tctggcccca   6540

gtgctgcaat gataccgcga gacccacgct caccggctcc agatttatca gcaataaacc   6600

agccagccgg aagggccgag cgcagaagtg gtcctgcaac tttatccgcc tccatccagt   6660

ctattaattg ttgccgggaa gctagagtaa gtagttcgcc agttaatagt ttgcgcaacg   6720

ttgttgccat tgctacaggc atcgtggtgt cacgctcgtc gtttggtatg gcttcattca   6780

gctccggttc ccaacgatca aggcgagtta catgatcccc catgttgtgc aaaaaagcgg   6840

ttagctcctt cggtcctccg atcgttgtca gaagtaagtt ggccgcagtg ttatcactca   6900

tggttatggc agcactgcat aattctctta ctgtcatgcc atccgtaaga tgcttttctg   6960

tgactggtga gtactcaacc aagtcattct gagaatagtg tatgcggcga ccgagttgct   7020

cttgcccggc gtcaatacgg gataataccg cgccacatag cagaacttta aaagtgctca   7080

tcattggaaa acgttcttcg gggcgaaaac tctcaaggat cttaccgctg ttgagatcca   7140

gttcgatgta acccactcgt gcacccaact gatcttcagc atcttttact ttcaccagcg   7200

tttctgggtg agcaaaaaca ggaaggcaaa atgccgcaaa aaagggaata agggcgacac   7260

ggaaatgttg aatactcata ctcttccttt ttcaatatta ttgaagcatt tatcagggtt   7320

attgtctcat gagcggatac atatttgaat gtatttagaa aaataaacaa ataggggttc   7380

cgcgcacatt tccccgaaaa gtgccacctg acgtc                              7415
```

```
<210> SEQ ID NO 29
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
```

```
ggatccgcca ccatgggatg gagctgtatc atcctcttct tggtagcaac agctacaggt     60

aaggggctca cagtagcagg cttgaggtct ggacatatat atgggtgaca atgacatcca    120

ctttgccttt ctctccacag gtgtccactc ccaggttcag ctggtgcagt ctggagctga    180

ggtgaagaag cctggggcct cagtgaaggt ctcctgcaag gcttctggtt acacctttac    240

cgactactgg attgagtggg tgcgacaggc ccctggacaa gggcttgagt ggatgggaga    300

tattttatgt ggaactggta gaactagata caatgagaag ttaaaggcca gagtcaccat    360

gaccgcagac acatccacga gcacagccta catggagctg aggagcctga gatctgacga    420

cacggccgtg tattactgtg cgagatcggc gtcatatggt gattacgctg actactgggg    480

gcaagggacc acggtcaccg tctcctcagg tggtggtggt tctggtggtg gtggttctgg    540

cggcggcggc tccgacatcg tgatgaccca atctccagac tctttggctg tgtctctagg    600

ggagagggcc accatcaact gcaaggccag tcaggacgtc tctactgctg tagcctggta    660

ccaacagaaa ccaggacagc cacccaaact cctcatctct tgggcatcca cccggcacac    720

tggggtccca gacaggttta gtggcagtgg gtctgggaca gacttcaccc tcaccatcag    780

cagcctgcag gctgaggatg tggcagttta ttactgtcag caacattata ccactcccct    840

cacgttcgga caagggacca agcttgagat caaagctagc gtggctgcac catctgtctt    900
```

```
catcttcccg ccatctgatg agcagttgaa atctggaact gcctctgttg tgtgcctgct     960

gaataacttc tatcccagag aggccaaagt acagtggaag gtggataacg ccctccaatc    1020

gggtaactcc caggagagtg tcacagagca ggacagcaag gacagcacct acagcctcag    1080

cagcaccctg acgctgagca aagcagacta cgagaaacac aaagtctacg cctgcgaagt    1140

cacccatcag ggcctgagct cgcccgtcac aaagagcttc aacaggggag agtgttaggc    1200

ggccgc                                                               1206
```

```
<210> SEQ ID NO 30
<211> LENGTH: 6164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gctggctagc     900

gtttaaactt aagcttggta ccgagctcgg atccgccacc atgggatgga gctgtatcat     960

cctcttcttg gtagcaacag ctacaggtaa ggggctcaca gtagcaggct tgaggtctgg    1020

acatatatat gggtgacaat gacatccact ttgcctttct ctccacaggt gtccactccc    1080

aggttcagct ggtgcagtct ggagctgagg tgaagaagcc tggggcctca gtgaaggtct    1140

cctgcaaggc ttctggttac acctttaccg actactggat tgagtgggtg cgacaggccc    1200

ctggacaagg gcttgagtgg atgggagata ttttatgtgg aactggtaga actagataca    1260

atgagaagtt aaaggccaga gtcaccatga ccgcagacac atccacgagc acagcctaca    1320

tggagctgag gagcctgaga tctgacgaca cggccgtgta ttactgtgcg agatcggcgt    1380

catatggtga ttacgctgac tactgggggc aagggaccac ggtcaccgtc tcctcaggtg    1440

gtggtggttc tggtggtggt ggttctggcg gcggcggctc cgacatcgtg atgacccaat    1500

ctccagactc tttggctgtg tctctagggg agagggccac catcaactgc aaggccagtc    1560

aggacgtctc tactgctgta gcctggtacc aacagaaacc aggacagcca cccaaactcc    1620

tcatctcttg ggcatccacc cggcacactg ggtcccagac aggtttagt ggcagtgggt     1680
```

```
ctgggacaga cttcaccctc accatcagca gcctgcaggc tgaggatgtg gcagtttatt   1740

actgtcagca acattatacc actcccctca cgttcggaca agggaccaag cttgagatca   1800

aagctagcgt ggctgcacca tctgtcttca tcttcccgcc atctgatgag cagttgaaat   1860

ctggaactgc ctctgttgtg tgcctgctga ataacttcta tcccagagag gccaaagtac   1920

agtggaaggt ggataacgcc ctccaatcgg gtaactccca ggagagtgtc acagagcagg   1980

acagcaagga cagcacctac agcctcagca gcaccctgac gctgagcaaa gcagactacg   2040

agaaacacaa agtctacgcc tgcgaagtca cccatcaggg cctgagctcg cccgtcacaa   2100

agagcttcaa caggggagag tgttaggcgg ccgctcgagt ctagagggcc cgtttaaacc   2160

cgctgatcag cctcgactgt gccttctagt tgccagccat ctgttgtttg cccctccccc   2220

gtgccttcct tgaccctgga aggtgccact cccactgtcc tttcctaata aaatgaggaa   2280

attgcatcgc attgtctgag taggtgtcat tctattctgg ggggtggggt ggggcaggac   2340

agcaaggggg aggattggga agacaatagc aggcatgctg gggatgcggt gggctctatg   2400

gcttctgagg cggaaagaac cagctggggc tctagggggt atccccacgc gccctgtagc   2460

ggcgcattaa gcgcggcggg tgtggtggtt acgcgcagcg tgaccgctac acttgccagc   2520

gccctagcgc ccgctccttt cgctttcttc ccttcctttc tcgccacgtt cgccggcttt   2580

ccccgtcaag ctctaaatcg ggcatccct ttagggttcc gatttagtgc tttacggcac    2640

ctcgacccca aaaaacttga ttagggtgat ggttcacgta gtgggccatc gccctgatag   2700

acggtttttc gccctttgac gttggagtcc acgttcttta atagtggact cttgttccaa   2760

actggaacaa cactcaaccc tatctcggtc tattcttttg atttataagg gattttgggg   2820

atttcggcct attggttaaa aaatgagctg atttaacaaa aatttaacgc gaattaattc   2880

tgtggaatgt gtgtcagtta gggtgtggaa agtccccagg ctccccaggc aggcagaagt   2940

atgcaaagca tgcatctcaa ttagtcagca accaggtgtg gaaagtcccc aggctcccca   3000

gcaggcagaa gtatgcaaag catgcatctc aattagtcag caaccatagt cccgccccta   3060

actccgccca tcccgcccct aactccgccc agttccgccc attctccgcc ccatggctga   3120

ctaatttttt ttatttatgc agaggccgag gccgcctctg cctctgagct attccagaag   3180

tagtgaggag gcttttttgg aggcctaggc ttttgcaaaa agctcccggg agcttgtata   3240

tccattttcg gatctgatca gcacgtgttg acaattaatc atcggcatag tatatcggca   3300

tagtataata cgacaaggtg aggaactaaa ccatggccaa gttgaccagt gccgttccgg   3360

tgctcaccgc gcgcgacgtc gccggagcgg tcgagttctg gaccgaccgg ctcgggttct   3420

cccgggactt cgtggaggac gacttcgccg gtgtggtccg ggacgacgtg accctgttca   3480

tcagcgcggt ccaggaccag gtggtgccgg acaacaccct ggcctgggtg tgggtgcgcg   3540

gcctggacga gctgtacgcc gagtggtcgg aggtcgtgtc cacgaacttc cgggacgcct   3600

ccgggccggc catgaccgag atcggcgagc agccgtgggg gcgggagttc gccctgcgcg   3660

acccggccgg caactgcgtg cacttcgtgg ccgaggagca ggactgacac gtgctacgag   3720

atttcgattc caccgccgcc ttctatgaaa ggttgggctt cggaatcgtt ttccgggacg   3780

ccggctggat gatcctccag cgcggggatc tcatgctgga gttcttcgcc caccccaact   3840

tgtttattgc agcttataat ggttacaaat aaagcaatag catcacaaat ttcacaaata   3900

aagcattttt ttcactgcat tctagttgtg gtttgtccaa actcatcaat gtatcttatc   3960

atgtctgtat accgtcgacc tctagctaga gcttggcgta atcatggtca tagctgtttc   4020
```

```
ctgtgtgaaa ttgttatccg ctcacaattc cacacaacat acgagccgga agcataaagt   4080

gtaaagcctg gggtgcctaa tgagtgagct aactcacatt aattgcgttg cgctcactgc   4140

ccgctttcca gtcgggaaac ctgtcgtgcc agctgcatta atgaatcggc caacgcgcgg   4200

ggagaggcgg tttgcgtatt gggcgctctt ccgcttcctc gctcactgac tcgctgcgct   4260

cggtcgttcg gctgcggcga gcggtatcag ctcactcaaa ggcggtaata cggttatcca   4320

cagaatcagg ggataacgca ggaaagaaca tgtgagcaaa aggccagcaa aaggccagga   4380

accgtaaaaa ggccgcgttg ctggcgtttt tccataggct ccgcccccct gacgagcatc   4440

acaaaaatcg acgctcaagt cagaggtggc gaaacccgac aggactataa agataccagg   4500

cgtttccccc tggaagctcc ctcgtgcgct ctcctgttcc gaccctgccg cttaccggat   4560

acctgtccgc ctttctccct tcgggaagcg tggcgctttc tcaatgctca cgctgtaggt   4620

atctcagttc ggtgtaggtc gttcgctcca agctgggctg tgtgcacgaa ccccccgttc   4680

agcccgaccg ctgcgcctta tccggtaact atcgtcttga gtccaacccg gtaagacacg   4740

acttatcgcc actggcagca gccactggta acaggattag cagagcgagg tatgtaggcg   4800

gtgctacaga gttcttgaag tggtggccta actacggcta cactagaagg acagtatttg   4860

gtatctgcgc tctgctgaag ccagttacct tcggaaaaag agttggtagc tcttgatccg   4920

gcaaacaaac caccgctggt agcggtggtt tttttgtttg caagcagcag attacgcgca   4980

gaaaaaaagg atctcaagaa gatcctttga tcttttctac ggggtctgac gctcagtgga   5040

acgaaaactc acgttaaggg attttggtca tgagattatc aaaaaggatc ttcacctaga   5100

tccttttaaa ttaaaaatga agttttaaat caatctaaag tatatatgag taaacttggt   5160

ctgacagtta ccaatgctta atcagtgagg cacctatctc agcgatctgt ctatttcgtt   5220

catccatagt tgcctgactc cccgtcgtgt agataactac gatacgggag ggcttaccat   5280

ctggccccag tgctgcaatg ataccgcgag acccacgctc accggctcca gatttatcag   5340

caataaacca gccagccgga agggccgagc gcagaagtgg tcctgcaact ttatccgcct   5400

ccatccagtc tattaattgt tgccgggaag ctagagtaag tagttcgcca gttaatagtt   5460

tgcgcaacgt tgttgccatt gctacaggca tcgtggtgtc acgctcgtcg tttggtatgg   5520

cttcattcag ctccggttcc caacgatcaa ggcgagttac atgatccccc atgttgtgca   5580

aaaaagcggt tagctccttc ggtcctccga tcgttgtcag aagtaagttg gccgcagtgt   5640

tatcactcat ggttatggca gcactgcata attctcttac tgtcatgcca tccgtaagat   5700

gcttttctgt gactggtgag tactcaacca agtcattctg agaatagtgt atgcggcgac   5760

cgagttgctc ttgcccggcg tcaatacggg ataataccgc gccacatagc agaactttaa   5820

aagtgctcat cattggaaaa cgttcttcgg ggcgaaaact ctcaaggatc ttaccgctgt   5880

tgagatccag ttcgatgtaa cccactcgtg cacccaactg atcttcagca tcttttactt   5940

tcaccagcgt ttctgggtga gcaaaaacag gaaggcaaaa tgccgcaaaa aagggaataa   6000

gggcgacacg gaaatgttga atactcatac tcttcctttt tcaatattat tgaagcattt   6060

atcagggtta ttgtctcatg agcggataca tatttgaatg tatttagaaa aataaacaaa   6120

taggggttcc gcgcacattt ccccgaaaag tgccacctga cgtc                    6164
```

<210> SEQ ID NO 31
<211> LENGTH: 6746
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccc   1080
aggttcagct ggtgcagtct ggagctgagg tgaagaagcc tggggcctca gtgaaggtct   1140
cctgcaaggc ttctggttac acctttaccg actactggat tgagtgggtg cgacaggccc   1200
ctggacaagg gcttgagtgg atgggagata ttttatgtgg aactggtaga actagataca   1260
atgagaagtt aaaggccaga gtcaccatga ccgcagacac atccacgagc acagcctaca   1320
tggagctgag gagcctgaga tctgacgaca cggccgtgta ttactgtgcg agatcggcgt   1380
catatggtga ttacgctgac tactgggggc aagggaccac ggtcaccgtc tcctcaggtg   1440
gtggtggttc tggtggtggt ggttctggcg gcggcggctc cgacatcgtg atgacccaat   1500
ctccagactc tttggctgtg tctctagggg agagggccac catcaactgc aaggccagtc   1560
aggacgtctc tactgctgta gcctggtacc aacagaaacc aggacagcca cccaaactcc   1620
tcatctcttg ggcatccacc cggcacactg gggtcccaga caggtttagt ggcagtgggt   1680
ctgggacaga cttcaccctc accatcagca gcctgcaggc tgaggatgtg gcagtttatt   1740
actgtcagca acattatacc actcccctca cgttcggaca agggaccaag cttgagatca   1800
aagctagcgt ggctgcacca tctgtcttca tcttcccgcc atctgatgag cagttgaaat   1860
ctggaactgc ctctgttgtg tgcctgctga ataacttcta tcccagagag gccaaagtac   1920
agtggaaggt ggataacgcc ctccaatcgg gtaactccca ggagagtgtc acagagcagg   1980
acagcaagga cagcacctac agcctcagca gcaccctgac gctgagcaaa gcagactacg   2040
agaaacacaa agtctacgcc tgcgaagtca cccatcaggg cctgagctcg cccgtcacaa   2100
agagcttcaa caggggagag tgttaggcgg ccgctcgagt ctagagggcc cgtttaaacc   2160
cgctgatcag cctcgactgt gccttctagt tgccagccat ctgttgtttg cccctccccc   2220
gtgccttcct tgaccctgga aggtgccact cccactgtcc tttcctaata aaatgaggaa   2280
```

```
attgcatcgc attgtctgag taggtgtcat tctattctgg ggggtggggt ggggcaggac   2340

agcaaggggg aggattggga agacaatagc aggcatgctg gggatgcggt gggctctatg   2400

gcttctgagg cggaaagaac cagctggggc tctagggggt atccccacgc gccctgtagc   2460

ggcgcattaa gcgcggcggg tgtggtggtt acgcgcagcg tgaccgctac acttgccagc   2520

gccctagcgc ccgctccttt cgctttcttc ccttcctttc tcgccacgtt cgccggcttt   2580

ccccgtcaag ctctaaatcg gggctccct ttagggttcc gatttagtgc tttacggcac   2640

ctcgacccca aaaaacttga ttagggtgat ggttcacgta gtgggccatc gccctgatag   2700

acggtttttc gccctttgac gttggagtcc acgttcttta atagtggact cttgttccaa   2760

actggaacaa cactcaaccc tatctcggtc tattcttttg atttataagg gattttgccg   2820

atttcggcct attggttaaa aaatgagctg atttaacaaa aatttaacgc gaattaattc   2880

tgtggaatgt gtgtcagtta gggtgtggaa agtccccagg ctccccagca ggcagaagta   2940

tgcaaagcat gcatctcaat tagtcagcaa ccaggtgtgg aaagtcccca ggctccccag   3000

caggcagaag tatgcaaagc atgcatctca attagtcagc aaccatagtc ccgcccctaa   3060

ctccgcccat cccgccccta actccgccca gttccgccca ttctccgccc catggctgac   3120

taattttttt tatttatgca gaggccgagg ccgcctctgc ctctgagcta ttccagaagt   3180

agtgaggagg cttttttgga ggcctaggct tttgcaaaaa gctcccggga gcttgtatat   3240

ccattttcgg atctgatcag cacgtgatga aaaagcctga actcaccgcg acgtctgtcg   3300

agaagtttct gatcgaaaag ttcgacagcg tctccgacct gatgcagctc tcggagggcg   3360

aagaatctcg tgctttcagc ttcgatgtag gagggcgtgg atatgtcctg cgggtaaata   3420

gctgcgccga tggtttctac aaagatcgtt atgtttatcg gcactttgca tcggccgcgc   3480

tcccgattcc ggaagtgctt gacattgggg aattcagcga gagcctgacc tattgcatct   3540

cccgccgtgc acagggtgtc acgttgcaag acctgcctga aaccgaactg cccgctgttc   3600

tgcagccggt cgcggaggcc atggatgcga tcgctgcggc cgatcttagc cagacgagcg   3660

ggttcggccc attcggaccg caaggaatcg gtcaatacac tacatggcgt gatttcatat   3720

gcgcgattgc tgatccccat gtgtatcact ggcaaactgt gatggacgac accgtcagtg   3780

cgtccgtcgc gcaggctctc gatgagctga tgctttgggc cgaggactgc cccgaagtcc   3840

ggcacctcgt gcacgcggat ttcggctcca acaatgtcct gacggacaat ggccgcataa   3900

cagcggtcat tgactggagc gaggcgatgt tcggggattc ccaatacgag gtcgccaaca   3960

tcttcttctg gaggccgtgg ttggcttgta tggagcagca gacgcgctac ttcgagcgga   4020

ggcatccgga gcttgcagga tcgccgcggc tccgggcgta tatgctccgc attggtcttg   4080

accaactcta tcagagcttg gttgacggca atttcgatga tgcagcttgg gcgcagggtc   4140

gatgcgacgc aatcgtccga tccggagccg ggactgtcgg gcgtacacaa atcgcccgca   4200

gaagcgcggc cgtctggacc gatggctgtg tagaagtact cgccgatagt ggaaaccgac   4260

gccccagcac tcgtccgagg gcaaaggaat agcacgtgct acgagatttc gattccaccg   4320

ccgccttcta tgaaaggttg ggcttcggaa tcgttttccg ggacgccggc tggatgatcc   4380

tccagcgcgg ggatctcatg ctggagttct tcgcccaccc caacttgttt attgcagctt   4440

ataatggtta caaataaagc aatagcatca caaatttcac aaataaagca tttttttcac   4500

tgcattctag ttgtggtttg tccaaactca tcaatgtatc ttatcatgtc tgtataccgt   4560

cgacctctag ctagagcttg gcgtaatcat ggtcatagct gtttcctgtg tgaaattgtt   4620
```

```
atccgctcac aattccacac aacatacgag ccggaagcat aaagtgtaaa gcctggggtg   4680

cctaatgagt gagctaactc acattaattg cgttgcgctc actgcccgct ttccagtcgg   4740

gaaacctgtc gtgccagctg cattaatgaa tcggccaacg cgcggggaga ggcggtttgc   4800

gtattgggcg ctcttccgct tcctcgctca ctgactcgct gcgctcggtc gttcggctgc   4860

ggcgagcggt atcagctcac tcaaaggcgg taatacggtt atccacagaa tcaggggata   4920

acgcaggaaa gaacatgtga gcaaaaggcc agcaaaaggc caggaaccgt aaaaaggccg   4980

cgttgctggc gtttttccat aggctccgcc cccctgacga gcatcacaaa aatcgacgct   5040

caagtcagag gtggcgaaac ccgacaggac tataaagata ccaggcgttt ccccctggaa   5100

gctccctcgt gcgctctcct gttccgaccc tgccgcttac cggatacctg tccgcctttc   5160

tcccttcggg aagcgtggcg ctttctcata gctcacgctg taggtatctc agttcggtgt   5220

aggtcgttcg ctccaagctg ggctgtgtgc acgaaccccc cgttcagccc gaccgctgcg   5280

ccttatccgg taactatcgt cttgagtcca acccggtaag acacgactta tcgccactgg   5340

cagcagccac tggtaacagg attagcagag cgaggtatgt aggcggtgct acagagttct   5400

tgaagtggtg gcctaactac ggctacacta gaagaacagt atttggtatc tgcgctctgc   5460

tgaagccagt taccttcgga aaaagagttg gtagctcttg atccggcaaa caaaccaccg   5520

ctggtagcgg tttttttgtt tgcaagcagc agattacgcg cagaaaaaaa ggatctcaag   5580

aagatccttt gatcttttct acggggtctg acgctcagtg gaacgaaaac tcacgttaag   5640

ggattttggt catgagatta tcaaaaagga tcttcaccta gatcctttta aattaaaaat   5700

gaagttttaa atcaatctaa agtatatatg agtaaacttg gtctgacagt taccaatgct   5760

taatcagtga ggcacctatc tcagcgatct gtctatttcg ttcatccata gttgcctgac   5820

tccccgtcgt gtagataact acgatacggg agggcttacc atctggcccc agtgctgcaa   5880

tgataccgcg agacccacgc tcaccggctc cagatttatc agcaataaac cagccagccg   5940

gaagggccga gcgcagaagt ggtcctgcaa ctttatccgc ctccatccag tctattaatt   6000

gttgccggga agctagagta agtagttcgc cagttaatag tttgcgcaac gttgttgcca   6060

ttgctacagg catcgtggtg tcacgctcgt cgtttggtat ggcttcattc agctccggtt   6120

cccaacgatc aaggcgagtt acatgatccc ccatgttgtg caaaaaagcg gttagctcct   6180

tcggtcctcc gatcgttgtc agaagtaagt tggccgcagt gttatcactc atggttatgg   6240

cagcactgca taattctctt actgtcatgc catccgtaag atgcttttct gtgactggtg   6300

agtactcaac caagtcattc tgagaatagt gtatgcggcg accgagttgc tcttgcccgg   6360

cgtcaatacg ggataatacc gcgccacata gcagaacttt aaaagtgctc atcattggaa   6420

aacgttcttc ggggcgaaaa ctctcaagga tcttaccgct gttgagatcc agttcgatgt   6480

aacccactcg tgcacccaac tgatcttcag catcttttac tttcaccagc gtttctgggt   6540

gagcaaaaac aggaaggcaa aatgccgcaa aaaagggaat aagggcgaca cggaaatgtt   6600

gaatactcat actcttcctt tttcaatatt attgaagcat ttatcagggt tattgtctca   6660

tgagcggata catatttgaa tgtatttaga aaaataaaca aataggggtt ccgcgcacat   6720

ttccccgaaa agtgccacct gacgtc                                        6746
```

<210> SEQ ID NO 32
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Gly Ser Thr Ser Gly Gly Gly Ser Gly
        115                 120                 125

Gly Gly Ser Gly Gly Gly Gly Ser Ser Asp Ile Val Met Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Asp Val Ser Thr Ala Val Ala Trp Tyr Gln Gln Lys
                165                 170                 175

Pro Gly Gln Pro Pro Lys Leu Leu Ile Ser Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln His Tyr Thr Thr Pro Leu Thr Phe Gly Gln Gly Thr Lys
225                 230                 235                 240

Leu Glu Ile Lys Ala Ser
                245
```

<210> SEQ ID NO 33
<211> LENGTH: 574
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Gly Ser Thr Ser Gly Gly Gly Ser Gly
        115                 120                 125

Gly Gly Ser Gly Gly Gly Gly Ser Ser Asp Ile Val Met Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Asp Val Ser Thr Ala Val Ala Trp Tyr Gln Gln Lys
                165                 170                 175

Pro Gly Gln Pro Pro Lys Leu Leu Ile Ser Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln His Tyr Thr Thr Pro Leu Thr Phe Gly Gln Gly Thr Lys
225                 230                 235                 240

Leu Glu Ile Lys Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Asp Glu Leu Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510
```

```
Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Lys
                565                 570


<210> SEQ ID NO 34
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Gly Ser Thr Ser Gly Gly Gly Ser Gly
        115                 120                 125

Gly Gly Ser Gly Gly Gly Gly Ser Ser Asp Ile Val Met Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Asp Val Ser Thr Ala Val Ala Trp Tyr Gln Gln Lys
                165                 170                 175

Pro Gly Gln Pro Pro Lys Leu Leu Ile Ser Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln His Tyr Thr Thr Pro Leu Thr Phe Gly Gln Gly Thr Lys
225                 230                 235                 240

Leu Glu Ile Lys Ala Ser Arg Thr Val Ala Ala Pro Ser Val Phe Ile
                245                 250                 255

Phe Pro Pro Ser Asp Glu Gln Leu Lys Ser Gly Thr Ala Ser Val Val
            260                 265                 270

Cys Leu Leu Asn Asn Phe Tyr Pro Arg Glu Ala Lys Val Gln Trp Lys
        275                 280                 285

Val Asp Asn Ala Leu Gln Ser Gly Asn Ser Gln Glu Ser Val Thr Glu
```

```
    290                 295                 300

Gln Asp Ser Lys Asp Ser Thr Tyr Ser Leu Ser Ser Thr Leu Thr Leu
305                 310                 315                 320

Ser Lys Ala Asp Tyr Glu Lys His Lys Val Tyr Ala Cys Glu Val Thr
                325                 330                 335

His Gln Gly Leu Ser Ser Pro Val Thr Lys Ser Phe Asn Arg Gly Glu
            340                 345                 350

Cys


<210> SEQ ID NO 35
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

gaattcgcca ccatgggatg gtcttgtatc atccttttct tggttgcaac agctactggt     60

gttcattctc aagtacaact tcaacaacct ggcgcagcac ttgtgaggcc tggcgcttca    120

atgagattgt cttgtaaagc tagtggatac tcattcacca catactggat gaattgggtg    180

aaacagcgtc cagggcaggg tttggaactt atagggatga tccatccaag tgatagtgaa    240

gtgagattga accagaagtt caaagataag gctacactta cagtagacac atctagttct    300

accgcatata tgcagcttaa ttctccaact agtgaggata gtgccgtcta ttattgcgct    360

cgttttggct tggattattg gggacagggt acaactctta ctgtttctag tggctctaca    420

agtggaggtg gtagtggtgg aggaagtgga ggaggtggtt caagtgacat tgtcattacc    480

caatctccat catctttgag tgcttctctt ggtgacacca tcttgattac ttgtcacgca    540

tcacagaata tcaatgtgtg gttgtcatgg tttcagcaaa aacctgggaa cgctccaaag    600

ttgcttatct acaaagcctc aaacttgcat acaggtgttc catcacgttt tagtgggagt    660

ggaagtggta ctggattcac tcttacaatc tcttcacttc aaccagagga tattgcaact    720

tactattgcc aacaaggaca aagttatcct tggacttttg gggaggcac taagttggaa    780

ataaaggcta gc                                                        792


<210> SEQ ID NO 36
<211> LENGTH: 1785
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

gaattcgcca ccatgggatg gtcttgtatc atccttttct tggttgcaac agctactggt     60

gttcattctc aagtacaact tcaacaacct ggcgcagcac ttgtgaggcc tggcgcttca    120

atgagattgt cttgtaaagc tagtggatac tcattcacca catactggat gaattgggtg    180

aaacagcgtc cagggcaggg tttggaactt atagggatga tccatccaag tgatagtgaa    240

gtgagattga accagaagtt caaagataag gctacactta cagtagacac atctagttct    300

accgcatata tgcagcttaa ttctccaact agtgaggata gtgccgtcta ttattgcgct    360

cgttttggct tggattattg gggacagggt acaactctta ctgtttctag tggctctaca    420

agtggaggtg gtagtggtgg aggaagtgga ggaggtggtt caagtgacat tgtcattacc    480
```

```
caatctccat catctttgag tgcttctctt ggtgacacca tcttgattac ttgtcacgca    540

tcacagaata tcaatgtgtg gttgtcatgg tttcagcaaa aacctgggaa cgctccaaag    600

ttgcttatct acaaagcctc aaacttgcat acaggtgttc catcacgttt tagtgggagt    660

ggaagtggta ctggattcac tcttacaatc tcttcacttc aaccagagga tattgcaact    720

tactattgcc aacaaggaca aagttatcct tggacttttg ggggaggcac taagttggaa    780

ataaaggcta gcaccaaggg accttctgtt tttccacttg ctccttcttc taagtctact    840

tctggtggaa ctgctgcttt gggttgtttg gtgaaagatt actttcctga gccagtgacc    900

gtttcttgga actcaggtgc tcttacatct ggtgttcata ctttcccagc tgttcttcaa    960

tcttcaggac tttactcact ttcttctgtt gttaccgttc cttcttcaag cttgggcact   1020

cagacctaca tctgcaatgt gaatcacaaa cccagcaaca ccaaggttga caagaaagtt   1080

gagcccaagt cttgtgacaa gactcatacg tgtccaccgt gcccagcacc tgaacttctt   1140

ggaggaccgt cagtcttctt gtttcctcca aagcctaagg ataccttgat gatctccagg   1200

actcctgaag tcacatgtgt agttgtggat gtgagccatg aagatcctga ggtgaagttc   1260

aactggtatg tggatggtgt ggaagtgcac aatgccaaga caaagccgag agaggaacag   1320

tacaacagca cgtacagggt tgtctcagtt ctcactgttc tccatcaaga ttggttgaat   1380

ggcaaagagt acaagtgcaa ggtctccaac aaagccctcc cagcccccat tgagaagacc   1440

atttccaaag cgaaagggca accccgtgaa ccacaagtgt acacacttcc tccatctcgc   1500

gatgaactga ccaagaacca ggtcagcttg acttgcctgg tgaaaggctt ctatccctct   1560

gacatagctg tagagtggga gagcaatggg caaccggaga acaactacaa gactacacct   1620

cccgttctcg attctgacgg ctccttcttc ctctacagca agctcacagt ggacaagagc   1680

aggtggcaac aagggaatgt cttctcatgc tccgtgatgc atgaggctct tcacaatcac   1740

tacacacaga agagtctctc cttgtctccg ggtaaatgag gatcc                   1785
```

```
<210> SEQ ID NO 37
<211> LENGTH: 8206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

tctagagtcg acctgcagaa gcttactaga gcgtggtgcg cacgatagcg catagtgttt     60

ttctctccac ttgaatcgaa gagatagact tacggtgtaa atccgtaggg gtggcgtaaa    120

ccaaattacg caatgttttg ggttccattt aaatcgaaac cccttatttc ctggatcacc    180

tgttaacgca cgtttgacgt gtattacagt gggaataagt aaaagtgaga ggttcgaatc    240

ctccctaacc ccgggtaggg gcccagcggc cgctctagct agagtcaagc agatcgttca    300

aacatttggc aataaagttt cttaagattg aatcctgttg ccggtcttgc gatgattatc    360

atataatttc tgttgaatta cgttaagcat gtaataatta acatgtaatg catgacgtta    420

tttatgagat gggtttttat gattagagtc ccgcaattat acatttaata cgcgatagaa    480

aacaaaatat agcgcgcaaa ctaggataaa ttatcgcgcg cggtgtcatc tatgttacta    540

gatcgaccag cttagatcag attgtcgttt cccgccttca gtttaaacta tcagtgtttg    600

acaggatata ttggcgggta aacctaagag aaaagagcgt ttattagaat aatcggatat    660

ttaaaagggc gtgaaaaggt ttatccgttc gtccatttgt atgtgccaac cacagggttc    720
```

```
cccagatcag taaagcgctg gctgctgaac ccccagccgg aactgacccc acaaggccct    780
agcgtttgca atgcaccagg tcatcattga cccaggcgtg ttccaccagg ccgctgcctc    840
gcaactcttc gcaggcttcg ccgacctgct cgcgccactt cttcacgcgg gtggaatccg    900
atccgcacat gaggcggaag gtttccagct tgagcgggta cggctcccgg tgcgagctga    960
aatagtcgaa catccgtcgg gccgtcggcg acagcttgcg gtacttctcc catatgaatt   1020
tcgtgtagtg gtcgccagca aacagcacga cgatttcctc gtcgatcagg acctggcaac   1080
gggacgtttt cttgccacgg tccaggacgc ggaagcggtg cagcagcgac accgattcca   1140
ggtgcccaac gcggtcggac gtgaagccca tcgccgtcgc ctgtaggcgc gacaggcatt   1200
cctcggcctt cgtgtaatac cggccattga tcgaccagcc caggtcctgg caaagctcgt   1260
agaacgtgaa ggtgatcggc tcgccgatag ggtgcgctt cgcgtactcc aacacctgct   1320
gccacaccag ttcgtcatcg tcggcccgca gctcgacgcc ggtgtaggtg atcttcacgt   1380
ccttgttgac gtggaaaatg accttgtttt gcagcgcctc gcgcgggatt ttcttgttgc   1440
gcgtggtgaa cagggcagag cggccgtgt cgtttggcat cgctcgcatc gtgtccggcc   1500
acggcgcaat atcgaacaag gaaagctgca tttccttgat ctgctgcttc gtgtgtttca   1560
gcaacgcggc ctgcttggcc tcgctgacct gttttgccag gtcctcgccg gcggtttttc   1620
gcttcttggt cgtcatagtt cctcgcgtgt cgatggtcat cgacttcgcc aaacctgccg   1680
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
```

```
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg    4020
aggccgttcg cggccgaggg gcgcagcccc tgggggggatg ggaggcccgc gttagcgggc  4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
```

```
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact ttttgttctt attgttgcag gtaccatggc   6420
agaattcgcc accatgggat ggtcttgtat catccttttc ttggttgcaa cagctactgg   6480
tgttcattct caagtacaac ttcaacaacc tggcgcagca cttgtgaggc ctggcgcttc   6540
aatgagattg tcttgtaaag ctagtggata ctcattcacc acatactgga tgaattgggt   6600
gaaacagcgt ccagggcagg gtttggaact tatagggatg atccatccaa gtgatagtga   6660
agtgagattg aaccagaagt tcaaagataa ggctacactt acagtagaca catctagttc   6720
taccgcatat atgcagctta attctccaac tagtgaggat agtgccgtct attattgcgc   6780
tcgttttggc ttggattatt ggggacaggg tacaactctt actgtttcta gtggctctac   6840
aagtggaggt ggtagtggtg gaggaagtgg aggaggtggt tcaagtgaca ttgtcattac   6900
ccaatctcca tcatctttga gtgcttctct tggtgacacc atcttgatta cttgtcacgc   6960
atcacagaat atcaatgtgt ggttgtcatg gtttcagcaa aaacctggga acgctccaaa   7020
gttgcttatc tacaaagcct caaacttgca tacaggtgtt ccatcacgtt ttagtgggag   7080
tggaagtggt actggattca ctcttacaat ctcttcactt caaccagagg atattgcaac   7140
ttactattgc caacaaggac aaagttatcc ttggactttt gggggaggca ctaagttgga   7200
aataaaggct agcaccaagg gaccttctgt ttttccactt gctccttctt ctaagtctac   7260
ttctggtgga actgctgctt tgggttgttt ggtgaaagat tactttcctg agccagtgac   7320
cgtttcttgg aactcaggtg ctcttacatc tggtgttcat actttcccag ctgttcttca   7380
atcttcagga ctttactcac tttcttctgt tgttaccgtt ccttcttcaa gcttgggcac   7440
tcagacctac atctgcaatg tgaatcacaa acccagcaac accaaggttg acaagaaagt   7500
tgagcccaag tcttgtgaca agactcatac gtgtccaccg tgcccagcac ctgaacttct   7560
tggaggaccg tcagtcttct tgtttcctcc aaagcctaag gataccttga tgatctccag   7620
gactcctgaa gtcacatgtg tagttgtgga tgtgagccat gaagatcctg aggtgaagtt   7680
caactggtat gtggatggtg tggaagtgca caatgccaag acaaagccga gagaggaaca   7740
gtacaacagc acgtacaggg ttgtctcagt tctcactgtt ctccatcaag attggttgaa   7800
tggcaaagag tacaagtgca aggtctccaa caaagccctc ccagccccca ttgagaagac   7860
```

```
catttccaaa gcgaaagggc aaccccgtga accacaagtg tacacacttc ctccatctcg   7920

cgatgaactg accaagaacc aggtcagctt gacttgcctg gtgaaaggct tctatccctc   7980

tgacatagct gtagagtggg agagcaatgg gcaaccggag aacaactaca agactacacc   8040

tcccgttctc gattctgacg gctccttctt cctctacagc aagctcacag tggacaagag   8100

caggtggcaa caagggaatg tcttctcatg ctccgtgatg catgaggctc ttcacaatca   8160

ctacacacag aagagtctct ccttgtctcc gggtaaatga ggatcc                   8206
```

```
<210> SEQ ID NO 38
<211> LENGTH: 8252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

```
agcttgaaga ctaggcgtgg tgcgcacgat agcgcatagt gtttttctct ccacttgaat     60

cgaagagata gacttacggt gtaaatccgt aggggtggcg taaaccaaat tacgcaatgt    120

tttgggttcc atttaaatcg aaacccctta tttcctggat cacctgttaa cgcacgtttg    180

acgtgtatta cagtgggaat aagtaaaagt gagaggttcg aatcctccct aaccccgggt    240

aggggcccag cggccgctct agctagagtc aagcagatcg ttcaaacatt tggcaataaa    300

gtttcttaag attgaatcct gttgccggtc ttgcgatgat tatcatataa tttctgttga    360

attacgttaa gcatgtaata attaacatgt aatgcatgac gttatttatg agatgggttt    420

ttatgattag agtcccgcaa ttatacattt aatacgcgat agaaaacaaa atatagcgcg    480

caaactagga taaattatcg cgcgcggtgt catctatgtt actagatcga ccagtcctat    540

ggtagtcttc agcttagatc agattgtcgt ttcccgcctt cagtttaaac tatcagtgtt    600

tgacaggata tattggcggg taaacctaag agaaaagagc gtttattaga ataatcggat    660

atttaaaagg gcgtgaaaag gtttatccgt tcgtccattt gtatgtgcat gccaaccaca    720

gggttcccca gatcagtaaa gcgctggctg ctgaaccccc agccggaact gaccccacaa    780

ggccctagcg tttgcaatgc accaggtcat cattgaccca ggcgtgttcc accaggccgc    840

tgcctcgcaa ctcttcgcag gcttcgccga cctgctcgcg ccacttcttc acgcgggtgg    900

aatccgatcc gcacatgagg cggaaggttt ccagcttgag cgggtacggc tcccggtgcg    960

agctgaaata gtcgaacatc cgtcgggccg tcggcgacag cttgcggtac ttctcccata   1020

tgaatttcgt gtagtggtcg ccagcaaaca gcacgacgat ttcctcgtcg atcaggacct   1080

ggcaacggga cgttttcttg ccacggtcca ggacgcggaa gcggtgcagc agcgacaccg   1140

attccaggtg cccaacgcgg tcggacgtga agcccatcgc cgtcgcctgt aggcgcgaca   1200

ggcattcctc ggccttcgtg taataccggc cattgatcga ccagcccagg tcctggcaaa   1260

gctcgtagaa cgtgaaggtg atcggctcgc cgataggggt gcgcttcgcg tactccaaca   1320

cctgctgcca caccagttcg tcatcgtcgg cccgcagctc gacgccggtg taggtgatct   1380

tcacgtcctt gttgacgtgg aaaatgacct tgttttgcag cgcctcgcgc gggattttct   1440

tgttgcgcgt ggtgaacagg gcagagcggg ccgtgtcgtt tggcatcgct cgcatcgtgt   1500

ccggccacgg cgcaatatcg aacaaggaaa gctgcatttc cttgatctgc tgcttcgtgt   1560

gtttcagcaa cgcggcctgc ttggcctcgc tgacctgttt tgccaggtcc tcgccggcgg   1620

tttttcgctt cttggtcgtc atagttcctc gcgtgtcgat ggtcatcgac ttcgccaaac   1680
```

```
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
```

```
ggggtgaggc cgttcgcggc cgaggggcgc agcccctggg gggatgggag gcccgcgtta   4080
gcgggccggg agggttcgag aagggggggc acccccttc ggcgtgcgcg gtcacgcgca   4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
```

```
agaccgaatt cgccaccatg ggatggtctt gtatcatcct tttcttggtt gcaacagcta   6480

ctggtgttca ttctcaagta caacttcaac aacctggcgc agcacttgtg aggcctggcg   6540

cttcaatgag attgtcttgt aaagctagtg gatactcatt caccacatac tggatgaatt   6600

gggtgaaaca gcgtccaggg cagggtttgg aacttatagg gatgatccat ccaagtgata   6660

gtgaagtgag attgaaccag aagttcaaag ataaggctac acttacagta gacacatcta   6720

gttctaccgc atatatgcag cttaattctc caactagtga ggatagtgcc gtctattatt   6780

gcgctcgttt tggcttggat tattggggac agggtacaac tcttactgtt tctagtggct   6840

ctacaagtgg aggtggtagt ggtggaggaa gtggaggagg tggttcaagt gacattgtca   6900

ttacccaatc tccatcatct ttgagtgctt ctcttggtga caccatcttg attacttgtc   6960

acgcatcaca gaatatcaat gtgtggttgt catggtttca gcaaaaacct gggaacgctc   7020

caaagttgct tatctacaaa gcctcaaact tgcatacagg tgttccatca cgttttagtg   7080

ggagtggaag tggtactgga ttcactctta caatctcttc acttcaacca gaggatattg   7140

caacttacta ttgccaacaa ggacaaagtt atccttggac ttttggggga ggcactaagt   7200

tggaaataaa ggctagcacc aagggacctt ctgtttttcc acttgctcct tcttctaagt   7260

ctacttctgg tggaactgct gctttgggtt gtttggtgaa agattacttt cctgagccag   7320

tgaccgtttc ttggaactca ggtgctctta catctggtgt tcatactttc ccagctgttc   7380

ttcaatcttc aggactttac tcactttctt ctgttgttac cgttccttct tcaagcttgg   7440

gcactcagac ctacatctgc aatgtgaatc acaaacccag caacaccaag gttgacaaga   7500

aagttgagcc caagtcttgt gacaagactc atacgtgtcc accgtgccca gcacctgaac   7560

ttcttggagg accgtcagtc ttcttgtttc ctccaaagcc taaggatacc ttgatgatct   7620

ccaggactcc tgaagtcaca tgtgtagttg tggatgtgag ccatgaagat cctgaggtga   7680

agttcaactg gtatgtggat ggtgtggaag tgcacaatgc caagacaaag ccgagagagg   7740

aacagtacaa cagcacgtac agggttgtct cagttctcac tgttctccat caagattggt   7800

tgaatggcaa agagtacaag tgcaaggtct ccaacaaagc cctcccagcc cccattgaga   7860

agaccatttc caaagcgaaa gggcaacccc gtgaaccaca agtgtacaca cttcctccat   7920

ctcgcgatga actgaccaag aaccaggtca gcttgacttg cctggtgaaa ggcttctatc   7980

cctctgacat agctgtagag tgggagagca atgggcaacc ggagaacaac tacaagacta   8040

cacctcccgt tctcgattct gacggctcct tcttcctcta cagcaagctc acagtggaca   8100

agagcaggtg gcaacaaggg aatgtcttct catgctccgt gatgcatgag gctcttcaca   8160

atcactacac acagaagagt ctctccttgt ctccgggtaa atgaggatcc tctagagtcg   8220

acctgcagaa gctggcagct aggatgggtc tc                                 8252
```

<210> SEQ ID NO 39
<211> LENGTH: 1122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gaattcgcca ccatgggatg gtcttgtatc atccttttct tggttgcaac agctactggt     60

gttcattctc aagtacaact tcaacaacct ggcgcagcac ttgtgaggcc tggcgcttca    120

atgagattgt cttgtaaagc tagtggatac tcattcacca catactggat gaattgggtg    180
```

```
aaacagcgtc cagggcaggg tttggaactt atagggatga tccatccaag tgatagtgaa    240

gtgagattga accagaagtt caaagataag gctacactta cagtagacac atctagttct    300

accgcatata tgcagcttaa ttctccaact agtgaggata gtgccgtcta ttattgcgct    360

cgttttggct tggattattg ggacagggt acaactctta ctgtttctag tggctctaca    420

agtggaggtg gtagtggtgg aggaagtgga ggaggtggtt caagtgacat tgtcattacc    480

caatctccat catctttgag tgcttctctt ggtgacacca tcttgattac ttgtcacgca    540

tcacagaata tcaatgtgtg gttgtcatgg tttcagcaaa aacctgggaa cgctccaaag    600

ttgcttatct acaaagcctc aaacttgcat acaggtgttc catcacgttt tagtgggagt    660

ggaagtggta ctggattcac tcttacaatc tcttcacttc aaccagagga tattgcaact    720

tactattgcc aacaaggaca aagttatcct tggacttttg gggaggcac taagttggaa    780

ataaaggcta gcagaactgt tgctgcacca tctgttttca tcttccctcc atctgatgag    840

cagttgaaat ctggaactgc ttctgttgtg tgccttctta ataacttcta tcctagagag    900

gctaaagttc agtggaaggt ggataacgca cttcaatctg gtaactctca agagtctgtt    960

acagagcaag attctaagga ctcaacttac tctctttcat ctacacttac tttgtcaaaa   1020

gcagattacg agaaacacaa agtttacgca tgcgaagtta ctcatcaagg actttcttca   1080

ccagttacaa agtctttcaa tagaggagag tgttaaggat cc                      1122
```

<210> SEQ ID NO 40
<211> LENGTH: 7543
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
tctagagtcg acctgcagaa gcttactaga gcgtggtgcg cacgatagcg catagtgttt     60

ttctctccac ttgaatcgaa gagatagact tacggtgtaa atccgtaggg gtggcgtaaa    120

ccaaattacg caatgttttg ggttccattt aaatcgaaac cccttatttc ctggatcacc    180

tgttaacgca cgtttgacgt gtattacagt gggaataagt aaaagtgaga ggttcgaatc    240

ctccctaacc ccgggtaggg gcccagcggc cgctctagct agagtcaagc agatcgttca    300

aacatttggc aataaagttt cttaagattg aatcctgttg ccggtcttgc gatgattatc    360

atataatttc tgttgaatta cgttaagcat gtaataatta acatgtaatg catgacgtta    420

tttatgagat gggtttttat gattagagtc ccgcaattat acatttaata cgcgatagaa    480

aacaaaatat agcgcgcaaa ctaggataaa ttatcgcgcg cggtgtcatc tatgttacta    540

gatcgaccag cttagatcag attgtcgttt cccgccttca gtttaaacta tcagtgtttg    600

acaggatata ttggcgggta aacctaagag aaaagagcgt ttattagaat aatcggatat    660

ttaaaagggc gtgaaaaggt ttatccgttc gtccatttgt atgtgccaac cacagggttc    720

cccagatcag taaagcgctg gctgctgaac ccccagccgg aactgacccc acaaggccct    780

agcgtttgca atgcaccagg tcatcattga cccaggcgtg ttccaccagg ccgctgcctc    840

gcaactcttc gcaggcttcg ccgacctgct cgcgccactt cttcacgcgg gtggaatccg    900

atccgcacat gaggcggaag gtttccagct tgagcgggta cggctcccgg tgcgagctga    960

aatagtcgaa catccgtcgg gccgtcggcg acagcttgcg gtacttctcc catatgaatt   1020

tcgtgtagtg gtcgccagca aacagcacga cgatttcctc gtcgatcagg acctggcaac   1080
```

```
gggacgtttt cttgccacgg tccaggacgc ggaagcggtg cagcagcgac accgattcca   1140
ggtgcccaac gcggtcggac gtgaagccca tcgccgtcgc ctgtaggcgc gacaggcatt   1200
cctcggcctt cgtgtaatac cggccattga tcgaccagcc caggtcctgg caaagctcgt   1260
agaacgtgaa ggtgatcggc tcgccgatag ggtgcgcttc cgcgtactcc aacacctgct   1320
gccacaccag ttcgtcatcg tcggcccgca gctcgacgcc ggtgtaggtg atcttcacgt   1380
ccttgttgac gtggaaaatg accttgtttt gcagcgcctc gcgcgggatt ttcttgttgc   1440
gcgtggtgaa cagggcagag cgggccgtgt cgtttggcat cgctcgcatc gtgtccggcc   1500
acggcgcaat atcgaacaag gaaagctgca tttccttgat ctgctgcttc gtgtgtttca   1560
gcaacgcggc ctgcttggcc tcgctgacct gttttgccag gtcctcgccg gcggtttttc   1620
gcttcttggt cgtcatagtt cctcgcgtgt cgatggtcat cgacttcgcc aaacctgccg   1680
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
```

```
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg    4020
aggccgttcg cggccgaggg gcgcagcccc tggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
```

```
aaaaagaacc gggcgcccct gcgctgacag ccggaacacg gcggcatcag agcagccgat   5880

tgtctgttgt gcccagtcat agccgaatag cctctccacc caagcggccg gagaacctgc   5940

gtgcaatcca tcttgttcaa tcatgcgaaa cgatccagat ccggtgcaga ttatttggat   6000

tgagagtgaa tatgagactc taattggata ccgaggggaa tttatggaac gtcagtggag   6060

catttttgac aagaaatatt tgctagctga tagtgacctt aggcgacttt tgaacgcgca   6120

ataatggttt ctgacgtatg tgcttagctc attaaactcc agaaacccgc ggctgagtgg   6180

ctccttcaac gttgcggttc tgtcagttcc aaacgtaaaa cggcttgtcc cgcgtcatcg   6240

gcgggggtca taacgtgact cccttaattc tccgctcatg gtacctcgaa gccgcggtgc   6300

gggtgccagg gcgtgccctt gggctccccg ggcgcgtact ccacctcacc catcttttat   6360

tacatgtttg aacttcaaca atttatgact ttttgttctt attgttgcag gtaccatggc   6420

agaattcgcc accatgggat ggtcttgtat catccttttc ttggttgcaa cagctactgg   6480

tgttcattct caagtacaac ttcaacaacc tggcgcagca cttgtgaggc ctggcgcttc   6540

aatgagattg tcttgtaaag ctagtggata ctcattcacc acatactgga tgaattgggt   6600

gaaacagcgt ccagggcagg gtttggaact tatagggatg atccatccaa gtgatagtga   6660

agtgagattg aaccagaagt tcaaagataa ggctacactt acagtagaca catctagttc   6720

taccgcatat atgcagctta attctccaac tagtgaggat agtgccgtct attattgcgc   6780

tcgttttggc ttggattatt ggggacaggg tacaactctt actgtttcta gtggctctac   6840

aagtggaggt ggtagtggtg gaggaagtgg aggaggtggt tcaagtgaca ttgtcattac   6900

ccaatctcca tcatctttga gtgcttctct tggtgacacc atcttgatta cttgtcacgc   6960

atcacagaat atcaatgtgt ggttgtcatg gtttcagcaa aaacctggga acgctccaaa   7020

gttgcttatc tacaaagcct caaacttgca tacaggtgtt ccatcacgtt ttagtgggag   7080

tggaagtggt actggattca ctcttacaat ctcttcactt caaccagagg atattgcaac   7140

ttactattgc caacaaggac aaagttatcc ttggactttt gggggaggca ctaagttgga   7200

aataaaggct agcagaactg ttgctgcacc atctgttttc atcttccctc catctgatga   7260

gcagttgaaa tctggaactg cttctgttgt gtgccttctt aataacttct atcctagaga   7320

ggctaaagtt cagtggaagg tggataacgc acttcaatct ggtaactctc aagagtctgt   7380

tacagagcaa gattctaagg actcaactta ctctctttca tctacactta ctttgtcaaa   7440

agcagattac gagaaacaca aagtttacgc atgcgaagtt actcatcaag gactttcttc   7500

accagttaca aagtctttca atagaggaga gtgttaagga tcc                     7543
```

<210> SEQ ID NO 41
<211> LENGTH: 7589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
agcttgaaga ctaggcgtgg tgcgcacgat agcgcatagt gtttttctct ccacttgaat     60

cgaagagata gacttacggt gtaaatccgt aggggtggcg taaaccaaat tacgcaatgt    120

tttgggttcc atttaaatcg aaacccctta tttcctggat cacctgttaa cgcacgtttg    180

acgtgtatta cagtgggaat aagtaaaagt gagaggttcg aatcctccct aaccccgggt    240

aggggcccag cggccgctct agctagagtc aagcagatcg ttcaaacatt tggcaataaa    300
```

```
gtttcttaag attgaatcct gttgccggtc ttgcgatgat tatcatataa tttctgttga    360
attacgttaa gcatgtaata attaacatgt aatgcatgac gttatttatg agatgggttt    420
ttatgattag agtcccgcaa ttatacattt aatacgcgat agaaaacaaa atatagcgcg    480
caaactagga taaattatcg cgcgcggtgt catctatgtt actagatcga ccagtcctat    540
ggtagtcttc agcttagatc agattgtcgt ttcccgcctt cagtttaaac tatcagtgtt    600
tgacaggata tattggcggg taaacctaag agaaaagagc gtttattaga ataatcggat    660
atttaaaagg gcgtgaaaag gtttatccgt tcgtccattt gtatgtgcat gccaaccaca    720
gggttcccca gatcagtaaa gcgctggctg ctgaaccccc agccggaact gaccccacaa    780
ggccctagcg tttgcaatgc accaggtcat cattgaccca ggcgtgttcc accaggccgc    840
tgcctcgcaa ctcttcgcag gcttcgccga cctgctcgcg ccacttcttc acgcgggtgg    900
aatccgatcc gcacatgagg cggaaggttt ccagcttgag cgggtacggc tcccggtgcg    960
agctgaaata gtcgaacatc cgtcgggccg tcggcgacag cttgcggtac ttctcccata   1020
tgaatttcgt gtagtggtcg ccagcaaaca gcacgacgat ttcctcgtcg atcaggacct   1080
ggcaacggga cgttttcttg ccacggtcca ggacgcggaa gcggtgcagc agcgacaccg   1140
attccaggtg cccaacgcgg tcggacgtga agcccatcgc cgtcgcctgt aggcgcgaca   1200
ggcattcctc ggccttcgtg taataccggc cattgatcga ccagcccagg tcctggcaaa   1260
gctcgtagaa cgtgaaggtg atcggctcgc cgataggggt gcgcttcgcg tactccaaca   1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggattttct   1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
```

```
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg ggatgggag gcccgcgtta    4080
gcgggccggg agggttcgag aaggggggc accccccttc ggcgtgcgcg gtcacgcgca    4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
```

```
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cgccaccatg ggatggtctt gtatcatcct tttcttggtt gcaacagcta   6480
ctggtgttca ttctcaagta caacttcaac aacctggcgc agcacttgtg aggcctggcg   6540
cttcaatgag attgtcttgt aaagctagtg gatactcatt caccacatac tggatgaatt   6600
gggtgaaaca gcgtccaggg cagggtttgg aacttatagg gatgatccat ccaagtgata   6660
gtgaagtgag attgaaccag aagttcaaag ataaggctac acttacagta gacacatcta   6720
gttctaccgc atatatgcag cttaattctc caactagtga ggatagtgcc gtctattatt   6780
gcgctcgttt tggcttggat tattggggac agggtacaac tcttactgtt tctagtggct   6840
ctacaagtgg aggtggtagt ggtggaggaa gtggaggagg tggttcaagt gacattgtca   6900
ttacccaatc tccatcatct ttgagtgctt ctcttggtga caccatcttg attacttgtc   6960
acgcatcaca gaatatcaat gtgtggttgt catggtttca gcaaaaacct gggaacgctc   7020
caaagttgct tatctacaaa gcctcaaact tgcatacagg tgttccatca cgttttagtg   7080
ggagtggaag tggtactgga ttcactctta caatctcttc acttcaacca gaggatattg   7140
caacttacta ttgccaacaa ggacaaagtt atccttggac ttttggggga ggcactaagt   7200
tggaaataaa ggctagcaga actgttgctg caccatctgt tttcatcttc cctccatctg   7260
atgagcagtt gaaatctgga actgcttctg ttgtgtgcct tcttaataac ttctatccta   7320
gagaggctaa agttcagtgg aaggtggata acgcacttca atctggtaac tctcaagagt   7380
```

ctgttacaga gcaagattct aaggactcaa cttactctct ttcatctaca cttactttgt 7440
caaaagcaga ttacgagaaa cacaaagttt acgcatgcga agttactcat caaggacttt 7500
cttcaccagt tacaaagtct ttcaatagag gagagtgtta aggatcctct agagtcgacc 7560
tgcagaagct ggcagctagg atgggtctc 7589

<210> SEQ ID NO 42
<211> LENGTH: 880
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
ggatccgcca ccatgggatg gagctgtatc atcctcttct tggtagcaac agctacaggt 60
aaggggctca cagtagcagg cttgaggtct ggacatatat atgggtgaca atgacatcca 120
ctttgccttt ctctccacag gtgtccactc ccaggtgcaa cttcagcagc ccggggctgc 180
cctggtgaga cccggtgcct ccatgcgatt gtcttgcaaa gcatctggct actcctttac 240
aacttattgg atgaattggg taaagcagcg gcccggccag ggactggagc tcatcggtat 300
gattcaccca agcgactctg aagtccgtct caaccaaaaa tttaaggata aagcaaccct 360
tacagtcgat acttcctcat ccacagctta catgcagttg aactctccca cctccgagga 420
cagtgccgtt tattattgtg ccaggttcgg actcgactac tgggggcaag gaacaaccct 480
gaccgtgtct tctgggagta ctagcggcgg aggcagtggt ggcggcagcg ggggaggcgg 540
gtcctcagat atcgttatta cacaaagtcc atcatccctg agcgcaagtc tgggcgacac 600
tatcctgata acatgtcatg cttcacaaaa catcaatgtc tggttgtcct ggttccagca 660
gaaaccaggg aacgccccta agctcctgat ctataaggct agtaatctgc acactggcgt 720
gcctagccgg ttctcaggta gcgggtctgg aactggcttt accctcacca taagctctct 780
gcaacctgaa gatattgcaa cctactactg ccagcagggt cagagctatc cttggacttt 840
tggcggtggg accaagttgg aaatcaagcg cgctgctagc 880

<210> SEQ ID NO 43
<211> LENGTH: 1875
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
ggatccgcca ccatgggatg gagctgtatc atcctcttct tggtagcaac agctacaggt 60
aaggggctca cagtagcagg cttgaggtct ggacatatat atgggtgaca atgacatcca 120
ctttgccttt ctctccacag gtgtccactc ccaggtgcaa cttcagcagc ccggggctgc 180
cctggtgaga cccggtgcct ccatgcgatt gtcttgcaaa gcatctggct actcctttac 240
aacttattgg atgaattggg taaagcagcg gcccggccag ggactggagc tcatcggtat 300
gattcaccca agcgactctg aagtccgtct caaccaaaaa tttaaggata aagcaaccct 360
tacagtcgat acttcctcat ccacagctta catgcagttg aactctccca cctccgagga 420
cagtgccgtt tattattgtg ccaggttcgg actcgactac tgggggcaag gaacaaccct 480
gaccgtgtct tctgggagta ctagcggcgg aggcagtggt ggcggcagcg ggggaggcgg 540
gtcctcagat atcgttatta cacaaagtcc atcatccctg agcgcaagtc tgggcgacac 600

```
tatcctgata acatgtcatg cttcacaaaa catcaatgtc tggttgtcct ggttccagca    660
gaaaccaggg aacgccccta agctcctgat ctataaggct agtaatctgc acactggcgt    720
gcctagccgg ttctcaggta gcgggtctgg aactggcttt accctcacca taagctctct    780
gcaacctgaa gatattgcaa cctactactg ccagcagggt cagagctatc cttggacttt    840
tggcggtggg accaagttgg aaatcaagcg cgctgctagc accaagggcc catcggtctt    900
cccctggca ccctcctcca agagcacctc tgggggcaca gcggccctgg gctgcctggt    960
caaggactac ttccccgaac cggtgacggt gtcgtggaac tcaggcgccc tgaccagcgg   1020
cgtgcacacc ttcccggctg tcctacagtc ctcaggactc tactccctca gcagcgtggt   1080
gaccgtgccc tccagcagct tgggcaccca gacctacatc tgcaacgtga atcacaagcc   1140
cagcaacacc aaggtggaca agagagttga gcccaaatct tgtgacaaaa ctcacacatg   1200
cccaccgtgc ccagcacctg aactcctggg gggaccgtca gtcttcctct tcccccaaa   1260
acccaaggac accctcatga tctcccggac ccctgaggtc acatgcgtgg tggtggacgt   1320
gagccacgaa gaccctgagg tcaagttcaa ctggtacgtg gacggcgtgg aggtgcataa   1380
tgccaagaca aagccgcggg aggagcagta caacagcacg taccgtgtgg tcagcgtcct   1440
caccgtcctg caccaggact ggctgaatgg caaggagtac aagtgcaagg tctccaacaa   1500
agccctccca gcccccatcg agaaaaccat ctccaaagcc aaagggcagc cccgagaacc   1560
acaggtgtac accctgcccc catcccggga tgagctgacc aagaaccagg tcagcctgac   1620
ctgcctggtc aaaggcttct atcccagcga catcgccgtg gagtgggaga gcaatgggca   1680
gccggagaac aactacaaga ccacgcctcc cgtgctggac tccgacggct ccttcttcct   1740
ctacagcaag ctcaccgtgg acaagagcag gtggcagcag gggaacgtct tctcatgctc   1800
cgtgatgcat gaggctctgc acaaccacta cacgcagaag agcctctccc tgtctccggg   1860
taaatgagcg gccgc                                                    1875
```

```
<210> SEQ ID NO 44
<211> LENGTH: 6833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
```

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccc   1080
aggtgcaact tcagcagccc ggggctgccc tggtgagacc cggtgcctcc atgcgattgt   1140
cttgcaaagc atctggctac tcctttacaa cttattggat gaattgggta aagcagcggc   1200
ccggccaggg actggagctc atcggtatga ttcacccaag cgactctgaa gtccgtctca   1260
accaaaaatt taaggataaa gcaaccctta cagtcgatac ttcctcatcc acagcttaca   1320
tgcagttgaa ctctcccacc tccgaggaca gtgccgttta ttattgtgcc aggttcggac   1380
tcgactactg gggcaagga acaaccctga ccgtgtcttc tgggagtact agcggcggag   1440
gcagtggtgg cggcagcggg ggaggcgggt cctcagatat cgttattaca caaagtccat   1500
catccctgag cgcaagtctg ggcgacacta tcctgataac atgtcatgct tcacaaaaca   1560
tcaatgtctg gttgtcctgg ttccagcaga aaccagggaa cgcccctaag ctcctgatct   1620
ataaggctag taatctgcac actggcgtgc ctagccggtt ctcaggtagc gggtctggaa   1680
ctggctttac cctcaccata agctctctgc aacctgaaga tattgcaacc tactactgcc   1740
agcagggtca gagctatcct tggacttttg gcggtgggac caagttggaa atcaagcgcg   1800
ctgctagcac caagggccca tcggtcttcc ccctggcacc ctcctccaag agcacctctg   1860
ggggcacagc ggccctgggc tgcctggtca aggactactt ccccgaaccg gtgacggtgt   1920
cgtggaactc aggcgccctg accagcggcg tgcacacctt cccggctgtc ctacagtcct   1980
caggactcta ctccctcagc agcgtggtga ccgtgccctc cagcagcttg ggcacccaga   2040
cctacatctg caacgtgaat cacaagccca gcaacaccaa ggtggacaag agagttgagc   2100
ccaaatcttg tgacaaaact cacacatgcc caccgtgccc agcacctgaa ctcctggggg   2160
gaccgtcagt cttcctcttc cccccaaaac ccaaggacac cctcatgatc tcccggaccc   2220
ctgaggtcac atgcgtggtg gtggacgtga gccacgaaga ccctgaggtc aagttcaact   2280
ggtacgtgga cggcgtggag gtgcataatg ccaagacaaa gccgcgggag gagcagtaca   2340
acagcacgta ccgtgtggtc agcgtcctca ccgtcctgca ccaggactgg ctgaatggca   2400
aggagtacaa gtgcaaggtc tccaacaaag ccctcccagc ccccatcgag aaaaccatct   2460
ccaaagccaa agggcagccc cgagaaccac aggtgtacac cctgccccca tcccgggatg   2520
agctgaccaa gaaccaggtc agcctgacct gcctggtcaa aggcttctat cccagcgaca   2580
tcgccgtgga gtgggagagc aatgggcagc cggagaacaa ctacaagacc acgcctcccg   2640
tgctggactc cgacggctcc ttcttcctct acagcaagct caccgtggac aagagcaggt   2700
ggcagcaggg gaacgtcttc tcatgctccg tgatgcatga ggctctgcac aaccactaca   2760
cgcagaagag cctctccctg tctccgggta aatgagcggc cgctcgagtc tagagggccc   2820
gtttaaaccc gctgatcagc ctcgactgtg ccttctagtt gccagccatc tgttgtttgc   2880
ccctcccccg tgccttcctt gaccctggaa ggtgccactc ccactgtcct ttcctaataa   2940
aatgaggaaa ttgcatcgca ttgtctgagt aggtgtcatt ctattctggg gggtggggtg   3000
gggcaggaca gcaaggggga ggattgggaa gacaatagca ggcatgctgg ggatgcggtg   3060
```

-continued

```
ggctctatgg cttctgaggc ggaaagaacc agctggggct ctaggggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg ggcatccctt tagggttccg atttagtgct   3300
ttacggcacc tcgaccccaa aaaacttgat tagggtgatg gttcacgtag tgggccatcg   3360
ccctgataga cggtttttcg ccctttgacg ttggagtcca cgttctttaa tagtggactc   3420
ttgttccaaa ctggaacaac actcaaccct atctcggtct attcttttga tttataaggg   3480
attttgggga tttcggccta ttggttaaaa aatgagctga tttaacaaaa atttaacgcg   3540
aattaattct gtggaatgtg tgtcagttag ggtgtggaaa gtccccaggc tccccaggca   3600
ggcagaagta tgcaaagcat gcatctcaat tagtcagcaa ccaggtgtgg aaagtcccca   3660
ggctccccag caggcagaag tatgcaaagc atgcatctca attagtcagc aaccatagtc   3720
ccgcccctaa ctccgcccat cccgccccta actccgccca gttccgccca ttctccgccc   3780
catggctgac taattttttt tatttatgca gaggccgagg ccgcctctgc ctctgagcta   3840
ttccagaagt agtgaggagg cttttttgga ggcctaggct tttgcaaaaa gctcccggga   3900
gcttgtatat ccattttcgg atctgatcag cacgtgttga caattaatca tcggcatagt   3960
atatcggcat agtataatac gacaaggtga ggaactaaac catggccaag ttgaccagtg   4020
ccgttccggt gctcaccgcg cgcgacgtcg ccggagcggt cgagttctgg accgaccggc   4080
tcgggttctc ccgggacttc gtggaggacg acttcgccgg tgtggtccgg gacgacgtga   4140
ccctgttcat cagcgcggtc caggaccagg tggtgccgga caacaccctg gcctgggtgt   4200
gggtgcgcgg cctggacgag ctgtacgccg agtggtcgga ggtcgtgtcc acgaacttcc   4260
gggacgcctc cgggccggcc atgaccgaga tcggcgagca gccgtggggg cgggagttcg   4320
ccctgcgcga cccggccggc aactgcgtgc acttcgtggc cgaggagcag gactgacacg   4380
tgctacgaga tttcgattcc accgccgcct tctatgaaag gttgggcttc ggaatcgttt   4440
tccgggacgc cggctggatg atcctccagc gcggggatct catgctggag ttcttcgccc   4500
accccaactt gtttattgca gcttataatg gttacaaata aagcaatagc atcacaaatt   4560
tcacaaataa agcatttttt tcactgcatt ctagttgtgg tttgtccaaa ctcatcaatg   4620
tatcttatca tgtctgtata ccgtcgacct ctagctagag cttggcgtaa tcatggtcat   4680
agctgtttcc tgtgtgaaat tgttatccgc tcacaattcc acacaacata cgagccggaa   4740
gcataaagtg taaagcctgg ggtgcctaat gagtgagcta actcacatta attgcgttgc   4800
gctcactgcc cgctttccag tcgggaaacc tgtcgtgcca gctgcattaa tgaatcggcc   4860
aacgcgcggg gagaggcggt ttgcgtattg ggcgctcttc cgcttcctcg ctcactgact   4920
cgctgcgctc ggtcgttcgg ctgcggcgag cggtatcagc tcactcaaag gcggtaatac   4980
ggttatccac agaatcaggg gataacgcag gaaagaacat gtgagcaaaa ggccagcaaa   5040
aggccaggaa ccgtaaaaag gccgcgttgc tggcgttttt ccataggctc cgcccccctg   5100
acgagcatca caaaaatcga cgctcaagtc agaggtggcg aaacccgaca ggactataaa   5160
gataccaggc gtttccccct ggaagctccc tcgtgcgctc tcctgttccg accctgccgc   5220
ttaccggata cctgtccgcc tttctccctt cgggaagcgt ggcgctttct caatgctcac   5280
gctgtaggta tctcagttcg gtgtaggtcg ttcgctccaa gctgggctgt gtgcacgaac   5340
cccccgttca gcccgaccgc tgcgccttat ccggtaacta tcgtcttgag tccaacccgg   5400
taagacacga cttatcgcca ctggcagcag ccactggtaa caggattagc agagcgaggt   5460
```

```
atgtaggcgg tgctacagag ttcttgaagt ggtggcctaa ctacggctac actagaagga   5520

cagtatttgg tatctgcgct ctgctgaagc cagttacctt cggaaaaaga gttggtagct   5580

cttgatccgg caaacaaacc accgctggta gcggtggttt ttttgtttgc aagcagcaga   5640

ttacgcgcag aaaaaaagga tctcaagaag atcctttgat cttttctacg gggtctgacg   5700

ctcagtggaa cgaaaactca cgttaaggga ttttggtcat gagattatca aaaaggatct   5760

tcacctagat ccttttaaat taaaaatgaa gttttaaatc aatctaaagt atatatgagt   5820

aaacttggtc tgacagttac caatgcttaa tcagtgaggc acctatctca gcgatctgtc   5880

tatttcgttc atccatagtt gcctgactcc ccgtcgtgta gataactacg atacgggagg   5940

gcttaccatc tggccccagt gctgcaatga taccgcgaga cccacgctca ccggctccag   6000

atttatcagc aataaaccag ccagccggaa gggccgagcg cagaagtggt cctgcaactt   6060

tatccgcctc catccagtct attaattgtt gccgggaagc tagagtaagt agttcgccag   6120

ttaatagttt gcgcaacgtt gttgccattg ctacaggcat cgtggtgtca cgctcgtcgt   6180

ttggtatggc ttcattcagc tccggttccc aacgatcaag gcgagttaca tgatccccca   6240

tgttgtgcaa aaaagcggtt agctccttcg gtcctccgat cgttgtcaga agtaagttgg   6300

ccgcagtgtt atcactcatg gttatggcag cactgcataa ttctcttact gtcatgccat   6360

ccgtaagatg cttttctgtg actggtgagt actcaaccaa gtcattctga gaatagtgta   6420

tgcggcgacc gagttgctct tgcccggcgt caatacggga taataccgcg ccacatagca   6480

gaactttaaa agtgctcatc attggaaaac gttcttcggg gcgaaaactc tcaaggatct   6540

taccgctgtt gagatccagt tcgatgtaac ccactcgtgc acccaactga tcttcagcat   6600

cttttacttt caccagcgtt tctgggtgag caaaaacagg aaggcaaaat gccgcaaaaa   6660

agggaataag ggcgacacgg aaatgttgaa tactcatact cttccttttt caatattatt   6720

gaagcattta tcagggttat tgtctcatga gcggatacat atttgaatgt atttagaaaa   6780

ataaacaaat aggggttccg cgcacatttc cccgaaaagt gccacctgac gtc          6833
```

```
<210> SEQ ID NO 45
<211> LENGTH: 7415
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
```

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660
```

```
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccc   1080
aggtgcaact tcagcagccc ggggctgccc tggtgagacc cggtgcctcc atgcgattgt   1140
cttgcaaagc atctggctac tcctttacaa cttattggat gaattgggta aagcagcggc   1200
ccggccaggg actggagctc atcggtatga ttcacccaag cgactctgaa gtccgtctca   1260
accaaaaatt taaggataaa gcaaccctta cagtcgatac ttcctcatcc acagcttaca   1320
tgcagttgaa ctctcccacc tccgaggaca gtgccgttta ttattgtgcc aggttcggac   1380
tcgactactg gggcaagga acaaccctga ccgtgtcttc tgggagtact agcggcggag   1440
gcagtggtgg cggcagcggg ggaggcgggt cctcagatat cgttattaca caaagtccat   1500
catccctgag cgcaagtctg ggcgacacta tcctgataac atgtcatgct tcacaaaaca   1560
tcaatgtctg gttgtcctgg ttccagcaga aaccagggaa cgcccctaag ctcctgatct   1620
ataaggctag taatctgcac actggcgtgc ctagccggtt ctcaggtagc gggtctggaa   1680
ctggctttac cctcaccata agctctctgc aacctgaaga tattgcaacc tactactgcc   1740
agcagggtca gagctatcct tggacttttg gcggtgggac caagttggaa atcaagcgcg   1800
ctgctagcac caagggccca tcggtcttcc ccctggcacc ctcctccaag agcacctctg   1860
ggggcacagc ggccctgggc tgcctggtca aggactactt ccccgaaccg gtgacggtgt   1920
cgtggaactc aggcgccctg accagcggcg tgcacacctt cccggctgtc ctacagtcct   1980
caggactcta ctccctcagc agcgtggtga ccgtgccctc cagcagcttg ggcacccaga   2040
cctacatctg caacgtgaat cacaagccca gcaacaccaa ggtggacaag agagttgagc   2100
ccaaatcttg tgacaaaact cacacatgcc caccgtgccc agcacctgaa ctcctggggg   2160
gaccgtcagt cttcctcttc cccccaaaac ccaaggacac cctcatgatc tcccggaccc   2220
ctgaggtcac atgcgtggtg gtggacgtga gccacgaaga ccctgaggtc aagttcaact   2280
ggtacgtgga cggcgtggag gtgcataatg ccaagacaaa gccgcgggag gagcagtaca   2340
acagcacgta ccgtgtggtc agcgtcctca ccgtcctgca ccaggactgg ctgaatggca   2400
aggagtacaa gtgcaaggtc tccaacaaag ccctcccagc ccccatcgag aaaaccatct   2460
ccaaagccaa agggcagccc cgagaaccac aggtgtacac cctgccccca tcccgggatg   2520
agctgaccaa gaaccaggtc agcctgacct gcctggtcaa aggcttctat cccagcgaca   2580
tcgccgtgga gtgggagagc aatgggcagc cggagaacaa ctacaagacc acgcctcccg   2640
tgctggactc cgacggctcc ttcttcctct acagcaagct caccgtggac aagagcaggt   2700
ggcagcaggg gaacgtcttc tcatgctccg tgatgcatga ggctctgcac aaccactaca   2760
cgcagaagag cctctccctg tctccgggta aatgagcggc cgctcgagtc tagagggccc   2820
gtttaaaccc gctgatcagc ctcgactgtg ccttctagtt gccagccatc tgttgtttgc   2880
ccctcccccg tgccttcctt gaccctggaa ggtgccactc ccactgtcct ttcctaataa   2940
aatgaggaaa ttgcatcgca ttgtctgagt aggtgtcatt ctattctggg gggtggggtg   3000
```

```
gggcaggaca gcaaggggga ggattgggaa gacaatagca ggcatgctgg ggatgcggtg   3060
ggctctatgg cttctgaggc ggaaagaacc agctggggct ctagggggta tccccacgcg   3120
ccctgtagcg gcgcattaag cgcggcgggt gtggtggtta cgcgcagcgt gaccgctaca   3180
cttgccagcg ccctagcgcc cgctcctttc gctttcttcc cttcctttct cgccacgttc   3240
gccggctttc cccgtcaagc tctaaatcgg gggctccctt tagggttccg atttagtgct   3300
ttacggcacc tcgaccccaa aaaacttgat tagggtgatg gttcacgtag tgggccatcg   3360
ccctgataga cggtttttcg ccctttgacg ttggagtcca cgttctttaa tagtggactc   3420
ttgttccaaa ctggaacaac actcaaccct atctcggtct attcttttga tttataaggg   3480
attttgccga tttcggccta ttggttaaaa aatgagctga tttaacaaaa atttaacgcg   3540
aattaattct gtggaatgtg tgtcagttag ggtgtggaaa gtccccaggc tccccagcag   3600
gcagaagtat gcaaagcatg catctcaatt agtcagcaac caggtgtgga aagtccccag   3660
gctccccagc aggcagaagt atgcaaagca tgcatctcaa ttagtcagca accatagtcc   3720
cgcccctaac tccgcccatc ccgcccctaa ctccgcccag ttccgcccat tctccgcccc   3780
atggctgact aatttttttt atttatgcag aggccgaggc cgcctctgcc tctgagctat   3840
tccagaagta gtgaggaggc ttttttggag gcctaggctt ttgcaaaaag ctcccgggag   3900
cttgtatatc cattttcgga tctgatcagc acgtgatgaa aaagcctgaa ctcaccgcga   3960
cgtctgtcga gaagtttctg atcgaaaagt tcgacagcgt ctccgacctg atgcagctct   4020
cggagggcga agaatctcgt gctttcagct tcgatgtagg agggcgtgga tatgtcctgc   4080
gggtaaatag ctgcgccgat ggtttctaca aagatcgtta tgtttatcgg cactttgcat   4140
cggccgcgct cccgattccg gaagtgcttg acattgggga attcagcgag agcctgacct   4200
attgcatctc ccgccgtgca cagggtgtca cgttgcaaga cctgcctgaa accgaactgc   4260
ccgctgttct gcagccggtc gcggaggcca tggatgcgat cgctgcggcc gatcttagcc   4320
agacgagcgg gttcggccca ttcggaccgc aaggaatcgg tcaatacact acatggcgtg   4380
atttcatatg cgcgattgct gatccccatg tgtatcactg gcaaactgtg atggacgaca   4440
ccgtcagtgc gtccgtcgcg caggctctcg atgagctgat gctttgggcc gaggactgcc   4500
ccgaagtccg gcacctcgtg cacgcggatt tcggctccaa caatgtcctg acggacaatg   4560
gccgcataac agcggtcatt gactggagcg aggcgatgtt cggggattcc caatacgagg   4620
tcgccaacat cttcttctgg aggccgtggt tggcttgtat ggagcagcag acgcgctact   4680
tcgagcggag gcatccggag cttgcaggat cgccgcggct ccgggcgtat atgctccgca   4740
ttggtcttga ccaactctat cagagcttgg ttgacggcaa tttcgatgat gcagcttggg   4800
cgcagggtcg atgcgacgca atcgtccgat ccggagccgg gactgtcggg cgtacacaaa   4860
tcgcccgcag aagcgcggcc gtctggaccg atggctgtgt agaagtactc gccgatagtg   4920
gaaaccgacg ccccagcact cgtccgaggg caaaggaata gcacgtgcta cgagatttcg   4980
attccaccgc cgccttctat gaaaggttgg gcttcggaat cgttttccgg gacgccggct   5040
ggatgatcct ccagcgcggg gatctcatgc tggagttctt cgcccacccc aacttgttta   5100
ttgcagctta taatggttac aaataaagca atagcatcac aaatttcaca aataaagcat   5160
ttttttcact gcattctagt tgtggtttgt ccaaactcat caatgtatct tatcatgtct   5220
gtataccgtc gacctctagc tagagcttgg cgtaatcatg gtcatagctg tttcctgtgt   5280
gaaattgtta tccgctcaca attccacaca acatacgagc cggaagcata aagtgtaaag   5340
cctggggtgc ctaatgagtg agctaactca cattaattgc gttgcgctca ctgcccgctt   5400
```

```
tccagtcggg aaacctgtcg tgccagctgc attaatgaat cggccaacgc gcggggagag   5460

gcggtttgcg tattgggcgc tcttccgctt cctcgctcac tgactcgctg cgctcggtcg   5520

ttcggctgcg gcgagcggta tcagctcact caaaggcggt aatacggtta tccacagaat   5580

caggggataa cgcaggaaag aacatgtgag caaaaggcca gcaaaaggcc aggaaccgta   5640

aaaaggccgc gttgctggcg tttttccata ggctccgccc ccctgacgag catcacaaaa   5700

atcgacgctc aagtcagagg tggcgaaacc cgacaggact ataaagatac caggcgtttc   5760

cccctggaag ctccctcgtg cgctctcctg ttccgaccct gccgcttacc ggatacctgt   5820

ccgcctttct cccttcggga agcgtggcgc tttctcatag ctcacgctgt aggtatctca   5880

gttcggtgta ggtcgttcgc tccaagctgg gctgtgtgca cgaacccccc gttcagcccg   5940

accgctgcgc cttatccggt aactatcgtc ttgagtccaa cccggtaaga cacgacttat   6000

cgccactggc agcagccact ggtaacagga ttagcagagc gaggtatgta ggcggtgcta   6060

cagagttctt gaagtggtgg cctaactacg gctacactag aagaacagta tttggtatct   6120

gcgctctgct gaagccagtt accttcggaa aaagagttgg tagctcttga tccggcaaac   6180

aaaccaccgc tggtagcggt ttttttgttt gcaagcagca gattacgcgc agaaaaaaag   6240

gatctcaaga agatcctttg atcttttcta cggggtctga cgctcagtgg aacgaaaact   6300

cacgttaagg gattttggtc atgagattat caaaaaggat cttcacctag atccttttaa   6360

attaaaaatg aagttttaaa tcaatctaaa gtatatatga gtaaacttgg tctgacagtt   6420

accaatgctt aatcagtgag gcacctatct cagcgatctg tctatttcgt tcatccatag   6480

ttgcctgact ccccgtcgtg tagataacta cgatacggga gggcttacca tctggcccca   6540

gtgctgcaat gataccgcga gacccacgct caccggctcc agatttatca gcaataaacc   6600

agccagccgg aagggccgag cgcagaagtg gtcctgcaac tttatccgcc tccatccagt   6660

ctattaattg ttgccgggaa gctagagtaa gtagttcgcc agttaatagt ttgcgcaacg   6720

ttgttgccat tgctacaggc atcgtggtgt cacgctcgtc gtttggtatg gcttcattca   6780

gctccggttc ccaacgatca aggcgagtta catgatcccc catgttgtgc aaaaaagcgg   6840

ttagctcctt cggtcctccg atcgttgtca gaagtaagtt ggccgcagtg ttatcactca   6900

tggttatggc agcactgcat aattctctta ctgtcatgcc atccgtaaga tgcttttctg   6960

tgactggtga gtactcaacc aagtcattct gagaatagtg tatgcggcga ccgagttgct   7020

cttgcccggc gtcaatacgg gataataccg cgccacatag cagaacttta aaagtgctca   7080

tcattggaaa acgttcttcg gggcgaaaac tctcaaggat cttaccgctg ttgagatcca   7140

gttcgatgta acccactcgt gcacccaact gatcttcagc atcttttact ttcaccagcg   7200

tttctgggtg agcaaaaaca ggaaggcaaa atgccgcaaa aaagggaata agggcgacac   7260

ggaaatgttg aatactcata ctcttccttt ttcaatatta ttgaagcatt tatcagggtt   7320

attgtctcat gagcggatac atatttgaat gtatttagaa aaataaacaa ataggggttc   7380

cgcgcacatt tccccgaaaa gtgccacctg acgtc                              7415
```

<210> SEQ ID NO 46
<211> LENGTH: 1206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
ggatccgcca ccatgggatg gagctgtatc atcctcttct tggtagcaac agctacaggt     60

aaggggctca cagtagcagg cttgaggtct ggacatatat atgggtgaca atgacatcca    120

ctttgccttt ctctccacag gtgtccactc ccaggtgcaa cttcagcagc ccggggctgc    180

cctggtgaga cccggtgcct ccatgcgatt gtcttgcaaa gcatctggct actcctttac    240

aacttattgg atgaattggg taaagcagcg gcccggccag ggactggagc tcatcggtat    300

gattcaccca agcgactctg aagtccgtct caaccaaaaa tttaaggata aagcaaccct    360

tacagtcgat acttcctcat ccacagctta catgcagttg aactctccca cctccgagga    420

cagtgccgtt tattattgtg ccaggttcgg actcgactac tgggggcaag gaacaaccct    480

gaccgtgtct tctgggagta ctagcggcgg aggcagtggt ggcggcagcg gggaggcgg     540

gtcctcagat atcgttatta cacaaagtcc atcatccctg agcgcaagtc tgggcgacac    600

tatcctgata acatgtcatg cttcacaaaa catcaatgtc tggttgtcct ggttccagca    660

gaaaccaggg aacgccccta agctcctgat ctataaggct agtaatctgc acactggcgt    720

gcctagccgg ttctcaggta gcgggtctgg aactggcttt accctcacca taagctctct    780

gcaacctgaa gatattgcaa cctactactg ccagcagggt cagagctatc cttggacttt    840

tggcggtggg accaagttgg aaatcaagcg cgctgctagc gtggctgcac catctgtctt    900

catcttcccg ccatctgatg agcagttgaa atctggaact gcctctgttg tgtgcctgct    960

gaataacttc tatcccagag aggccaaagt acagtggaag gtggataacg ccctccaatc   1020

gggtaactcc caggagagtg tcacagagca ggacagcaag gacagcacct acagcctcag   1080

cagcaccctg acgctgagca aagcagacta cgagaaacac aaagtctacg cctgcgaagt   1140

cacccatcag ggcctgagct cgcccgtcac aaagagcttc aacaggggag agtgttaggc   1200

ggccgc                                                              1206
```

<210> SEQ ID NO 47
<211> LENGTH: 6164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780
```

```
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccc   1080
aggtgcaact tcagcagccc ggggctgccc tggtgagacc cggtgcctcc atgcgattgt   1140
cttgcaaagc atctggctac tcctttacaa cttattggat gaattgggta aagcagcggc   1200
ccggccaggg actggagctc atcggtatga ttcacccaag cgactctgaa gtccgtctca   1260
accaaaaatt taaggataaa gcaaccctta cagtcgatac ttcctcatcc acagcttaca   1320
tgcagttgaa ctctcccacc tccgaggaca gtgccgttta ttattgtgcc aggttcggac   1380
tcgactactg gggcaagga acaaccctga ccgtgtcttc tgggagtact agcggcggag   1440
gcagtggtgg cggcagcggg ggaggcgggt cctcagatat cgttattaca caaagtccat   1500
catccctgag cgcaagtctg ggcgacacta tcctgataac atgtcatgct tcacaaaaca   1560
tcaatgtctg gttgtcctgg ttccagcaga aaccagggaa cgcccctaag ctcctgatct   1620
ataaggctag taatctgcac actggcgtgc ctagccggtt ctcaggtagc gggtctggaa   1680
ctggctttac cctcaccata agctctctgc aacctgaaga tattgcaacc tactactgcc   1740
agcagggtca gagctatcct tggacttttg gcggtgggac caagttggaa atcaagcgcg   1800
ctgctagcgt ggctgcacca tctgtcttca tcttcccgcc atctgatgag cagttgaaat   1860
ctggaactgc ctctgttgtg tgcctgctga ataacttcta tcccagagag gccaaagtac   1920
agtggaaggt ggataacgcc ctccaatcgg gtaactccca ggagagtgtc acagagcagg   1980
acagcaagga cagcacctac agcctcagca gcaccctgac gctgagcaaa gcagactacg   2040
agaaacacaa agtctacgcc tgcgaagtca cccatcaggg cctgagctcg cccgtcacaa   2100
agagcttcaa caggggagag tgttaggcgg ccgctcgagt ctagagggcc cgtttaaacc   2160
cgctgatcag cctcgactgt gccttctagt tgccagccat ctgttgtttg cccctccccc   2220
gtgccttcct tgaccctgga aggtgccact cccactgtcc tttcctaata aaatgaggaa   2280
attgcatcgc attgtctgag taggtgtcat tctattctgg ggggtggggt ggggcaggac   2340
agcaaggggg aggattggga agacaatagc aggcatgctg gggatgcggt gggctctatg   2400
gcttctgagg cggaaagaac cagctggggc tctagggggt atccccacgc gccctgtagc   2460
ggcgcattaa gcgcggcggg tgtggtggtt acgcgcagcg tgaccgctac acttgccagc   2520
gccctagcgc ccgctccttt cgctttcttc ccttcctttc tcgccacgtt cgccggcttt   2580
ccccgtcaag ctctaaatcg ggcatccct ttagggttcc gatttagtgc tttacggcac   2640
ctcgacccca aaaaacttga ttagggtgat ggttcacgta gtgggccatc gccctgatag   2700
acggtttttc gccctttgac gttggagtcc acgttcttta atagtggact cttgttccaa   2760
actggaacaa cactcaaccc tatctcggtc tattcttttg atttataagg gattttgggg   2820
atttcggcct attggttaaa aaatgagctg atttaacaaa aatttaacgc gaattaattc   2880
tgtggaatgt gtgtcagtta gggtgtggaa agtccccagg ctccccaggc aggcagaagt   2940
atgcaaagca tgcatctcaa ttagtcagca accaggtgtg gaaagtcccc aggctcccca   3000
gcaggcagaa gtatgcaaag catgcatctc aattagtcag caaccatagt cccgccccta   3060
actccgccca tcccgcccct aactccgccc agttccgccc attctccgcc ccatggctga   3120
```

```
ctaatttttt ttatttatgc agaggccgag gccgcctctg cctctgagct attccagaag   3180

tagtgaggag gcttttttgg aggcctaggc ttttgcaaaa agctcccggg agcttgtata   3240

tccattttcg gatctgatca gcacgtgttg acaattaatc atcggcatag tatatcggca   3300

tagtataata cgacaaggtg aggaactaaa ccatggccaa gttgaccagt gccgttccgg   3360

tgctcaccgc gcgcgacgtc gccggagcgg tcgagttctg gaccgaccgg ctcgggttct   3420

cccgggactt cgtggaggac gacttcgccg gtgtggtccg ggacgacgtg accctgttca   3480

tcagcgcggt ccaggaccag gtggtgccgg acaacaccct ggcctgggtg tgggtgcgcg   3540

gcctggacga gctgtacgcc gagtggtcgg aggtcgtgtc cacgaacttc cgggacgcct   3600

ccgggccggc catgaccgag atcggcgagc agccgtgggg gcgggagttc gccctgcgcg   3660

acccggccgg caactgcgtg cacttcgtgg ccgaggagca ggactgacac gtgctacgag   3720

atttcgattc caccgccgcc ttctatgaaa ggttgggctt cggaatcgtt ttccgggacg   3780

ccggctggat gatcctccag cgcggggatc tcatgctgga gttcttcgcc caccccaact   3840

tgtttattgc agcttataat ggttacaaat aaagcaatag catcacaaat ttcacaaata   3900

aagcattttt ttcactgcat tctagttgtg gtttgtccaa actcatcaat gtatcttatc   3960

atgtctgtat accgtcgacc tctagctaga gcttggcgta atcatggtca tagctgtttc   4020

ctgtgtgaaa ttgttatccg ctcacaattc cacacaacat acgagccgga agcataaagt   4080

gtaaagcctg gggtgcctaa tgagtgagct aactcacatt aattgcgttg cgctcactgc   4140

ccgctttcca gtcgggaaac ctgtcgtgcc agctgcatta atgaatcggc caacgcgcgg   4200

ggagaggcgg tttgcgtatt gggcgctctt ccgcttcctc gctcactgac tcgctgcgct   4260

cggtcgttcg gctgcggcga gcggtatcag ctcactcaaa ggcggtaata cggttatcca   4320

cagaatcagg ggataacgca ggaaagaaca tgtgagcaaa aggccagcaa aaggccagga   4380

accgtaaaaa ggccgcgttg ctggcgtttt tccataggct ccgcccccct gacgagcatc   4440

acaaaaatcg acgctcaagt cagaggtggc gaaacccgac aggactataa agataccagg   4500

cgtttccccc tggaagctcc ctcgtgcgct ctcctgttcc gaccctgccg cttaccggat   4560

acctgtccgc ctttctccct tcgggaagcg tggcgctttc tcaatgctca cgctgtaggt   4620

atctcagttc ggtgtaggtc gttcgctcca agctgggctg tgtgcacgaa ccccccgttc   4680

agcccgaccg ctgcgcctta tccggtaact atcgtcttga gtccaacccg gtaagacacg   4740

acttatcgcc actggcagca gccactggta acaggattag cagagcgagg tatgtaggcg   4800

gtgctacaga gttcttgaag tggtggccta actacggcta cactagaagg acagtatttg   4860

gtatctgcgc tctgctgaag ccagttacct tcggaaaaag agttggtagc tcttgatccg   4920

gcaaacaaac caccgctggt agcggtggtt tttttgtttg caagcagcag attacgcgca   4980

gaaaaaaagg atctcaagaa gatcctttga tcttttctac ggggtctgac gctcagtgga   5040

acgaaaactc acgttaaggg attttggtca tgagattatc aaaaaggatc ttcacctaga   5100

tccttttaaa ttaaaaatga agttttaaat caatctaaag tatatatgag taaacttggt   5160

ctgacagtta ccaatgctta atcagtgagg cacctatctc agcgatctgt ctatttcgtt   5220

catccatagt tgcctgactc cccgtcgtgt agataactac gatacgggag ggcttaccat   5280

ctggccccag tgctgcaatg ataccgcgag acccacgctc accggctcca gatttatcag   5340

caataaacca gccagccgga agggccgagc gcagaagtgg tcctgcaact ttatccgcct   5400

ccatccagtc tattaattgt tgccgggaag ctagagtaag tagttcgcca gttaatagtt   5460

tgcgcaacgt tgttgccatt gctacaggca tcgtggtgtc acgctcgtcg tttggtatgg   5520
```

```
cttcattcag ctccggttcc caacgatcaa ggcgagttac atgatccccc atgttgtgca   5580
aaaaagcggt tagctccttc ggtcctccga tcgttgtcag aagtaagttg gccgcagtgt   5640
tatcactcat ggttatggca gcactgcata attctcttac tgtcatgcca tccgtaagat   5700
gcttttctgt gactggtgag tactcaacca agtcattctg agaatagtgt atgcggcgac   5760
cgagttgctc ttgcccggcg tcaatacggg ataataccgc gccacatagc agaactttaa   5820
aagtgctcat cattggaaaa cgttcttcgg ggcgaaaact ctcaaggatc ttaccgctgt   5880
tgagatccag ttcgatgtaa cccactcgtg cacccaactg atcttcagca tcttttactt   5940
tcaccagcgt ttctgggtga gcaaaaacag gaaggcaaaa tgccgcaaaa aagggaataa   6000
gggcgacacg gaaatgttga atactcatac tcttcctttt tcaatattat tgaagcattt   6060
atcagggtta ttgtctcatg agcggataca tatttgaatg tatttagaaa aataaacaaa   6120
taggggttcc gcgcacattt ccccgaaaag tgccacctga cgtc                     6164
```

<210> SEQ ID NO 48
<211> LENGTH: 6746
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccc   1080
aggtgcaact tcagcagccc ggggctgccc tggtgagacc cggtgcctcc atgcgattgt   1140
cttgcaaagc atctggctac tcctttacaa cttattggat gaattgggta aagcagcggc   1200
ccggccaggg actggagctc atcggtatga ttcacccaag cgactctgaa gtccgtctca   1260
accaaaaatt taaggataaa gcaaccctta cagtcgatac ttcctcatcc acagcttaca   1320
tgcagttgaa ctctcccacc tccgaggaca gtgccgttta ttattgtgcc aggttcggac   1380
```

```
tcgactactg gggcaagga acaaccctga ccgtgtcttc tgggagtact agcggcggag   1440
gcagtggtgg cggcagcggg ggaggcgggt cctcagatat cgttattaca caaagtccat   1500
catccctgag cgcaagtctg ggcgacacta tcctgataac atgtcatgct tcacaaaaca   1560
tcaatgtctg gttgtcctgg ttccagcaga aaccagggaa cgcccctaag ctcctgatct   1620
ataaggctag taatctgcac actggcgtgc ctagccggtt ctcaggtagc gggtctggaa   1680
ctggctttac cctcaccata agctctctgc aacctgaaga tattgcaacc tactactgcc   1740
agcagggtca gagctatcct tggacttttg gcggtgggac caagttggaa atcaagcgcg   1800
ctgctagcgt ggctgcacca tctgtcttca tcttcccgcc atctgatgag cagttgaaat   1860
ctggaactgc ctctgttgtg tgcctgctga ataacttcta tcccagagag gccaaagtac   1920
agtggaaggt ggataacgcc ctccaatcgg gtaactccca ggagagtgtc acagagcagg   1980
acagcaagga cagcacctac agcctcagca gcaccctgac gctgagcaaa gcagactacg   2040
agaaacacaa agtctacgcc tgcgaagtca cccatcaggg cctgagctcg cccgtcacaa   2100
agagcttcaa caggggagag tgttaggcgg ccgctcgagt ctagagggcc cgtttaaacc   2160
cgctgatcag cctcgactgt gccttctagt tgccagccat ctgttgtttg cccctccccc   2220
gtgccttcct tgaccctgga aggtgccact cccactgtcc tttcctaata aaatgaggaa   2280
attgcatcgc attgtctgag taggtgtcat tctattctgg ggggtggggt ggggcaggac   2340
agcaaggggg aggattggga agacaatagc aggcatgctg gggatgcggt gggctctatg   2400
gcttctgagg cggaaagaac cagctggggc tctagggggt atccccacgc gccctgtagc   2460
ggcgcattaa gcgcggcggg tgtggtggtt acgcgcagcg tgaccgctac acttgccagc   2520
gccctagcgc ccgctccttt cgctttcttc ccttcctttc tcgccacgtt cgccggcttt   2580
ccccgtcaag ctctaaatcg ggggctccct ttagggttcc gatttagtgc tttacggcac   2640
ctcgacccca aaaaacttga ttagggtgat ggttcacgta gtgggccatc gccctgatag   2700
acggtttttc gccctttgac gttggagtcc acgttcttta atagtggact cttgttccaa   2760
actggaacaa cactcaaccc tatctcggtc tattcttttg atttataagg gattttgccg   2820
atttcggcct attggttaaa aaatgagctg atttaacaaa aatttaacgc gaattaattc   2880
tgtggaatgt gtgtcagtta gggtgtggaa agtccccagg ctccccagca ggcagaagta   2940
tgcaaagcat gcatctcaat tagtcagcaa ccaggtgtgg aaagtcccca ggctccccag   3000
caggcagaag tatgcaaagc atgcatctca attagtcagc aaccatagtc ccgcccctaa   3060
ctccgcccat cccgccccta actccgccca gttccgccca ttctccgccc catggctgac   3120
taattttttt tatttatgca gaggccgagg ccgcctctgc ctctgagcta ttccagaagt   3180
agtgaggagg cttttttgga ggcctaggct tttgcaaaaa gctcccggga gcttgtatat   3240
ccattttcgg atctgatcag cacgtgatga aaaagcctga actcaccgcg acgtctgtcg   3300
agaagtttct gatcgaaaag ttcgacagcg tctccgacct gatgcagctc tcggagggcg   3360
aagaatctcg tgctttcagc ttcgatgtag gagggcgtgg atatgtcctg cgggtaaata   3420
gctgcgccga tggtttctac aaagatcgtt atgtttatcg gcactttgca tcggccgcgc   3480
tcccgattcc ggaagtgctt gacattgggg aattcagcga gagcctgacc tattgcatct   3540
cccgccgtgc acagggtgtc acgttgcaag acctgcctga aaccgaactg cccgctgttc   3600
tgcagccggt cgcggaggcc atggatgcga tcgctgcggc cgatcttagc cagacgagcg   3660
ggttcggccc attcggaccg caaggaatcg gtcaatacac tacatggcgt gatttcatat   3720
```

-continued

```
gcgcgattgc tgatccccat gtgtatcact ggcaaactgt gatggacgac accgtcagtg   3780

cgtccgtcgc gcaggctctc gatgagctga tgctttgggc cgaggactgc cccgaagtcc   3840

ggcacctcgt gcacgcggat ttcggctcca acaatgtcct gacggacaat ggccgcataa   3900

cagcggtcat tgactggagc gaggcgatgt tcggggattc ccaatacgag gtcgccaaca   3960

tcttcttctg gaggccgtgg ttggcttgta tggagcagca gacgcgctac ttcgagcgga   4020

ggcatccgga gcttgcagga tcgccgcggc tccgggcgta tatgctccgc attggtcttg   4080

accaactcta tcagagcttg gttgacggca atttcgatga tgcagcttgg gcgcagggtc   4140

gatgcgacgc aatcgtccga tccggagccg ggactgtcgg gcgtacacaa atcgcccgca   4200

gaagcgcggc cgtctggacc gatggctgtg tagaagtact cgccgatagt ggaaaccgac   4260

gccccagcac tcgtccgagg gcaaaggaat agcacgtgct acgagatttc gattccaccg   4320

ccgccttcta tgaaaggttg ggcttcggaa tcgttttccg ggacgccggc tggatgatcc   4380

tccagcgcgg ggatctcatg ctggagttct tcgcccaccc caacttgttt attgcagctt   4440

ataatggtta caaataaagc aatagcatca caaatttcac aaataaagca tttttttcac   4500

tgcattctag ttgtggtttg tccaaactca tcaatgtatc ttatcatgtc tgtataccgt   4560

cgacctctag ctagagcttg gcgtaatcat ggtcatagct gtttcctgtg tgaaattgtt   4620

atccgctcac aattccacac aacatacgag ccggaagcat aaagtgtaaa gcctggggtg   4680

cctaatgagt gagctaactc acattaattg cgttgcgctc actgcccgct ttccagtcgg   4740

gaaacctgtc gtgccagctg cattaatgaa tcggccaacg cgcggggaga ggcggtttgc   4800

gtattgggcg ctcttccgct tcctcgctca ctgactcgct gcgctcggtc gttcggctgc   4860

ggcgagcggt atcagctcac tcaaaggcgg taatacggtt atccacagaa tcaggggata   4920

acgcaggaaa gaacatgtga gcaaaaggcc agcaaaaggc caggaaccgt aaaaaggccg   4980

cgttgctggc gtttttccat aggctccgcc cccctgacga gcatcacaaa aatcgacgct   5040

caagtcagag gtggcgaaac ccgacaggac tataaagata ccaggcgttt ccccctggaa   5100

gctccctcgt gcgctctcct gttccgaccc tgccgcttac cggatacctg tccgcctttc   5160

tcccttcggg aagcgtggcg ctttctcata gctcacgctg taggtatctc agttcggtgt   5220

aggtcgttcg ctccaagctg ggctgtgtgc acgaaccccc cgttcagccc gaccgctgcg   5280

ccttatccgg taactatcgt cttgagtcca acccggtaag acacgactta tcgccactgg   5340

cagcagccac tggtaacagg attagcagag cgaggtatgt aggcggtgct acagagttct   5400

tgaagtggtg gcctaactac ggctacacta gaagaacagt atttggtatc tgcgctctgc   5460

tgaagccagt taccttcgga aaaagagttg gtagctcttg atccggcaaa caaaccaccg   5520

ctggtagcgg tttttttgtt tgcaagcagc agattacgcg cagaaaaaaa ggatctcaag   5580

aagatccttt gatcttttct acggggtctg acgctcagtg gaacgaaaac tcacgttaag   5640

ggattttggt catgagatta tcaaaaagga tcttcaccta gatcctttta aattaaaaat   5700

gaagttttaa atcaatctaa agtatatatg agtaaacttg gtctgacagt taccaatgct   5760

taatcagtga ggcacctatc tcagcgatct gtctatttcg ttcatccata gttgcctgac   5820

tccccgtcgt gtagataact acgatacggg agggcttacc atctggcccc agtgctgcaa   5880

tgataccgcg agacccacgc tcaccggctc cagatttatc agcaataaac cagccagccg   5940

gaagggccga gcgcagaagt ggtcctgcaa ctttatccgc ctccatccag tctattaatt   6000

gttgccggga agctagagta agtagttcgc cagttaatag tttgcgcaac gttgttgcca   6060

ttgctacagg catcgtggtg tcacgctcgt cgtttggtat ggcttcattc agctccggtt   6120
```

```
cccaacgatc aaggcgagtt acatgatccc ccatgttgtg caaaaaagcg gttagctcct   6180

tcggtcctcc gatcgttgtc agaagtaagt tggccgcagt gttatcactc atggttatgg   6240

cagcactgca taattctctt actgtcatgc catccgtaag atgcttttct gtgactggtg   6300

agtactcaac caagtcattc tgagaatagt gtatgcggcg accgagttgc tcttgcccgg   6360

cgtcaatacg ggataatacc gcgccacata gcagaacttt aaaagtgctc atcattggaa   6420

aacgttcttc ggggcgaaaa ctctcaagga tcttaccgct gttgagatcc agttcgatgt   6480

aacccactcg tgcacccaac tgatcttcag catcttttac tttcaccagc gtttctgggt   6540

gagcaaaaac aggaaggcaa aatgccgcaa aaaagggaat aagggcgaca cggaaatgtt   6600

gaatactcat actcttcctt tttcaatatt attgaagcat ttatcagggt tattgtctca   6660

tgagcggata catatttgaa tgtatttaga aaaataaaca aataggggtt ccgcgcacat   6720

ttccccgaaa agtgccacct gacgtc                                         6746
```

<210> SEQ ID NO 49
<211> LENGTH: 243
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gln Val Gln Leu Gln Gln Pro Gly Ala Ala Leu Val Arg Pro Gly Ala
1               5                   10                  15

Ser Met Arg Leu Ser Cys Lys Ala Ser Gly Tyr Ser Phe Thr Thr Tyr
            20                  25                  30

Trp Met Asn Trp Val Lys Gln Arg Pro Gly Gln Gly Leu Glu Leu Ile
        35                  40                  45

Gly Met Ile His Pro Ser Asp Ser Glu Val Arg Leu Asn Gln Lys Phe
    50                  55                  60

Lys Asp Lys Ala Thr Leu Thr Val Asp Thr Ser Ser Ser Thr Ala Tyr
65                  70                  75                  80

Met Gln Leu Asn Ser Pro Thr Ser Glu Asp Ser Ala Val Tyr Tyr Cys
                85                  90                  95

Ala Arg Phe Gly Leu Asp Tyr Trp Gly Gln Gly Thr Thr Leu Thr Val
            100                 105                 110

Ser Ser Gly Ser Thr Ser Gly Gly Gly Ser Gly Gly Gly Ser Gly Gly
        115                 120                 125

Gly Gly Ser Ser Asp Ile Val Ile Thr Gln Ser Pro Ser Ser Leu Ser
    130                 135                 140

Ala Ser Leu Gly Asp Thr Ile Leu Ile Thr Cys His Ala Ser Gln Asn
145                 150                 155                 160

Ile Asn Val Trp Leu Ser Trp Phe Gln Gln Lys Pro Gly Asn Ala Pro
                165                 170                 175

Lys Leu Leu Ile Tyr Lys Ala Ser Asn Leu His Thr Gly Val Pro Ser
            180                 185                 190

Arg Phe Ser Gly Ser Gly Ser Gly Thr Gly Phe Thr Leu Thr Ile Ser
        195                 200                 205

Ser Leu Gln Pro Glu Asp Ile Ala Thr Tyr Tyr Cys Gln Gln Gly Gln
    210                 215                 220

Ser Tyr Pro Trp Thr Phe Gly Gly Gly Thr Lys Leu Glu Ile Lys Arg
225                 230                 235                 240
```

Ala Ala Ser

<210> SEQ ID NO 50
<211> LENGTH: 571
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Gln Val Gln Leu Gln Gln Pro Gly Ala Ala Leu Val Arg Pro Gly Ala
1               5                   10                  15

Ser Met Arg Leu Ser Cys Lys Ala Ser Gly Tyr Ser Phe Thr Thr Tyr
            20                  25                  30

Trp Met Asn Trp Val Lys Gln Arg Pro Gly Gln Gly Leu Glu Leu Ile
        35                  40                  45

Gly Met Ile His Pro Ser Asp Ser Glu Val Arg Leu Asn Gln Lys Phe
    50                  55                  60

Lys Asp Lys Ala Thr Leu Thr Val Asp Thr Ser Ser Ser Thr Ala Tyr
65                  70                  75                  80

Met Gln Leu Asn Ser Pro Thr Ser Glu Asp Ser Ala Val Tyr Tyr Cys
                85                  90                  95

Ala Arg Phe Gly Leu Asp Tyr Trp Gly Gln Gly Thr Thr Leu Thr Val
            100                 105                 110

Ser Ser Gly Ser Thr Ser Gly Gly Gly Ser Gly Gly Gly Ser Gly Gly
        115                 120                 125

Gly Gly Ser Ser Asp Ile Val Ile Thr Gln Ser Pro Ser Ser Leu Ser
    130                 135                 140

Ala Ser Leu Gly Asp Thr Ile Leu Ile Thr Cys His Ala Ser Gln Asn
145                 150                 155                 160

Ile Asn Val Trp Leu Ser Trp Phe Gln Gln Lys Pro Gly Asn Ala Pro
                165                 170                 175

Lys Leu Leu Ile Tyr Lys Ala Ser Asn Leu His Thr Gly Val Pro Ser
            180                 185                 190

Arg Phe Ser Gly Ser Gly Ser Gly Thr Gly Phe Thr Leu Thr Ile Ser
        195                 200                 205

Ser Leu Gln Pro Glu Asp Ile Ala Thr Tyr Tyr Cys Gln Gln Gly Gln
    210                 215                 220

Ser Tyr Pro Trp Thr Phe Gly Gly Gly Thr Lys Leu Glu Ile Lys Arg
225                 230                 235                 240

Ala Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350
```

```
Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570


<210> SEQ ID NO 51
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Gln Gln Pro Gly Ala Ala Leu Val Arg Pro Gly Ala
1               5                   10                  15

Ser Met Arg Leu Ser Cys Lys Ala Ser Gly Tyr Ser Phe Thr Thr Tyr
            20                  25                  30

Trp Met Asn Trp Val Lys Gln Arg Pro Gly Gln Gly Leu Glu Leu Ile
        35                  40                  45

Gly Met Ile His Pro Ser Asp Ser Glu Val Arg Leu Asn Gln Lys Phe
    50                  55                  60

Lys Asp Lys Ala Thr Leu Thr Val Asp Thr Ser Ser Ser Thr Ala Tyr
65                  70                  75                  80

Met Gln Leu Asn Ser Pro Thr Ser Glu Asp Ser Ala Val Tyr Tyr Cys
                85                  90                  95

Ala Arg Phe Gly Leu Asp Tyr Trp Gly Gln Gly Thr Thr Leu Thr Val
            100                 105                 110

Ser Ser Gly Ser Thr Ser Gly Gly Gly Ser Gly Gly Gly Ser Gly Gly
        115                 120                 125

Gly Gly Ser Ser Asp Ile Val Ile Thr Gln Ser Pro Ser Ser Leu Ser
    130                 135                 140
```

```
Ala Ser Leu Gly Asp Thr Ile Leu Ile Thr Cys His Ala Ser Gln Asn
145                 150                 155                 160

Ile Asn Val Trp Leu Ser Trp Phe Gln Gln Lys Pro Gly Asn Ala Pro
                165                 170                 175

Lys Leu Leu Ile Tyr Lys Ala Ser Asn Leu His Thr Gly Val Pro Ser
            180                 185                 190

Arg Phe Ser Gly Ser Gly Ser Gly Thr Gly Phe Thr Leu Thr Ile Ser
        195                 200                 205

Ser Leu Gln Pro Glu Asp Ile Ala Thr Tyr Tyr Cys Gln Gln Gly Gln
    210                 215                 220

Ser Tyr Pro Trp Thr Phe Gly Gly Gly Thr Lys Leu Glu Ile Lys Arg
225                 230                 235                 240

Ala Ala Ser Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345
```

<210> SEQ ID NO 52
<211> LENGTH: 805
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gaattcacaa tgggatggtc ttgtatcatc cttttcttgg ttgcaacagc tactggtgtt      60

cattctgaag tgcaacttgt ggagtctggt ggtggtcttg ttcaaccagg aaactcactt     120

actttgtctt gcgtggcttc tggtttcact ttctcaaatt atggtatgca ttggataaga     180

caagctccaa agaagggtct tgagtggata gctatgattt attacgactc ttctaagatg     240

aactatgctg atacagtgaa gggtagattt actatatcta gagataactc taagaacaca     300

ctttacttgg agatgaactc tttgagatca gaggacactg caatgtacta ctgcgcagtg     360

ccaacttctc actacgttgt ggacgtgtgg ggacaaggag tttctgttac tgtttcttca     420

ggttcaactt caggaggagg atcaggtggt ggttcaggag gtggaggatc ttctgacatc     480

caaatgactc aatctccagc ttcactttct gcatctcttg aggagatagt tacaatcact     540

tgtcaagcat ctcaagacat tggaaattgg ttggcttggt accaacaaaa acctggtaag     600

tcaccacaac ttcttatcta tggagctact tctcttgcag acggagtgcc atctagattc     660

tcaggttcaa gatcaggaac tcaattctca cttaagatct ctagagtgca agtggaggac     720

attggtatat actattgtct tcaagcatac aacacaccat ggacttttgg aggaggaact     780

aagttggaac ttaagagggc tagct                                           805
```

<210> SEQ ID NO 53
<211> LENGTH: 1797
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
gaattcacaa tgggatggtc ttgtatcatc cttttcttgg ttgcaacagc tactggtgtt     60
cattctgaag tgcaacttgt ggagtctggt ggtggtcttg ttcaaccagg aaactcactt    120
actttgtctt gcgtggcttc tggtttcact ttctcaaatt atggtatgca ttggataaga    180
caagctccaa agaagggtct tgagtggata gctatgattt attacgactc ttctaagatg    240
aactatgctg atacagtgaa gggtagattt actatatcta gagataactc taagaacaca    300
ctttacttgg agatgaactc tttgagatca gaggacactg caatgtacta ctgcgcagtg    360
ccaacttctc actacgttgt ggacgtgtgg ggacaaggag tttctgttac tgtttcttca    420
ggttcaactt caggaggagg atcaggtggt ggttcaggag gtggaggatc ttctgacatc    480
caaatgactc aatctccagc ttcactttct gcatctcttg aggagatagt tacaatcact    540
tgtcaagcat ctcaagacat tggaaattgg ttggcttggt accaacaaaa acctggtaag    600
tcaccacaac ttcttatcta tggagctact tctcttgcag acggagtgcc atctagattc    660
tcaggttcaa gatcaggaac tcaattctca cttaagatct ctagagtgca agtggaggac    720
attggtatat actattgtct tcaagcatac aacacaccat ggacttttgg aggaggaact    780
aagttggaac ttaagagggc tagcaccaag ggaccttctg tttttccact tgctccttct    840
tctaagtcta cttctggtgg aactgctgct ttgggttgtt tggtgaaaga ttactttcct    900
gagccagtga ccgtttcttg gaactcaggt gctcttacat ctggtgttca tactttccca    960
gctgttcttc aatcttcagg actttactca ctttcttctg ttgttaccgt tccttcttca   1020
agcttgggca ctcagaccta catctgcaat gtgaatcaca aacccagcaa caccaaggtt   1080
gacaagaaag ttgagcccaa gtcttgtgac aagactcata cgtgtccacc gtgcccagca   1140
cctgaacttc ttggaggacc gtcagtcttc ttgtttcctc caaagcctaa ggataccttg   1200
atgatctcca ggactcctga agtcacatgt gtagttgtgg atgtgagcca tgaagatcct   1260
gaggtgaagt tcaactggta tgtggatggt gtggaagtgc acaatgccaa gacaaagccg   1320
agagaggaac agtacaacag cacgtacagg gttgtctcag ttctcactgt tctccatcaa   1380
gattggttga atggcaaaga gtacaagtgc aaggtctcca acaaagccct cccagccccc   1440
attgagaaga ccatttccaa agcgaaaggg caaccccgtg aaccacaagt gtacacactt   1500
cctccatctc gcgatgaact gaccaagaac caggtcagct tgacttgcct ggtgaaaggc   1560
ttctatccct ctgacatagc tgtagagtgg gagagcaatg ggcaaccgga gaacaactac   1620
aagactacac ctcccgttct cgattctgac ggctccttct tcctctacag caagctcaca   1680
gtggacaaga gcaggtggca acaagggaat gtcttctcat gctccgtgat gcatgaggct   1740
cttcacaatc actacacaca gaagagtctc tccttgtctc cgggtaaatg aggatcc      1797
```

<210> SEQ ID NO 54
<211> LENGTH: 8218
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
tctagagtcg acctgcagaa gcttactaga gcgtggtgcg cacgatagcg catagtgttt     60
ttctctccac ttgaatcgaa gagatagact tacggtgtaa atccgtaggg gtggcgtaaa    120
ccaaattacg caatgttttg ggttccattt aaatcgaaac cccttatttc ctggatcacc    180
tgttaacgca cgtttgacgt gtattacagt gggaataagt aaaagtgaga ggttcgaatc    240
ctccctaacc ccgggtaggg gcccagcggc cgctctagct agagtcaagc agatcgttca    300
aacatttggc aataaagttt cttaagattg aatcctgttg ccggtcttgc gatgattatc    360
atataatttc tgttgaatta cgttaagcat gtaataatta acatgtaatg catgacgtta    420
tttatgagat gggtttttat gattagagtc ccgcaattat acatttaata cgcgatagaa    480
aacaaaatat agcgcgcaaa ctaggataaa ttatcgcgcg cggtgtcatc tatgttacta    540
gatcgaccag cttagatcag attgtcgttt cccgccttca gtttaaacta tcagtgtttg    600
acaggatata ttggcgggta aacctaagag aaaagagcgt ttattagaat aatcggatat    660
ttaaaagggc gtgaaaaggt ttatccgttc gtccatttgt atgtgccaac cacagggttc    720
cccagatcag taaagcgctg gctgctgaac ccccagccgg aactgacccc acaaggccct    780
agcgtttgca atgcaccagg tcatcattga cccaggcgtg ttccaccagg ccgctgcctc    840
gcaactcttc gcaggcttcg ccgacctgct cgcgccactt cttcacgcgg gtggaatccg    900
atccgcacat gaggcggaag gtttccagct tgagcgggta cggctcccgg tgcgagctga    960
aatagtcgaa catccgtcgg gccgtcggcg acagcttgcg gtacttctcc catatgaatt   1020
tcgtgtagtg gtcgccagca aacagcacga cgatttcctc gtcgatcagg acctggcaac   1080
gggacgtttt cttgccacgg tccaggacgc ggaagcggtg cagcagcgac accgattcca   1140
ggtgcccaac gcggtcggac gtgaagccca tcgccgtcgc ctgtaggcgc gacaggcatt   1200
cctcggcctt cgtgtaatac cggccattga tcgaccagcc caggtcctgg caaagctcgt   1260
agaacgtgaa ggtgatcggc tcgccgatag gggtgcgctt cgcgtactcc aacacctgct   1320
gccacaccag ttcgtcatcg tcggcccgca gctcgacgcc ggtgtaggtg atcttcacgt   1380
ccttgttgac gtggaaaatg accttgtttt gcagcgcctc gcgcgggatt ttcttgttgc   1440
gcgtggtgaa cagggcagag cgggccgtgt cgtttggcat cgctcgcatc gtgtccggcc   1500
acggcgcaat atcgaacaag gaaagctgca tttccttgat ctgctgcttc gtgtgtttca   1560
gcaacgcggc ctgcttggcc tcgctgacct gttttgccag gtcctcgccg gcggtttttc   1620
gcttcttggt cgtcatagtt cctcgcgtgt cgatggtcat cgacttcgcc aaacctgccg   1680
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
```

-continued ccctgacgag catcacaaaa atcgacgctc aagtcagagg tggcgaaacc cgacaggact 2340
ataaagatac caggcgtttc cccctggaag ctccctcgtg cgctctcctg ttccgaccct 2400
gccgcttacc ggatacctgt ccgcctttct cccttcggga agcgtggcgc tttctcatag 2460
ctcacgctgt aggtatctca gttcggtgta ggtcgttcgc tccaagctgg gctgtgtgca 2520
cgaacccccc gttcagcccg accgctgcgc cttatccggt aactatcgtc ttgagtccaa 2580
cccggtaaga cacgacttat cgccactggc agcagccact ggtaacagga ttagcagagc 2640
gaggtatgta ggcggtgcta cagagttctt gaagtggtgg cctaactacg gctacactag 2700
aagaacagta tttggtatct gcgctctgct gaagccagtt accttcggaa aaagagttgg 2760
tagctcttga tccggcaaac aaaccaccgc tggtagcggt ggtttttttg tttgcaagca 2820
gcagattacg cgcagaaaaa aaggatctca agaagatcct ttgatctttt ctacggggtc 2880
tgacgctcag tggaacgaaa actcacgtta agggattttg gtcatgagat tatcaaaaag 2940
gatcttcacc tagatccttt taaattaaaa atgaagtttt aaatcaatct aaagtatata 3000
tgagtaaact tggtctgaca gttaccaatg cttaatcagt gaggcaccta tctcagcgat 3060
ctgtctattt cgttcatcca tagttgcctg actccccgtc gtgtagataa ctacgatacg 3120
ggagggctta ccatctggcc ccagtgctgc aatgataccg cgagacccac gctcaccggc 3180
tccagattta tcagcaataa accagccagc cggaagggcc gagcgcagaa gtggtcctgc 3240
aactttatcc gcctccatcc agtctattaa ttgttgccgg gaagctagag taagtagttc 3300
gccagttaat agtttgcgca acgttgttgc cattgctaca ggcatcgtgg tgtcacgctc 3360
gtcgtttggt atggcttcat tcagctccgg ttcccaacga tcaaggcgag ttacatgatc 3420
ccccatgttg tgcaaaaaag cggttagctc cttcggtcct ccgatcgttg tcagaagtaa 3480
gttggccgca gtgttatcac tcatggttat ggcagcactg cataattctc ttactgtcat 3540
gccatccgta agatgctttt ctgtgactgg tgagtactca accaagtcat tctgagaata 3600
gtgtatgcgg cgaccgagtt gctcttgccc ggcgtcaata cgggataata ccgcgccaca 3660
tagcagaact ttaaaagtgc tcatcattgg aaaacgttct tcggggcgaa aactctcaag 3720
gatcttaccg ctgttgagat ccagttcgat gtaacccact cgtgcaccca actgatcttc 3780
agcatctttt actttcacca gcgtttctgg gtgagcaaaa acaggaaggc aaaatgccgc 3840
aaaaaaggga ataagggcga cacggaaatg ttgaatactc atactcttcc tttttcaata 3900
ttattgaagc atttatcagg gttattgtct catgagcgga tacatatttg aatgtattta 3960
gaaaaataaa caaatagggg ttccgcgcac gaattggcca gcgctgccat ttttggggtg 4020
aggccgttcg cggccgaggg gcgcagcccc tgggggggatg ggaggcccgc gttagcgggc 4080
cgggagggtt cgagaagggg gggcaccccc cttcggcgtg cgcggtcacg cgcacagggc 4140
gcagccctgg ttaaaaacaa ggtttataaa tattggttta aaagcaggtt aaaagacagg 4200
ttagcggtgg ccgaaaaacg ggcggaaacc cttgcaaatg ctggattttc tgcctgtgga 4260
cagcccctca aatgtcaata ggtgcgcccc tcatctgtca gcactctgcc cctcaagtgt 4320
caaggatcgc gcccctcatc tgtcagtagt cgcgcccctc aagtgtcaat accgcagggc 4380
acttatcccc aggcttgtcc acatcatctg tgggaaactc gcgtaaaatc aggcgttttc 4440
gccgatttgc gaggctggcc agctccacgt cgccggccga aatcgagcct gcccctcatc 4500
tgtcaacgcc gcgccgggtg agtcggcccc tcaagtgtca acgtccgccc ctcatctgtc 4560
agtgagggcc aagttttccg cgaggtatcc acaacgccgg cggccgcggt gtctcgcaca 4620
cggcttcgac ggcgtttctg gcgcgtttgc agggccatag acggccgcca gcccagcggc 4680

```
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact ttttgttctt attgttgcag gtaccatggc   6420
agaattcaca atgggatggt cttgtatcat ccttttcttg gttgcaacag ctactggtgt   6480
tcattctgaa gtgcaacttg tggagtctgg tggtggtctt gttcaaccag gaaactcact   6540
tactttgtct tgcgtggctt ctggtttcac tttctcaaat tatggtatgc attggataag   6600
acaagctcca aagaagggtc ttgagtggat agctatgatt tattacgact cttctaagat   6660
gaactatgct gatacagtga agggtagatt tactatatct agagataact ctaagaacac   6720
actttacttg gagatgaact ctttgagatc agaggacact gcaatgtact actgcgcagt   6780
gccaacttct cactacgttg tggacgtgtg gggacaagga gtttctgtta ctgtttcttc   6840
aggttcaact tcaggaggag gatcaggtgg tggttcagga ggtggaggat cttctgacat   6900
ccaaatgact caatctccag cttcactttc tgcatctctt gaggagatag ttacaatcac   6960
ttgtcaagca tctcaagaca ttggaaattg gttggcttgg taccaacaaa aacctggtaa   7020
```

gtcaccacaa cttcttatct atggagctac ttctcttgca gacggagtgc catctagatt 7080
ctcaggttca agatcaggaa ctcaattctc acttaagatc tctagagtgc aagtggagga 7140
cattggtata tactattgtc ttcaagcata caacacacca tggacttttg gaggaggaac 7200
taagttggaa cttaagaggg ctagcaccaa gggaccttct gtttttccac ttgctccttc 7260
ttctaagtct acttctggtg gaactgctgc tttgggttgt ttggtgaaag attactttcc 7320
tgagccagtg accgtttctt ggaactcagg tgctcttaca tctggtgttc atactttccc 7380
agctgttctt caatcttcag gactttactc actttcttct gttgttaccg ttccttcttc 7440
aagcttgggc actcagacct acatctgcaa tgtgaatcac aaacccagca acaccaaggt 7500
tgacaagaaa gttgagccca agtcttgtga caagactcat acgtgtccac cgtgcccagc 7560
acctgaactt cttggaggac cgtcagtctt cttgtttcct ccaaagccta aggatacctt 7620
gatgatctcc aggactcctg aagtcacatg tgtagttgtg gatgtgagcc atgaagatcc 7680
tgaggtgaag ttcaactggt atgtggatgg tgtggaagtg cacaatgcca agacaaagcc 7740
gagagaggaa cagtacaaca gcacgtacag ggttgtctca gttctcactg ttctccatca 7800
agattggttg aatggcaaag agtacaagtg caaggtctcc aacaaagccc tcccagcccc 7860
cattgagaag accatttcca aagcgaaagg gcaaccccgt gaaccacaag tgtacacact 7920
tcctccatct cgcgatgaac tgaccaagaa ccaggtcagc ttgacttgcc tggtgaaagg 7980
cttctatccc tctgacatag ctgtagagtg ggagagcaat gggcaaccgg agaacaacta 8040
caagactaca cctcccgttc tcgattctga cggctccttc ttcctctaca gcaagctcac 8100
agtggacaag agcaggtggc aacaagggaa tgtcttctca tgctccgtga tgcatgaggc 8160
tcttcacaat cactacacac agaagagtct ctccttgtct ccgggtaaat gaggatcc 8218

<210> SEQ ID NO 55
<211> LENGTH: 8270
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
agcttgaaga ctaggcgtgg tgcgcacgat agcgcatagt gtttttctct ccacttgaat 60
cgaagagata gacttacggt gtaaatccgt aggggtggcg taaaccaaat tacgcaatgt 120
tttgggttcc atttaaatcg aaacccctta tttcctggat cacctgttaa cgcacgtttg 180
acgtgtatta cagtgggaat aagtaaaagt gagaggttcg aatcctccct aaccccgggt 240
aggggcccag cggccgctct agctagagtc aagcagatcg ttcaaacatt tggcaataaa 300
gtttcttaag attgaatcct gttgccggtc ttgcgatgat tatcatataa tttctgttga 360
attacgttaa gcatgtaata attaacatgt aatgcatgac gttatttatg agatgggttt 420
ttatgattag agtcccgcaa ttatacattt aatacgcgat agaaaacaaa atatagcgcg 480
caaactagga taaattatcg cgcgcggtgt catctatgtt actagatcga ccagtcctat 540
ggtagtcttc agcttagatc agattgtcgt ttcccgcctt cagtttaaac tatcagtgtt 600
tgacaggata tattggcggg taaacctaag agaaaagagc gtttattaga ataatcggat 660
atttaaaagg gcgtgaaaag gtttatccgt tcgtccattt gtatgtgcat gccaaccaca 720
gggttcccca gatcagtaaa gcgctggctg ctgaaccccc agccggaact gaccccacaa 780
ggccctagcg tttgcaatgc accaggtcat cattgaccca ggcgtgttcc accaggccgc 840

```
tgcctcgcaa ctcttcgcag gcttcgccga cctgctcgcg ccacttcttc acgcgggtgg    900
aatccgatcc gcacatgagg cggaaggttt ccagcttgag cgggtacggc tcccggtgcg    960
agctgaaata gtcgaacatc cgtcgggccg tcggcgacag cttgcggtac ttctcccata   1020
tgaatttcgt gtagtggtcg ccagcaaaca gcacgacgat ttcctcgtcg atcaggacct   1080
ggcaacggga cgttttcttg ccacggtcca ggacgcggaa gcggtgcagc agcgacaccg   1140
attccaggtg cccaacgcgg tcggacgtga agcccatcgc cgtcgcctgt aggcgcgaca   1200
ggcattcctc ggccttcgtg taataccggc cattgatcga ccagcccagg tcctggcaaa   1260
gctcgtagaa cgtgaaggtg atcggctcgc cgataggggt gcgcttcgcg tactccaaca   1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggatttttct  1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac ccgcgtcga tcagttcttg cctgtatgcc ttccggtcaa    1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
```

```
tcctgcaact ttatccgcct ccatccagtc tattaattgt tgccgggaag ctagagtaag   3300

tagttcgcca gttaatagtt tgcgcaacgt tgttgccatt gctacaggca tcgtggtgtc   3360

acgctcgtcg tttggtatgg cttcattcag ctccggttcc caacgatcaa ggcgagttac   3420

atgatccccc atgttgtgca aaaaagcggt tagctccttc ggtcctccga tcgttgtcag   3480

aagtaagttg gccgcagtgt tatcactcat ggttatggca gcactgcata attctcttac   3540

tgtcatgcca tccgtaagat gcttttctgt gactggtgag tactcaacca agtcattctg   3600

agaatagtgt atgcggcgac cgagttgctc ttgcccggcg tcaatacggg ataataccgc   3660

gccacatagc agaactttaa aagtgctcat cattggaaaa cgttcttcgg ggcgaaaact   3720

ctcaaggatc ttaccgctgt tgagatccag ttcgatgtaa cccactcgtg cacccaactg   3780

atcttcagca tcttttactt tcaccagcgt ttctgggtga gcaaaaacag gaaggcaaaa   3840

tgccgcaaaa aagggaataa gggcgacacg gaaatgttga atactcatac tcttcctttt   3900

tcaatattat tgaagcattt atcagggtta ttgtctcatg agcggataca tatttgaatg   3960

tatttagaaa aataaacaaa taggggttcc gcgcacgaat tggccagcgc tgccattttt   4020

ggggtgaggc cgttcgcggc cgaggggcgc agcccctggg gggatgggag gcccgcgtta   4080

gcgggccggg agggttcgag aagggggggc acccccctc ggcgtgcgcg gtcacgcgca   4140

cagggcgcag ccctggttaa aaacaaggtt tataaatatt ggtttaaaag caggttaaaa   4200

gacaggttag cggtggccga aaaacgggcg gaaacccttg caaatgctgg attttctgcc   4260

tgtggacagc ccctcaaatg tcaataggtg cgcccctcat ctgtcagcac tctgcccctc   4320

aagtgtcaag gatcgcgccc ctcatctgtc agtagtcgcg cccctcaagt gtcaataccg   4380

cagggcactt atccccaggc ttgtccacat catctgtggg aaactcgcgt aaaatcaggc   4440

gttttcgccg atttgcgagg ctggccagct ccacgtcgcc ggccgaaatc gagcctgccc   4500

ctcatctgtc aacgccgcgc cgggtgagtc ggcccctcaa gtgtcaacgt ccgcccctca   4560

tctgtcagtg agggccaagt tttccgcgag gtatccacaa cgccggcggc cgcggtgtct   4620

cgcacacggc ttcgacggcg tttctggcgc gtttgcaggg ccatagacgg ccgccagccc   4680

agcggcgagg gcaaccagcc cggtgagcgt cgcaaaggag atcctgatct gactgatggg   4740

ctgcctgtat cgagtggtga ttttgtgccg agctgccggt cggggagctg ttggctggct   4800

ggtggcagga tatattgtgg tgtaaacaaa ttgacgctta gacaacttaa taacacattg   4860

cggacgtttt taatgtactg gggtggatgc aggtcgatct agtaacatag atgacaccgc   4920

gcgcgataat ttatcctagt ttgcgcgcta tattttgttt tctatcgcgt attaaatgta   4980

taattgcggg actctaatca taaaaaccca tctcataaat aacgtcatgc attacatgtt   5040

aattattaca tgcttaacgt aattcaacag aaattatatg ataatcatcg caagaccggc   5100

aacaggattc aatcttaaga aactttattg ccaaatgttt gaacgatctg cttgactcta   5160

gatccagagt cccgctcaga agaactcgtc aagaaggcga tagaaggcga tgcgctgcga   5220

atcgggagcg gcgataccgt aaagcacgag gaagcggtca gcccattcgc cgccaagctc   5280

ttcagcaata tcacgggtag ccaacgctat gtcctgatag cggtccgcca cacccagccg   5340

gccacagtcg atgaatccag aaaagcggcc attttccacc atgatattcg gcaagcaggc   5400

atcgccatga gtcacgacga gatcctcgcc gtcgggcata cgcgccttga gcctggcgaa   5460

cagttcggct ggcgcgagcc cctgatgctc ttcgtccaga tcatcctgat cgacaagacc   5520

ggcttccatc cgagtacgtg ctcgctcgat gcgatgtttc gcttggtggt cgaatgggca   5580
```

```
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cacaatggga tggtcttgta tcatcctttt cttggttgca acagctactg   6480
gtgttcattc tgaagtgcaa cttgtggagt ctggtggtgg tcttgttcaa ccaggaaact   6540
cacttacttt gtcttgcgtg gcttctggtt tcactttctc aaattatggt atgcattgga   6600
taagacaagc tccaaagaag ggtcttgagt ggatagctat gatttattac gactcttcta   6660
agatgaacta tgctgataca gtgaagggta gatttactat atctagagat aactctaaga   6720
acacacttta cttggagatg aactctttga gatcagagga cactgcaatg tactactgcg   6780
cagtgccaac ttctcactac gttgtggacg tgtggggaca aggagtttct gttactgttt   6840
cttcaggttc aacttcagga ggaggatcag gtggtggttc aggaggtgga ggatcttctg   6900
acatccaaat gactcaatct ccagcttcac tttctgcatc tcttgaggag atagttacaa   6960
tcacttgtca agcatctcaa gacattggaa attggttggc ttggtaccaa caaaaacctg   7020
gtaagtcacc acaacttctt atctatggag ctacttctct tgcagacgga gtgccatcta   7080
gattctcagg ttcaagatca ggaactcaat tctcacttaa gatctctaga gtgcaagtgg   7140
aggacattgg tatatactat tgtcttcaag catacaacac accatggact tttggaggag   7200
gaactaagtt ggaacttaag agggctagca ccaagggacc ttctgttttt ccacttgctc   7260
cttcttctaa gtctacttct ggtggaactg ctgctttggg ttgtttggtg aaagattact   7320
ttcctgagcc agtgaccgtt tcttggaact caggtgctct tacatctggt gttcatactt   7380
tcccagctgt tcttcaatct tcaggacttt actcactttc ttctgttgtt accgttcctt   7440
cttcaagctt gggcactcag acctacatct gcaatgtgaa tcacaaaccc agcaacacca   7500
aggttgacaa gaaagttgag cccaagtctt gtgacaagac tcatacgtgt ccaccgtgcc   7560
cagcacctga acttcttgga ggaccgtcag tcttcttgtt tcctccaaag cctaaggata   7620
ccttgatgat ctccaggact cctgaagtca catgtgtagt tgtggatgtg agccatgaag   7680
atcctgaggt gaagttcaac tggtatgtgg atggtgtgga agtgcacaat gccaagacaa   7740
agccgagaga ggaacagtac aacagcacgt acagggttgt ctcagttctc actgttctcc   7800
atcaagattg gttgaatggc aaagagtaca agtgcaaggt ctccaacaaa gccctcccag   7860
cccccattga gaagaccatt tccaaagcga aagggcaacc ccgtgaacca caagtgtaca   7920
cacttcctcc atctcgcgat gaactgacca agaaccaggt cagcttgact tgcctggtga   7980
```

```
aaggcttcta tccctctgac atagctgtag agtgggagag caatgggcaa ccggagaaca   8040

actacaagac tacacctccc gttctcgatt ctgacggctc cttcttcctc tacagcaagc   8100

tcacagtgga caagagcagg tggcaacaag ggaatgtctt ctcatgctcc gtgatgcatg   8160

aggctcttca caatcactac acacagaaga gtctctcctt gtctccgggt aaatgaggat   8220

ccggatcctc tagagtcgac ctgcagaagc tggcagctag gatgggtctc              8270
```

```
<210> SEQ ID NO 56
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

gaattcacaa tgggatggtc ttgtatcatc cttttcttgg ttgcaacagc tactggtgtt     60

cattctgaag tgcaacttgt ggagtctggt ggtggtcttg ttcaaccagg aaactcactt    120

actttgtctt gcgtggcttc tggtttcact ttctcaaatt atggtatgca ttggataaga    180

caagctccaa agaagggtct tgagtggata gctatgattt attacgactc ttctaagatg    240

aactatgctg atacagtgaa gggtagattt actatatcta gagataactc taagaacaca    300

ctttacttgg agatgaactc tttgagatca gaggacactg caatgtacta ctgcgcagtg    360

ccaacttctc actacgttgt ggacgtgtgg ggacaaggag tttctgttac tgtttcttca    420

ggttcaactt caggaggagg atcaggtggt ggttcaggag gtggaggatc ttctgacatc    480

caaatgactc aatctccagc ttcactttct gcatctcttg aggagatagt tacaatcact    540

tgtcaagcat ctcaagacat tggaaattgg ttggcttggt accaacaaaa acctggtaag    600

tcaccacaac ttcttatcta tggagctact tctcttgcag acggagtgcc atctagattc    660

tcaggttcaa gatcaggaac tcaattctca cttaagatct ctagagtgca agtggaggac    720

attggtatat actattgtct tcaagcatac aacacaccat ggacttttgg aggaggaact    780

aagttggaac ttaagagggc tagcagaact gttgctgcac catctgtttt catcttccct    840

ccatctgatg agcagttgaa atctggaact gcttctgttg tgtgccttct taataacttc    900

tatcctagag aggctaaagt tcagtggaag gtggataacg cacttcaatc tggtaactct    960

caagagtctg ttacagagca agattctaag gactcaactt actctctttc atctacactt   1020

actttgtcaa aagcagatta cgagaaacac aaagtttacg catgcgaagt tactcatcaa   1080

ggactttctt caccagttac aaagtctttc aatagaggag agtgttaagg atcc         1134
```

```
<210> SEQ ID NO 57
<211> LENGTH: 7555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

tctagagtcg acctgcagaa gcttactaga gcgtggtgcg cacgatagcg catagtgttt     60

ttctctccac ttgaatcgaa gagatagact tacggtgtaa atccgtaggg gtggcgtaaa    120

ccaaattacg caatgttttg ggttccattt aaatcgaaac cccttatttc ctggatcacc    180

tgttaacgca cgtttgacgt gtattacagt gggaataagt aaaagtgaga ggttcgaatc    240
```

```
ctccctaacc ccgggtaggg gcccagcggc cgctctagct agagtcaagc agatcgttca    300
aacatttggc aataaagttt cttaagattg aatcctgttg ccggtcttgc gatgattatc    360
atataatttc tgttgaatta cgttaagcat gtaataatta acatgtaatg catgacgtta    420
tttatgagat gggtttttat gattagagtc ccgcaattat acatttaata cgcgatagaa    480
aacaaaatat agcgcgcaaa ctaggataaa ttatcgcgcg cggtgtcatc tatgttacta    540
gatcgaccag cttagatcag attgtcgttt cccgccttca gtttaaacta tcagtgtttg    600
acaggatata ttggcgggta aacctaagag aaaagagcgt ttattagaat aatcggatat    660
ttaaaagggc gtgaaaaggt ttatccgttc gtccatttgt atgtgccaac cacagggttc    720
cccagatcag taaagcgctg gctgctgaac ccccagccgg aactgacccc acaaggccct    780
agcgtttgca atgcaccagg tcatcattga cccaggcgtg ttccaccagg ccgctgcctc    840
gcaactcttc gcaggcttcg ccgacctgct cgcgccactt cttcacgcgg gtggaatccg    900
atccgcacat gaggcggaag gtttccagct tgagcgggta cggctcccgg tgcgagctga    960
aatagtcgaa catccgtcgg gccgtcggcg acagcttgcg gtacttctcc catatgaatt   1020
tcgtgtagtg gtcgccagca aacagcacga cgatttcctc gtcgatcagg acctggcaac   1080
gggacgtttt cttgccacgg tccaggacgc ggaagcggtg cagcagcgac accgattcca   1140
ggtgcccaac gcggtcggac gtgaagccca tcgccgtcgc ctgtaggcgc gacaggcatt   1200
cctcggcctt cgtgtaatac cggccattga tcgaccagcc caggtcctgg caaagctcgt   1260
agaacgtgaa ggtgatcggc tcgccgatag gggtgcgctt cgcgtactcc aacacctgct   1320
gccacaccag ttcgtcatcg tcggcccgca gctcgacgcc ggtgtaggtg atcttcacgt   1380
ccttgttgac gtggaaaatg accttgtttt gcagcgcctc gcgcgggatt ttcttgttgc   1440
gcgtggtgaa cagggcagag cgggccgtgt cgtttggcat cgctcgcatc gtgtccggcc   1500
acggcgcaat atcgaacaag gaaagctgca tttccttgat ctgctgcttc gtgtgtttca   1560
gcaacgcggc ctgcttggcc tcgctgacct gttttgccag gtcctcgccg gcggtttttc   1620
gcttcttggt cgtcatagtt cctcgcgtgt cgatggtcat cgacttcgcc aaacctgccg   1680
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
```

```
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg    4020
aggccgttcg cggccgaggg gcgcagcccc tggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
```

```
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact ttttgttctt attgttgcag gtaccatggc   6420
agaattcaca atgggatggt cttgtatcat ccttttcttg gttgcaacag ctactggtgt   6480
tcattctgaa gtgcaacttg tggagtctgg tggtggtctt gttcaaccag gaaactcact   6540
tactttgtct tgcgtggctt ctggtttcac tttctcaaat tatggtatgc attggataag   6600
acaagctcca aagaagggtc ttgagtggat agctatgatt tattacgact cttctaagat   6660
gaactatgct gatacagtga agggtagatt tactatatct agagataact ctaagaacac   6720
actttacttg gagatgaact ctttgagatc agaggacact gcaatgtact actgcgcagt   6780
gccaacttct cactacgttg tggacgtgtg gggacaagga gtttctgtta ctgtttcttc   6840
aggttcaact tcaggaggag gatcaggtgg tggttcagga ggtggaggat cttctgacat   6900
ccaaatgact caatctccag cttcactttc tgcatctctt gaggagatag ttacaatcac   6960
ttgtcaagca tctcaagaca ttggaaattg gttggcttgg taccaacaaa aacctggtaa   7020
gtcaccacaa cttcttatct atggagctac ttctcttgca gacggagtgc catctagatt   7080
ctcaggttca agatcaggaa ctcaattctc acttaagatc tctagagtgc aagtggagga   7140
cattggtata tactattgtc ttcaagcata caacacacca tggacttttg gaggaggaac   7200
taagttggaa cttaagaggg ctagcagaac tgttgctgca ccatctgttt tcatcttccc   7260
tccatctgat gagcagttga aatctggaac tgcttctgtt gtgtgccttc ttaataactt   7320
ctatcctaga gaggctaaag ttcagtggaa ggtggataac gcacttcaat ctggtaactc   7380
```

tcaagagtct gttacagagc aagattctaa ggactcaact tactctcttt catctacact 7440
tactttgtca aaagcagatt acgagaaaca caaagtttac gcatgcgaag ttactcatca 7500
aggactttct tcaccagtta caaagtcttt caatagagga gagtgttaag gatcc 7555

<210> SEQ ID NO 58
<211> LENGTH: 7601
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
agcttgaaga ctaggcgtgg tgcgcacgat agcgcatagt gtttttctct ccacttgaat 60
cgaagagata gacttacggt gtaaatccgt aggggtggcg taaaccaaat tacgcaatgt 120
tttgggttcc atttaaatcg aaacccctta tttcctggat cacctgttaa cgcacgtttg 180
acgtgtatta cagtgggaat aagtaaaagt gagaggttcg aatcctccct aaccccgggt 240
aggggcccag cggccgctct agctagagtc aagcagatcg ttcaaacatt tggcaataaa 300
gtttcttaag attgaatcct gttgccggtc ttgcgatgat tatcatataa tttctgttga 360
attacgttaa gcatgtaata attaacatgt aatgcatgac gttatttatg agatgggttt 420
ttatgattag agtcccgcaa ttatacattt aatacgcgat agaaaacaaa atatagcgcg 480
caaactagga taaattatcg cgcgcggtgt catctatgtt actagatcga ccagtcctat 540
ggtagtcttc agcttagatc agattgtcgt ttcccgcctt cagtttaaac tatcagtgtt 600
tgacaggata tattggcggg taaacctaag agaaaagagc gtttattaga ataatcggat 660
atttaaaagg gcgtgaaaag gtttatccgt tcgtccattt gtatgtgcat gccaaccaca 720
gggttcccca gatcagtaaa gcgctggctg ctgaaccccc agccggaact gaccccacaa 780
ggccctagcg tttgcaatgc accaggtcat cattgaccca ggcgtgttcc accaggccgc 840
tgcctcgcaa ctcttcgcag gcttcgccga cctgctcgcg ccacttcttc acgcgggtgg 900
aatccgatcc gcacatgagg cggaaggttt ccagcttgag cgggtacggc tcccggtgcg 960
agctgaaata gtcgaacatc cgtcgggccg tcggcgacag cttgcggtac ttctcccata 1020
tgaatttcgt gtagtggtcg ccagcaaaca gcacgacgat ttcctcgtcg atcaggacct 1080
ggcaacggga cgttttcttg ccacggtcca ggacgcggaa gcggtgcagc agcgacaccg 1140
attccaggtg cccaacgcgg tcggacgtga agcccatcgc cgtcgcctgt aggcgcgaca 1200
ggcattcctc ggccttcgtg taataccggc cattgatcga ccagcccagg tcctggcaaa 1260
gctcgtagaa cgtgaaggtg atcggctcgc cgataggggt gcgcttcgcg tactccaaca 1320
cctgctgcca caccagttcg tcatcgtcgg cccgcagctc gacgccggtg taggtgatct 1380
tcacgtcctt gttgacgtgg aaaatgacct tgttttgcag cgcctcgcgc gggattttct 1440
tgttgcgcgt ggtgaacagg gcagagcggg ccgtgtcgtt tggcatcgct cgcatcgtgt 1500
ccggccacgg cgcaatatcg aacaaggaaa gctgcatttc cttgatctgc tgcttcgtgt 1560
gtttcagcaa cgcggcctgc ttggcctcgc tgacctgttt tgccaggtcc tcgccggcgg 1620
tttttcgctt cttggtcgtc atagttcctc gcgtgtcgat ggtcatcgac ttcgccaaac 1680
ctgccgcctc ctgttcgaga cgacgcgaac gctccacggc ggccgatggc gcgggcaggg 1740
cagggggagc cagttgcacg ctgtcgcgct cgatcttggc cgtagcttgc tggaccatcg 1800
agccgacgga ctggaaggtt tcgcggggcg cacgcatgac ggtgcggctt gcgatggttt 1860

```
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg gggatgggag gcccgcgtta   4080
gcgggccggg agggttcgag aagggggggc acccccccttc ggcgtgcgcg gtcacgcgca   4140
cagggcgcag ccctggttaa aaacaaggtt tataaatatt ggtttaaaag caggttaaaa   4200
```

```
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cacaatggga tggtcttgta tcatcctttt cttggttgca acagctactg   6480
gtgttcattc tgaagtgcaa cttgtggagt ctggtggtgg tcttgttcaa ccaggaaact   6540
cacttacttt gtcttgcgtg gcttctggtt tcactttctc aaattatggt atgcattgga   6600
```

```
taagacaagc tccaaagaag ggtcttgagt ggatagctat gatttattac gactcttcta   6660

agatgaacta tgctgataca gtgaagggta gatttactat atctagagat aactctaaga   6720

acacacttta cttggagatg aactctttga gatcagagga cactgcaatg tactactgcg   6780

cagtgccaac ttctcactac gttgtggacg tgtggggaca aggagtttct gttactgttt   6840

cttcaggttc aacttcagga ggaggatcag gtggtggttc aggaggtgga ggatcttctg   6900

acatccaaat gactcaatct ccagcttcac tttctgcatc tcttgaggag atagttacaa   6960

tcacttgtca agcatctcaa gacattggaa attggttggc ttggtaccaa caaaaacctg   7020

gtaagtcacc acaacttctt atctatggag ctacttctct tgcagacgga gtgccatcta   7080

gattctcagg ttcaagatca ggaactcaat tctcacttaa gatctctaga gtgcaagtgg   7140

aggacattgg tatatactat tgtcttcaag catacaacac accatggact tttggaggag   7200

gaactaagtt ggaacttaag agggctagca gaactgttgc tgcaccatct gttttcatct   7260

tccctccatc tgatgagcag ttgaaatctg gaactgcttc tgttgtgtgc cttcttaata   7320

acttctatcc tagagaggct aaagttcagt ggaaggtgga taacgcactt caatctggta   7380

actctcaaga gtctgttaca gagcaagatt ctaaggactc aacttactct ctttcatcta   7440

cacttacttt gtcaaaagca gattacgaga aacacaaagt ttacgcatgc gaagttactc   7500

atcaaggact ttcttcacca gttacaaagt ctttcaatag aggagagtgt taaggatcct   7560

ctagagtcga cctgcagaag ctggcagcta ggatgggtct c                       7601
```

```
<210> SEQ ID NO 59
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

tggatccgcc accatgggat ggagctgtat catcctcttc ttggtagcaa cagctacagg     60

taaggggctc acagtagcag gcttgaggtc tggacatata tatgggtgac aatgacatcc    120

actttgcctt tctctccaca ggtgtccact ccgaagtgca gcttgtggag agcggaggtg    180

gccttgtgca gccggggaac tcactcacac tctcgtgcgt cgcttcggga ttcacctttt    240

cgaattacgg gatgcactgg atcagacagg cacccaagaa agggctcgaa tggattgcga    300

tgatctacta cgatagctcg aagatgaact acgcagacac agtgaagggg cggtttacaa    360

tttcccgaga taactcaaag aatacgcttt atcttgagat gaactccctg agatccgagg    420

acactgcgat gtactattgc gcagtcccta cttcacatta tgtagtcgat gtgtggggcc    480

agggtgtgtc agtaactgtc agctccggga gcacgtcggg agggggttcg ggcggaggga    540

gcggtggagg aggatcgtcg gatattcaga tgacgcaatc acccgcctcg ttgtccgcga    600

gcctcgaaga gatcgtgaca atcacctgtc aggcctccca agatatcgga aattggctgg    660

cgtggtatca gcagaaacca gggaagtcac cgcagttgct gatctacgga gcgacctccc    720

tcgccgacgg ggtcccctcg cgcttctcgg gctcaaggtc cggcacgcag ttctcgctga    780

agattagcag ggtacaagtg gaggacattg gcatctacta ctgtttgcaa gcctataaca    840

ccccgtggac gtttggtggg ggtacgaaat tggagcttaa acgggctagc t             891

<210> SEQ ID NO 60
<211> LENGTH: 1885
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
tggatccgcc accatgggat ggagctgtat catcctcttc ttggtagcaa cagctacagg 60
taaggggctc acagtagcag gcttgaggtc tggacatata tatgggtgac aatgacatcc 120
actttgcctt tctctccaca ggtgtccact ccgaagtgca gcttgtggag agcggaggtg 180
gccttgtgca gccggggaac tcactcacac tctcgtgcgt cgcttcggga ttcacctttt 240
cgaattacgg gatgcactgg atcagacagg cacccaagaa agggctcgaa tggattgcga 300
tgatctacta cgatagctcg aagatgaact acgcagacac agtgaagggg cggtttacaa 360
tttcccgaga taactcaaag aatacgcttt atcttgagat gaactccctg agatccgagg 420
acactgcgat gtactattgc gcagtcccta cttcacatta tgtagtcgat gtgtggggcc 480
agggtgtgtc agtaactgtc agctccggga gcacgtcggg agggggttcg ggcggaggga 540
gcggtggagg aggatcgtcg gatattcaga tgacgcaatc acccgcctcg ttgtccgcga 600
gcctcgaaga gatcgtgaca atcacctgtc aggcctccca agatatcgga aattggctgg 660
cgtggtatca gcagaaacca gggaagtcac cgcagttgct gatctacgga gcgacctccc 720
tcgccgacgg ggtcccctcg cgcttctcgg gctcaaggtc cggcacgcag ttctcgctga 780
agattagcag ggtacaagtg gaggacattg gcatctacta ctgtttgcaa gcctataaca 840
ccccgtggac gtttggtggg ggtacgaaat tggagcttaa acgggctagc accaagggcc 900
catcggtctt ccccctggca ccctcctcca agagcacctc tgggggcaca gcggccctgg 960
gctgcctggt caaggactac ttccccgaac cggtgacggt gtcgtggaac tcaggcgccc 1020
tgaccagcgg cgtgcacacc ttcccggctg tcctacagtc ctcaggactc tactccctca 1080
gcagcgtggt gaccgtgccc tccagcagct tgggcaccca gacctacatc tgcaacgtga 1140
atcacaagcc cagcaacacc aaggtggaca agagagttga gcccaaatct tgtgacaaaa 1200
ctcacacatg cccaccgtgc ccagcacctg aactcctggg gggaccgtca gtcttcctct 1260
tccccccaaa acccaaggac accctcatga tctcccggac ccctgaggtc acatgcgtgg 1320
tggtggacgt gagccacgaa gaccctgagg tcaagttcaa ctggtacgtg gacggcgtgg 1380
aggtgcataa tgccaagaca aagccgcggg aggagcagta caacagcacg taccgtgtgg 1440
tcagcgtcct caccgtcctg caccaggact ggctgaatgg caaggagtac aagtgcaagg 1500
tctccaacaa agccctccca gcccccatcg agaaaaccat ctccaaagcc aaagggcagc 1560
cccgagaacc acaggtgtac accctgcccc catcccggga tgagctgacc aagaaccagg 1620
tcagcctgac ctgcctggtc aaaggcttct atcccagcga catcgccgtg gagtgggaga 1680
gcaatgggca gccggagaac aactacaaga ccacgcctcc cgtgctggac tccgacggct 1740
ccttcttcct ctacagcaag ctcaccgtgg acaagagcag gtggcagcag gggaacgtct 1800
tctcatgctc cgtgatgcat gaggctctgc acaaccacta cacgcagaag agcctctccc 1860
tgtctccggg taaatgagcg gccgc 1885

<210> SEQ ID NO 61
<211> LENGTH: 6842
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccg   1080
aagtgcagct tgtggagagc ggaggtggcc ttgtgcagcc ggggaactca ctcacactct   1140
cgtgcgtcgc ttcgggattc accttttcga attacgggat gcactggatc agacaggcac   1200
ccaagaaagg gctcgaatgg attgcgatga tctactacga tagctcgaag atgaactacg   1260
cagacacagt gaaggggcgg tttacaattt cccgagataa ctcaaagaat acgctttatc   1320
ttgagatgaa ctccctgaga tccgaggaca ctgcgatgta ctattgcgca gtccctactt   1380
cacattatgt agtcgatgtg tggggccagg gtgtgtcagt aactgtcagc tccgggagca   1440
cgtcgggagg gggttcgggc ggagggagcg gtggaggagg atcgtcggat attcagatga   1500
cgcaatcacc cgcctcgttg tccgcgagcc tcgaagagat cgtgacaatc acctgtcagg   1560
cctcccaaga tatcggaaat tggctggcgt ggtatcagca gaaaccaggg aagtcaccgc   1620
agttgctgat ctacggagcg acctccctcg ccgacggggt cccctcgcgc ttctcgggct   1680
caaggtccgg cacgcagttc tcgctgaaga ttagcagggt acaagtggag gacattggca   1740
tctactactg tttgcaagcc tataacaccc cgtggacgtt tggtgggggt acgaaattgg   1800
agcttaaacg ggctagcacc aagggcccat cggtcttccc cctggcaccc tcctccaaga   1860
gcacctctgg gggcacagcg gccctgggct gcctggtcaa ggactacttc cccgaaccgg   1920
tgacggtgtc gtggaactca ggcgccctga ccagcggcgt gcacaccttc ccggctgtcc   1980
tacagtcctc aggactctac tccctcagca gcgtggtgac cgtgccctcc agcagcttgg   2040
gcacccagac ctacatctgc aacgtgaatc acaagcccag caacaccaag gtggacaaga   2100
gagttgagcc caaatcttgt gacaaaactc acacatgccc accgtgccca gcacctgaac   2160
tcctgggggg accgtcagtc ttcctcttcc ccccaaaacc caaggacacc ctcatgatct   2220
cccggacccc tgaggtcaca tgcgtggtgg tggacgtgag ccacgaagac cctgaggtca   2280
```

```
agttcaactg gtacgtggac ggcgtggagg tgcataatgc caagacaaag ccgcgggagg   2340
agcagtacaa cagcacgtac cgtgtggtca gcgtcctcac cgtcctgcac caggactggc   2400
tgaatggcaa ggagtacaag tgcaaggtct ccaacaaagc cctcccagcc cccatcgaga   2460
aaaccatctc caaagccaaa gggcagcccc gagaaccaca ggtgtacacc ctgcccccat   2520
cccgggatga gctgaccaag aaccaggtca gcctgacctg cctggtcaaa ggcttctatc   2580
ccagcgacat cgccgtggag tgggagagca atgggcagcc ggagaacaac tacaagacca   2640
cgcctcccgt gctggactcc gacggctcct tcttcctcta cagcaagctc accgtggaca   2700
agagcaggtg gcagcagggg aacgtcttct catgctccgt gatgcatgag gctctgcaca   2760
accactacac gcagaagagc ctctccctgt ctccgggtaa atgagcggcc gctcgagtct   2820
agagggcccg tttaaacccg ctgatcagcc tcgactgtgc cttctagttg ccagccatct   2880
gttgtttgcc cctcccccgt gccttccttg accctggaag gtgccactcc cactgtcctt   2940
tcctaataaa atgaggaaat tgcatcgcat tgtctgagta ggtgtcattc tattctgggg   3000
ggtggggtgg ggcaggacag caagggggag gattgggaag acaatagcag gcatgctggg   3060
gatgcggtgg gctctatggc ttctgaggcg gaaagaacca gctggggctc taggggggtat   3120
ccccacgcgc cctgtagcgg cgcattaagc gcggcgggtg tggtggttac gcgcagcgtg   3180
accgctacac ttgccagcgc cctagcgccc gctcctttcg ctttcttccc ttcctttctc   3240
gccacgttcg ccggctttcc ccgtcaagct ctaaatcggg gcatcccttt agggttccga   3300
tttagtgctt tacggcacct cgaccccaaa aaacttgatt agggtgatgg ttcacgtagt   3360
gggccatcgc cctgatagac ggtttttcgc cctttgacgt tggagtccac gttctttaat   3420
agtggactct tgttccaaac tggaacaaca ctcaacccta tctcggtcta ttcttttgat   3480
ttataaggga ttttggggat ttcggcctat tggttaaaaa atgagctgat ttaacaaaaa   3540
tttaacgcga attaattctg tggaatgtgt gtcagttagg gtgtggaaag tccccaggct   3600
ccccaggcag gcagaagtat gcaaagcatg catctcaatt agtcagcaac caggtgtgga   3660
aagtccccag gctccccagc aggcagaagt atgcaaagca tgcatctcaa ttagtcagca   3720
accatagtcc cgcccctaac tccgcccatc ccgcccctaa ctccgcccag ttccgcccat   3780
tctccgcccc atggctgact aatttttttt atttatgcag aggccgaggc cgcctctgcc   3840
tctgagctat tccagaagta gtgaggaggc ttttttggag gcctaggctt ttgcaaaaag   3900
ctcccgggag cttgtatatc cattttcgga tctgatcagc acgtgttgac aattaatcat   3960
cggcatagta tatcggcata gtataatacg acaaggtgag gaactaaacc atggccaagt   4020
tgaccagtgc cgttccggtg ctcaccgcgc gcgacgtcgc cggagcggtc gagttctgga   4080
ccgaccggct cgggttctcc cgggacttcg tggaggacga cttcgccggt gtggtccggg   4140
acgacgtgac cctgttcatc agcgcggtcc aggaccaggt ggtgccggac aacaccctgg   4200
cctgggtgtg ggtgcgcggc ctggacgagc tgtacgccga gtggtcggag gtcgtgtcca   4260
cgaacttccg ggacgcctcc gggccggcca tgaccgagat cggcgagcag ccgtgggggc   4320
gggagttcgc cctgcgcgac ccggccggca actgcgtgca cttcgtggcc gaggagcagg   4380
actgacacgt gctacgagat ttcgattcca ccgccgcctt ctatgaaagg ttgggcttcg   4440
gaatcgtttt ccgggacgcc ggctggatga tcctccagcg cggggatctc atgctggagt   4500
tcttcgccca ccccaacttg tttattgcag cttataatgg ttacaaataa agcaatagca   4560
tcacaaattt cacaaataaa gcattttttt cactgcattc tagttgtggt ttgtccaaac   4620
```

```
tcatcaatgt atcttatcat gtctgtatac cgtcgacctc tagctagagc ttggcgtaat   4680

catggtcata gctgtttcct gtgtgaaatt gttatccgct cacaattcca cacaacatac   4740

gagccggaag cataaagtgt aaagcctggg gtgcctaatg agtgagctaa ctcacattaa   4800

ttgcgttgcg ctcactgccc gctttccagt cgggaaacct gtcgtgccag ctgcattaat   4860

gaatcggcca acgcgcgggg agaggcggtt tgcgtattgg gcgctcttcc gcttcctcgc   4920

tcactgactc gctgcgctcg gtcgttcggc tgcggcgagc ggtatcagct cactcaaagg   4980

cggtaatacg gttatccaca gaatcagggg ataacgcagg aaagaacatg tgagcaaaag   5040

gccagcaaaa ggccaggaac cgtaaaaagg ccgcgttgct ggcgtttttc cataggctcc   5100

gcccccctga cgagcatcac aaaaatcgac gctcaagtca gaggtggcga aacccgacag   5160

gactataaag ataccaggcg tttccccctg gaagctccct cgtgcgctct cctgttccga   5220

ccctgccgct taccggatac ctgtccgcct ttctcccttc gggaagcgtg gcgctttctc   5280

aatgctcacg ctgtaggtat ctcagttcgg tgtaggtcgt tcgctccaag ctgggctgtg   5340

tgcacgaacc ccccgttcag cccgaccgct gcgccttatc cggtaactat cgtcttgagt   5400

ccaacccggt aagacacgac ttatcgccac tggcagcagc cactggtaac aggattagca   5460

gagcgaggta tgtaggcggt gctacagagt tcttgaagtg gtggcctaac tacggctaca   5520

ctagaaggac agtatttggt atctgcgctc tgctgaagcc agttaccttc ggaaaaagag   5580

ttggtagctc ttgatccggc aaacaaacca ccgctggtag cggtggtttt tttgtttgca   5640

agcagcagat tacgcgcaga aaaaaaggat ctcaagaaga tcctttgatc ttttctacgg   5700

ggtctgacgc tcagtggaac gaaaactcac gttaagggat tttggtcatg agattatcaa   5760

aaaggatctt cacctagatc cttttaaatt aaaaatgaag ttttaaatca atctaaagta   5820

tatatgagta aacttggtct gacagttacc aatgcttaat cagtgaggca cctatctcag   5880

cgatctgtct atttcgttca tccatagttg cctgactccc cgtcgtgtag ataactacga   5940

tacgggaggg cttaccatct ggccccagtg ctgcaatgat accgcgagac ccacgctcac   6000

cggctccaga tttatcagca ataaaccagc cagccggaag ggccgagcgc agaagtggtc   6060

ctgcaacttt atccgcctcc atccagtcta ttaattgttg ccgggaagct agagtaagta   6120

gttcgccagt taatagtttg cgcaacgttg ttgccattgc tacaggcatc gtggtgtcac   6180

gctcgtcgtt tggtatggct tcattcagct ccggttccca acgatcaagg cgagttacat   6240

gatcccccat gttgtgcaaa aaagcggtta gctccttcgg tcctccgatc gttgtcagaa   6300

gtaagttggc cgcagtgtta tcactcatgg ttatggcagc actgcataat tctcttactg   6360

tcatgccatc cgtaagatgc ttttctgtga ctggtgagta ctcaaccaag tcattctgag   6420

aatagtgtat gcggcgaccg agttgctctt gcccggcgtc aatacgggat aataccgcgc   6480

cacatagcag aactttaaaa gtgctcatca ttggaaaacg ttcttcgggg cgaaaactct   6540

caaggatctt accgctgttg agatccagtt cgatgtaacc cactcgtgca cccaactgat   6600

cttcagcatc ttttactttc accagcgttt ctgggtgagc aaaaacagga aggcaaaatg   6660

ccgcaaaaaa gggaataagg gcgacacgga aatgttgaat actcatactc ttcctttttc   6720

aatattattg aagcatttat cagggttatt gtctcatgag cggatacata tttgaatgta   6780

tttagaaaaa taaacaaata ggggttccgc gcacatttcc ccgaaaagtg ccacctgacg   6840

tc                                                                  6842
```

```
<210> SEQ ID NO 62
<211> LENGTH: 7424
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccgccacc atgggatgga gctgtatcat 960
cctcttcttg gtagcaacag ctacaggtaa ggggctcaca gtagcaggct tgaggtctgg 1020
acatatatat gggtgacaat gacatccact ttgcctttct ctccacaggt gtccactccg 1080
aagtgcagct tgtggagagc ggaggtggcc ttgtgcagcc ggggaactca ctcacactct 1140
cgtgcgtcgc ttcgggattc accttttcga attacgggat gcactggatc agacaggcac 1200
ccaagaaagg gctcgaatgg attgcgatga tctactacga tagctcgaag atgaactacg 1260
cagacacagt gaaggggcgg tttacaattt cccgagataa ctcaaagaat acgctttatc 1320
ttgagatgaa ctccctgaga tccgaggaca ctgcgatgta ctattgcgca gtccctactt 1380
cacattatgt agtcgatgtg tggggccagg gtgtgtcagt aactgtcagc tccgggagca 1440
cgtcgggagg gggttcgggc ggagggagcg gtggaggagg atcgtcggat attcagatga 1500
cgcaatcacc cgcctcgttg tccgcgagcc tcgaagagat cgtgacaatc acctgtcagg 1560
cctcccaaga tatcggaaat tggctggcgt ggtatcagca gaaaccaggg aagtcaccgc 1620
agttgctgat ctacggagcg acctccctcg ccgacggggt cccctcgcgc ttctcgggct 1680
caaggtccgg cacgcagttc tcgctgaaga ttagcagggt acaagtggag gacattggca 1740
tctactactg tttgcaagcc tataacaccc cgtggacgtt tggtgggggt acgaaattgg 1800
agcttaaacg ggctagcacc aagggcccat cggtcttccc cctggcaccc tcctccaaga 1860
gcacctctgg gggcacagcg gccctgggct gcctggtcaa ggactacttc cccgaaccgg 1920
tgacggtgtc gtggaactca ggcgccctga ccagcggcgt gcacaccttc ccggctgtcc 1980
tacagtcctc aggactctac tccctcagca gcgtggtgac cgtgccctcc agcagcttgg 2040
gcacccagac ctacatctgc aacgtgaatc acaagcccag caacaccaag gtggacaaga 2100
gagttgagcc caaatcttgt gacaaaactc acacatgccc accgtgccca gcacctgaac 2160

```
tcctgggggg accgtcagtc ttcctcttcc ccccaaaacc caaggacacc ctcatgatct   2220
cccggacccc tgaggtcaca tgcgtggtgg tggacgtgag ccacgaagac cctgaggtca   2280
agttcaactg gtacgtggac ggcgtggagg tgcataatgc caagacaaag ccgcgggagg   2340
agcagtacaa cagcacgtac cgtgtggtca gcgtcctcac cgtcctgcac caggactggc   2400
tgaatggcaa ggagtacaag tgcaaggtct ccaacaaagc cctcccagcc cccatcgaga   2460
aaaccatctc caaagccaaa gggcagcccc gagaaccaca ggtgtacacc ctgcccccat   2520
cccgggatga gctgaccaag aaccaggtca gcctgacctg cctggtcaaa ggcttctatc   2580
ccagcgacat cgccgtggag tgggagagca atgggcagcc ggagaacaac tacaagacca   2640
cgcctcccgt gctggactcc gacggctcct tcttcctcta cagcaagctc accgtggaca   2700
agagcaggtg gcagcagggg aacgtcttct catgctccgt gatgcatgag gctctgcaca   2760
accactacac gcagaagagc ctctccctgt ctccgggtaa atgagcggcc gctcgagtct   2820
agagggcccg tttaaacccg ctgatcagcc tcgactgtgc cttctagttg ccagccatct   2880
gttgtttgcc cctcccccgt gccttccttg accctggaag gtgccactcc cactgtcctt   2940
tcctaataaa atgaggaaat tgcatcgcat tgtctgagta ggtgtcattc tattctgggg   3000
ggtggggtgg ggcaggacag caagggggag gattgggaag acaatagcag gcatgctggg   3060
gatgcggtgg gctctatggc ttctgaggcg gaaagaacca gctggggctc tagggggtat   3120
ccccacgcgc cctgtagcgg cgcattaagc gcggcgggtg tggtggttac gcgcagcgtg   3180
accgctacac ttgccagcgc cctagcgccc gctcctttcg ctttcttccc ttcctttctc   3240
gccacgttcg ccggctttcc ccgtcaagct ctaaatcggg ggctcccttt agggttccga   3300
tttagtgctt tacggcacct cgaccccaaa aaacttgatt agggtgatgg ttcacgtagt   3360
gggccatcgc cctgatagac ggtttttcgc cctttgacgt tggagtccac gttctttaat   3420
agtggactct tgttccaaac tggaacaaca ctcaacccta tctcggtcta ttcttttgat   3480
ttataaggga ttttgccgat ttcggcctat tggttaaaaa atgagctgat ttaacaaaaa   3540
tttaacgcga attaattctg tggaatgtgt gtcagttagg gtgtggaaag tccccaggct   3600
ccccagcagg cagaagtatg caaagcatgc atctcaatta gtcagcaacc aggtgtggaa   3660
agtccccagg ctccccagca ggcagaagta tgcaaagcat gcatctcaat tagtcagcaa   3720
ccatagtccc gcccctaact ccgcccatcc cgcccctaac tccgcccagt tccgcccatt   3780
ctccgcccca tggctgacta attttttta tttatgcaga ggccgaggcc gcctctgcct   3840
ctgagctatt ccagaagtag tgaggaggct tttttggagg cctaggcttt tgcaaaaagc   3900
tcccgggagc ttgtatatcc attttcggat ctgatcagca cgtgatgaaa aagcctgaac   3960
tcaccgcgac gtctgtcgag aagtttctga tcgaaaagtt cgacagcgtc tccgacctga   4020
tgcagctctc ggagggcgaa gaatctcgtg ctttcagctt cgatgtagga gggcgtggat   4080
atgtcctgcg ggtaaatagc tgcgccgatg gtttctacaa agatcgttat gtttatcggc   4140
actttgcatc ggccgcgctc ccgattccgg aagtgcttga cattggggaa ttcagcgaga   4200
gcctgaccta ttgcatctcc cgccgtgcac agggtgtcac gttgcaagac ctgcctgaaa   4260
ccgaactgcc cgctgttctg cagccggtcg cggaggccat ggatgcgatc gctgcggccg   4320
atcttagcca gacgagcggg ttcggcccat tcggaccgca aggaatcggt caatacacta   4380
catggcgtga tttcatatgc gcgattgctg atccccatgt gtatcactgg caaactgtga   4440
tggacgacac cgtcagtgcg tccgtcgcgc aggctctcga tgagctgatg ctttgggccg   4500
```

```
aggactgccc cgaagtccgg cacctcgtgc acgcggattt cggctccaac aatgtcctga   4560
cggacaatgg ccgcataaca gcggtcattg actggagcga ggcgatgttc ggggattccc   4620
aatacgaggt cgccaacatc ttcttctgga ggccgtggtt ggcttgtatg gagcagcaga   4680
cgcgctactt cgagcggagg catccggagc ttgcaggatc gccgcggctc cgggcgtata   4740
tgctccgcat tggtcttgac caactctatc agagcttggt tgacggcaat ttcgatgatg   4800
cagcttgggc gcagggtcga tgcgacgcaa tcgtccgatc cggagccggg actgtcgggc   4860
gtacacaaat cgcccgcaga agcgcggccg tctggaccga tggctgtgta gaagtactcg   4920
ccgatagtgg aaaccgacgc cccagcactc gtccgagggc aaaggaatag cacgtgctac   4980
gagatttcga ttccaccgcc gccttctatg aaaggttggg cttcggaatc gttttccggg   5040
acgccggctg gatgatcctc cagcgcgggg atctcatgct ggagttcttc gcccacccca   5100
acttgtttat tgcagcttat aatggttaca aataaagcaa tagcatcaca aatttcacaa   5160
ataaagcatt tttttcactg cattctagtt gtggtttgtc caaactcatc aatgtatctt   5220
atcatgtctg tataccgtcg acctctagct agagcttggc gtaatcatgg tcatagctgt   5280
ttcctgtgtg aaattgttat ccgctcacaa ttccacacaa catacgagcc ggaagcataa   5340
agtgtaaagc ctggggtgcc taatgagtga gctaactcac attaattgcg ttgcgctcac   5400
tgcccgcttt ccagtcggga aacctgtcgt gccagctgca ttaatgaatc ggccaacgcg   5460
cggggagagg cggtttgcgt attgggcgct cttccgcttc ctcgctcact gactcgctgc   5520
gctcggtcgt tcggctgcgg cgagcggtat cagctcactc aaaggcggta atacggttat   5580
ccacagaatc aggggataac gcaggaaaga acatgtgagc aaaaggccag caaaaggcca   5640
ggaaccgtaa aaaggccgcg ttgctggcgt ttttccatag gctccgcccc cctgacgagc   5700
atcacaaaaa tcgacgctca agtcagaggt ggcgaaaccc gacaggacta taaagatacc   5760
aggcgtttcc ccctggaagc tccctcgtgc gctctcctgt tccgaccctg ccgcttaccg   5820
gatacctgtc cgcctttctc ccttcgggaa gcgtggcgct ttctcatagc tcacgctgta   5880
ggtatctcag ttcggtgtag gtcgttcgct ccaagctggg ctgtgtgcac gaaccccccg   5940
ttcagcccga ccgctgcgcc ttatccggta actatcgtct tgagtccaac ccggtaagac   6000
acgacttatc gccactggca gcagccactg gtaacaggat tagcagagcg aggtatgtag   6060
gcggtgctac agagttcttg aagtggtggc ctaactacgg ctacactaga agaacagtat   6120
ttggtatctg cgctctgctg aagccagtta ccttcggaaa aagagttggt agctcttgat   6180
ccggcaaaca aaccaccgct ggtagcggtt tttttgtttg caagcagcag attacgcgca   6240
gaaaaaaagg atctcaagaa gatcctttga tcttttctac ggggtctgac gctcagtgga   6300
acgaaaactc acgttaaggg attttggtca tgagattatc aaaaaggatc ttcacctaga   6360
tccttttaaa ttaaaaatga agttttaaat caatctaaag tatatatgag taaacttggt   6420
ctgacagtta ccaatgctta atcagtgagg cacctatctc agcgatctgt ctatttcgtt   6480
catccatagt tgcctgactc cccgtcgtgt agataactac gatacgggag ggcttaccat   6540
ctggccccag tgctgcaatg ataccgcgag acccacgctc accggctcca gatttatcag   6600
caataaacca gccagccgga agggccgagc gcagaagtgg tcctgcaact ttatccgcct   6660
ccatccagtc tattaattgt tgccgggaag ctagagtaag tagttcgcca gttaatagtt   6720
tgcgcaacgt tgttgccatt gctacaggca tcgtggtgtc acgctcgtcg tttggtatgg   6780
cttcattcag ctccggttcc caacgatcaa ggcgagttac atgatccccc atgttgtgca   6840
aaaaagcggt tagctccttc ggtcctccga tcgttgtcag aagtaagttg gccgcagtgt   6900
```

```
tatcactcat ggttatggca gcactgcata attctcttac tgtcatgcca tccgtaagat   6960
gcttttctgt gactggtgag tactcaacca agtcattctg agaatagtgt atgcggcgac   7020
cgagttgctc ttgcccggcg tcaatacggg ataataccgc gccacatagc agaactttaa   7080
aagtgctcat cattggaaaa cgttcttcgg ggcgaaaact ctcaaggatc ttaccgctgt   7140
tgagatccag ttcgatgtaa cccactcgtg cacccaactg atcttcagca tcttttactt   7200
tcaccagcgt ttctgggtga gcaaaaacag gaaggcaaaa tgccgcaaaa aagggaataa   7260
gggcgacacg gaaatgttga atactcatac tcttcctttt tcaatattat tgaagcattt   7320
atcagggtta ttgtctcatg agcggataca tatttgaatg tatttagaaa aataaacaaa   7380
taggggttcc gcgcacattt ccccgaaaag tgccacctga cgtc                    7424
```

<210> SEQ ID NO 63
<211> LENGTH: 1216
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
tggatccgcc accatgggat ggagctgtat catcctcttc ttggtagcaa cagctacagg     60
taaggggctc acagtagcag gcttgaggtc tggacatata tatgggtgac aatgacatcc    120
actttgcctt tctctccaca ggtgtccact ccgaagtgca gcttgtggag agcggaggtg    180
gccttgtgca gccggggaac tcactcacac tctcgtgcgt cgcttcggga ttcacctttt    240
cgaattacgg gatgcactgg atcagacagg cacccaagaa agggctcgaa tggattgcga    300
tgatctacta cgatagctcg aagatgaact acgcagacac agtgaagggg cggtttacaa    360
tttcccgaga taactcaaag aatacgcttt atcttgagat gaactccctg agatccgagg    420
acactgcgat gtactattgc gcagtcccta cttcacatta tgtagtcgat gtgtggggcc    480
agggtgtgtc agtaactgtc agctccggga gcacgtcggg agggggttcg ggcggaggga    540
gcggtggagg aggatcgtcg gatattcaga tgacgcaatc acccgcctcg ttgtccgcga    600
gcctcgaaga gatcgtgaca atcacctgtc aggcctccca agatatcgga aattggctgg    660
cgtggtatca gcagaaacca gggaagtcac cgcagttgct gatctacgga gcgacctccc    720
tcgccgacgg ggtcccctcg cgcttctcgg gctcaaggtc cggcacgcag ttctcgctga    780
agattagcag ggtacaagtg gaggacattg gcatctacta ctgtttgcaa gcctataaca    840
ccccgtggac gtttggtggg ggtacgaaat tggagcttaa acgggctagc gtggctgcac    900
catctgtctt catcttcccg ccatctgatg agcagttgaa atctggaact gcctctgttg    960
tgtgcctgct gaataacttc tatcccagag aggccaaagt acagtggaag gtggataacg   1020
ccctccaatc gggtaactcc caggagagtg tcacagagca ggacagcaag gacagcacct   1080
acagcctcag cagcaccctg acgctgagca aagcagacta cgagaaacac aaagtctacg   1140
cctgcgaagt cacccatcag ggcctgagct cgcccgtcac aaagagcttc aacaggggag   1200
agtgttaggc ggccgc                                                   1216
```

<210> SEQ ID NO 64
<211> LENGTH: 6173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccgccacc atgggatgga gctgtatcat    960
cctcttcttg gtagcaacag ctacaggtaa ggggctcaca gtagcaggct tgaggtctgg   1020
acatatatat gggtgacaat gacatccact ttgcctttct ctccacaggt gtccactccg   1080
aagtgcagct tgtggagagc ggaggtggcc ttgtgcagcc ggggaactca ctcacactct   1140
cgtgcgtcgc ttcgggattc accttttcga attacgggat gcactggatc agacaggcac   1200
ccaagaaagg gctcgaatgg attgcgatga tctactacga tagctcgaag atgaactacg   1260
cagacacagt gaaggggcgg tttacaattt cccgagataa ctcaaagaat acgctttatc   1320
ttgagatgaa ctccctgaga tccgaggaca ctgcgatgta ctattgcgca gtccctactt   1380
cacattatgt agtcgatgtg tggggccagg gtgtgtcagt aactgtcagc tccgggagca   1440
cgtcgggagg gggttcgggc ggagggagcg gtggaggagg atcgtcggat attcagatga   1500
cgcaatcacc cgcctcgttg tccgcgagcc tcgaagagat cgtgacaatc acctgtcagg   1560
cctcccaaga tatcggaaat tggctggcgt ggtatcagca gaaaccaggg aagtcaccgc   1620
agttgctgat ctacggagcg acctccctcg ccgacggggt cccctcgcgc ttctcgggct   1680
caaggtccgg cacgcagttc tcgctgaaga ttagcagggt acaagtggag gacattggca   1740
tctactactg tttgcaagcc tataacaccc cgtggacgtt tggtgggggt acgaaattgg   1800
agcttaaacg ggctagcgtg gctgcaccat ctgtcttcat cttcccgcca tctgatgagc   1860
agttgaaatc tggaactgcc tctgttgtgt gcctgctgaa taacttctat cccagagagg   1920
ccaaagtaca gtggaaggtg gataacgccc tccaatcggg taactcccag gagagtgtca   1980
cagagcagga cagcaaggac agcacctaca gcctcagcag caccctgacg ctgagcaaag   2040
cagactacga gaaacacaaa gtctacgcct gcgaagtcac ccatcagggc ctgagctcgc   2100
ccgtcacaaa gagcttcaac aggggagagt gttaggcggc cgctcgagtc tagagggccc   2160
gtttaaaccc gctgatcagc ctcgactgtg ccttctagtt gccagccatc tgttgtttgc   2220
ccctcccccg tgccttcctt gaccctggaa ggtgccactc ccactgtcct ttcctaataa   2280
```

```
aatgaggaaa ttgcatcgca ttgtctgagt aggtgtcatt ctattctggg gggtggggtg   2340
gggcaggaca gcaaggggga ggattgggaa gacaatagca ggcatgctgg ggatgcggtg   2400
ggctctatgg cttctgaggc ggaaagaacc agctggggct ctagggggta tccccacgcg   2460
ccctgtagcg gcgcattaag cgcggcgggt gtggtggtta cgcgcagcgt gaccgctaca   2520
cttgccagcg ccctagcgcc cgctcctttc gctttcttcc cttcctttct cgccacgttc   2580
gccggctttc cccgtcaagc tctaaatcgg ggcatccctt tagggttccg atttagtgct   2640
ttacggcacc tcgaccccaa aaaacttgat tagggtgatg gttcacgtag tgggccatcg   2700
ccctgataga cggtttttcg ccctttgacg ttggagtcca cgttctttaa tagtggactc   2760
ttgttccaaa ctggaacaac actcaaccct atctcggtct attcttttga tttataaggg   2820
attttgggga tttcggccta ttggttaaaa aatgagctga tttaacaaaa atttaacgcg   2880
aattaattct gtggaatgtg tgtcagttag ggtgtggaaa gtccccaggc tccccaggca   2940
ggcagaagta tgcaaagcat gcatctcaat tagtcagcaa ccaggtgtgg aaagtcccca   3000
ggctccccag caggcagaag tatgcaaagc atgcatctca attagtcagc aaccatagtc   3060
ccgcccctaa ctccgcccat cccgccccta actccgccca gttccgccca ttctccgccc   3120
catggctgac taattttttt tatttatgca gaggccgagg ccgcctctgc ctctgagcta   3180
ttccagaagt agtgaggagg cttttttgga ggcctaggct tttgcaaaaa gctcccggga   3240
gcttgtatat ccattttcgg atctgatcag cacgtgttga caattaatca tcggcatagt   3300
atatcggcat agtataatac gacaaggtga ggaactaaac catggccaag ttgaccagtg   3360
ccgttccggt gctcaccgcg cgcgacgtcg ccggagcggt cgagttctgg accgaccggc   3420
tcgggttctc ccgggacttc gtggaggacg acttcgccgg tgtggtccgg gacgacgtga   3480
ccctgttcat cagcgcggtc caggaccagg tggtgccgga caacaccctg gcctgggtgt   3540
gggtgcgcgg cctggacgag ctgtacgccg agtggtcgga ggtcgtgtcc acgaacttcc   3600
gggacgcctc cgggccggcc atgaccgaga tcggcgagca gccgtggggg cgggagttcg   3660
ccctgcgcga cccggccggc aactgcgtgc acttcgtggc cgaggagcag gactgacacg   3720
tgctacgaga tttcgattcc accgccgcct tctatgaaag gttgggcttc ggaatcgttt   3780
tccgggacgc cggctggatg atcctccagc gcggggatct catgctggag ttcttcgccc   3840
accccaactt gtttattgca gcttataatg gttacaaata aagcaatagc atcacaaatt   3900
tcacaaataa agcatttttt tcactgcatt ctagttgtgg tttgtccaaa ctcatcaatg   3960
tatcttatca tgtctgtata ccgtcgacct ctagctagag cttggcgtaa tcatggtcat   4020
agctgtttcc tgtgtgaaat tgttatccgc tcacaattcc acacaacata cgagccggaa   4080
gcataaagtg taaagcctgg ggtgcctaat gagtgagcta actcacatta attgcgttgc   4140
gctcactgcc cgctttccag tcgggaaacc tgtcgtgcca gctgcattaa tgaatcggcc   4200
aacgcgcggg gagaggcggt ttgcgtattg ggcgctcttc cgcttcctcg ctcactgact   4260
cgctgcgctc ggtcgttcgg ctgcggcgag cggtatcagc tcactcaaag gcggtaatac   4320
ggttatccac agaatcaggg gataacgcag gaaagaacat gtgagcaaaa ggccagcaaa   4380
aggccaggaa ccgtaaaaag gccgcgttgc tggcgttttt ccataggctc cgcccccctg   4440
acgagcatca caaaaatcga cgctcaagtc agaggtggcg aaacccgaca ggactataaa   4500
gataccaggc gtttccccct ggaagctccc tcgtgcgctc tcctgttccg accctgccgc   4560
ttaccggata cctgtccgcc tttctccctt cgggaagcgt ggcgctttct caatgctcac   4620
```

```
gctgtaggta tctcagttcg gtgtaggtcg ttcgctccaa gctgggctgt gtgcacgaac   4680

cccccgttca gcccgaccgc tgcgccttat ccggtaacta tcgtcttgag tccaacccgg   4740

taagacacga cttatcgcca ctggcagcag ccactggtaa caggattagc agagcgaggt   4800

atgtaggcgg tgctacagag ttcttgaagt ggtggcctaa ctacggctac actagaagga   4860

cagtatttgg tatctgcgct ctgctgaagc cagttacctt cggaaaaaga gttggtagct   4920

cttgatccgg caaacaaacc accgctggta gcggtggttt ttttgtttgc aagcagcaga   4980

ttacgcgcag aaaaaaagga tctcaagaag atcctttgat cttttctacg gggtctgacg   5040

ctcagtggaa cgaaaactca cgttaaggga ttttggtcat gagattatca aaaaggatct   5100

tcacctagat ccttttaaat taaaaatgaa gttttaaatc aatctaaagt atatatgagt   5160

aaacttggtc tgacagttac caatgcttaa tcagtgaggc acctatctca gcgatctgtc   5220

tatttcgttc atccatagtt gcctgactcc ccgtcgtgta gataactacg atacgggagg   5280

gcttaccatc tggccccagt gctgcaatga taccgcgaga cccacgctca ccggctccag   5340

atttatcagc aataaaccag ccagccggaa gggccgagcg cagaagtggt cctgcaactt   5400

tatccgcctc catccagtct attaattgtt gccgggaagc tagagtaagt agttcgccag   5460

ttaatagttt gcgcaacgtt gttgccattg ctacaggcat cgtggtgtca cgctcgtcgt   5520

ttggtatggc ttcattcagc tccggttccc aacgatcaag gcgagttaca tgatccccca   5580

tgttgtgcaa aaaagcggtt agctccttcg gtcctccgat cgttgtcaga agtaagttgg   5640

ccgcagtgtt atcactcatg gttatggcag cactgcataa ttctcttact gtcatgccat   5700

ccgtaagatg cttttctgtg actggtgagt actcaaccaa gtcattctga gaatagtgta   5760

tgcggcgacc gagttgctct tgcccggcgt caatacggga taataccgcg ccacatagca   5820

gaactttaaa agtgctcatc attggaaaac gttcttcggg gcgaaaactc tcaaggatct   5880

taccgctgtt gagatccagt tcgatgtaac ccactcgtgc acccaactga tcttcagcat   5940

cttttacttt caccagcgtt tctgggtgag caaaaacagg aaggcaaaat gccgcaaaaa   6000

agggaataag ggcgacacgg aaatgttgaa tactcatact cttccttttt caatattatt   6060

gaagcattta tcagggttat tgtctcatga gcggatacat atttgaatgt atttagaaaa   6120

ataaacaaat aggggttccg cgcacatttc cccgaaaagt gccacctgac gtc          6173
```

<210> SEQ ID NO 65
<211> LENGTH: 6755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480
```

```
atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccgccacc atgggatgga gctgtatcat    960

cctcttcttg gtagcaacag ctacaggtaa ggggctcaca gtagcaggct tgaggtctgg   1020

acatatatat gggtgacaat gacatccact ttgcctttct ctccacaggt gtccactccg   1080

aagtgcagct tgtggagagc ggaggtggcc ttgtgcagcc ggggaactca ctcacactct   1140

cgtgcgtcgc ttcgggattc accttttcga attacgggat gcactggatc agacaggcac   1200

ccaagaaagg gctcgaatgg attgcgatga tctactacga tagctcgaag atgaactacg   1260

cagacacagt gaaggggcgg tttacaattt cccgagataa ctcaaagaat acgctttatc   1320

ttgagatgaa ctccctgaga tccgaggaca ctgcgatgta ctattgcgca gtccctactt   1380

cacattatgt agtcgatgtg tggggccagg gtgtgtcagt aactgtcagc tccgggagca   1440

cgtcgggagg gggttcgggc ggagggagcg gtggaggagg atcgtcggat attcagatga   1500

cgcaatcacc cgcctcgttg tccgcgagcc tcgaagagat cgtgacaatc acctgtcagg   1560

cctcccaaga tatcggaaat tggctggcgt ggtatcagca gaaaccaggg aagtcaccgc   1620

agttgctgat ctacggagcg acctccctcg ccgacggggt cccctcgcgc ttctcgggct   1680

caaggtccgg cacgcagttc tcgctgaaga ttagcagggt acaagtggag gacattggca   1740

tctactactg tttgcaagcc tataacaccc cgtggacgtt tggtgggggt acgaaattgg   1800

agcttaaacg ggctagcgtg gctgcaccat ctgtcttcat cttcccgcca tctgatgagc   1860

agttgaaatc tggaactgcc tctgttgtgt gcctgctgaa taacttctat cccagagagg   1920

ccaaagtaca gtggaaggtg gataacgccc tccaatcggg taactcccag gagagtgtca   1980

cagagcagga cagcaaggac agcacctaca gcctcagcag caccctgacg ctgagcaaag   2040

cagactacga gaaacacaaa gtctacgcct gcgaagtcac ccatcagggc ctgagctcgc   2100

ccgtcacaaa gagcttcaac aggggagagt gttaggcggc cgctcgagtc tagagggccc   2160

gtttaaaccc gctgatcagc ctcgactgtg ccttctagtt gccagccatc tgttgtttgc   2220

ccctcccccg tgccttcctt gaccctggaa ggtgccactc ccactgtcct ttcctaataa   2280

aatgaggaaa ttgcatcgca ttgtctgagt aggtgtcatt ctattctggg gggtggggtg   2340

gggcaggaca gcaaggggga ggattgggaa gacaatagca ggcatgctgg ggatgcggtg   2400

ggctctatgg cttctgaggc ggaaagaacc agctggggct ctagggggta tccccacgcg   2460

ccctgtagcg gcgcattaag cgcggcgggt gtggtggtta cgcgcagcgt gaccgctaca   2520

cttgccagcg ccctagcgcc cgctcctttc gctttcttcc cttcctttct cgccacgttc   2580

gccggctttc cccgtcaagc tctaaatcgg gggctccctt tagggttccg atttagtgct   2640

ttacggcacc tcgaccccaa aaaacttgat tagggtgatg gttcacgtag tgggccatcg   2700

ccctgataga cggtttttcg ccctttgacg ttggagtcca cgttctttaa tagtggactc   2760

ttgttccaaa ctggaacaac actcaaccct atctcggtct attcttttga tttataaggg   2820

attttgccga tttcggccta ttggttaaaa aatgagctga tttaacaaaa atttaacgcg   2880
```

```
aattaattct gtggaatgtg tgtcagttag ggtgtggaaa gtccccaggc tccccagcag   2940
gcagaagtat gcaaagcatg catctcaatt agtcagcaac caggtgtgga aagtccccag   3000
gctccccagc aggcagaagt atgcaaagca tgcatctcaa ttagtcagca accatagtcc   3060
cgcccctaac tccgcccatc ccgcccctaa ctccgcccag ttccgcccat tctccgcccc   3120
atggctgact aatttttttt atttatgcag aggccgaggc cgcctctgcc tctgagctat   3180
tccagaagta gtgaggaggc ttttttggag gcctaggctt ttgcaaaaag ctcccgggag   3240
cttgtatatc cattttcgga tctgatcagc acgtgatgaa aaagcctgaa ctcaccgcga   3300
cgtctgtcga gaagtttctg atcgaaaagt tcgacagcgt ctccgacctg atgcagctct   3360
cggagggcga agaatctcgt gctttcagct tcgatgtagg agggcgtgga tatgtcctgc   3420
gggtaaatag ctgcgccgat ggtttctaca aagatcgtta tgtttatcgg cactttgcat   3480
cggccgcgct cccgattccg gaagtgcttg acattgggga attcagcgag agcctgacct   3540
attgcatctc ccgccgtgca cagggtgtca cgttgcaaga cctgcctgaa accgaactgc   3600
ccgctgttct gcagccggtc gcggaggcca tggatgcgat cgctgcggcc gatcttagcc   3660
agacgagcgg gttcggccca ttcggaccgc aaggaatcgg tcaatacact acatggcgtg   3720
atttcatatg cgcgattgct gatccccatg tgtatcactg gcaaactgtg atggacgaca   3780
ccgtcagtgc gtccgtcgcg caggctctcg atgagctgat gctttgggcc gaggactgcc   3840
ccgaagtccg gcacctcgtg cacgcggatt tcggctccaa caatgtcctg acggacaatg   3900
gccgcataac agcggtcatt gactggagcg aggcgatgtt cggggattcc caatacgagg   3960
tcgccaacat cttcttctgg aggccgtggt tggcttgtat ggagcagcag acgcgctact   4020
tcgagcggag gcatccggag cttgcaggat cgccgcggct ccgggcgtat atgctccgca   4080
ttggtcttga ccaactctat cagagcttgg ttgacggcaa tttcgatgat gcagcttggg   4140
cgcagggtcg atgcgacgca atcgtccgat ccggagccgg gactgtcggg cgtacacaaa   4200
tcgcccgcag aagcgcggcc gtctggaccg atggctgtgt agaagtactc gccgatagtg   4260
gaaaccgacg ccccagcact cgtccgaggg caaaggaata gcacgtgcta cgagatttcg   4320
attccaccgc cgccttctat gaaaggttgg gcttcggaat cgttttccgg gacgccggct   4380
ggatgatcct ccagcgcggg gatctcatgc tggagttctt cgcccacccc aacttgttta   4440
ttgcagctta taatggttac aaataaagca atagcatcac aaatttcaca aataaagcat   4500
ttttttcact gcattctagt tgtggtttgt ccaaactcat caatgtatct tatcatgtct   4560
gtataccgtc gacctctagc tagagcttgg cgtaatcatg gtcatagctg tttcctgtgt   4620
gaaattgtta tccgctcaca attccacaca acatacgagc cggaagcata aagtgtaaag   4680
cctggggtgc ctaatgagtg agctaactca cattaattgc gttgcgctca ctgcccgctt   4740
tccagtcggg aaacctgtcg tgccagctgc attaatgaat cggccaacgc gcggggagag   4800
gcggtttgcg tattgggcgc tcttccgctt cctcgctcac tgactcgctg cgctcggtcg   4860
ttcggctgcg gcgagcggta tcagctcact caaaggcggt aatacggtta tccacagaat   4920
caggggataa cgcaggaaag aacatgtgag caaaaggcca gcaaaaggcc aggaaccgta   4980
aaaaggccgc gttgctggcg tttttccata ggctccgccc ccctgacgag catcacaaaa   5040
atcgacgctc aagtcagagg tggcgaaacc cgacaggact ataaagatac caggcgtttc   5100
cccctggaag ctccctcgtg cgctctcctg ttccgaccct gccgcttacc ggatacctgt   5160
ccgcctttct cccttcggga agcgtggcgc tttctcatag ctcacgctgt aggtatctca   5220
```

```
gttcggtgta ggtcgttcgc tccaagctgg gctgtgtgca cgaacccccc gttcagcccg   5280

accgctgcgc cttatccggt aactatcgtc ttgagtccaa cccggtaaga cacgacttat   5340

cgccactggc agcagccact ggtaacagga ttagcagagc gaggtatgta ggcggtgcta   5400

cagagttctt gaagtggtgg cctaactacg gctacactag aagaacagta tttggtatct   5460

gcgctctgct gaagccagtt accttcggaa aaagagttgg tagctcttga tccggcaaac   5520

aaaccaccgc tggtagcggt ttttttgttt gcaagcagca gattacgcgc agaaaaaaag   5580

gatctcaaga agatcctttg atcttttcta cggggtctga cgctcagtgg aacgaaaact   5640

cacgttaagg gattttggtc atgagattat caaaaaggat cttcacctag atccttttaa   5700

attaaaaatg aagttttaaa tcaatctaaa gtatatatga gtaaacttgg tctgacagtt   5760

accaatgctt aatcagtgag gcacctatct cagcgatctg tctatttcgt tcatccatag   5820

ttgcctgact ccccgtcgtg tagataacta cgatacggga gggcttacca tctggcccca   5880

gtgctgcaat gataccgcga gacccacgct caccggctcc agatttatca gcaataaacc   5940

agccagccgg aagggccgag cgcagaagtg gtcctgcaac tttatccgcc tccatccagt   6000

ctattaattg ttgccgggaa gctagagtaa gtagttcgcc agttaatagt ttgcgcaacg   6060

ttgttgccat tgctacaggc atcgtggtgt cacgctcgtc gtttggtatg gcttcattca   6120

gctccggttc ccaacgatca aggcgagtta catgatcccc catgttgtgc aaaaaagcgg   6180

ttagctcctt cggtcctccg atcgttgtca gaagtaagtt ggccgcagtg ttatcactca   6240

tggttatggc agcactgcat aattctctta ctgtcatgcc atccgtaaga tgcttttctg   6300

tgactggtga gtactcaacc aagtcattct gagaatagtg tatgcggcga ccgagttgct   6360

cttgcccggc gtcaatacgg gataataccg cgccacatag cagaacttta aaagtgctca   6420

tcattggaaa acgttcttcg gggcgaaaac tctcaaggat cttaccgctg ttgagatcca   6480

gttcgatgta acccactcgt gcacccaact gatcttcagc atcttttact ttcaccagcg   6540

tttctgggtg agcaaaaaca ggaaggcaaa atgccgcaaa aaagggaata agggcgacac   6600

ggaaatgttg aatactcata ctcttccttt ttcaatatta ttgaagcatt tatcagggtt   6660

attgtctcat gagcggatac atatttgaat gtatttagaa aaataaacaa ataggggttc   6720

cgcgcacatt tccccgaaaa gtgccacctg acgtc                              6755
```

<210> SEQ ID NO 66
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
```

```
                85                  90                  95

Ala Val Pro Thr Ser His Tyr Val Val Asp Val Trp Gly Gln Gly Val
            100                 105                 110

Ser Val Thr Val Ser Ser Gly Ser Thr Ser Gly Gly Gly Ser Gly Gly
        115                 120                 125

Gly Ser Gly Gly Gly Gly Ser Ser Asp Ile Gln Met Thr Gln Ser Pro
    130                 135                 140

Ala Ser Leu Ser Ala Ser Leu Glu Glu Ile Val Thr Ile Thr Cys Gln
145                 150                 155                 160

Ala Ser Gln Asp Ile Gly Asn Trp Leu Ala Trp Tyr Gln Gln Lys Pro
                165                 170                 175

Gly Lys Ser Pro Gln Leu Leu Ile Tyr Gly Ala Thr Ser Leu Ala Asp
            180                 185                 190

Gly Val Pro Ser Arg Phe Ser Gly Ser Arg Ser Gly Thr Gln Phe Ser
        195                 200                 205

Leu Lys Ile Ser Arg Val Gln Val Glu Asp Ile Gly Ile Tyr Tyr Cys
    210                 215                 220

Leu Gln Ala Tyr Asn Thr Pro Trp Thr Phe Gly Gly Gly Thr Lys Leu
225                 230                 235                 240

Glu Leu Lys Arg Ala Ser
                245


<210> SEQ ID NO 67
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser Gly Ser Thr Ser Gly Gly Gly Ser Gly Gly
        115                 120                 125

Gly Ser Gly Gly Gly Gly Ser Ser Asp Ile Gln Met Thr Gln Ser Pro
    130                 135                 140

Ala Ser Leu Ser Ala Ser Leu Glu Glu Ile Val Thr Ile Thr Cys Gln
145                 150                 155                 160

Ala Ser Gln Asp Ile Gly Asn Trp Leu Ala Trp Tyr Gln Gln Lys Pro
                165                 170                 175

Gly Lys Ser Pro Gln Leu Leu Ile Tyr Gly Ala Thr Ser Leu Ala Asp
            180                 185                 190
```

```
Gly Val Pro Ser Arg Phe Ser Gly Ser Arg Ser Gly Thr Gln Phe Ser
        195                 200                 205

Leu Lys Ile Ser Arg Val Gln Val Glu Asp Ile Gly Ile Tyr Tyr Cys
    210                 215                 220

Leu Gln Ala Tyr Asn Thr Pro Trp Thr Phe Gly Gly Gly Thr Lys Leu
225                 230                 235                 240

Glu Leu Lys Arg Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Asp Glu Leu Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Lys
                565                 570
```

<210> SEQ ID NO 68
<211> LENGTH: 353
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser Gly Ser Thr Ser Gly Gly Gly Ser Gly Gly
        115                 120                 125

Gly Ser Gly Gly Gly Gly Ser Ser Asp Ile Gln Met Thr Gln Ser Pro
    130                 135                 140

Ala Ser Leu Ser Ala Ser Leu Glu Glu Ile Val Thr Ile Thr Cys Gln
145                 150                 155                 160

Ala Ser Gln Asp Ile Gly Asn Trp Leu Ala Trp Tyr Gln Gln Lys Pro
                165                 170                 175

Gly Lys Ser Pro Gln Leu Leu Ile Tyr Gly Ala Thr Ser Leu Ala Asp
            180                 185                 190

Gly Val Pro Ser Arg Phe Ser Gly Ser Arg Ser Gly Thr Gln Phe Ser
        195                 200                 205

Leu Lys Ile Ser Arg Val Gln Val Glu Asp Ile Gly Ile Tyr Tyr Cys
    210                 215                 220

Leu Gln Ala Tyr Asn Thr Pro Trp Thr Phe Gly Gly Gly Thr Lys Leu
225                 230                 235                 240

Glu Leu Lys Arg Ala Ser Arg Thr Val Ala Ala Pro Ser Val Phe Ile
                245                 250                 255

Phe Pro Pro Ser Asp Glu Gln Leu Lys Ser Gly Thr Ala Ser Val Val
            260                 265                 270

Cys Leu Leu Asn Asn Phe Tyr Pro Arg Glu Ala Lys Val Gln Trp Lys
        275                 280                 285

Val Asp Asn Ala Leu Gln Ser Gly Asn Ser Gln Glu Ser Val Thr Glu
    290                 295                 300

Gln Asp Ser Lys Asp Ser Thr Tyr Ser Leu Ser Ser Thr Leu Thr Leu
305                 310                 315                 320

Ser Lys Ala Asp Tyr Glu Lys His Lys Val Tyr Ala Cys Glu Val Thr
                325                 330                 335

His Gln Gly Leu Ser Ser Pro Val Thr Lys Ser Phe Asn Arg Gly Glu
            340                 345                 350

Cys
```

<210> SEQ ID NO 69
<211> LENGTH: 787
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gaattcacaa tgggatggtc ttgtatcatc cttttcttgg ttgcaacagc tactggtgtt     60
cattctcaag tgcaactttt ggagtctggt gctgagcttg tgaggcctgg ttcttcagtg    120
aagatctctt gtaaagcttc aggttataca tttacaaatt acgacatcca ttgggtgaag    180
caaaggccag gtcaaggtct tgagtggatt ggatggatat acccaggtga tggttctact    240
aagtacaacg agaaatttaa gggaaaagca actcttacag ctgataagtc ttcatcaact    300
gcatatatgc acttgtcatc tcttacttct gaaaagtctg cagtttactt ttgtgcaaga    360
gagtgggctt attggggaca aggtacaact gtgacagttt caggttcaac ttcaggagga    420
ggatcaggtg gtggttcagg aggtggagga tcttctgaca tccaaatgac acaatctcca    480
tcatcacttt cagcatcagt tggagataga gtgactatca cttgtagagc ttcacaagac    540
attggtggaa atctttattg gtaccaacaa aaaccaggaa aagctccaaa gttgttgata    600
tacgcaactt cttctttgga ctctggtgtt ccatctagat ttctggatc aggatctgga     660
actgactaca ctttcactat ctcatctctt caaccagagg acattgctac ttactattgc    720
ttgcaatact cttcttctcc atggactttt ggacaaggta caaaagtgga aatcaagaga    780
gctagcc                                                              787
```

<210> SEQ ID NO 70
<211> LENGTH: 1779
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70

```
gaattcacaa tgggatggtc ttgtatcatc cttttcttgg ttgcaacagc tactggtgtt     60
cattctcaag tgcaactttt ggagtctggt gctgagcttg tgaggcctgg ttcttcagtg    120
aagatctctt gtaaagcttc aggttataca tttacaaatt acgacatcca ttgggtgaag    180
caaaggccag gtcaaggtct tgagtggatt ggatggatat acccaggtga tggttctact    240
aagtacaacg agaaatttaa gggaaaagca actcttacag ctgataagtc ttcatcaact    300
gcatatatgc acttgtcatc tcttacttct gaaaagtctg cagtttactt ttgtgcaaga    360
gagtgggctt attggggaca aggtacaact gtgacagttt caggttcaac ttcaggagga    420
ggatcaggtg gtggttcagg aggtggagga tcttctgaca tccaaatgac acaatctcca    480
tcatcacttt cagcatcagt tggagataga gtgactatca cttgtagagc ttcacaagac    540
attggtggaa atctttattg gtaccaacaa aaaccaggaa aagctccaaa gttgttgata    600
tacgcaactt cttctttgga ctctggtgtt ccatctagat ttctggatc aggatctgga     660
actgactaca ctttcactat ctcatctctt caaccagagg acattgctac ttactattgc    720
ttgcaatact cttcttctcc atggactttt ggacaaggta caaaagtgga aatcaagaga    780
gctagcacca agggaccttc tgtttttcca cttgctcctt cttctaagtc tacttctggt    840
ggaactgctg ctttgggttg tttggtgaaa gattactttc ctgagccagt gaccgtttct    900
tggaactcag gtgctcttac atctggtgtt catactttcc cagctgttct tcaatcttca    960
ggactttact cactttcttc tgttgttacc gttccttctt caagcttggg cactcagacc   1020
tacatctgca atgtgaatca caaacccagc aacaccaagg ttgacaagaa agttgagccc   1080
```

```
aagtcttgtg acaagactca tacgtgtcca ccgtgcccag cacctgaact tcttggagga   1140

ccgtcagtct tcttgtttcc tccaaagcct aaggatacct tgatgatctc caggactcct   1200

gaagtcacat gtgtagttgt ggatgtgagc catgaagatc ctgaggtgaa gttcaactgg   1260

tatgtggatg gtgtggaagt gcacaatgcc aagacaaagc cgagagagga acagtacaac   1320

agcacgtaca gggttgtctc agttctcact gttctccatc aagattggtt gaatggcaaa   1380

gagtacaagt gcaaggtctc caacaaagcc ctcccagccc ccattgagaa gaccatttcc   1440

aaagcgaaag ggcaaccccg tgaaccacaa gtgtacacac ttcctccatc tcgcgatgaa   1500

ctgaccaaga accaggtcag cttgacttgc ctggtgaaag gcttctatcc ctctgacata   1560

gctgtagagt gggagagcaa tgggcaaccg gagaacaact acaagactac acctcccgtt   1620

ctcgattctg acggctcctt cttcctctac agcaagctca cagtggacaa gagcaggtgg   1680

caacaaggga atgtcttctc atgctccgtg atgcatgagg ctcttcacaa tcactacaca   1740

cagaagagtc tctccttgtc tccgggtaaa tgaggatcc                          1779
```

<210> SEQ ID NO 71
<211> LENGTH: 8200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
tctagagtcg acctgcagaa gcttactaga gcgtggtgcg cacgatagcg catagtgttt     60

ttctctccac ttgaatcgaa gagatagact tacggtgtaa atccgtaggg gtggcgtaaa    120

ccaaattacg caatgttttg ggttccattt aaatcgaaac cccttatttc ctggatcacc    180

tgttaacgca cgtttgacgt gtattacagt gggaataagt aaaagtgaga ggttcgaatc    240

ctccctaacc ccgggtaggg gcccagcggc cgctctagct agagtcaagc agatcgttca    300

aacatttggc aataaagttt cttaagattg aatcctgttg ccggtcttgc gatgattatc    360

atataatttc tgttgaatta cgttaagcat gtaataatta acatgtaatg catgacgtta    420

tttatgagat gggtttttat gattagagtc ccgcaattat acatttaata cgcgatagaa    480

aacaaaatat agcgcgcaaa ctaggataaa ttatcgcgcg cggtgtcatc tatgttacta    540

gatcgaccag cttagatcag attgtcgttt cccgccttca gtttaaacta tcagtgtttg    600

acaggatata ttggcgggta aacctaagag aaaagagcgt ttattagaat aatcggatat    660

ttaaaagggc gtgaaaaggt ttatccgttc gtccatttgt atgtgccaac cacagggttc    720

cccagatcag taaagcgctg gctgctgaac cccagccgg aactgacccc acaaggccct     780

agcgtttgca atgcaccagg tcatcattga cccaggcgtg ttccaccagg ccgctgcctc    840

gcaactcttc gcaggcttcg ccgacctgct cgcgccactt cttcacgcgg gtggaatccg    900

atccgcacat gaggcggaag gtttccagct tgagcgggta cggctcccgg tgcgagctga    960

aatagtcgaa catccgtcgg gccgtcggcg acagcttgcg gtacttctcc catatgaatt   1020

tcgtgtagtg gtcgccagca aacagcacga cgatttcctc gtcgatcagg acctggcaac   1080

gggacgtttt cttgccacgg tccaggacgc ggaagcggtg cagcagcgac accgattcca   1140

ggtgcccaac gcggtcggac gtgaagccca tcgccgtcgc ctgtaggcgc gacaggcatt   1200

cctcggcctt cgtgtaatac cggccattga tcgaccagcc caggtcctgg caaagctcgt   1260

agaacgtgaa ggtgatcggc tcgccgatag gggtgcgctt cgcgtactcc aacacctgct   1320
```

-continued

```
gccacaccag ttcgtcatcg tcggcccgca gctcgacgcc ggtgtaggtg atcttcacgt   1380
ccttgttgac gtggaaaatg accttgtttt gcagcgcctc gcgcgggatt ttcttgttgc   1440
gcgtggtgaa cagggcagag cgggccgtgt cgtttggcat cgctcgcatc gtgtccggcc   1500
acggcgcaat atcgaacaag gaaagctgca tttccttgat ctgctgcttc gtgtgtttca   1560
gcaacgcggc ctgcttggcc tcgctgacct gttttgccag gtcctcgccg gcggtttttc   1620
gcttcttggt cgtcatagtt cctcgcgtgt cgatggtcat cgacttcgcc aaacctgccg   1680
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
```

```
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg    4020
aggccgttcg cggccgaggg gcgcagcccc tggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
```

```
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact ttttgttctt attgttgcag gtaccatggc   6420
agaattcaca atgggatggt cttgtatcat ccttttcttg gttgcaacag ctactggtgt   6480
tcattctcaa gtgcaacttt tggagtctgg tgctgagctt gtgaggcctg gttcttcagt   6540
gaagatctct tgtaaagctt caggttatac atttacaaat tacgacatcc attgggtgaa   6600
gcaaaggcca ggtcaaggtc ttgagtggat tggatggata tacccaggtg atggttctac   6660
taagtacaac gagaaattta agggaaaagc aactcttaca gctgataagt cttcatcaac   6720
tgcatatatg cacttgtcat ctcttacttc tgaaaagtct gcagtttact tttgtgcaag   6780
agagtgggct tattggggac aaggtacaac tgtgacagtt tcaggttcaa cttcaggagg   6840
aggatcaggt ggtggttcag gaggtggagg atcttctgac atccaaatga cacaatctcc   6900
atcatcactt tcagcatcag ttggagatag agtgactatc acttgtagag cttcacaaga   6960
cattggtgga aatctttatt ggtaccaaca aaaaccagga aaagctccaa agttgttgat   7020
atacgcaact tcttctttgg actctggtgt tccatctaga ttttctggat caggatctgg   7080
aactgactac actttcacta tctcatctct tcaaccagag gacattgcta cttactattg   7140
cttgcaatac tcttcttctc catggacttt tggacaaggt acaaaagtgg aaatcaagag   7200
agctagcacc aagggacctt ctgtttttcc acttgctcct tcttctaagt ctacttctgg   7260
tggaactgct gctttgggtt gtttggtgaa agattacttt cctgagccag tgaccgtttc   7320
ttggaactca ggtgctctta catctggtgt tcatactttc ccagctgttc ttcaatcttc   7380
aggactttac tcactttctt ctgttgttac cgttccttct tcaagcttgg gcactcagac   7440
ctacatctgc aatgtgaatc acaaacccag caacaccaag gttgacaaga aagttgagcc   7500
caagtcttgt gacaagactc atacgtgtcc accgtgccca gcacctgaac ttcttggagg   7560
accgtcagtc ttcttgtttc ctccaaagcc taaggatacc ttgatgatct ccaggactcc   7620
tgaagtcaca tgtgtagttg tggatgtgag ccatgaagat cctgaggtga agttcaactg   7680
gtatgtggat ggtgtggaag tgcacaatgc caagacaaag ccgagagagg aacagtacaa   7740
cagcacgtac agggttgtct cagttctcac tgttctccat caagattggt tgaatggcaa   7800
agagtacaag tgcaaggtct ccaacaaagc cctcccagcc cccattgaga agaccatttc   7860
caaagcgaaa gggcaacccc gtgaaccaca agtgtacaca cttcctccat ctcgcgatga   7920
actgaccaag aaccaggtca gcttgacttg cctggtgaaa ggcttctatc cctctgacat   7980
agctgtagag tgggagagca atgggcaacc ggagaacaac tacaagacta cacctcccgt   8040
tctcgattct gacggctcct tcttcctcta cagcaagctc acagtggaca agagcaggtg   8100
gcaacaaggg aatgtcttct catgctccgt gatgcatgag gctcttcaca atcactacac   8160
acagaagagt ctctccttgt ctccgggtaa atgaggatcc                         8200
```

<210> SEQ ID NO 72
<211> LENGTH: 8246
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
agcttgaaga ctaggcgtgg tgcgcacgat agcgcatagt gtttttctct ccacttgaat     60
cgaagagata gacttacggt gtaaatccgt aggggtggcg taaaccaaat tacgcaatgt    120
tttgggttcc atttaaatcg aaacccctta tttcctggat cacctgttaa cgcacgtttg    180
acgtgtatta cagtgggaat aagtaaaagt gagaggttcg aatcctccct aaccccgggt    240
aggggcccag cggccgctct agctagagtc aagcagatcg ttcaaacatt tggcaataaa    300
gtttcttaag attgaatcct gttgccggtc ttgcgatgat tatcatataa tttctgttga    360
attacgttaa gcatgtaata attaacatgt aatgcatgac gttatttatg agatgggttt    420
ttatgattag agtcccgcaa ttatacattt aatacgcgat agaaaacaaa atatagcgcg    480
caaactagga taaattatcg cgcgcggtgt catctatgtt actagatcga ccagtcctat    540
ggtagtcttc agcttagatc agattgtcgt ttcccgcctt cagtttaaac tatcagtgtt    600
tgacaggata tattggcggg taaacctaag agaaaagagc gtttattaga ataatcggat    660
atttaaaagg gcgtgaaaag gtttatccgt tcgtccattt gtatgtgcat gccaaccaca    720
gggttcccca gatcagtaaa gcgctggctg ctgaaccccc agccggaact gaccccacaa    780
ggccctagcg tttgcaatgc accaggtcat cattgaccca ggcgtgttcc accaggccgc    840
tgcctcgcaa ctcttcgcag gcttcgccga cctgctcgcg ccacttcttc acgcgggtgg    900
aatccgatcc gcacatgagg cggaaggttt ccagcttgag cgggtacggc tcccggtgcg    960
agctgaaata gtcgaacatc cgtcgggccg tcggcgacag cttgcggtac ttctcccata   1020
tgaatttcgt gtagtggtcg ccagcaaaca gcacgacgat ttcctcgtcg atcaggacct   1080
ggcaacggga cgttttcttg ccacggtcca ggacgcggaa gcggtgcagc agcgacaccg   1140
attccaggtg cccaacgcgg tcggacgtga agcccatcgc cgtcgcctgt aggcgcgaca   1200
ggcattcctc ggccttcgtg taataccggc cattgatcga ccagcccagg tcctggcaaa   1260
gctcgtagaa cgtgaaggtg atcggctcgc cgataggggt gcgcttcgcg tactccaaca   1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggattttct   1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
caggggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
```

```
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg gggatgggag gcccgcgtta   4080
gcgggccggg agggttcgag aaggggggc accccccttc ggcgtgcgcg gtcacgcgca   4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
```

```
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
ggcaggagca aggtgagatg acaggagatc ctgccccggc acttcgccca atagcagcca   5700
gtcccttccc gcttcagtga caacgtcgag cacagctgcg caaggaacgc ccgtcgtggc   5760
cagccacgat agccgcgctg cctcgtcctg gagttcattc agggcaccgg acaggtcggt   5820
cttgacaaaa agaaccgggc gcccctgcgc tgacagccgg aacacggcgg catcagagca   5880
gccgattgtc tgttgtgccc agtcatagcc gaatagcctc tccacccaag cggccggaga   5940
acctgcgtgc aatccatctt gttcaatcat gcgaaacgat ccagatccgg tgcagattat   6000
ttggattgag agtgaatatg agactctaat tggataccga ggggaattta tggaacgtca   6060
gtggagcatt tttgacaaga aatatttgct agctgatagt gaccttaggc gacttttgaa   6120
cgcgcaataa tggtttctga cgtatgtgct tagctcatta aactccagaa acccgcggct   6180
gagtggctcc ttcaacgttg cggttctgtc agttccaaac gtaaaacggc ttgtcccgcg   6240
tcatcggcgg gggtcataac gtgactccct taattctccg ctcatggtac ctcgaagccg   6300
cggtgcgggt gccagggcgt gcccttgggc tccccgggcg cgtactccac ctcacccatc   6360
ttttattaca tgtttgaact tcaacaattt atgacttttt gttcttattg ttgcaggtag   6420
agaccgaatt cacaatggga tggtcttgta tcatcctttt cttggttgca acagctactg   6480
gtgttcattc tcaagtgcaa cttttggagt ctggtgctga gcttgtgagg cctggttctt   6540
cagtgaagat ctcttgtaaa gcttcaggtt atacatttac aaattacgac atccattggg   6600
tgaagcaaag gccaggtcaa ggtcttgagt ggattggatg gatataccca ggtgatggtt   6660
ctactaagta caacgagaaa tttaagggaa aagcaactct tacagctgat aagtcttcat   6720
caactgcata tatgcacttg tcatctctta cttctgaaaa gtctgcagtt tacttttgtg   6780
caagagagtg ggcttattgg ggacaaggta caactgtgac agtttcaggt tcaacttcag   6840
gaggaggatc aggtggtggt tcaggaggtg gaggatcttc tgacatccaa atgacacaat   6900
ctccatcatc actttcagca tcagttggag atagagtgac tatcacttgt agagcttcac   6960
aagacattgg tggaaatctt tattggtacc aacaaaaacc aggaaaagct ccaaagttgt   7020
```

tgatatacgc aacttcttct ttggactctg gtgttccatc tagattttct ggatcaggat 7080
ctggaactga ctacactttc actatctcat ctcttcaacc agaggacatt gctacttact 7140
attgcttgca atactcttct tctccatgga cttttggaca aggtacaaaa gtggaaatca 7200
agagagctag caccaaggga ccttctgttt ttccacttgc tccttcttct aagtctactt 7260
ctggtggaac tgctgctttg ggttgtttgg tgaaagatta ctttcctgag ccagtgaccg 7320
tttcttggaa ctcaggtgct cttacatctg gtgttcatac tttcccagct gttcttcaat 7380
cttcaggact ttactcactt tcttctgttg ttaccgttcc ttcttcaagc ttgggcactc 7440
agacctacat ctgcaatgtg aatcacaaac ccagcaacac caaggttgac aagaaagttg 7500
agcccaagtc ttgtgacaag actcatacgt gtccaccgtg cccagcacct gaacttcttg 7560
gaggaccgtc agtcttcttg tttcctccaa agcctaagga taccttgatg atctccagga 7620
ctcctgaagt cacatgtgta gttgtggatg tgagccatga agatcctgag gtgaagttca 7680
actggtatgt ggatggtgtg gaagtgcaca atgccaagac aaagccgaga gaggaacagt 7740
acaacagcac gtacagggtt gtctcagttc tcactgttct ccatcaagat tggttgaatg 7800
gcaaagagta caagtgcaag gtctccaaca aagccctccc agcccccatt gagaagacca 7860
tttccaaagc gaaagggcaa ccccgtgaac cacaagtgta cacacttcct ccatctcgcg 7920
atgaactgac caagaaccag gtcagcttga cttgcctggt gaaaggcttc tatccctctg 7980
acatagctgt agagtgggag agcaatgggc aaccggagaa caactacaag actacacctc 8040
ccgttctcga ttctgacggc tccttcttcc tctacagcaa gctcacagtg gacaagagca 8100
ggtggcaaca agggaatgtc ttctcatgct ccgtgatgca tgaggctctt cacaatcact 8160
acacacagaa gagtctctcc ttgtctccgg gtaaatgagg atcctctaga gtcgacctgc 8220
agaagctggc agctaggatg ggtctc 8246

<210> SEQ ID NO 73
<211> LENGTH: 1116
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73
gaattcacaa tgggatggtc ttgtatcatc cttttcttgg ttgcaacagc tactggtgtt 60
cattctcaag tgcaactttt ggagtctggt gctgagcttg tgaggcctgg ttcttcagtg 120
aagatctctt gtaaagcttc aggttataca tttacaaatt acgacatcca ttgggtgaag 180
caaaggccag gtcaaggtct tgagtggatt ggatggatat acccaggtga tggttctact 240
aagtacaacg agaaatttaa gggaaaagca actcttacag ctgataagtc ttcatcaact 300
gcatatatgc acttgtcatc tcttacttct gaaaagtctg cagtttactt ttgtgcaaga 360
gagtgggctt attggggaca aggtacaact gtgacagttt caggttcaac ttcaggagga 420
ggatcaggtg gtggttcagg aggtggagga tcttctgaca tccaaatgac acaatctcca 480
tcatcacttt cagcatcagt tggagataga gtgactatca cttgtagagc ttcacaagac 540
attggtggaa atctttattg gtaccaacaa aaaccaggaa aagctccaaa gttgttgata 600
tacgcaactt cttctttgga ctctggtgtt ccatctagat tttctggatc aggatctgga 660
actgactaca ctttcactat ctcatctctt caaccagagg acattgctac ttactattgc 720
ttgcaatact cttcttctcc atggactttt ggacaaggta caaaagtgga aatcaagaga 780

```
gctagcagaa ctgttgctgc accatctgtt ttcatcttcc ctccatctga tgagcagttg    840

aaatctggaa ctgcttctgt tgtgtgcctt cttaataact tctatcctag agaggctaaa    900

gttcagtgga aggtggataa cgcacttcaa tctggtaact ctcaagagtc tgttacagag    960

caagattcta aggactcaac ttactctctt tcatctacac ttactttgtc aaaagcagat   1020

tacgagaaac acaaagttta cgcatgcgaa gttactcatc aaggactttc ttcaccagtt   1080

acaaagtctt tcaatagagg agagtgttaa ggatcc                             1116
```

<210> SEQ ID NO 74
<211> LENGTH: 7537
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
tctagagtcg acctgcagaa gcttactaga gcgtggtgcg cacgatagcg catagtgttt     60

ttctctccac ttgaatcgaa gagatagact tacggtgtaa atccgtaggg gtggcgtaaa    120

ccaaattacg caatgttttg ggttccattt aaatcgaaac cccttatttc ctggatcacc    180

tgttaacgca cgtttgacgt gtattacagt gggaataagt aaaagtgaga ggttcgaatc    240

ctccctaacc ccgggtaggg gcccagcggc cgctctagct agagtcaagc agatcgttca    300

aacatttggc aataaagttt cttaagattg aatcctgttg ccggtcttgc gatgattatc    360

atataatttc tgttgaatta cgttaagcat gtaataatta acatgtaatg catgacgtta    420

tttatgagat gggtttttat gattagagtc ccgcaattat acatttaata cgcgatagaa    480

aacaaaatat agcgcgcaaa ctaggataaa ttatcgcgcg cggtgtcatc tatgttacta    540

gatcgaccag cttagatcag attgtcgttt cccgccttca gtttaaacta tcagtgtttg    600

acaggatata ttggcgggta aacctaagag aaaagagcgt ttattagaat aatcggatat    660

ttaaaagggc gtgaaaaggt ttatccgttc gtccatttgt atgtgccaac cacagggttc    720

cccagatcag taaagcgctg gctgctgaac cccagccgg aactgacccc acaaggccct     780

agcgtttgca atgcaccagg tcatcattga cccaggcgtg ttccaccagg ccgctgcctc    840

gcaactcttc gcaggcttcg ccgacctgct cgcgccactt cttcacgcgg gtggaatccg    900

atccgcacat gaggcggaag gtttccagct tgagcgggta cggctcccgg tgcgagctga    960

aatagtcgaa catccgtcgg gccgtcggcg acagcttgcg gtacttctcc catatgaatt   1020

tcgtgtagtg gtcgccagca aacagcacga cgatttcctc gtcgatcagg acctggcaac   1080

gggacgtttt cttgccacgg tccaggacgc ggaagcggtg cagcagcgac accgattcca   1140

ggtgcccaac gcggtcggac gtgaagccca tcgccgtcgc ctgtaggcgc gacaggcatt   1200

cctcggcctt cgtgtaatac cggccattga tcgaccagcc caggtcctgg caaagctcgt   1260

agaacgtgaa ggtgatcggc tcgccgatag gggtgcgctt cgcgtactcc aacacctgct   1320

gccacaccag ttcgtcatcg tcggcccgca gctcgacgcc ggtgtaggtg atcttcacgt   1380

ccttgttgac gtggaaaatg accttgtttt gcagcgcctc gcgcgggatt ttcttgttgc   1440

gcgtggtgaa cagggcagag cgggccgtgt cgtttggcat cgctcgcatc gtgtccggcc   1500

acggcgcaat atcgaacaag gaaagctgca tttccttgat ctgctgcttc gtgtgtttca   1560

gcaacgcggc ctgcttggcc tcgctgacct gttttgccag gtcctcgccg gcggtttttc   1620

gcttcttggt cgtcatagtt cctcgcgtgt cgatggtcat cgacttcgcc aaacctgccg   1680
```

```
cctcctgttc gagacgacgc gaacgctcca cggcggccga tggcgcgggc agggcagggg   1740
gagccagttg cacgctgtcg cgctcgatct tggccgtagc ttgctggacc atcgagccga   1800
cggactggaa ggtttcgcgg ggcgcacgca tgacggtgcg gcttgcgatg gtttcggcat   1860
cctcggcgga aaaccccgcg tcgatcagtt cttgcctgta tgccttccgg tcaaacgtcc   1920
gattcattca ccctccttgc gggattgccc cgactcacgc cggggcaatg tgcccttatt   1980
cctgatttga cccgcctggt gccttggtgt ccagataatc caccttatcg gcaatgaagt   2040
cggtcccgta gaccgtctgg ccgtccttct cgtacttggt attccgaatc ttgccctgca   2100
cgaataccag cgaccccttg cccaaatact tgccgtgggc ctcggcctga gagccaaaac   2160
acttgatgcg gaagaagtcg gtgcgctcct gcttgtcgcc ggcatcgttg cgccacatct   2220
aggatctgcc aggaaccgta aaaaggccgc gttgctggcg tttttccata ggctccgccc   2280
ccctgacgag catcacaaaa atcgacgctc aagtcagagg tggcgaaacc cgacaggact   2340
ataaagatac caggcgtttc cccctggaag ctccctcgtg cgctctcctg ttccgaccct   2400
gccgcttacc ggatacctgt ccgcctttct cccttcggga agcgtggcgc tttctcatag   2460
ctcacgctgt aggtatctca gttcggtgta ggtcgttcgc tccaagctgg gctgtgtgca   2520
cgaacccccc gttcagcccg accgctgcgc cttatccggt aactatcgtc ttgagtccaa   2580
cccggtaaga cacgacttat cgccactggc agcagccact ggtaacagga ttagcagagc   2640
gaggtatgta ggcggtgcta cagagttctt gaagtggtgg cctaactacg gctacactag   2700
aagaacagta tttggtatct gcgctctgct gaagccagtt accttcggaa aaagagttgg   2760
tagctcttga tccggcaaac aaaccaccgc tggtagcggt ggtttttttg tttgcaagca   2820
gcagattacg cgcagaaaaa aaggatctca agaagatcct ttgatctttt ctacggggtc   2880
tgacgctcag tggaacgaaa actcacgtta agggattttg gtcatgagat tatcaaaaag   2940
gatcttcacc tagatccttt taaattaaaa atgaagtttt aaatcaatct aaagtatata   3000
tgagtaaact tggtctgaca gttaccaatg cttaatcagt gaggcaccta tctcagcgat   3060
ctgtctattt cgttcatcca tagttgcctg actccccgtc gtgtagataa ctacgatacg   3120
ggagggctta ccatctggcc ccagtgctgc aatgataccg cgagacccac gctcaccggc   3180
tccagattta tcagcaataa accagccagc cggaagggcc gagcgcagaa gtggtcctgc   3240
aactttatcc gcctccatcc agtctattaa ttgttgccgg gaagctagag taagtagttc   3300
gccagttaat agtttgcgca acgttgttgc cattgctaca ggcatcgtgg tgtcacgctc   3360
gtcgtttggt atggcttcat tcagctccgg ttcccaacga tcaaggcgag ttacatgatc   3420
ccccatgttg tgcaaaaaag cggttagctc cttcggtcct ccgatcgttg tcagaagtaa   3480
gttggccgca gtgttatcac tcatggttat ggcagcactg cataattctc ttactgtcat   3540
gccatccgta agatgctttt ctgtgactgg tgagtactca accaagtcat tctgagaata   3600
gtgtatgcgg cgaccgagtt gctcttgccc ggcgtcaata cgggataata ccgcgccaca   3660
tagcagaact ttaaaagtgc tcatcattgg aaaacgttct tcggggcgaa aactctcaag   3720
gatcttaccg ctgttgagat ccagttcgat gtaacccact cgtgcaccca actgatcttc   3780
agcatctttt actttcacca gcgtttctgg gtgagcaaaa acaggaaggc aaaatgccgc   3840
aaaaaaggga ataagggcga cacggaaatg ttgaatactc atactcttcc tttttcaata   3900
ttattgaagc atttatcagg gttattgtct catgagcgga tacatatttg aatgtattta   3960
gaaaaataaa caaatagggg ttccgcgcac gaattggcca gcgctgccat tttggggtg   4020
```

```
aggccgttcg cggccgaggg gcgcagcccc tggggggatg ggaggcccgc gttagcgggc   4080
cgggagggtt cgagaagggg gggcaccccc cttcggcgtg cgcggtcacg cgcacagggc   4140
gcagccctgg ttaaaaacaa ggtttataaa tattggttta aaagcaggtt aaaagacagg   4200
ttagcggtgg ccgaaaaacg ggcggaaacc cttgcaaatg ctggattttc tgcctgtgga   4260
cagcccctca aatgtcaata ggtgcgcccc tcatctgtca gcactctgcc cctcaagtgt   4320
caaggatcgc gcccctcatc tgtcagtagt cgcgcccctc aagtgtcaat accgcagggc   4380
acttatcccc aggcttgtcc acatcatctg tgggaaactc gcgtaaaatc aggcgttttc   4440
gccgatttgc gaggctggcc agctccacgt cgccggccga aatcgagcct gcccctcatc   4500
tgtcaacgcc gcgccgggtg agtcggcccc tcaagtgtca acgtccgccc ctcatctgtc   4560
agtgagggcc aagttttccg cgaggtatcc acaacgccgg cggccgcggt gtctcgcaca   4620
cggcttcgac ggcgtttctg gcgcgtttgc agggccatag acggccgcca gcccagcggc   4680
gagggcaacc agcccggtga gcgtcgcaaa ggagatcctg atctgactga tgggctgcct   4740
gtatcgagtg gtgattttgt gccgagctgc cggtcgggga gctgttggct ggctggtggc   4800
aggatatatt gtggtgtaaa caaattgacg cttagacaac ttaataacac attgcggacg   4860
tttttaatgt actggggtgg atgcaggtcg atctagtaac atagatgaca ccgcgcgcga   4920
taatttatcc tagtttgcgc gctatatttt gttttctatc gcgtattaaa tgtataattg   4980
cgggactcta atcataaaaa cccatctcat aaataacgtc atgcattaca tgttaattat   5040
tacatgctta acgtaattca acagaaatta tatgataatc atcgcaagac cggcaacagg   5100
attcaatctt aagaaacttt attgccaaat gtttgaacga tctgcttgac tctagatcca   5160
gagtcccgct cagaagaact cgtcaagaag gcgatagaag gcgatgcgct gcgaatcggg   5220
agcggcgata ccgtaaagca cgaggaagcg gtcagcccat tcgccgccaa gctcttcagc   5280
aatatcacgg gtagccaacg ctatgtcctg atagcggtcc gccacaccca gccggccaca   5340
gtcgatgaat ccagaaaagc ggccattttc caccatgata ttcggcaagc aggcatcgcc   5400
atgagtcacg acgagatcct cgccgtcggg catacgcgcc ttgagcctgg cgaacagttc   5460
ggctggcgcg agcccctgat gctcttcgtc cagatcatcc tgatcgacaa gaccggcttc   5520
catccgagta cgtgctcgct cgatgcgatg tttcgcttgg tggtcgaatg ggcaggtagc   5580
cggatcaagc gtatgcagcc gccgcattgc atcagccatg atggatactt tctcggcagg   5640
agcaaggtga gatgacagga gatcctgccc cggcacttcg cccaatagca gccagtccct   5700
tcccgcttca gtgacaacgt cgagcacagc tgcgcaagga acgcccgtcg tggccagcca   5760
cgatagccgc gctgcctcgt cctggagttc attcagggca ccggacaggt cggtcttgac   5820
aaaaagaacc gggcgcccct gcgctgacag ccggaacacg gcggcatcag agcagccgat   5880
tgtctgttgt gcccagtcat agccgaatag cctctccacc caagcggccg gagaacctgc   5940
gtgcaatcca tcttgttcaa tcatgcgaaa cgatccagat ccggtgcaga ttatttggat   6000
tgagagtgaa tatgagactc taattggata ccgaggggaa tttatggaac gtcagtggag   6060
catttttgac aagaaatatt tgctagctga tagtgacctt aggcgacttt tgaacgcgca   6120
ataatggttt ctgacgtatg tgcttagctc attaaactcc agaaacccgc ggctgagtgg   6180
ctccttcaac gttgcggttc tgtcagttcc aaacgtaaaa cggcttgtcc cgcgtcatcg   6240
gcgggggtca taacgtgact cccttaattc tccgctcatg gtacctcgaa gccgcggtgc   6300
gggtgccagg gcgtgccctt gggctccccg ggcgcgtact ccacctcacc catcttttat   6360
tacatgtttg aacttcaaca atttatgact tttgttctt attgttgcag gtaccatggc   6420
```

```
agaattcaca atgggatggt cttgtatcat ccttttcttg gttgcaacag ctactggtgt   6480
tcattctcaa gtgcaacttt tggagtctgg tgctgagctt gtgaggcctg gttcttcagt   6540
gaagatctct tgtaaagctt caggttatac atttacaaat tacgacatcc attgggtgaa   6600
gcaaaggcca ggtcaaggtc ttgagtggat tggatggata tacccaggtg atggttctac   6660
taagtacaac gagaaattta agggaaaagc aactcttaca gctgataagt cttcatcaac   6720
tgcatatatg cacttgtcat ctcttacttc tgaaaagtct gcagtttact tttgtgcaag   6780
agagtgggct tattggggac aaggtacaac tgtgacagtt tcaggttcaa cttcaggagg   6840
aggatcaggt ggtggttcag gaggtggagg atcttctgac atccaaatga cacaatctcc   6900
atcatcactt tcagcatcag ttggagatag agtgactatc acttgtagag cttcacaaga   6960
cattggtgga aatctttatt ggtaccaaca aaaaccagga aaagctccaa agttgttgat   7020
atacgcaact tcttctttgg actctggtgt tccatctaga ttttctggat caggatctgg   7080
aactgactac actttcacta tctcatctct tcaaccagag gacattgcta cttactattg   7140
cttgcaatac tcttcttctc catggacttt tggacaaggt acaaaagtgg aaatcaagag   7200
agctagcaga actgttgctg caccatctgt tttcatcttc cctccatctg atgagcagtt   7260
gaaatctgga actgcttctg ttgtgtgcct tcttaataac ttctatccta gagaggctaa   7320
agttcagtgg aaggtggata acgcacttca atctggtaac tctcaagagt ctgttacaga   7380
gcaagattct aaggactcaa cttactctct ttcatctaca cttactttgt caaaagcaga   7440
ttacgagaaa cacaaagttt acgcatgcga agttactcat caaggacttt cttcaccagt   7500
tacaaagtct ttcaatagag gagagtgtta aggatcc                            7537
```

<210> SEQ ID NO 75
<211> LENGTH: 7583
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
agcttgaaga ctaggcgtgg tgcgcacgat agcgcatagt gtttttctct ccacttgaat     60
cgaagagata gacttacggt gtaaatccgt aggggtggcg taaaccaaat tacgcaatgt    120
tttgggttcc atttaaatcg aaacccctta tttcctggat cacctgttaa cgcacgtttg    180
acgtgtatta cagtgggaat aagtaaaagt gagaggttcg aatcctccct aaccccgggt    240
aggggcccag cggccgctct agctagagtc aagcagatcg ttcaaacatt tggcaataaa    300
gtttcttaag attgaatcct gttgccggtc ttgcgatgat tatcatataa tttctgttga    360
attacgttaa gcatgtaata attaacatgt aatgcatgac gttatttatg agatgggttt    420
ttatgattag agtcccgcaa ttatacattt aatacgcgat agaaaacaaa atatagcgcg    480
caaactagga taaattatcg cgcgcggtgt catctatgtt actagatcga ccagtcctat    540
ggtagtcttc agcttagatc agattgtcgt ttcccgcctt cagtttaaac tatcagtgtt    600
tgacaggata tattggcggg taaacctaag agaaaagagc gtttattaga ataatcggat    660
atttaaaagg gcgtgaaaag gtttatccgt tcgtccattt gtatgtgcat gccaaccaca    720
gggttcccca gatcagtaaa gcgctggctg ctgaaccccc agccggaact gaccccacaa    780
ggccctagcg tttgcaatgc accaggtcat cattgaccca ggcgtgttcc accaggccgc    840
tgcctcgcaa ctcttcgcag gcttcgccga cctgctcgcg ccacttcttc acgcgggtgg    900
```

```
aatccgatcc gcacatgagg cggaaggttt ccagcttgag cgggtacggc tcccggtgcg    960
agctgaaata gtcgaacatc cgtcgggccg tcggcgacag cttgcggtac ttctcccata   1020
tgaatttcgt gtagtggtcg ccagcaaaca gcacgacgat ttcctcgtcg atcaggacct   1080
ggcaacggga cgttttcttg ccacggtcca ggacgcggaa gcggtgcagc agcgacaccg   1140
attccaggtg cccaacgcgg tcggacgtga agcccatcgc cgtcgcctgt aggcgcgaca   1200
ggcattcctc ggccttcgtg taataccggc cattgatcga ccagcccagg tcctggcaaa   1260
gctcgtagaa cgtgaaggtg atcggctcgc cgataggggt gcgcttcgcg tactccaaca   1320
cctgctgcca caccagttcg tcatcgtcgg cccgcagctc gacgccggtg taggtgatct   1380
tcacgtcctt gttgacgtgg aaaatgacct tgttttgcag cgcctcgcgc gggattttct   1440
tgttgcgcgt ggtgaacagg gcagagcggg ccgtgtcgtt tggcatcgct cgcatcgtgt   1500
ccggccacgg cgcaatatcg aacaaggaaa gctgcatttc cttgatctgc tgcttcgtgt   1560
gtttcagcaa cgcggcctgc ttggcctcgc tgacctgttt tgccaggtcc tcgccggcgg   1620
tttttcgctt cttggtcgtc atagttcctc gcgtgtcgat ggtcatcgac ttcgccaaac   1680
ctgccgcctc ctgttcgaga cgacgcgaac gctccacggc ggccgatggc gcgggcaggg   1740
cagggggagc cagttgcacg ctgtcgcgct cgatcttggc cgtagcttgc tggaccatcg   1800
agccgacgga ctggaaggtt tcgcggggcg cacgcatgac ggtgcggctt gcgatggttt   1860
cggcatcctc ggcggaaaac cccgcgtcga tcagttcttg cctgtatgcc ttccggtcaa   1920
acgtccgatt cattcaccct ccttgcggga ttgccccgac tcacgccggg gcaatgtgcc   1980
cttattcctg atttgacccg cctggtgcct tggtgtccag ataatccacc ttatcggcaa   2040
tgaagtcggt cccgtagacc gtctggccgt ccttctcgta cttggtattc cgaatcttgc   2100
cctgcacgaa taccagcgac cccttgccca aatacttgcc gtgggcctcg gcctgagagc   2160
caaaacactt gatgcggaag aagtcggtgc gctcctgctt gtcgccggca tcgttgcgcc   2220
acatctagga tctgccagga accgtaaaaa ggccgcgttg ctggcgtttt tccataggct   2280
ccgcccccct gacgagcatc acaaaaatcg acgctcaagt cagaggtggc gaaacccgac   2340
aggactataa agataccagg cgtttccccc tggaagctcc ctcgtgcgct ctcctgttcc   2400
gaccctgccg cttaccggat acctgtccgc ctttctccct tcgggaagcg tggcgctttc   2460
tcatagctca cgctgtaggt atctcagttc ggtgtaggtc gttcgctcca agctgggctg   2520
tgtgcacgaa ccccccgttc agcccgaccg ctgcgcctta tccggtaact atcgtcttga   2580
gtccaacccg gtaagacacg acttatcgcc actggcagca gccactggta acaggattag   2640
cagagcgagg tatgtaggcg gtgctacaga gttcttgaag tggtggccta actacggcta   2700
cactagaaga acagtatttg gtatctgcgc tctgctgaag ccagttacct tcggaaaaag   2760
agttggtagc tcttgatccg gcaaacaaac caccgctggt agcggtggtt tttttgtttg   2820
caagcagcag attacgcgca gaaaaaaagg atctcaagaa gatcctttga tcttttctac   2880
ggggtctgac gctcagtgga acgaaaactc acgttaaggg attttggtca tgagattatc   2940
aaaaaggatc ttcacctaga tccttttaaa ttaaaaatga agttttaaat caatctaaag   3000
tatatatgag taaacttggt ctgacagtta ccaatgctta atcagtgagg cacctatctc   3060
agcgatctgt ctatttcgtt catccatagt tgcctgactc cccgtcgtgt agataactac   3120
gatacgggag ggcttaccat ctggccccag tgctgcaatg ataccgcgag acccacgctc   3180
accggctcca gatttatcag caataaacca gccagccgga agggccgagc gcagaagtgg   3240
```

```
tcctgcaact ttatccgcct ccatccagtc tattaattgt tgccgggaag ctagagtaag   3300
tagttcgcca gttaatagtt tgcgcaacgt tgttgccatt gctacaggca tcgtggtgtc   3360
acgctcgtcg tttggtatgg cttcattcag ctccggttcc caacgatcaa ggcgagttac   3420
atgatccccc atgttgtgca aaaaagcggt tagctccttc ggtcctccga tcgttgtcag   3480
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatattat tgaagcattt atcagggtta ttgtctcatg agcggataca tatttgaatg   3960
tatttagaaa aataaacaaa taggggttcc gcgcacgaat tggccagcgc tgccattttt   4020
ggggtgaggc cgttcgcggc cgaggggcgc agcccctggg gggatgggag gcccgcgtta   4080
gcgggccggg agggttcgag aagggggggc acccccttc ggcgtgcgcg gtcacgcgca   4140
cagggcgcag ccctggttaa aaacaaggtt tataaatatt ggtttaaaag caggttaaaa   4200
gacaggttag cggtggccga aaaacgggcg gaaacccttg caaatgctgg attttctgcc   4260
tgtggacagc ccctcaaatg tcaataggtg cgcccctcat ctgtcagcac tctgcccctc   4320
aagtgtcaag gatcgcgccc ctcatctgtc agtagtcgcg cccctcaagt gtcaataccg   4380
cagggcactt atccccaggc ttgtccacat catctgtggg aaactcgcgt aaaatcaggc   4440
gttttcgccg atttgcgagg ctggccagct ccacgtcgcc ggccgaaatc gagcctgccc   4500
ctcatctgtc aacgccgcgc cgggtgagtc ggcccctcaa gtgtcaacgt ccgcccctca   4560
tctgtcagtg agggccaagt tttccgcgag gtatccacaa cgccggcggc cgcggtgtct   4620
cgcacacggc ttcgacggcg tttctggcgc gtttgcaggg ccatagacgg ccgccagccc   4680
agcggcgagg gcaaccagcc cggtgagcgt cgcaaaggag atcctgatct gactgatggg   4740
ctgcctgtat cgagtggtga ttttgtgccg agctgccggt cggggagctg ttggctggct   4800
ggtggcagga tatattgtgg tgtaaacaaa ttgacgctta gacaacttaa taacacattg   4860
cggacgtttt taatgtactg gggtggatgc aggtcgatct agtaacatag atgacaccgc   4920
gcgcgataat ttatcctagt ttgcgcgcta tattttgttt tctatcgcgt attaaatgta   4980
taattgcggg actctaatca taaaaaccca tctcataaat aacgtcatgc attacatgtt   5040
aattattaca tgcttaacgt aattcaacag aaattatatg ataatcatcg caagaccggc   5100
aacaggattc aatcttaaga aactttattg ccaaatgttt gaacgatctg cttgactcta   5160
gatccagagt cccgctcaga agaactcgtc aagaaggcga tagaaggcga tgcgctgcga   5220
atcgggagcg gcgataccgt aaagcacgag gaagcggtca gcccattcgc cgccaagctc   5280
ttcagcaata tcacgggtag ccaacgctat gtcctgatag cggtccgcca cacccagccg   5340
gccacagtcg atgaatccag aaaagcggcc attttccacc atgatattcg gcaagcaggc   5400
atcgccatga gtcacgacga gatcctcgcc gtcgggcata cgcgccttga gcctggcgaa   5460
cagttcggct ggcgcgagcc cctgatgctc ttcgtccaga tcatcctgat cgacaagacc   5520
ggcttccatc cgagtacgtg ctcgctcgat gcgatgtttc gcttggtggt cgaatgggca   5580
ggtagccgga tcaagcgtat gcagccgccg cattgcatca gccatgatgg atactttctc   5640
```

```
ggcaggagca aggtgagatg acaggagatc ctgccccggc acttcgccca atagcagcca   5700

gtcccttccc gcttcagtga caacgtcgag cacagctgcg caaggaacgc ccgtcgtggc   5760

cagccacgat agccgcgctg cctcgtcctg gagttcattc agggcaccgg acaggtcggt   5820

cttgacaaaa agaaccgggc gcccctgcgc tgacagccgg aacacggcgg catcagagca   5880

gccgattgtc tgttgtgccc agtcatagcc gaatagcctc tccacccaag cggccggaga   5940

acctgcgtgc aatccatctt gttcaatcat gcgaaacgat ccagatccgg tgcagattat   6000

ttggattgag agtgaatatg agactctaat tggataccga ggggaattta tggaacgtca   6060

gtggagcatt tttgacaaga aatatttgct agctgatagt gaccttaggc gacttttgaa   6120

cgcgcaataa tggtttctga cgtatgtgct tagctcatta aactccagaa acccgcggct   6180

gagtggctcc ttcaacgttg cggttctgtc agttccaaac gtaaaacggc ttgtcccgcg   6240

tcatcggcgg gggtcataac gtgactccct taattctccg ctcatggtac ctcgaagccg   6300

cggtgcgggt gccagggcgt gcccttgggc tccccgggcg cgtactccac ctcacccatc   6360

ttttattaca tgtttgaact tcaacaattt atgacttttt gttcttattg ttgcaggtag   6420

agaccgaatt cacaatggga tggtcttgta tcatcctttt cttggttgca acagctactg   6480

gtgttcattc tcaagtgcaa cttttggagt ctggtgctga gcttgtgagg cctggttctt   6540

cagtgaagat ctcttgtaaa gcttcaggtt atacatttac aaattacgac atccattggg   6600

tgaagcaaag gccaggtcaa ggtcttgagt ggattggatg gatataccca ggtgatggtt   6660

ctactaagta caacgagaaa tttaagggaa aagcaactct tacagctgat aagtcttcat   6720

caactgcata tatgcacttg tcatctctta cttctgaaaa gtctgcagtt tacttttgtg   6780

caagagagtg ggcttattgg ggacaaggta caactgtgac agtttcaggt tcaacttcag   6840

gaggaggatc aggtggtggt tcaggaggtg gaggatcttc tgacatccaa atgacacaat   6900

ctccatcatc actttcagca tcagttggag atagagtgac tatcacttgt agagcttcac   6960

aagacattgg tggaaatctt tattggtacc aacaaaaacc aggaaaagct ccaaagttgt   7020

tgatatacgc aacttcttct ttggactctg gtgttccatc tagattttct ggatcaggat   7080

ctggaactga ctacactttc actatctcat ctcttcaacc agaggacatt gctacttact   7140

attgcttgca atactcttct tctccatgga cttttggaca aggtacaaaa gtggaaatca   7200

agagagctag cagaactgtt gctgcaccat ctgttttcat cttccctcca tctgatgagc   7260

agttgaaatc tggaactgct tctgttgtgt gccttcttaa taacttctat cctagagagg   7320

ctaaagttca gtggaaggtg gataacgcac ttcaatctgg taactctcaa gagtctgtta   7380

cagagcaaga ttctaaggac tcaacttact ctctttcatc tacacttact ttgtcaaaag   7440

cagattacga gaaacacaaa gtttacgcat gcgaagttac tcatcaagga ctttcttcac   7500

cagttacaaa gtctttcaat agaggagagt gttaaggatc ctctagagtc gacctgcaga   7560

agctggcagc taggatgggt ctc                                           7583
```

```
<210> SEQ ID NO 76
<211> LENGTH: 872
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

tggatccgcc accatgggat ggagctgtat catcctcttc ttggtagcaa cagctacagg     60
```

```
taaggggctc acagtagcag gcttgaggtc tggacatata tatgggtgac aatgacatcc    120

actttgcctt tctctccaca ggtgtccact cccaagtgca gctgctcgag tctggggctg    180

agctggtgag gcctgggtcc tcagtgaaga tttcctgcaa ggcttctggt tacaccttca    240

caaactacga tatacactgg gtgaagcaga ggcctggaca gggtcttgag tggattggat    300

ggatttatcc tggagatggt agtactaagt acaatgagaa attcaagggc aaggccacac    360

tgactgcaga caaatcctcc agcacagcct acatgcacct cagcagcctg acttctgaga    420

aatctgcagt ctatttctgt gcaagagagt gggcttactg gggacaaggg accacagtca    480

ccgtctctgg cagcaccagc ggcggaggct ccggcggagg cagcggcgga ggcgggagct    540

ccgacatcca gatgacccag agcccaagca gcctgagcgc cagcgtgggt gacagagtga    600

ccattacttg tcgggctagt caggacattg gaggaaactt atattggtac caacaaaagc    660

caggtaaagc tccaaagtta ctgatctacg ccacatctag tttagattct ggtgtgccaa    720

gcagattcag tggtagtggt agcggtaccg actacacctt caccatcagc agcttacagc    780

cagaggacat cgccacctac tattgcctac agtattctag ttctccatgg acgttcggac    840

aagggaccaa ggtggaaatc aaaagggcta gc                                  872
```

<210> SEQ ID NO 77
<211> LENGTH: 1867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
tggatccgcc accatgggat ggagctgtat catcctcttc ttggtagcaa cagctacagg     60

taaggggctc acagtagcag gcttgaggtc tggacatata tatgggtgac aatgacatcc    120

actttgcctt tctctccaca ggtgtccact cccaagtgca gctgctcgag tctggggctg    180

agctggtgag gcctgggtcc tcagtgaaga tttcctgcaa ggcttctggt tacaccttca    240

caaactacga tatacactgg gtgaagcaga ggcctggaca gggtcttgag tggattggat    300

ggatttatcc tggagatggt agtactaagt acaatgagaa attcaagggc aaggccacac    360

tgactgcaga caaatcctcc agcacagcct acatgcacct cagcagcctg acttctgaga    420

aatctgcagt ctatttctgt gcaagagagt gggcttactg gggacaaggg accacagtca    480

ccgtctctgg cagcaccagc ggcggaggct ccggcggagg cagcggcgga ggcgggagct    540

ccgacatcca gatgacccag agcccaagca gcctgagcgc cagcgtgggt gacagagtga    600

ccattacttg tcgggctagt caggacattg gaggaaactt atattggtac caacaaaagc    660

caggtaaagc tccaaagtta ctgatctacg ccacatctag tttagattct ggtgtgccaa    720

gcagattcag tggtagtggt agcggtaccg actacacctt caccatcagc agcttacagc    780

cagaggacat cgccacctac tattgcctac agtattctag ttctccatgg acgttcggac    840

aagggaccaa ggtggaaatc aaaagggcta gcaccaaggg cccatcggtc ttccccctgg    900

caccctcctc caagagcacc tctgggggca cagcggccct gggctgcctg gtcaaggact    960

acttccccga accggtgacg gtgtcgtgga actcaggcgc cctgaccagc ggcgtgcaca   1020

ccttcccggc tgtcctacag tcctcaggac tctactccct cagcagcgtg gtgaccgtgc   1080

cctccagcag cttgggcacc cagacctaca tctgcaacgt gaatcacaag cccagcaaca   1140

ccaaggtgga caagagagtt gagcccaaat cttgtgacaa aactcacaca tgcccaccgt   1200
```

gcccagcacc tgaactcctg gggggaccgt cagtcttcct cttcccccca aaacccaagg 1260
acaccctcat gatctcccgg acccctgagg tcacatgcgt ggtggtggac gtgagccacg 1320
aagaccctga ggtcaagttc aactggtacg tggacggcgt ggaggtgcat aatgccaaga 1380
caaagccgcg ggaggagcag tacaacagca cgtaccgtgt ggtcagcgtc ctcaccgtcc 1440
tgcaccagga ctggctgaat ggcaaggagt acaagtgcaa ggtctccaac aaagccctcc 1500
cagcccccat cgagaaaacc atctccaaag ccaaagggca gccccgagaa ccacaggtgt 1560
acaccctgcc cccatcccgg gatgagctga ccaagaacca ggtcagcctg acctgcctgg 1620
tcaaaggctt ctatcccagc gacatcgccg tggagtggga gagcaatggg cagccggaga 1680
acaactacaa gaccacgcct cccgtgctgg actccgacgg ctccttcttc ctctacagca 1740
agctcaccgt ggacaagagc aggtggcagc aggggaacgt cttctcatgc tccgtgatgc 1800
atgaggctct gcacaaccac tacacgcaga agagcctctc cctgtctccg ggtaaatgag 1860
cggccgc 1867

<210> SEQ ID NO 78
<211> LENGTH: 6824
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccgccacc atgggatgga gctgtatcat 960
cctcttcttg gtagcaacag ctacaggtaa ggggctcaca gtagcaggct tgaggtctgg 1020
acatatatat gggtgacaat gacatccact ttgcctttct ctccacaggt gtccactccc 1080
aagtgcagct gctcgagtct ggggctgagc tggtgaggcc tgggtcctca gtgaagattt 1140
cctgcaaggc ttctggttac accttcacaa actacgatat acactgggtg aagcagaggc 1200
ctggacaggg tcttgagtgg attggatgga tttatcctgg agatggtagt actaagtaca 1260
atgagaaatt caagggcaag gccacactga ctgcagacaa atcctccagc acagcctaca 1320

```
tgcacctcag cagcctgact tctgagaaat ctgcagtcta tttctgtgca agagagtggg   1380
cttactgggg acaagggacc acagtcaccg tctctggcag caccagcggc ggaggctccg   1440
gcggaggcag cggcggaggc gggagctccg acatccagat gacccagagc ccaagcagcc   1500
tgagcgccag cgtgggtgac agagtgacca ttacttgtcg ggctagtcag gacattggag   1560
gaaacttata ttggtaccaa caaaagccag gtaaagctcc aaagttactg atctacgcca   1620
catctagttt agattctggt gtgccaagca gattcagtgg tagtggtagc ggtaccgact   1680
acaccttcac catcagcagc ttacagccag aggacatcgc cacctactat tgcctacagt   1740
attctagttc tccatggacg ttcggacaag ggaccaaggt ggaaatcaaa agggctagca   1800
ccaagggccc atcggtcttc cccctggcac cctcctccaa gagcacctct gggggcacag   1860
cggccctggg ctgcctggtc aaggactact tccccgaacc ggtgacggtg tcgtggaact   1920
caggcgccct gaccagcggc gtgcacacct tcccggctgt cctacagtcc tcaggactct   1980
actccctcag cagcgtggtg accgtgccct ccagcagctt gggcacccag acctacatct   2040
gcaacgtgaa tcacaagccc agcaacacca aggtggacaa gagagttgag cccaaatctt   2100
gtgacaaaac tcacacatgc ccaccgtgcc cagcacctga actcctgggg ggaccgtcag   2160
tcttcctctt ccccccaaaa cccaaggaca ccctcatgat ctcccggacc cctgaggtca   2220
catgcgtggt ggtggacgtg agccacgaag accctgaggt caagttcaac tggtacgtgg   2280
acggcgtgga ggtgcataat gccaagacaa agccgcggga ggagcagtac aacagcacgt   2340
accgtgtggt cagcgtcctc accgtcctgc accaggactg gctgaatggc aaggagtaca   2400
agtgcaaggt ctccaacaaa gccctcccag cccccatcga gaaaaccatc tccaaagcca   2460
aagggcagcc ccgagaacca caggtgtaca ccctgccccc atcccgggat gagctgacca   2520
agaaccaggt cagcctgacc tgcctggtca aaggcttcta tcccagcgac atcgccgtgg   2580
agtgggagag caatgggcag ccggagaaca actacaagac cacgcctccc gtgctggact   2640
ccgacggctc cttcttcctc tacagcaagc tcaccgtgga caagagcagg tggcagcagg   2700
ggaacgtctt ctcatgctcc gtgatgcatg aggctctgca caaccactac acgcagaaga   2760
gcctctccct gtctccgggt aaatgagcgg ccgctcgagt ctagagggcc cgtttaaacc   2820
cgctgatcag cctcgactgt gccttctagt tgccagccat ctgttgtttg cccctccccc   2880
gtgccttcct tgaccctgga aggtgccact cccactgtcc tttcctaata aaatgaggaa   2940
attgcatcgc attgtctgag taggtgtcat tctattctgg ggggtggggt ggggcaggac   3000
agcaaggggg aggattggga agacaatagc aggcatgctg gggatgcggt gggctctatg   3060
gcttctgagg cggaaagaac cagctggggc tctagggggt atccccacgc gccctgtagc   3120
ggcgcattaa gcgcggcggg tgtggtggtt acgcgcagcg tgaccgctac acttgccagc   3180
gccctagcgc ccgctccttt cgctttcttc ccttcctttc tcgccacgtt cgccggcttt   3240
ccccgtcaag ctctaaatcg ggcatccct ttagggttcc gatttagtgc tttacggcac   3300
ctcgacccca aaaaacttga ttagggtgat ggttcacgta gtgggccatc gccctgatag   3360
acggtttttc gccctttgac gttggagtcc acgttcttta atagtggact cttgttccaa   3420
actggaacaa cactcaaccc tatctcggtc tattcttttg atttataagg gattttgggg   3480
atttcggcct attggttaaa aaatgagctg atttaacaaa aatttaacgc gaattaattc   3540
tgtggaatgt gtgtcagtta gggtgtggaa agtccccagg ctccccaggc aggcagaagt   3600
atgcaaagca tgcatctcaa ttagtcagca accaggtgtg gaaagtcccc aggctcccca   3660
```

```
gcaggcagaa gtatgcaaag catgcatctc aattagtcag caaccatagt cccgccccta   3720
actccgccca tcccgcccct aactccgccc agttccgccc attctccgcc ccatggctga   3780
ctaatttttt ttatttatgc agaggccgag gccgcctctg cctctgagct attccagaag   3840
tagtgaggag gcttttttgg aggcctaggc ttttgcaaaa agctcccggg agcttgtata   3900
tccattttcg gatctgatca gcacgtgttg acaattaatc atcggcatag tatatcggca   3960
tagtataata cgacaaggtg aggaactaaa ccatggccaa gttgaccagt gccgttccgg   4020
tgctcaccgc gcgcgacgtc gccggagcgg tcgagttctg gaccgaccgg ctcgggttct   4080
cccgggactt cgtggaggac gacttcgccg gtgtggtccg ggacgacgtg accctgttca   4140
tcagcgcggt ccaggaccag gtggtgccgg acaacaccct ggcctgggtg tgggtgcgcg   4200
gcctggacga gctgtacgcc gagtggtcgg aggtcgtgtc cacgaacttc cgggacgcct   4260
ccgggccggc catgaccgag atcggcgagc agccgtgggg gcgggagttc gccctgcgcg   4320
acccggccgg caactgcgtg cacttcgtgg ccgaggagca ggactgacac gtgctacgag   4380
atttcgattc caccgccgcc ttctatgaaa ggttgggctt cggaatcgtt ttccgggacg   4440
ccggctggat gatcctccag cgcggggatc tcatgctgga gttcttcgcc caccccaact   4500
tgtttattgc agcttataat ggttacaaat aaagcaatag catcacaaat ttcacaaata   4560
aagcattttt ttcactgcat tctagttgtg gtttgtccaa actcatcaat gtatcttatc   4620
atgtctgtat accgtcgacc tctagctaga gcttggcgta atcatggtca tagctgtttc   4680
ctgtgtgaaa ttgttatccg ctcacaattc cacacaacat acgagccgga agcataaagt   4740
gtaaagcctg gggtgcctaa tgagtgagct aactcacatt aattgcgttg cgctcactgc   4800
ccgctttcca gtcgggaaac ctgtcgtgcc agctgcatta atgaatcggc caacgcgcgg   4860
ggagaggcgg tttgcgtatt gggcgctctt ccgcttcctc gctcactgac tcgctgcgct   4920
cggtcgttcg gctgcggcga gcggtatcag ctcactcaaa ggcggtaata cggttatcca   4980
cagaatcagg ggataacgca ggaaagaaca tgtgagcaaa aggccagcaa aaggccagga   5040
accgtaaaaa ggccgcgttg ctggcgtttt tccataggct ccgcccccct gacgagcatc   5100
acaaaaatcg acgctcaagt cagaggtggc gaaacccgac aggactataa agataccagg   5160
cgtttccccc tggaagctcc ctcgtgcgct ctcctgttcc gaccctgccg cttaccggat   5220
acctgtccgc ctttctccct tcgggaagcg tggcgctttc tcaatgctca cgctgtaggt   5280
atctcagttc ggtgtaggtc gttcgctcca agctgggctg tgtgcacgaa ccccccgttc   5340
agcccgaccg ctgcgcctta tccggtaact atcgtcttga gtccaacccg gtaagacacg   5400
acttatcgcc actggcagca gccactggta acaggattag cagagcgagg tatgtaggcg   5460
gtgctacaga gttcttgaag tggtggccta actacggcta cactagaagg acagtatttg   5520
gtatctgcgc tctgctgaag ccagttacct tcggaaaaag agttggtagc tcttgatccg   5580
gcaaacaaac caccgctggt agcggtggtt tttttgtttg caagcagcag attacgcgca   5640
gaaaaaaagg atctcaagaa gatcctttga tcttttctac ggggtctgac gctcagtgga   5700
acgaaaactc acgttaaggg attttggtca tgagattatc aaaaaggatc ttcacctaga   5760
tccttttaaa ttaaaaatga agttttaaat caatctaaag tatatatgag taaacttggt   5820
ctgacagtta ccaatgctta atcagtgagg cacctatctc agcgatctgt ctatttcgtt   5880
catccatagt tgcctgactc cccgtcgtgt agataactac gatacgggag ggcttaccat   5940
ctggccccag tgctgcaatg ataccgcgag acccacgctc accggctcca gatttatcag   6000
caataaacca gccagccgga agggccgagc gcagaagtgg tcctgcaact ttatccgcct   6060
```

ccatccagtc tattaattgt tgccgggaag ctagagtaag tagttcgcca gttaatagtt 6120
tgcgcaacgt tgttgccatt gctacaggca tcgtggtgtc acgctcgtcg tttggtatgg 6180
cttcattcag ctccggttcc caacgatcaa ggcgagttac atgatccccc atgttgtgca 6240
aaaaagcggt tagctccttc ggtcctccga tcgttgtcag aagtaagttg gccgcagtgt 6300
tatcactcat ggttatggca gcactgcata attctcttac tgtcatgcca tccgtaagat 6360
gcttttctgt gactggtgag tactcaacca agtcattctg agaatagtgt atgcggcgac 6420
cgagttgctc ttgcccggcg tcaatacggg ataataccgc gccacatagc agaactttaa 6480
aagtgctcat cattggaaaa cgttcttcgg ggcgaaaact ctcaaggatc ttaccgctgt 6540
tgagatccag ttcgatgtaa cccactcgtg cacccaactg atcttcagca tcttttactt 6600
tcaccagcgt ttctgggtga gcaaaaacag gaaggcaaaa tgccgcaaaa aagggaataa 6660
gggcgacacg gaaatgttga atactcatac tcttcctttt tcaatattat tgaagcattt 6720
atcagggtta ttgtctcatg agcggataca tatttgaatg tatttagaaa aataaacaaa 6780
taggggttcc gcgcacattt ccccgaaaag tgccacctga cgtc 6824

<210> SEQ ID NO 79
<211> LENGTH: 7406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccgccacc atgggatgga gctgtatcat 960
cctcttcttg gtagcaacag ctacaggtaa ggggctcaca gtagcaggct tgaggtctgg 1020
acatatatat gggtgacaat gacatccact ttgcctttct ctccacaggt gtccactccc 1080
aagtgcagct gctcgagtct ggggctgagc tggtgaggcc tgggtcctca gtgaagattt 1140
cctgcaaggc ttctggttac accttcacaa actacgatat acactgggtg aagcagaggc 1200
ctggacaggg tcttgagtgg attggatgga tttatcctgg agatggtagt actaagtaca 1260

```
atgagaaatt caagggcaag gccacactga ctgcagacaa atcctccagc acagcctaca   1320

tgcacctcag cagcctgact tctgagaaat ctgcagtcta tttctgtgca agagagtggg   1380

cttactgggg acaagggacc acagtcaccg tctctggcag caccagcggc ggaggctccg   1440

gcggaggcag cggcggaggc gggagctccg acatccagat gacccagagc ccaagcagcc   1500

tgagcgccag cgtgggtgac agagtgacca ttacttgtcg ggctagtcag gacattggag   1560

gaaacttata ttggtaccaa caaaagccag gtaaagctcc aaagttactg atctacgcca   1620

catctagttt agattctggt gtgccaagca gattcagtgg tagtggtagc ggtaccgact   1680

acaccttcac catcagcagc ttacagccag aggacatcgc cacctactat tgcctacagt   1740

attctagttc tccatggacg ttcggacaag ggaccaaggt ggaaatcaaa agggctagca   1800

ccaagggccc atcggtcttc cccctggcac cctcctccaa gagcacctct gggggcacag   1860

cggccctggg ctgcctggtc aaggactact tccccgaacc ggtgacggtg tcgtggaact   1920

caggcgccct gaccagcggc gtgcacacct tcccggctgt cctacagtcc tcaggactct   1980

actccctcag cagcgtggtg accgtgccct ccagcagctt gggcacccag acctacatct   2040

gcaacgtgaa tcacaagccc agcaacacca aggtggacaa gagagttgag cccaaatctt   2100

gtgacaaaac tcacacatgc ccaccgtgcc cagcacctga actcctgggg ggaccgtcag   2160

tcttcctctt ccccccaaaa cccaaggaca ccctcatgat ctcccggacc cctgaggtca   2220

catgcgtggt ggtggacgtg agccacgaag accctgaggt caagttcaac tggtacgtgg   2280

acggcgtgga ggtgcataat gccaagacaa agccgcggga ggagcagtac aacagcacgt   2340

accgtgtggt cagcgtcctc accgtcctgc accaggactg gctgaatggc aaggagtaca   2400

agtgcaaggt ctccaacaaa gccctcccag cccccatcga gaaaaccatc tccaaagcca   2460

aagggcagcc ccgagaacca caggtgtaca ccctgccccc atcccgggat gagctgacca   2520

agaaccaggt cagcctgacc tgcctggtca aaggcttcta tcccagcgac atcgccgtgg   2580

agtgggagag caatgggcag ccggagaaca actacaagac cacgcctccc gtgctggact   2640

ccgacggctc cttcttcctc tacagcaagc tcaccgtgga caagagcagg tggcagcagg   2700

ggaacgtctt ctcatgctcc gtgatgcatg aggctctgca caaccactac acgcagaaga   2760

gcctctccct gtctccgggt aaatgagcgg ccgctcgagt ctagagggcc cgtttaaacc   2820

cgctgatcag cctcgactgt gccttctagt tgccagccat ctgttgtttg cccctccccc   2880

gtgccttcct tgaccctgga aggtgccact cccactgtcc tttcctaata aaatgaggaa   2940

attgcatcgc attgtctgag taggtgtcat tctattctgg ggggtggggt ggggcaggac   3000

agcaaggggg aggattggga agacaatagc aggcatgctg gggatgcggt gggctctatg   3060

gcttctgagg cggaaagaac cagctggggc tctagggggt atccccacgc gccctgtagc   3120

ggcgcattaa gcgcggcggg tgtggtggtt acgcgcagcg tgaccgctac acttgccagc   3180

gccctagcgc ccgctccttt cgctttcttc ccttcctttc tcgccacgtt cgccggcttt   3240

ccccgtcaag ctctaaatcg ggggctccct ttagggttcc gatttagtgc tttacggcac   3300

ctcgacccca aaaaacttga ttagggtgat ggttcacgta gtgggccatc gccctgatag   3360

acggtttttc gccctttgac gttggagtcc acgttcttta atagtggact cttgttccaa   3420

actggaacaa cactcaaccc tatctcggtc tattcttttg atttataagg gattttgccg   3480

atttcggcct attggttaaa aaatgagctg atttaacaaa aatttaacgc gaattaattc   3540

tgtggaatgt gtgtcagtta gggtgtggaa agtccccagg ctccccagca ggcagaagta   3600
```

```
tgcaaagcat gcatctcaat tagtcagcaa ccaggtgtgg aaagtcccca ggctccccag   3660

caggcagaag tatgcaaagc atgcatctca attagtcagc aaccatagtc ccgcccctaa   3720

ctccgcccat cccgccccta actccgccca gttccgccca ttctccgccc catggctgac   3780

taattttttt tatttatgca gaggccgagg ccgcctctgc ctctgagcta ttccagaagt   3840

agtgaggagg cttttttgga ggcctaggct tttgcaaaaa gctcccggga gcttgtatat   3900

ccattttcgg atctgatcag cacgtgatga aaaagcctga actcaccgcg acgtctgtcg   3960

agaagtttct gatcgaaaag ttcgacagcg tctccgacct gatgcagctc tcggagggcg   4020

aagaatctcg tgctttcagc ttcgatgtag gagggcgtgg atatgtcctg cgggtaaata   4080

gctgcgccga tggtttctac aaagatcgtt atgtttatcg gcactttgca tcggccgcgc   4140

tcccgattcc ggaagtgctt gacattgggg aattcagcga gagcctgacc tattgcatct   4200

cccgccgtgc acagggtgtc acgttgcaag acctgcctga aaccgaactg cccgctgttc   4260

tgcagccggt cgcggaggcc atggatgcga tcgctgcggc cgatcttagc cagacgagcg   4320

ggttcggccc attcggaccg caaggaatcg gtcaatacac tacatggcgt gatttcatat   4380

gcgcgattgc tgatccccat gtgtatcact ggcaaactgt gatggacgac accgtcagtg   4440

cgtccgtcgc gcaggctctc gatgagctga tgctttgggc cgaggactgc cccgaagtcc   4500

ggcacctcgt gcacgcggat ttcggctcca acaatgtcct gacggacaat ggccgcataa   4560

cagcggtcat tgactggagc gaggcgatgt tcggggattc ccaatacgag gtcgccaaca   4620

tcttcttctg gaggccgtgg ttggcttgta tggagcagca gacgcgctac ttcgagcgga   4680

ggcatccgga gcttgcagga tcgccgcggc tccgggcgta tatgctccgc attggtcttg   4740

accaactcta tcagagcttg gttgacggca atttcgatga tgcagcttgg gcgcagggtc   4800

gatgcgacgc aatcgtccga tccggagccg ggactgtcgg gcgtacacaa atcgcccgca   4860

gaagcgcggc cgtctggacc gatggctgtg tagaagtact cgccgatagt ggaaaccgac   4920

gccccagcac tcgtccgagg gcaaaggaat agcacgtgct acgagatttc gattccaccg   4980

ccgccttcta tgaaaggttg ggcttcggaa tcgttttccg ggacgccggc tggatgatcc   5040

tccagcgcgg ggatctcatg ctggagttct tcgcccaccc caacttgttt attgcagctt   5100

ataatggtta caaataaagc aatagcatca caaatttcac aaataaagca tttttttcac   5160

tgcattctag ttgtggtttg tccaaactca tcaatgtatc ttatcatgtc tgtataccgt   5220

cgacctctag ctagagcttg gcgtaatcat ggtcatagct gtttcctgtg tgaaattgtt   5280

atccgctcac aattccacac aacatacgag ccggaagcat aaagtgtaaa gcctggggtg   5340

cctaatgagt gagctaactc acattaattg cgttgcgctc actgcccgct ttccagtcgg   5400

gaaacctgtc gtgccagctg cattaatgaa tcggccaacg cgcggggaga ggcggtttgc   5460

gtattgggcg ctcttccgct tcctcgctca ctgactcgct gcgctcggtc gttcggctgc   5520

ggcgagcggt atcagctcac tcaaaggcgg taatacggtt atccacagaa tcaggggata   5580

acgcaggaaa gaacatgtga gcaaaaggcc agcaaaaggc caggaaccgt aaaaaggccg   5640

cgttgctggc gtttttccat aggctccgcc cccctgacga gcatcacaaa aatcgacgct   5700

caagtcagag gtggcgaaac ccgacaggac tataaagata ccaggcgttt ccccctggaa   5760

gctccctcgt gcgctctcct gttccgaccc tgccgcttac cggatacctg tccgcctttc   5820

tcccttcggg aagcgtggcg ctttctcata gctcacgctg taggtatctc agttcggtgt   5880

aggtcgttcg ctccaagctg ggctgtgtgc acgaaccccc cgttcagccc gaccgctgcg   5940

ccttatccgg taactatcgt cttgagtcca acccggtaag acacgactta tcgccactgg   6000
```

cagcagccac tggtaacagg attagcagag cgaggtatgt aggcggtgct acagagttct 6060
tgaagtggtg gcctaactac ggctacacta gaagaacagt atttggtatc tgcgctctgc 6120
tgaagccagt taccttcgga aaaagagttg gtagctcttg atccggcaaa caaaccaccg 6180
ctggtagcgg tttttttgtt tgcaagcagc agattacgcg cagaaaaaaa ggatctcaag 6240
aagatccttt gatcttttct acggggtctg acgctcagtg gaacgaaaac tcacgttaag 6300
ggattttggt catgagatta tcaaaaagga tcttcaccta gatcctttta aattaaaaat 6360
gaagttttaa atcaatctaa agtatatatg agtaaacttg gtctgacagt taccaatgct 6420
taatcagtga ggcacctatc tcagcgatct gtctatttcg ttcatccata gttgcctgac 6480
tccccgtcgt gtagataact acgatacggg agggcttacc atctggcccc agtgctgcaa 6540
tgataccgcg agacccacgc tcaccggctc cagatttatc agcaataaac cagccagccg 6600
gaagggccga gcgcagaagt ggtcctgcaa ctttatccgc ctccatccag tctattaatt 6660
gttgccggga agctagagta agtagttcgc cagttaatag tttgcgcaac gttgttgcca 6720
ttgctacagg catcgtggtg tcacgctcgt cgtttggtat ggcttcattc agctccggtt 6780
cccaacgatc aaggcgagtt acatgatccc ccatgttgtg caaaaaagcg gttagctcct 6840
tcggtcctcc gatcgttgtc agaagtaagt tggccgcagt gttatcactc atggttatgg 6900
cagcactgca taattctctt actgtcatgc catccgtaag atgcttttct gtgactggtg 6960
agtactcaac caagtcattc tgagaatagt gtatgcggcg accgagttgc tcttgcccgg 7020
cgtcaatacg ggataatacc gcgccacata gcagaacttt aaaagtgctc atcattggaa 7080
aacgttcttc ggggcgaaaa ctctcaagga tcttaccgct gttgagatcc agttcgatgt 7140
aacccactcg tgcacccaac tgatcttcag catcttttac tttcaccagc gtttctgggt 7200
gagcaaaaac aggaaggcaa aatgccgcaa aaaagggaat aagggcgaca cggaaatgtt 7260
gaatactcat actcttcctt tttcaatatt attgaagcat ttatcagggt tattgtctca 7320
tgagcggata catatttgaa tgtatttaga aaaataaaca aataggggtt ccgcgcacat 7380
ttccccgaaa agtgccacct gacgtc 7406

<210> SEQ ID NO 80
<211> LENGTH: 1198
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 80
tggatccgcc accatgggat ggagctgtat catcctcttc ttggtagcaa cagctacagg 60
taaggggctc acagtagcag gcttgaggtc tggacatata tatgggtgac aatgacatcc 120
actttgcctt tctctccaca ggtgtccact cccaagtgca gctgctcgag tctggggctg 180
agctggtgag gcctgggtcc tcagtgaaga tttcctgcaa ggcttctggt tacaccttca 240
caaactacga tatacactgg gtgaagcaga ggcctggaca gggtcttgag tggattggat 300
ggatttatcc tggagatggt agtactaagt acaatgagaa attcaagggc aaggccacac 360
tgactgcaga caaatcctcc agcacagcct acatgcacct cagcagcctg acttctgaga 420
aatctgcagt ctatttctgt gcaagagagt gggcttactg gggacaaggg accacagtca 480
ccgtctctgg cagcaccagc ggcggaggct ccggcggagg cagcggcgga ggcgggagct 540
ccgacatcca gatgacccag agcccaagca gcctgagcgc cagcgtgggt gacagagtga 600

```
ccattacttg tcgggctagt caggacattg gaggaaactt atattggtac caacaaaagc    660

caggtaaagc tccaaagtta ctgatctacg ccacatctag tttagattct ggtgtgccaa    720

gcagattcag tggtagtggt agcggtaccg actacacctt caccatcagc agcttacagc    780

cagaggacat cgccacctac tattgcctac agtattctag ttctccatgg acgttcggac    840

aagggaccaa ggtggaaatc aaaagggcta gcgtggctgc accatctgtc ttcatcttcc    900

cgccatctga tgagcagttg aaatctggaa ctgcctctgt tgtgtgcctg ctgaataact    960

tctatcccag agaggccaaa gtacagtgga aggtggataa cgccctccaa tcgggtaact   1020

cccaggagag tgtcacagag caggacagca aggacagcac ctacagcctc agcagcaccc   1080

tgacgctgag caaagcagac tacgagaaac acaaagtcta cgcctgcgaa gtcacccatc   1140

agggcctgag ctcgcccgtc acaaagagct tcaacagggg agagtgttag gcggccgc     1198
```

```
<210> SEQ ID NO 81
<211> LENGTH: 6155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
```

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccgccacc atgggatgga gctgtatcat    960

cctcttcttg gtagcaacag ctacaggtaa ggggctcaca gtagcaggct tgaggtctgg   1020

acatatatat gggtgacaat gacatccact ttgcctttct ctccacaggt gtccactccc   1080

aagtgcagct gctcgagtct ggggctgagc tggtgaggcc tgggtcctca gtgaagattt   1140

cctgcaaggc ttctggttac accttcacaa actacgatat acactgggtg aagcagaggc   1200

ctggacaggg tcttgagtgg attggatgga tttatcctgg agatggtagt actaagtaca   1260

atgagaaatt caagggcaag gccacactga ctgcagacaa atcctccagc acagcctaca   1320

tgcacctcag cagcctgact tctgagaaat ctgcagtcta tttctgtgca agagagtggg   1380

cttactgggg acaagggacc acagtcaccg tctctggcag caccagcggc ggaggctccg   1440
```

```
gcggaggcag cggcggaggc gggagctccg acatccagat gacccagagc ccaagcagcc   1500
tgagcgccag cgtgggtgac agagtgacca ttacttgtcg ggctagtcag gacattggag   1560
gaaacttata ttggtaccaa caaaagccag gtaaagctcc aaagttactg atctacgcca   1620
catctagttt agattctggt gtgccaagca gattcagtgg tagtggtagc ggtaccgact   1680
acaccttcac catcagcagc ttacagccag aggacatcgc cacctactat tgcctacagt   1740
attctagttc tccatggacg ttcggacaag ggaccaaggt ggaaatcaaa agggctagcg   1800
tggctgcacc atctgtcttc atcttcccgc catctgatga gcagttgaaa tctggaactg   1860
cctctgttgt gtgcctgctg aataacttct atcccagaga ggccaaagta cagtggaagg   1920
tggataacgc cctccaatcg ggtaactccc aggagagtgt cacagagcag gacagcaagg   1980
acagcaccta cagcctcagc agcaccctga cgctgagcaa agcagactac gagaaacaca   2040
aagtctacgc ctgcgaagtc acccatcagg gcctgagctc gcccgtcaca aagagcttca   2100
acaggggaga gtgttaggcg gccgctcgag tctagagggc ccgtttaaac ccgctgatca   2160
gcctcgactg tgccttctag ttgccagcca tctgttgttt gcccctcccc cgtgccttcc   2220
ttgaccctgg aaggtgccac tcccactgtc ctttcctaat aaaatgagga aattgcatcg   2280
cattgtctga gtaggtgtca ttctattctg gggggtgggg tggggcagga cagcaagggg   2340
gaggattggg aagacaatag caggcatgct ggggatgcgg tgggctctat ggcttctgag   2400
gcggaaagaa ccagctgggg ctctaggggg tatccccacg cgccctgtag cggcgcatta   2460
agcgcggcgg gtgtggtggt tacgcgcagc gtgaccgcta cacttgccag cgccctagcg   2520
cccgctcctt tcgctttctt cccttccttt ctcgccacgt tcgccggctt tccccgtcaa   2580
gctctaaatc ggggcatccc tttagggttc cgatttagtg ctttacggca cctcgacccc   2640
aaaaaacttg attagggtga tggttcacgt agtgggccat cgccctgata gacggttttt   2700
cgccctttga cgttggagtc cacgttcttt aatagtggac tcttgttcca aactggaaca   2760
acactcaacc ctatctcggt ctattctttt gatttataag ggattttggg gatttcggcc   2820
tattggttaa aaaatgagct gatttaacaa aaatttaacg cgaattaatt ctgtggaatg   2880
tgtgtcagtt agggtgtgga aagtccccag gctccccagg caggcagaag tatgcaaagc   2940
atgcatctca attagtcagc aaccaggtgt ggaaagtccc caggctcccc agcaggcaga   3000
agtatgcaaa gcatgcatct caattagtca gcaaccatag tcccgcccct aactccgccc   3060
atcccgcccc taactccgcc cagttccgcc cattctccgc cccatggctg actaattttt   3120
tttatttatg cagaggccga ggccgcctct gcctctgagc tattccagaa gtagtgagga   3180
ggcttttttg gaggcctagg cttttgcaaa aagctcccgg gagcttgtat atccattttc   3240
ggatctgatc agcacgtgtt gacaattaat catcggcata gtatatcggc atagtataat   3300
acgacaaggt gaggaactaa accatggcca agttgaccag tgccgttccg gtgctcaccg   3360
cgcgcgacgt cgccggagcg gtcgagttct ggaccgaccg gctcgggttc tcccgggact   3420
tcgtggagga cgacttcgcc ggtgtggtcc gggacgacgt gaccctgttc atcagcgcgg   3480
tccaggacca ggtggtgccg gacaacaccc tggcctgggt gtgggtgcgc ggcctggacg   3540
agctgtacgc cgagtggtcg gaggtcgtgt ccacgaactt ccgggacgcc tccgggccgg   3600
ccatgaccga gatcggcgag cagccgtggg ggcgggagtt cgccctgcgc gacccggccg   3660
gcaactgcgt gcacttcgtg gccgaggagc aggactgaca cgtgctacga gatttcgatt   3720
ccaccgccgc cttctatgaa aggttgggct tcggaatcgt tttccgggac gccggctgga   3780
```

```
tgatcctcca gcgcggggat ctcatgctgg agttcttcgc ccaccccaac ttgtttattg   3840
cagcttataa tggttacaaa taaagcaata gcatcacaaa tttcacaaat aaagcatttt   3900
tttcactgca ttctagttgt ggtttgtcca aactcatcaa tgtatcttat catgtctgta   3960
taccgtcgac ctctagctag agcttggcgt aatcatggtc atagctgttt cctgtgtgaa   4020
attgttatcc gctcacaatt ccacacaaca tacgagccgg aagcataaag tgtaaagcct   4080
ggggtgccta atgagtgagc taactcacat taattgcgtt gcgctcactg cccgctttcc   4140
agtcgggaaa cctgtcgtgc cagctgcatt aatgaatcgg ccaacgcgcg gggagaggcg   4200
gtttgcgtat tgggcgctct tccgcttcct cgctcactga ctcgctgcgc tcggtcgttc   4260
ggctgcggcg agcggtatca gctcactcaa aggcggtaat acggttatcc acagaatcag   4320
gggataacgc aggaaagaac atgtgagcaa aaggccagca aaaggccagg aaccgtaaaa   4380
aggccgcgtt gctggcgttt ttccataggc tccgcccccc tgacgagcat cacaaaaatc   4440
gacgctcaag tcagaggtgg cgaaacccga caggactata aagataccag gcgtttcccc   4500
ctggaagctc cctcgtgcgc tctcctgttc cgaccctgcc gcttaccgga tacctgtccg   4560
cctttctccc ttcgggaagc gtggcgcttt ctcaatgctc acgctgtagg tatctcagtt   4620
cggtgtaggt cgttcgctcc aagctgggct gtgtgcacga accccccgtt cagcccgacc   4680
gctgcgcctt atccggtaac tatcgtcttg agtccaaccc ggtaagacac gacttatcgc   4740
cactggcagc agccactggt aacaggatta gcagagcgag gtatgtaggc ggtgctacag   4800
agttcttgaa gtggtggcct aactacggct acactagaag gacagtattt ggtatctgcg   4860
ctctgctgaa gccagttacc ttcggaaaaa gagttggtag ctcttgatcc ggcaaacaaa   4920
ccaccgctgg tagcggtggt ttttttgttt gcaagcagca gattacgcgc agaaaaaaag   4980
gatctcaaga agatcctttg atcttttcta cggggtctga cgctcagtgg aacgaaaact   5040
cacgttaagg gattttggtc atgagattat caaaaaggat cttcacctag atccttttaa   5100
attaaaaatg aagttttaaa tcaatctaaa gtatatatga gtaaacttgg tctgacagtt   5160
accaatgctt aatcagtgag gcacctatct cagcgatctg tctatttcgt tcatccatag   5220
ttgcctgact ccccgtcgtg tagataacta cgatacggga gggcttacca tctggcccca   5280
gtgctgcaat gataccgcga gacccacgct caccggctcc agatttatca gcaataaacc   5340
agccagccgg aagggccgag cgcagaagtg gtcctgcaac tttatccgcc tccatccagt   5400
ctattaattg ttgccgggaa gctagagtaa gtagttcgcc agttaatagt ttgcgcaacg   5460
ttgttgccat tgctacaggc atcgtggtgt cacgctcgtc gtttggtatg gcttcattca   5520
gctccggttc ccaacgatca aggcgagtta catgatcccc catgttgtgc aaaaaagcgg   5580
ttagctcctt cggtcctccg atcgttgtca gaagtaagtt ggccgcagtg ttatcactca   5640
tggttatggc agcactgcat aattctctta ctgtcatgcc atccgtaaga tgcttttctg   5700
tgactggtga gtactcaacc aagtcattct gagaatagtg tatgcggcga ccgagttgct   5760
cttgcccggc gtcaatacgg gataataccg cgccacatag cagaacttta aaagtgctca   5820
tcattggaaa acgttcttcg gggcgaaaac tctcaaggat cttaccgctg ttgagatcca   5880
gttcgatgta acccactcgt gcacccaact gatcttcagc atcttttact ttcaccagcg   5940
tttctgggtg agcaaaaaca ggaaggcaaa atgccgcaaa aaagggaata agggcgacac   6000
ggaaatgttg aatactcata ctcttccttt ttcaatatta ttgaagcatt tatcagggtt   6060
attgtctcat gagcggatac atatttgaat gtatttagaa aaataaacaa ataggggttc   6120
cgcgcacatt tccccgaaaa gtgccacctg acgtc                              6155
```

<210> SEQ ID NO 82
<211> LENGTH: 6737
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccgccacc atgggatgga gctgtatcat    960

cctcttcttg gtagcaacag ctacaggtaa ggggctcaca gtagcaggct tgaggtctgg   1020

acatatatat gggtgacaat gacatccact ttgcctttct ctccacaggt gtccactccc   1080

aagtgcagct gctcgagtct ggggctgagc tggtgaggcc tgggtcctca gtgaagattt   1140

cctgcaaggc ttctggttac accttcacaa actacgatat acactgggtg aagcagaggc   1200

ctggacaggg tcttgagtgg attggatgga tttatcctgg agatggtagt actaagtaca   1260

atgagaaatt caagggcaag gccacactga ctgcagacaa atcctccagc acagcctaca   1320

tgcacctcag cagcctgact tctgagaaat ctgcagtcta tttctgtgca agagagtggg   1380

cttactgggg acaagggacc acagtcaccg tctctggcag caccagcggc ggaggctccg   1440

gcggaggcag cggcggaggc gggagctccg acatccagat gacccagagc ccaagcagcc   1500

tgagcgccag cgtgggtgac agagtgacca ttacttgtcg ggctagtcag gacattggag   1560

gaaacttata ttggtaccaa caaaagccag gtaaagctcc aaagttactg atctacgcca   1620

catctagttt agattctggt gtgccaagca gattcagtgg tagtggtagc ggtaccgact   1680

acaccttcac catcagcagc ttacagccag aggacatcgc cacctactat tgcctacagt   1740

attctagttc tccatggacg ttcggacaag ggaccaaggt ggaaatcaaa agggctagcg   1800

tggctgcacc atctgtcttc atcttcccgc catctgatga gcagttgaaa tctggaactg   1860

cctctgttgt gtgcctgctg aataacttct atcccagaga ggccaaagta cagtggaagg   1920

tggataacgc cctccaatcg ggtaactccc aggagagtgt cacagagcag gacagcaagg   1980

acagcaccta cagcctcagc agcaccctga cgctgagcaa agcagactac gagaaacaca   2040
```

```
aagtctacgc ctgcgaagtc acccatcagg gcctgagctc gcccgtcaca aagagcttca   2100
acaggggaga gtgttaggcg gccgctcgag tctagagggc ccgtttaaac ccgctgatca   2160
gcctcgactg tgccttctag ttgccagcca tctgttgttt gcccctcccc cgtgccttcc   2220
ttgaccctgg aaggtgccac tcccactgtc ctttcctaat aaaatgagga aattgcatcg   2280
cattgtctga gtaggtgtca ttctattctg gggggtgggg tggggcagga cagcaagggg   2340
gaggattggg aagacaatag caggcatgct ggggatgcgg tgggctctat ggcttctgag   2400
gcggaaagaa ccagctgggg ctctaggggg tatccccacg cgccctgtag cggcgcatta   2460
agcgcggcgg gtgtggtggt tacgcgcagc gtgaccgcta cacttgccag cgccctagcg   2520
cccgctcctt tcgctttctt cccttccttt ctcgccacgt tcgccggctt tccccgtcaa   2580
gctctaaatc gggggctccc tttagggttc cgatttagtg ctttacggca cctcgacccc   2640
aaaaaacttg attagggtga tggttcacgt agtgggccat cgccctgata gacggttttt   2700
cgccctttga cgttggagtc cacgttcttt aatagtggac tcttgttcca aactggaaca   2760
acactcaacc ctatctcggt ctattctttt gatttataag ggattttgcc gatttcggcc   2820
tattggttaa aaaatgagct gatttaacaa aaatttaacg cgaattaatt ctgtggaatg   2880
tgtgtcagtt agggtgtgga aagtccccag gctccccagc aggcagaagt atgcaaagca   2940
tgcatctcaa ttagtcagca accaggtgtg gaaagtcccc aggctcccca gcaggcagaa   3000
gtatgcaaag catgcatctc aattagtcag caaccatagt cccgccccta actccgccca   3060
tcccgcccct aactccgccc agttccgccc attctccgcc ccatggctga ctaatttttt   3120
ttatttatgc agaggccgag gccgcctctg cctctgagct attccagaag tagtgaggag   3180
gcttttttgg aggcctaggc ttttgcaaaa agctcccggg agcttgtata tccattttcg   3240
gatctgatca gcacgtgatg aaaaagcctg aactcaccgc gacgtctgtc gagaagtttc   3300
tgatcgaaaa gttcgacagc gtctccgacc tgatgcagct ctcggagggc gaagaatctc   3360
gtgctttcag cttcgatgta ggagggcgtg gatatgtcct gcgggtaaat agctgcgccg   3420
atggtttcta caaagatcgt tatgtttatc ggcactttgc atcggccgcg ctcccgattc   3480
cggaagtgct tgacattggg gaattcagcg agagcctgac ctattgcatc tcccgccgtg   3540
cacagggtgt cacgttgcaa gacctgcctg aaaccgaact gcccgctgtt ctgcagccgg   3600
tcgcggaggc catggatgcg atcgctgcgg ccgatcttag ccagacgagc gggttcggcc   3660
cattcggacc gcaaggaatc ggtcaataca ctacatggcg tgatttcata tgcgcgattg   3720
ctgatcccca tgtgtatcac tggcaaactg tgatggacga caccgtcagt gcgtccgtcg   3780
cgcaggctct cgatgagctg atgctttggg ccgaggactg ccccgaagtc cggcacctcg   3840
tgcacgcgga tttcggctcc aacaatgtcc tgacggacaa tggccgcata acagcggtca   3900
ttgactggag cgaggcgatg ttcggggatt cccaatacga ggtcgccaac atcttcttct   3960
ggaggccgtg gttggcttgt atggagcagc agacgcgcta cttcgagcgg aggcatccgg   4020
agcttgcagg atcgccgcgg ctccgggcgt atatgctccg cattggtctt gaccaactct   4080
atcagagctt ggttgacggc aatttcgatg atgcagcttg ggcgcagggt cgatgcgacg   4140
caatcgtccg atccggagcc gggactgtcg ggcgtacaca aatcgcccgc agaagcgcgg   4200
ccgtctggac cgatggctgt gtagaagtac tcgccgatag tggaaaccga cgccccagca   4260
ctcgtccgag ggcaaaggaa tagcacgtgc tacgagattt cgattccacc gccgccttct   4320
atgaaaggtt gggcttcgga atcgttttcc gggacgccgg ctggatgatc ctccagcgcg   4380
```

```
gggatctcat gctggagttc ttcgcccacc ccaacttgtt tattgcagct tataatggtt   4440
acaaataaag caatagcatc acaaatttca caaataaagc atttttttca ctgcattcta   4500
gttgtggttt gtccaaactc atcaatgtat cttatcatgt ctgtataccg tcgacctcta   4560
gctagagctt ggcgtaatca tggtcatagc tgtttcctgt gtgaaattgt tatccgctca   4620
caattccaca caacatacga gccggaagca taaagtgtaa agcctggggt gcctaatgag   4680
tgagctaact cacattaatt gcgttgcgct cactgcccgc tttccagtcg ggaaacctgt   4740
cgtgccagct gcattaatga atcggccaac gcgcggggag aggcggtttg cgtattgggc   4800
gctcttccgc ttcctcgctc actgactcgc tgcgctcggt cgttcggctg cggcgagcgg   4860
tatcagctca ctcaaaggcg gtaatacggt tatccacaga atcaggggat aacgcaggaa   4920
agaacatgtg agcaaaaggc cagcaaaagg ccaggaaccg taaaaaggcc gcgttgctgg   4980
cgtttttcca taggctccgc ccccctgacg agcatcacaa aaatcgacgc tcaagtcaga   5040
ggtggcgaaa cccgacagga ctataaagat accaggcgtt tccccctgga agctccctcg   5100
tgcgctctcc tgttccgacc ctgccgctta ccggatacct gtccgccttt ctcccttcgg   5160
gaagcgtggc gctttctcat agctcacgct gtaggtatct cagttcggtg taggtcgttc   5220
gctccaagct gggctgtgtg cacgaacccc ccgttcagcc cgaccgctgc gccttatccg   5280
gtaactatcg tcttgagtcc aacccggtaa gacacgactt atcgccactg gcagcagcca   5340
ctggtaacag gattagcaga gcgaggtatg taggcggtgc tacagagttc ttgaagtggt   5400
ggcctaacta cggctacact agaagaacag tatttggtat ctgcgctctg ctgaagccag   5460
ttaccttcgg aaaaagagtt ggtagctctt gatccggcaa acaaaccacc gctggtagcg   5520
gtttttttgt ttgcaagcag cagattacgc gcagaaaaaa aggatctcaa gaagatcctt   5580
tgatcttttc tacggggtct gacgctcagt ggaacgaaaa ctcacgttaa gggattttgg   5640
tcatgagatt atcaaaaagg atcttcacct agatcctttt aaattaaaaa tgaagtttta   5700
aatcaatcta aagtatatat gagtaaactt ggtctgacag ttaccaatgc ttaatcagtg   5760
aggcacctat ctcagcgatc tgtctatttc gttcatccat agttgcctga ctccccgtcg   5820
tgtagataac tacgatacgg gagggcttac catctggccc cagtgctgca atgataccgc   5880
gagacccacg ctcaccggct ccagatttat cagcaataaa ccagccagcc ggaagggccg   5940
agcgcagaag tggtcctgca actttatccg cctccatcca gtctattaat tgttgccggg   6000
aagctagagt aagtagttcg ccagttaata gtttgcgcaa cgttgttgcc attgctacag   6060
gcatcgtggt gtcacgctcg tcgtttggta tggcttcatt cagctccggt tcccaacgat   6120
caaggcgagt tacatgatcc cccatgttgt gcaaaaaagc ggttagctcc ttcggtcctc   6180
cgatcgttgt cagaagtaag ttggccgcag tgttatcact catggttatg gcagcactgc   6240
ataattctct tactgtcatg ccatccgtaa gatgcttttc tgtgactggt gagtactcaa   6300
ccaagtcatt ctgagaatag tgtatgcggc gaccgagttg ctcttgcccg gcgtcaatac   6360
gggataatac cgcgccacat agcagaactt taaaagtgct catcattgga aaacgttctt   6420
cggggcgaaa actctcaagg atcttaccgc tgttgagatc cagttcgatg taacccactc   6480
gtgcacccaa ctgatcttca gcatctttta ctttcaccag cgtttctggg tgagcaaaaa   6540
caggaaggca aaatgccgca aaaaagggaa taagggcgac acggaaatgt tgaatactca   6600
tactcttcct ttttcaatat tattgaagca tttatcaggg ttattgtctc atgagcggat   6660
acatatttga atgtatttag aaaaataaac aaataggggt tccgcgcaca tttccccgaa   6720
aagtgccacc tgacgtc                                                   6737
```

<210> SEQ ID NO 83
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Thr Phe Thr Asn Tyr
            20                  25                  30

Asp Ile His Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Lys Ser Ala Val Tyr Phe Cys
                85                  90                  95

Ala Arg Glu Trp Ala Tyr Trp Gly Gln Gly Thr Thr Val Thr Val Ser
            100                 105                 110

Gly Ser Thr Ser Gly Gly Gly Ser Gly Gly Gly Ser Gly Gly Gly Gly
        115                 120                 125

Ser Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Asp Ile Gly
145                 150                 155                 160

Gly Asn Leu Tyr Trp Tyr Gln Gln Lys Pro Gly Lys Ala Pro Lys Leu
                165                 170                 175

Leu Ile Tyr Ala Thr Ser Ser Leu Asp Ser Gly Val Pro Ser Arg Phe
            180                 185                 190

Ser Gly Ser Gly Ser Gly Thr Asp Tyr Thr Phe Thr Ile Ser Ser Leu
        195                 200                 205

Gln Pro Glu Asp Ile Ala Thr Tyr Tyr Cys Leu Gln Tyr Ser Ser Ser
    210                 215                 220

Pro Trp Thr Phe Gly Gln Gly Thr Lys Val Glu Ile Lys Arg Ala Ser
225                 230                 235                 240
```

<210> SEQ ID NO 84
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Thr Phe Thr Asn Tyr
            20                  25                  30

Asp Ile His Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60
```

```
Lys Gly Lys Ala Thr Leu Thr Ala Asp Lys Ser Ser Ser Thr Ala Tyr
65                  70                  75                  80

Met His Leu Ser Ser Leu Thr Ser Glu Lys Ser Ala Val Tyr Phe Cys
                85                  90                  95

Ala Arg Glu Trp Ala Tyr Trp Gly Gln Gly Thr Thr Val Thr Val Ser
            100                 105                 110

Gly Ser Thr Ser Gly Gly Gly Ser Gly Gly Gly Ser Gly Gly Gly Gly
        115                 120                 125

Ser Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Asp Ile Gly
145                 150                 155                 160

Gly Asn Leu Tyr Trp Tyr Gln Gln Lys Pro Gly Lys Ala Pro Lys Leu
                165                 170                 175

Leu Ile Tyr Ala Thr Ser Ser Leu Asp Ser Gly Val Pro Ser Arg Phe
            180                 185                 190

Ser Gly Ser Gly Ser Gly Thr Asp Tyr Thr Phe Thr Ile Ser Ser Leu
        195                 200                 205

Gln Pro Glu Asp Ile Ala Thr Tyr Tyr Cys Leu Gln Tyr Ser Ser Ser
    210                 215                 220

Pro Trp Thr Phe Gly Gln Gly Thr Lys Val Glu Ile Lys Arg Ala Ser
225                 230                 235                 240

Thr Lys Gly Pro Ser Val Phe Pro Leu Ala Pro Ser Ser Lys Ser Thr
                245                 250                 255

Ser Gly Gly Thr Ala Ala Leu Gly Cys Leu Val Lys Asp Tyr Phe Pro
            260                 265                 270

Glu Pro Val Thr Val Ser Trp Asn Ser Gly Ala Leu Thr Ser Gly Val
        275                 280                 285

His Thr Phe Pro Ala Val Leu Gln Ser Ser Gly Leu Tyr Ser Leu Ser
    290                 295                 300

Ser Val Val Thr Val Pro Ser Ser Ser Leu Gly Thr Gln Thr Tyr Ile
305                 310                 315                 320

Cys Asn Val Asn His Lys Pro Ser Asn Thr Lys Val Asp Lys Lys Val
                325                 330                 335

Glu Pro Lys Ser Cys Asp Lys Thr His Thr Cys Pro Pro Cys Pro Ala
            340                 345                 350

Pro Glu Leu Leu Gly Gly Pro Ser Val Phe Leu Phe Pro Pro Lys Pro
        355                 360                 365

Lys Asp Thr Leu Met Ile Ser Arg Thr Pro Glu Val Thr Cys Val Val
    370                 375                 380

Val Asp Val Ser His Glu Asp Pro Glu Val Lys Phe Asn Trp Tyr Val
385                 390                 395                 400

Asp Gly Val Glu Val His Asn Ala Lys Thr Lys Pro Arg Glu Glu Gln
                405                 410                 415

Tyr Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Ala
        435                 440                 445

Leu Pro Ala Pro Ile Glu Lys Thr Ile Ser Lys Ala Lys Gly Gln Pro
    450                 455                 460

Arg Glu Pro Gln Val Tyr Thr Leu Pro Pro Ser Arg Asp Glu Leu Thr
465                 470                 475                 480
```

```
Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Lys Leu Thr Val Asp Lys Ser Arg Trp Gln Gln Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Pro Gly Lys
                565


<210> SEQ ID NO 85
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Thr Phe Thr Asn Tyr
            20                  25                  30

Asp Ile His Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Lys Ser Ala Val Tyr Phe Cys
                85                  90                  95

Ala Arg Glu Trp Ala Tyr Trp Gly Gln Gly Thr Thr Val Thr Val Ser
            100                 105                 110

Gly Ser Thr Ser Gly Gly Gly Ser Gly Gly Gly Ser Gly Gly Gly Gly
        115                 120                 125

Ser Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Asp Ile Gly
145                 150                 155                 160

Gly Asn Leu Tyr Trp Tyr Gln Gln Lys Pro Gly Lys Ala Pro Lys Leu
                165                 170                 175

Leu Ile Tyr Ala Thr Ser Ser Leu Asp Ser Gly Val Pro Ser Arg Phe
            180                 185                 190

Ser Gly Ser Gly Ser Gly Thr Asp Tyr Thr Phe Thr Ile Ser Ser Leu
        195                 200                 205

Gln Pro Glu Asp Ile Ala Thr Tyr Tyr Cys Leu Gln Tyr Ser Ser Ser
    210                 215                 220

Pro Trp Thr Phe Gly Gln Gly Thr Lys Val Glu Ile Lys Arg Ala Ser
225                 230                 235                 240

Arg Thr Val Ala Ala Pro Ser Val Phe Ile Phe Pro Pro Ser Asp Glu
                245                 250                 255

Gln Leu Lys Ser Gly Thr Ala Ser Val Val Cys Leu Leu Asn Asn Phe
            260                 265                 270
```

```
Tyr Pro Arg Glu Ala Lys Val Gln Trp Lys Val Asp Asn Ala Leu Gln
        275                 280                 285

Ser Gly Asn Ser Gln Glu Ser Val Thr Glu Gln Asp Ser Lys Asp Ser
    290                 295                 300

Thr Tyr Ser Leu Ser Ser Thr Leu Thr Leu Ser Lys Ala Asp Tyr Glu
305                 310                 315                 320

Lys His Lys Val Tyr Ala Cys Glu Val Thr His Gln Gly Leu Ser Ser
                325                 330                 335

Pro Val Thr Lys Ser Phe Asn Arg Gly Glu Cys
            340                 345


<210> SEQ ID NO 86
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asn Glu Lys Leu Lys Ala Arg Val Thr Met Thr Ala Asp Thr Ser Thr
1               5                   10                  15

Ser Thr Ala Tyr Met Glu Leu Arg Ser Leu Arg Ser Asp Asp Thr Ala
            20                  25                  30

Val Tyr Tyr Cys Ala Arg Ser Ala Ser Tyr Gly Asp Tyr Ala Asp Tyr
        35                  40                  45

Trp Gly Gln Gly Thr Thr Val Thr Val Ser Ser Ala Ser Thr Lys Gly
    50                  55                  60

Pro Ser Val Phe Pro Leu Ala Pro Ser Ser Lys Ser Thr Ser Gly Gly
65                  70                  75                  80

Thr Ala Ala Leu Gly Cys Leu Val Lys Asp Tyr Phe Pro Glu Pro Val
                85                  90                  95

Thr Val Ser Trp Asn Ser Gly Ala Leu Thr Ser Gly Val His Thr Phe
            100                 105                 110

Pro Ala Val Leu Gln Ser Ser Gly Leu Tyr Ser Leu Ser Ser Val Val
        115                 120                 125

Thr Val Pro Ser Ser Ser Leu Gly Thr Gln Thr Tyr Ile Cys Asn Val
    130                 135                 140

Asn His Lys Pro Ser Asn Thr Lys Val Asp Lys Arg
145                 150                 155
```

BISPECIFIC MONOCLONAL ANTIBODY THERAPEUTICS AGAINST WEST NILE VIRUS WITH IMPROVED CNS PENETRATION

RELATED APPLICATION

This application claims priority under 35 U.S.C 119(e) to provisional U.S. Ser. No. 61/494,612 filed Jun. 8, 2011, which application is incorporated hereby by reference,

FEDERALLY SPONSORED RESEARCH OR DEVELOPMENT

This invention was made with government support under U01 AI075549 awarded by NIH-NIAID. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 27, 2012, is named 175551 WO.txt and is 451,050 bytes in size.

FIELD OF THE INVENTION

The present invention relates to a bifunctional antibody that has improved blood-brain barrier penetration. In exemplary embodiments the antibodies are plant-, mammalian- or other eukaryotic cell-produced antibodies against West Nile Virus that have an improved efficacy and therapeutic window for crossing the blood-brain barrier.

BACKGROUND OF THE INVENTION

West Nile virus (WNV) is a member of the *Flavivirus* genus of the Flaviviridae which also includes the Japanese encephalitis virus (JE), Tick-borne encephalitis virus (TBE), St. Louis Encephalitis virus (SLEV), Murray Valley encephalitis virus, dengue virus (including the four serotypes of: DEN-1, DEN-2, DEN-3, and DEN-4), and the family prototype, yellow fever virus (YF). *Flavivirus* infections are a global public health problem [C. G. Hayes, in The Arboviruses: Epidemiology and Ecology, T. P. Monathy, ed., CRC, Boca Raton, Fla., vol. 5, chap. 49 (1989); M. J. Cardosa, Br Med Bull, 54, pp, 395-405 (1998); Z. Hubalek and J. Halouzka, Emerg Infect Dis, 5, pp. 643-50 (1999)] with about half of the *flaviviruses* causing human diseases.

WNV is a neurotropic, enveloped virus with a single-stranded, positive polarity, 11 kilobase RNA genome. Until 1999, WNV was found in the Eastern Hemisphere, with wide distribution in Africa, Asia, the Middle East, and Europe (1). In 1999, WNV entered the Western Hemisphere as a point introduction in New York City (2), Greater than 29,000 human cases have been diagnosed with severe WNV infection in the continental United States during the last decade, and many more have been infected and remain undiagnosed. Advanced age is by far the greatest risk factor for severe neurological disease, long-term morbidity, and death (3), although a genetic basis of susceptibility has also been recently identified (4-7).

Historically, there has been a lack of effective and specific antiviral treatment for infection by WNV or other *flaviviruses* (reviewed in 8). While several small molecules compounds have been recently described with antiviral activity against WNV in vitro, only few have demonstrated efficacy in vivo (9, 10). Interferon (IFN), which is used as part of combination therapy against the distantly related, hepatitis C virus, potently inhibits *flaviviruses* including WNV when used as prophylaxis. However, its effect is markedly attenuated once viral replication has commenced as *flavivirus* non-structural proteins antagonize IFN signaling pathways (reviewed in 11). Current treatment for WNV infection is supportive and no vaccine or therapeutic agent has been approved for human use. New threats of WNV globally and lack of available treatments warrant studies to develop effective therapeutics and production technologies that can rapidly transfer the candidates into the clinical care settings in a cost-conscious manner.

Recently, a plant-derived humanized murine MAb was developed with promising therapeutic potential. This MAb (E16) binds to a highly conserved epitope on the envelope protein of WNV in all North American isolates, blocks viral fusion, and shows promising post-exposure therapeutic activity. Nonetheless, detailed studies show that while the E16 is therapeutically effective, peripheral delivery of this antibody has a limited window of efficacy in rodents. For example, administration of a single dose of hu-E16 through an intravenous or intraperitonreal route at day 5 postinfection or earlier improves survival rates. However, delivers of E.16 directly into the brain at day 6 after infection can protect hamsters against lethal WNV infection, Thus, even though antibodies have been identified as potential prophylactic and or therapeutic medicaments for WNV or other infectious diseases, their ultimate application as beneficial therapeutics is limited lack of efficacy due to the short therapeutic window. Thus, there remains a need for blood-brain barrier permeable variants of antibodies that can achieve higher levels in the CNS, increase its therapeutic efficacy, and extend the window of treatment. In addition, the there is a need to alleviate the high production costs and scalability associated with the mammalian cell culture production system. Moreover, if biological drugs are too costly to produce for resource poor health care systems and cannot be easily made into generics, their therapeutic potential may never be realized. As such, the development of production platforms that are cost-effective, scalable, and safe for biological therapeutics is urgently needed.

BRIEF SUMMARY OF THE INVENTION

The present invention describes the plant-based production of a bispecific therapeutic antibody against West Nile Virus. More specifically, the bifunctional antibody comprises a first scFV specific for a first antigen, a second scFV specific for a second antigen that is distinct from the first antigen, a heavy chain constant domain (CH) and a light chain constant domain (CL), wherein: the first scFV is linked to either the CH or the CL to produce a first scFV linked to constant domain; and the second scFV is linked to the CH when the first scFV is linked to CL or the second scFV is linked to CL when the first scFV is linked to CH to produce a second scFV-linked to a constant domain.

The bifunctional antibody may be one in which the first scFV linked to constant domain is produced separately from the second scFV linked to constant domain and the two linked scFVs are admixed together to form a bifunctional antibody.

The bifunctional antibody may be one wherein the first scFV linked to a constant domain and the second scFV linked to a constant domain are prepared by co-expression of at nucleic acid that encodes each of the linked scFVs in a host cell produces a tetravalent molecule with divalent binding to two different epitopes and an intact Fc domain.

In certain embodiments, the first scFV specifically binds to an antigen or epitope from an antigen selected from the group consisting of the Domain III or any other parts of the Envelope protein of the West Nile virus or other *flavivirus*. In additional embodiments, the second scFV specifically binds to an antigen or epitope from an antigen selected from the group consisting of transferrin receptors and insulin receptors of mouse, rat, rhesus monkey, and human cells wherein the antigen or epitope is different from the antigen or epitope to which the fist scFV binds.

Thus, in some embodiments either the first scFV or the second scFV specifically binds to West Nile Virus. More specifically, such an antibody that binds WNV is a humanized E16 antibody comprising a heavy chain variable domain sequence comprising the CDR1, CDR2 and CDR3 sequences from the heavy chain variable domain sequence of SEQ ID NO: 1. For example, the humanized E16 antibody comprising to heavy chain variable domain sequence selected from the group consisting of SEQ ID NO: 1, SEQ ID NO: 2, SEQ ID NO: 3, SEQ ID NO: 4, and SEQ ID NO: 5.

In certain embodiments, the bifunctional antibody is a humanized E16 antibody comprising a light chain variable domain sequence comprising the CDR1, CDR2 and CDR3 sequences from the light chain variable domain sequence of SEQ ID NO: 6.

Alternatively, the bifunctional antibody is a humanized E16 antibody comprising a light chain variable domain sequence selected from the group consisting of SEQ ID NO: 6 and SEQ ID NO: 7.

In the bifunctional antibody the alternative to the scFV to the one that specifically binds to West Nile Virus binds to an entity expressed on the blood-brain barrier to uptake of the bifunctional antibody through the blood brain barrier. For example, the scFV that binds to the blood brain barrier entity binds to a receptor expressed on the blood brain barrier. Exemplary such receptors are the receptor is a transferrin receptor or insulin receptor.

Also contemplated is an isolated humanized E16 antibody that is specific for West Nile Virus wherein the antibody is a bifunctional antibody comprising two scFVs wherein one of the scFVs is from humanized E16 and the second scFV specifically binds to a receptor or other blood-brain barrier targeting sequence, wherein the first scFV is linked to either a CH or the CL domain to produce a first scFV linked to constant domain; and the second scFV is linked to a CH domain when the first scFV is linked to a CL domain or the second scFV is linked to a CL when the first scFV is linked to a CH domain to produce a second scFV-linked to a constant domain. In exemplary embodiments, the isolated humanized E16 antibody has an increased in vivo efficacy as compared to humanized E16 antibody that is not bifunctional. In other embodiments, it is a humanized E16 antibody comprising a heavy chain variable domain sequence comprising the CDR1, CDR2 and CDR3 sequences from the heavy chain variable domain sequence of SEQ ID NO: 1. In still other embodiments, the antibody is a humanized E16 antibody comprising a heavy chain variable domain sequence selected from the group consisting of SEQ ID NO: 1, SEQ ID NO: 2, SEQ ID NO: 3, SEQ ID NO: 4, and SEQ ID NO: 5.

In certain embodiments, the antibody is a humanized E16 antibody comprising a light chain variable domain sequence comprising the CDR1, CDR2 and CDR3 sequences from the light chain variable domain sequence of SEQ ID NO: 6.

In exemplary embodiments, the antibody is a humanized E16 antibody comprising a light chain variable domain sequence selected from the group consisting of SEQ ID NO: 6 and SEQ ID NO: 7.

Also contemplated are pharmaceutical compositions that comprise the isolated bifunctional antibodies of the present invention.

Further, the invention also contemplates use of the antibodies or pharmaceutical compositions comprising the same for methods of treating a West Nile Virus infection.

BRIEF DESCRIPTION OF SEVERAL VIEWS OF THE DRAWINGS

FIGS. 7A-7B. FIG. 7A depicts Hu-E16 bifunctional mAb plant expression vectors. (PA1-D1) TMV-based provectors: 3' module cloning vectors for Hu-E16 (PA), 8D3 (PB), OX26 (PC) or anti-HIR (PD) scFV-Fc and scFv-CL. (PA2-D2) PVX-based provectors: 3' module cloning vectors f or Hu-E16 (PA), 8D3 (PB), OX26 (PC) or anti-HIR (PD) scFv-Fc and scFv-CL. scFv, single chain variable fragment; HIR, human insulin receptor; LB and RB, binary left and right, borders, respectively; T, nos terminator; int, intron; 3'TMV and 3'PVX, 3' untranslated regions of TMV and PVX, respectively; SP, signal peptide. FIG. 7B depicts Hu-E16 bifunctional mAb mammalian expression vectors. Coding sequence of Hu-E16 (MA), 8D3 (MB), OX26 (MC) or anti-HIR (MD) was fused to that of constant region of light chain (CL) or constant region of heavy chain (Fc). The combination of scFv-CL were either cloned in pcDNA3.1 vector with hygromycin resistant gene (hygro) (MA1-MD1) or with zeocin resistant gene (Zeo) (MA2-MD2). Pcmv, cytomegalovirus promoter: Tbgh, bovine growth hormone terminator. The sequences for the gene and vector are attached in Appendix A.

DETAILED DESCRIPTION OF THE INVENTION

Figure 1:
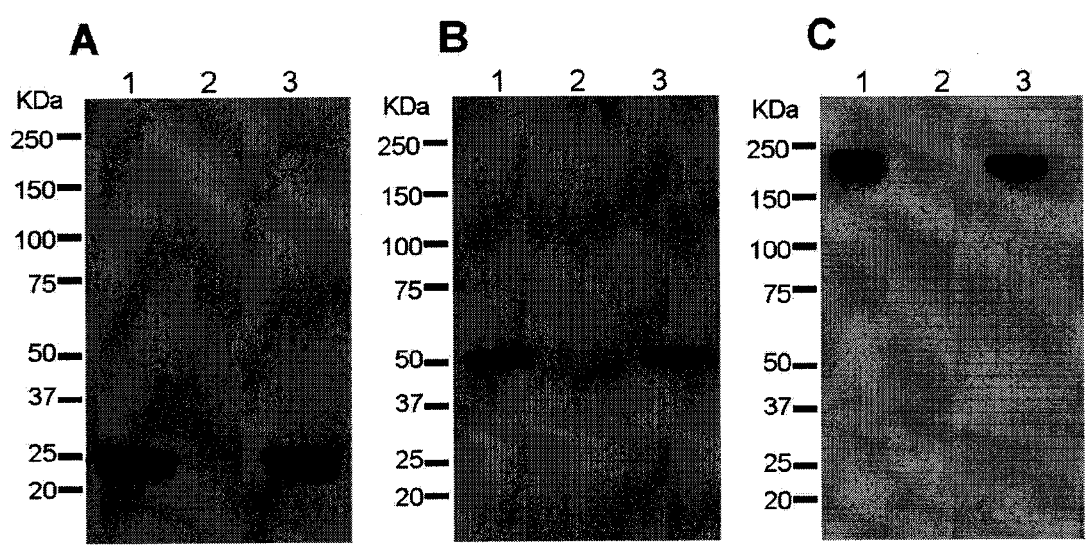
FIGS. 1A-1C. Western blot analysis of pHu-E16. Leaf protein extracts were separated on 4-20% SDS-PAGE gradient gels under reducing (A and B) or nonreducing (C) condition and blotted onto PVDF membranes. The membranes were incubated with a goat anti-human kappa chain antibody or a goat anti-human gamma chain antibody to detect light chain (A and C) or heavy chain (B). Lane 1, mHu-E16 as a reference standard; lane 2, Protein sample extracted from un-infiltrated leaves; lane 3, Extract from leaves co-infiltrated with Hu-E16 LC and HC constructs.

Despite annual WNV outbreaks in North America there is a lack of effective and specific antiviral treatment (reviewed in 8). The high production costs and limited scalability associated with mammalian cell culture production may restrict the use of therapeutic antibodies against WNV and other *flaviviruses* in resource-poor settings in the future. Here, we investigated the feasibility of producing in plants a candidate MAb therapeutic against WNV infection. The inventors have shown that plant-derived MAb therapeutics have similar potency as their mammalian-cell counterparts, and production of biological therapeutics in plants provides a platform that can address the cost and scalability issues associated with the mammalian cell culture production system.

While pHu-E16 retained high-affinity binding and potent neutralizing activity in vitro against WNV and a single dose protected mice against WNV-induced mortality even 4 days after infection at rates that were indistinguishable from mHu-E16 there remains an issue of peripheral delivery of E16 has a limited window of efficacy in rodents. The administration of a single dose of huE16 through intravenous or intraperitoneal route at day 5 post-infection or earlier improves survival rate.

In this invention, the inventors generated several bispecific and bifunctional Hu-E16 monoclonal antibody (MAb) therapeutics in plants and in mammalian culture cells that can effectively treat West Nile virus (WNV) infection, can pass the blood brain barrier (BBB) to extend the window of treatment, and can also be rapidly scaled-up for commercial production.

The plant and mammalian cell-produced bifunctional Hu-E16 MAbs retain the biological and therapeutic activity of the parental Hu-E16 mAb in high-affinity binding and potent neutralizing activity in vitro against WNV, and in protecting mice against WNV-induced mortality within 4 days after infection. Moreover, these bifunctional MAbs have gained the ability in binding to specific receptors on the endothelial cells of the BBB, and therefore, are able to pass the BBB and enter the brain through transcytosis. These BBB permeable variants of the E16 MAb can be used to achieve higher levels in the central nervous system (CNS), increase their therapeutic efficacy, and extend the window of treatment. In addition, the plant-produced bifunctional Hu-E16s with optimized DNA sequences for both Hu-E16 and MAb against BBB endothelial receptor moieties are as efficacious as their mammalian cell-derived counterparts in treating WNV infection but have superior characteristics in their production cost, production scalability, and product safety. This invention is the first to demonstrate the efficacy of MAb variants against WNV in binding to BBB endothelial cell receptors and in passing the BBB to enter the CNS. Thus, this invention can provide a platform for delivery of MAbs to the CNS, which can be broadly applicable to the treatment of other infectious, inflammatory, or neoplastic CNS diseases.

Thus, in one aspect, the present invention provides generation of a bifunctional fusion protein with two distinct antigen-binding moieties that efficiently crosses the BBB and enhances treatment efficacy against lethal WNV infection is innovative. Most bifunctional antibodies developed to date have been aimed at recognizing two cell surface proteins on different cell types, and thus, bringing the two populations (such as cytotoxic cells and tumor or infected cells) in proximity. Currently, there is no report of using such an approach to treat an infectious disease. If successful, this platform can be applied broadly to treatment of infectious and non-infectious CNS diseases and open an avenue to the development of specific therapeutic agents that target the brain.

The approach on the design of the bifunctional antibody is novel. Although bispecific antibody fragments have been developed, many of them (such as diabody and mini-antibody) lack Fc regions and thus, lose effector functions and are cleared rapidly from circulation. Current Bif-MAbs with Fc region are produced either with two VL and two VH domains tandemly linked together to form an extended light (LC) and heavy (HC) chain (FIG. 6*d*), or with two tandemly linked scFvs (FIG. 6*c*). The bifunctional antibody design of the present invention links two scFvs of different specificity to the constant region of the LC (CL) and HC (CH) respectively (FIG. 6*a*). It is unique in that each scFv can be formed independently. When scFV-CH and scFv-CL are co-expressed, a tetravalent molecule with divalent binding to two different epitopes and an intact Fe region (and potentially effector functions) assembles. This design may enhance product yield since tandemly-linked long peptide chains with multiple linkers are not required. It may also provide the versatility of targeting a therapeutic MAb to different tissues by co-expressing with different targeting scFv-fusions. Finally, it retains bivalent binding to the target of interest, in this case the WNV E protein for the MAb E16.

The production technology for the bifunctional antibody is novel. Most of the current bifunctional antibodies and their fragments are developed in either mammalian cell or bacterial cultures, but so far, none have been described in plants. Generation of these molecules in current systems has been hindered by difficulties especially in obtaining properly folded full-length molecules in sufficient quantities that retain conformationally-sensitive epitopes. Our invention showed that in addition to mammalian cells, plants can also be readily used to produce a Bif-MAb successfully without any of these production issues (see FIG. 8-9). Since plants can rapidly express, accumulate and assemble MAb, and this can be expanded for commercial production without high-capital investments, plants may be a novel system for large-scale manufacture of Bif-MAbs.

The DNA sequences for scFvs of huE16, OX26. 8D3, and anti-HIR and the linkers that link them to the constant region of IgG light chain and Heavy chain for plant expression are novel and can be produced using plant-based antibody production as described herein. See Appendix A for sequence information.

Transgenic plants are suitable for MAb production as they can be rapidly expanded in commercial production without the high-capital investment associated with traditional MAb bioreactor facilities (reviewed in 19), pHu-E16 was expressed rapidly in *N. benthamiana* leaves within 4 to 8 days of infiltration and efficiently assembled into a native IgG form. Without any genetic optimization, pHu-E16 accumulated at an average of 0.8 mg/g of fresh leaf weight, greater than the highest expression level for MAbs in plants ever reported (22). The rapid high-level production and assembly of pHu-E16 convincingly demonstrate the viability of this system for the more large-scale cost effective production of MAbs.

It is well-known that downstream processing is an important component of a pharmaceutical protein production technology. In the present invention, there is described a simple three-step extraction and purification scheme that can be used to purify plant-generated Hu-E16 efficiently and in a manner that is scalable for mass production and conforms to cGMP regulations, thereby providing a method for the production of a pharmaceutically acceptable preparation of HU-E16. The rapid high-level accumulation of pHu-E16 in plants and the availability of a scalable and cGMP compliant processing scheme provides advantages over the mammalian cell culture for future low-cost commercial production of Hu-E16 or other therapeutic MAbs.

Hu-E16 derived from mammalian cells is highly potent against almost all WNV strains because it binds a conserved epitope and blocks viral fusion (14). Compared to the parent mHu- E16, pHu-E16 showed equivalent binding kinetics and neutralization activity in vitro. However, pHu-E16 did not show a shift in the neutralization curve to lower antibody concentrations in the presence of human Clq. Clq augments the neutralization potency of mHu-E16 IgG1 by approximately 3-fold (29). SPR studies confirmed that pHu-E16 bound less well to human Clq compared to mHu-E16. This impairment was likely caused by the slightly different carbohydrate modifications on plant-derived antibodies (see Examples). Overall, the functional studies in vitro suggest that pHu-E16 and mHu-E16 had similar but not identical properties.

While plant-derived MAbs or MAb fragments are currently in clinical trials as a cancer vaccine or as topical treatment for tooth decay, and a MAb as post-exposure rabies prophylaxis has been reported (24, 31, 32), our results are the first to demonstrate the efficacy of a plant-produced MAb against a lethal infection several days after exposure. A single dose of pHu-E16 protected mice when administered 2 or 4 days after WNV infection. As WNV has already disseminated to the brain by day 4 (12, 30, 33), pHu-E16 improves survival after the virus has spread into the CNS. Although our in vitro results showed a decrease in the binding to human Clq and an absence of Clq augmented WNV neutralization by pHu-E16, this did not affect potency in vivo in mice. This is likely because Hu-E16 binds mouse Clq less well than human Clq. Indeed, we previously did not observe a difference in protection of the mHu-E16 IgGI between wild type and Clq−/− mice, and reported a smaller shift in the neutralization potency in vitro of mHu-E16 with marine Clq (29). The N-linked glycosylation of proteins in plants is generally similar to that in mammalian cells. However, plants have unique plant-specific β-1,2-xylose and core α-1,3-fucose residues on complex N-linked glycans and lack terminal β-1,4-Gal and N acetylneuraminic acid (Neu5Ac) residues (21). The impact of such differences on the activity of MAb therapeutics in vivo has not been evaluated although glycan variations in the Fc region of IgG modulate the binding and activation of Clq (34, 35). Since pHu-E16 HC has an ER-retention KDEL sequence (SEQ ID NO: 12), it is likely retained in the ER resulting in a predominately high mannose form of glycosylation (31), which contributes to the reduced affinity to Clq (36).

The difference between plant and mammalian glycosylation patterns raises concerns for the immunogenicity of plant-derived MAb therapeutics. The possibility of inducing plant-glycan specific antibodies could reduce therapeutic efficacy by accelerating clearance from plasma, or cause potential adverse effects through immune complex formation. Immunization studies with plant glycoproteins in different animal models have yielded inconsistent results: rats and rabbits develop antibodies to plant specific xylose and α-1 ,3-fucose, yet mice generate no antibody response against these glycans (37, 38), Moreover, no adverse effects were observed in patients with topical application of plant-produced MAbs with plant unique carbohydrates (39, 40). To date, the immunogenicity of systemic administered plant-produced MAbs has not been evaluated in humans.

To avoid problems associated with plant-specific glycans, "humanized" *N. benthamiana, Arabidopsis thaliana* and *Lemna minor* plant lines have been generated by genetic knockout or RNA interference (RNAi) strategies (41-43). In these plants, enzymes for the biosynthesis of plant specific glycans are inactivated, resulting in structurally equivalent MAbs as those derived in mammalian cells. Moreover, the glycan uniformity of MAbs produced by these optimized plant lines is better than those from mammalian cell cultures. Indeed, an anti-human CD30 MAb produced from these genetically modified plants had only a single predominant N-glycan species and showed improved antibody-dependent cell-mediated cytotoxicity (ADCC) compared to the same MAb produced in mammalian cells (43). This improvement is most likely due to the removal of fucose, which results in improved FcγR binding of MAbs (44). The therapeutic utility of pHu-E16 can be improved by expression in such "humanized" *N. benthamiana* lines.

In brief, the Examples provided below demonstrate that plant-derived MAbs can function effectively as post-exposure therapy against a potentially lethal infectious disease. Plants are an efficient platform to produce Hu-E16 with high-yield, speed, enhanced scalability, and cost-effectiveness, satisfying all major metrics for a successful therapeutic candidate. This technology can be readily applied in the future to antiviral antibodies against other emerging infectious disease threats, and may be most useful in resource poor settings such as the developing world. E16 is a monoclonal antibody that strongly neutralizes WNV and a humanized version of this antibody has been described in the art that retains its neutralizing activity and avidity (12). In the present invention this antibody was optimized for production of the antibody in a plant-based system. Attached as Appendix A are the Sequence materials showing the optimized sequences for the heavy and light chain for huE16 generated for use in the methods described herein. SEQ ID NO: 1. shows the optimized new E16p sequence-HC variable region (EcoRI-intronless signal sequence-HC-HindIII) used in the present invention. The sequence is translated into an amino acid sequence of SEQ ID NO: 2 in which the sequence: QVQLVQSGAEVKKPGASVKVSCKASGYTFTDYWIEWVRQAPGQGLEWMGDILCGTG RTRYNEKLKARVTMTADTSTSTAYMELRSLRSDDTAVYYCARSASYGDYADYWGQG TTVTVSS (SEQ ID NO: 3) is the VH portion of the sequences, NEKLKARVTMTADTSTSTAYMELRSLRSDDTAVYYCARSASYGDYADYWGQGTTVT VSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRV (SEQ ID NO: 8) depicts the CH1 region of the heavy chain, EPKSCDKTHTCPPCP (SEQ ID NO: 9) is the hinge region of the heavy chain, APELLGGP SVFLFPPKPKDTLMISRTPEVTCVVVDVSHEDPEVKFNWYVDGVEVHNAKTKPREEQY NSTYRVVSVLTVL- HQDWLNGKEYKCKVSNKALPAPIEKTISKAK (SEQ ID NO: 10) annotates as the CH2 region and GQPREPQVYTLPPSRDEL TKNQVSLTCLVKGFYPS-DIAVEWESNGQPENNYKTTPPVLDSDGSFFLYSKLT-VDKSRW QQGNVFSCSVMHEALHNHYTQK-SLSLSPGK-(SEQ ID NO: 11) is the CH3 region of the heavy chain. The entire optimized heavy chain encoding nucleic acid sequence is depicted in SEQ ID NO: 4, which encodes a sequence of SEQ ID NO: 5. The sequence of SEQ ID NO: 4 is co-expressed in the *N. benthamiana* with a sequence that encodes the humanized light chain of the huE16 antibody. The optimized light chain of huE16 is encoded by the sequence of SEQ ID NO: 6 and encodes the amino acid sequence of the light chain of the huE16 as depicted in SEQ ID NO: 7. Coexpression of these two separate chains in *N. benthamiana* as detailed below yields a therapeutic huE16 antibody that has therapeutic and prophylactic properties.

The bispecific antibodies of the present invention recognize specific West Nile Virus epitopes. As used herein these terms refer to a molecule (e.g., a peptide) or a fragment of a molecule capable of immunoreactivity with an anti-huE16 antibody and, for example, include a WNV antigenic determinant domain III recognized by the any of the antibodies having a heavy chain/light chain sequence combination of SEQ ID NO: 5/SEQ ID NO: 7. WNC antigen epitopes can be included in proteins, protein fragments, peptides or the like.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked, to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain (VH), followed by three or four constant domains (CH1, CH2, CH3, and CH4). as well as a hinge region between CH1 and CH2. Each light chain has two domains, an amino-terminal variable domain (VL) and a carboxy-terminal constant domain (CL). The VL domain associates non-covalently with the VH domain, whereas the CL domain is commonly covalently linked to the CHI domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol I. pages 647-669), although not all CDR residues are necessarily directly involved in antigen binding.

The terms, "antibody" is used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., WNV binding and or neutralizing.

The term "monoclonal antibody", (mAb) refers to an antibody of a population of substantially homogeneous antibodies: that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art: including e.g., the hybridoma method ( Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g., human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus sequence. Chimeric antibodies can include fragments of such antibodies, provided that the antibody fragment exhibits the desired biological activity of its parent antibody, for example binding to the same epitope (see, e.g., U.S. Pat. No. 4,816,567: and Morrison et al., 1984, Proc. Natl. Acad. Sci. USA 81: 6851-6855).

The methods of the invention can also be used to prepare antibody fragments. The terms "antibody fragment", refer to a portion of a full length huE16 antibody, in which a variable region or a functional capability is retained, for example, specific West Nile Virus epitope binding. Examples of antibody fragments include, but are not limited to, a Fab, Fab', F(ab')2, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the CH1 domain of the heavy chain. Pepsin treatment yields a F(ab')2 fragment that has two antigen-binding sites and is still capable of cross-linking antigen.

Fab' fragments differ from Fab fragments by the presence of additional residues including one or more cysteines from the antibody hinge region at the C-terminus of the CH1 domain. F(ab')2 antibody fragments are pairs of Fab' fragments linked by cysteine residues in the hinge region. Other chemical couplings of antibody fragments are also known.

"Fv" fragment is contains a complete antigen-recognition and binding site consisting of a dimer of one heavy and one light chain variable domain in tight, non-covalent association. In this configuration, the three CDRs of each variable domain interact to define an antigen-biding site on the surface of the VH-VL dimer. Collectively, the six CDRs confer antigen-binding specificity to the antibody.

A "single-chain Fv" or "scFv" antibody fragment is a single chain Fv variant comprising the VH and VL domains of an antibody where the domains are present in a single polypeptide chain. The single chain Fv is capable of recognizing and binding antigen. The scFv polypeptide may optionally also contain a polypeptide linker positioned between the VH and VL domains in order to facilitate formation of a desired three-dimensional structure for antigen binding by the scFv (see e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments (VH-CH1-VH-CH1) to form a pair of antigen binding regions. These "linear antibodies" can be bispecific or monospecific as described in, for example, Zapata et al. 1995, Protein Eng. 8(10):1057-1062.

Any of the above antibody fragments or variants can be produced by the methods described herein and isolated for use as therapeutic and or prophylactic medicaments. As such, the antibody compositions of the invention may advantageously be prepared as pharmaceutical formulations in suitable pharmaceutical excipients or deliver vehicles. The antibody formulations will be prepared by at least one purification step in which the recombinant cellular material is removed. The methods described below are scaleable for the production of large quantities of the huE16 antibody for therapeutic and or prophylactic uses against WNV infection.

EXAMPLES

Example 1

Materials and Methods for Production of Hu-E16

Construction of pHu-E16 MAb Expression Vectors. The coding sequences of Hu-E16 MAb LC and HC (12) were optimized in silico with *N. benthamiana*-optimized codons using an algorithm described in (26). An 18-bp sequence coding for a 'SEKDEL' hexapeptide (SEQ ID NO: 13) ER-retention signal was added to the C-terminus of the HC gene. Optimized LC and HC sequences were synthesized (DNA 2.0) and cloned into the 5' modules of plant expression vectors pICH21595 and pICH11599 of the MagnICON system as described previously (22).

Agroinfiltration of *N. benthamiana.* Plant expression vectors were individually transformed into *Agrobacterium tumefaciens* GV3101 by electroporation as previously described (45). Wild-type N. benthamiana plants were grown in a greenhouse with 16/8 hr light/dark cycle at 25° C. for 5 weeks. Plant leaves were co-Agroinfiltrated with GV3101 strains containing the LC and HC 5' modules along with their respective 3' modules and an integrase construct as described previously (22).

Extraction of total protein from plant leaves. Agroinfiltrated *N. benthamiana* leaves were harvested on days 4, 5, 6, 7, 8, 9, and 10 days post infiltration (dpi) for evaluating the temporal pattern of pHu-E16 MAb expression, For other protein analysis, plant leaves were harvested 7 dpi. Total leaf protein was extracted by homogenization with extraction buffer (PBS, 1 mM EDTA, 10 mg/ml sodium ascorbate, 10 μg/ml leupeptin, 0.3 mg/ml phenylmethylsufonylflouride) using a FastPrep machine (Bio101) following the manufacture's instruction. The crude plant extract was clarified by centrifugation at 14,000×g for 10 min at 4° C.

SDS-PAGE and Western blot. SDS-PAGE and Western blotting were performed as described previously (46). Protein samples were subjected to 4-20% gradient SDS-PAGE under reducing (5% v/v β-mercaptoethanol) or non-reducing conditions. Gels were then either stained with Coomassie blue or used to transfer proteins onto PVDF membranes. HRP-conjugated antibodies against human-kappa LC or gamma HC (Southern Biotech) were used for western blot analysis.

ELISA. An ELISA designed to detect the assembled form of MAb (with both LC and HC) was performed to quantify pHu-E16 expression as described previously (22). Plates were coated with a goat anti-human gamma HC antibody (Southern Biotech). After incubation with plant protein extract, a HRP-conjugated anti-human-kappa LC antibody was used as the detection antibody. mHu-E16 was used as reference standard (12).

The ELISA for examining the binding of pHu-E16 to WNV E DIII was performed based on an earlier publication (27). DIII (amino acids 296-415) protein of the New York 1999 strain of WNV purified from *E. coli* (27) was immobilized on microtiter plates. An HRP-conjugated anti-human-kappa LC antibody was used as the detection antibody. The plates were developed with TMB substrate (KPL Inc).

Purification of pHu-E16. pHu-E16 was purified from *N. benthamiana* leaves by a three- step purification protocol comprised of ammonium sulfate precipitation, protein A affinity and DEAE-anion exchange chromatographies.

*N. benthamiana* leaves Infiltrated with hu-E16 MAb constructs were harvested on 7 dpi and homogenized with the extraction buffer (PBS, 1 mM EDTA, 10 mg/ml sodium ascorbate, 10 μg/ml leupeptin, 0.3 mg/ml PMSF). Crude extract was filtered through Miracloth and centrifuged at 17,700×g for 30 min at 40° C. to remove cell debris. Ammonium sulfate was added slowly to the clarified plant extracts to 25% saturation with thorough mixing at 4° C. The sample was centrifuged at 17,700×g for 30 min at 4° C and the pellet was saved for analysis. The 25% ammonium sulfate supernatant was further processed by adding ammonium sulfate to 50% saturation. The sample was again centrifuged at 17,700×g for 30 min and the supernatant was discarded. The 50% ammonium sulfate pellet was resuspended in PBS and then applied to a MabSelect Protein A column (GE Healthcare, Piscataway, N.J.). After washing with PBS, the column was eluted with 50 mM sodium citrate, pH 2.5. The eluate was neutralized immediately with 1M Tris-base to a final pH of 7.0 and further purified by DEAE anion exchange chromatography with DEAE Sepharose FF 26/20 resin (GE Healthcare, Piscataway, N.J.). Purified pHu-E16 was collected in the DEAE flow-through fraction. The purity of pHu-E16 was determined by quantitating Coomassie blue-stained protein bands on SDS-PAGE using a densitameter. Levels of residual DNA, Protein A and endotoxin in the final purified samples were quantified by using commercial PicoGreen dsDNA quantitation (Invitrogen, Carlsbad, Calif.), protein A ELISA (Cygnus Technologies, Southport, N.C.), and QCL-1000 Chromogenic LAL Endpoint assay kits (Lonza, Allendale, N.J.), respectively, based on the manufactures' instructions.

Cells, reporter virus particles, and antibody neutralization. BHK21-15, C6/36, and Raji-DC-SIGNR cells were maintained as described (13, 28, 47). WNV reporter virus particles (RVP), which encode GFP, were produced in HEK293T cells as described (13, 28). The neutralization potency of pHu-E16 or mHu-E16 was measured in the presence or absence of purified human Clq protein (Complement Technologies). Neutralization potency was calculated as a function of the concentration of antibody required to block 50% of the infection events using non-linear regression analysis (GraphPadPrism4). mHu-E16 was produced in CHO cells and purified by protein A affinity and size exclusion chromatography as described (12).

Recombinant protein expression and yeast surface display. The WNV E ectodomain (residues 1-404) and DIII (residues 296-404) of the New York 1999 strain were cloned into the pET21a bacterial expression plasmid (EMD Biosciences) as described previously (27). All constructs were expressed in *E. coli* and purified using an oxidative refolding protocol (27). Refolded protein was separated from aggregates on a Superdex 75 or 200, 16/60 size-exclusion column using fast protein liquid chromatography (GE Healthcare). Yeast expressing WNV DIII were generated and stained with MAbs as described (12). Yeast cells were analyzed with a Becton Dickinson FACSCalibur flow cytometer.

Surface plasmon resonance. Affinity measurement of MAb for DIII or E ectodomain of WNV was performed by surface plasmon resonance (SPR). The binding of human Clq to mHu-E16 and pHu-E16 was also analyzed by SPR.

Affinity measurement of MAb for DIII of WNV was performed by surface plasmon resonance (SPR, BIAcore 3000 biosensor, Biacore, Inc). pHu-E16 or mHu-E16 were immobilized on the CM-5 sensor chip (~500RU) by amine coupling kit as recommended by the manufacturer. Subsequently, purified DIII or E ectodomain was injected at concentrations of 3.1, 6.3, 12.5, 25, 50 and 100 nM, a flow rate of 70 μl/minute for 180 sec, and then allowed to dissociate over 180 sec. Regeneration of antibody surfaces was performed by pulse injection of 10 mM glycine pH 1.5. Binding responses were normalized to the same level of immobilized antibody and analyzed using the BIA evaluation 4.1 software. Kinetic constants, k (a) and k (d), were estimated by global fitting analysis of the association/dissociation curves to the 1:1 Langmuir interaction model. The equilibrium dissociation constant (KD) was calculated as $KD=k_{(d)}/k_{(a)}$.

The binding of human Clq to mHu-E16 and pHu-E16 was analyzed by SPR. WNV DIII was immobilized on the CM-5 sensor chip by amine coupling. MAb was bound to the DIII surface at approximately 1000 RU, followed by injection of Clq at 24 nM and a flow rate of 30 μl/min for 60 sec with dissociation time of 60 sec. Between experiments, the naked antigen surface was regenerated by pulse injection of 10 mM glycine pH 1.5. All binding experiments were performed in 10 mM Hepes, pH 7.4, 150 mM NaCl, 3 mM EDTA, and 0.005% P20 surfactant.

Efficacy of MAbs in vivo. All mice were housed in a pathogen-free mouse facility. Studies were performed with approval from the Washington University School of Medicine Animal Safety Committee. Mice received a single dose of purified pHu-E16 or mHu-E16 by intraperitoneal injection the same day, two days after, or four days after footpad infection with $10^2$ plaque forming units (PFU) of WNV strain 3000.0259. Five week-old wild type C57BL/6 mice were purchased commercially (Jackson Laboratories). Kaplan-Meier analysis of survival data was performed using the log-rank test. IC50 analyses were performed by non-linear regression and statistical significances were determined using analysis of variance (ANOVA) and F-tests.

Example 2

Expression and Assembly of Hu-E16 MAb in Plants

Figure 2:
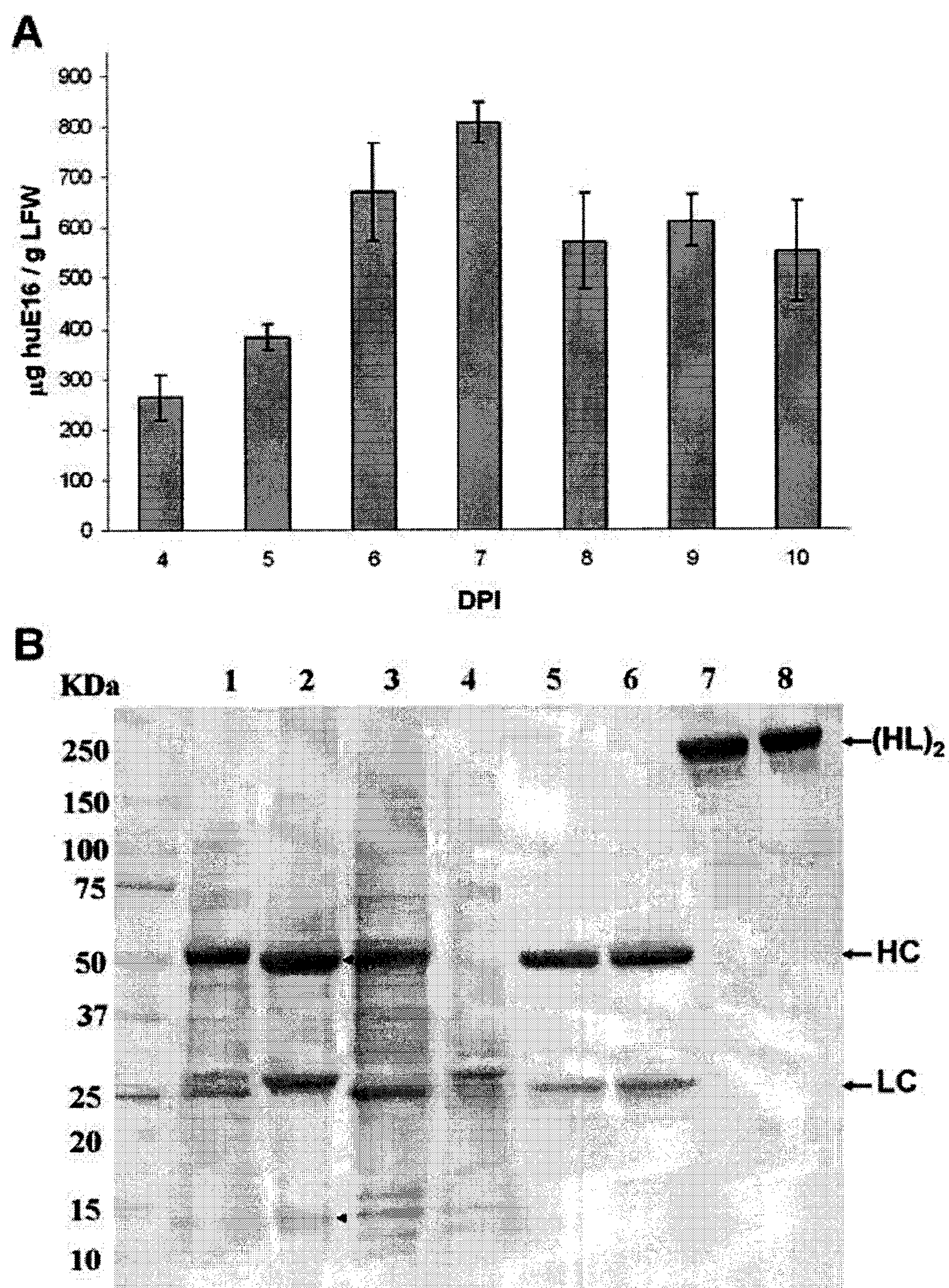
FIGS. 2A-2B. Expression and purification of Hu-E16 mAb in *N. benthamiana* plants. *N. benthamiana* leaves were co-infiltrated with Hu-E16 LC and HC constructs. Leaf proteins were extracted on days 4 to 10 after agroinfiltration (A) or on day 7 after agroinfiltration (B). A. Protein extracts were analyzed with an ELISA that detects the assembled form of pHu-E16 MAb. Mean ± standard deviation (SD) of samples from three independent infiltration experiments are presented. B. Leaf protein extract was purified and analyzed on a 4-20% SDS-PAGE gel under reducing (Lanes 1-6) or nonreducing (Lanes 7 and 8) condition. Lane 1, Clarified plant extract; lane 2, Plant proteins removed by 25% ammonium sulfate precipitation; lane 3, 50% ammonium sulfate pellet fraction resuspended for Protein A Chromatography: lane 4, Protein A flow-through fraction; lanes 5 and 7, Purified pHu-E16 mAb in the Protein A eluate; lanes 6 and 8, mHu-E16 as a reference standard. ◄: RuBisCo large and small subunits; light (LC), heavy (HC) chain, and assembled form (HL)2 of Hu-E16 MAb.

As a first test of the feasibility of developing a plant-derived Hu-E16 therapeutic, we needed to demonstrate that plants could express and assemble Hu-E16. To ensure high-level expression of Hu-E16 in plants, the coding sequences of Hu-E16 light chain (LC) and heavy chain (HC) were optimized in silico with *N. benthamiana*-optimized codons (26). Optimized LC and HC sequences were cloned into the 5' modules of plant expression vectors of the MagnICON system (22) and transformed into *Agrobacterium tumefacient*. To co-express Hu-E16 LC and HC, A. tumefacient strains harboring the LC and HC 5' modules were co-delivered into *N. benthamiana* leaves along with their respective 3' modules and an integrase construct through vacuum infiltration (22). Western blot analysis confirmed that the LC and HC of pHu-E16 were produced in leaves with the expected molecular weights of 25 kDa and 50 kDa, respectively (FIGS. 1A and B). Western blot analysis under non-reducing conditions showed a pHu-E16 MAb band with a molecular weight of ~170 kDa, indicating assembly into its tetrameric (2HC+2 LC) form (FIG. 1C). Comparison of bands from reducing and non-reducing gels also confirmed no cleavage of the fully assembled MAb since only intact LC and HC bands. The assembly of pHu-E16 was corroborated by an ELISA that detects the assembled form of E16 (HC capture, LC probe) (FIG. 2A). ELISA results also indicated that pHu-E16 reached the highest level of production 7 days post infiltration with *A. tumefacient* containing the HC and LC constructs, with an average accumulation of 8.1 mg/g leaf fresh weight (LFW). This level is greater than the highest expression level for MAbs in plants ever reported (22) and convincingly demonstrates that plants can rapidly express fully-assembled pHu-E16 at high levels.

Example 3

Purification and Scale-Up Production of pHu-E16

For plant-produced pHu-E16 to become a viable WNV therapeutic candidate, an efficient purification scheme from plant tissue must be developed. pHu-E16 was extracted and purified by a three-step purification protocol comprised of ammonium sulfate precipitation, protein A affinity and DEAE-anion exchange chromatographies. Precipitation with 35% ammonium sulfate effectively removed the most abundant plant host protein, the photosynthetic enzyme RuBisCo, and other plant proteins (FIG. 2B, Lane 2). Protein A affinity chromatography removed the remaining contaminating proteins and enriched pHu-E16 to greater than 95% purity (FIG. 2B, Lane 5). In the presence of a reducing agent, purified pHu-E16 was detected as the HC and LC (migration at ~50 and 25 kDa) in the same stoichiometric ratio as the Hu-E16 produced in mammalian cells (FIG. 2B, Lanes 5 and 6). Under oxidizing conditions, purified pHu-E16 antibody assembled in its tetrameric form (FIG. 2B, Lane 7). For future clinical testing and cGMP production, an ion exchange chromatographic step was added to eliminate residual DNA, endotoxin, and Protein A from the final purified product. Contaminants and/or impurities were efficiently removed using this purification scheme so that levels in the final pHu-E16 product were below the Food and Drug Administration specifications for injectable human MAb pharmaceuticals (Table 1). To validate the scalability of our purification protocol, we purified pHu-E16 purification at different scales of plant materials ranging from 10 to 5,000 grams. Our protocol produced highly purified pHu-E16 from *N. benthamiana* plants with consistent recovery among batches of different scale (Table 1). In total, >5 g of hu-E16 was purified from 16 kg of plant material for in vitro and in vivo studies.

TABLE 1

Characterization of pHu-E16 mAb purification scheme

| LFW (g) | Recovery (%) | Purity | Residual DNA (ng/ml) | Residual Protein A (ng/ml) | Endotoxin (EU/ml) |
|---|---|---|---|---|---|
| 10 | 57.52 ± 2.59 | >95% | <1 | 9.77 ± 3.02 | 3.78 ± 1.52 |
| 100 | 51.71 ± 2.86 | >95% | <1 | 11.65 ± 2.15 | 3.57 ± 2.6 |
| 500 | 45.77 ± 4.84 | >95% | <1 | 12.04 ± 2.42 | 2.94 ± 1.57 |
| 5000 | 48.76 ± 6.06 | >95% | <1 | 10.33 ± 6.65 | 4.12 ± 2.93 |

Example 4 pHu-E16 Retains Antigen Binding Activity

Figure 3:
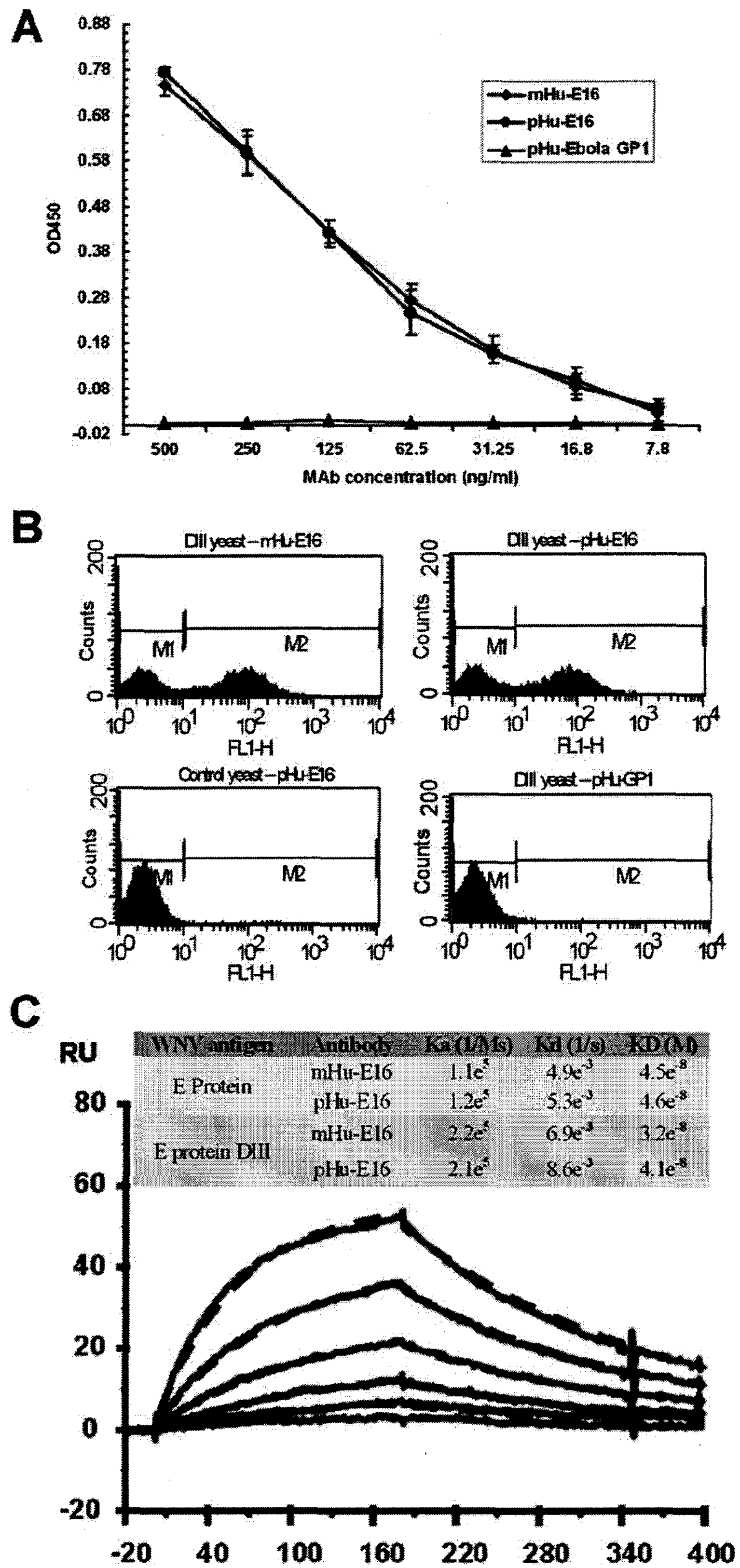
FIGS. 3A-3C. Antigen recognition and binding kinetics of pHu-E16 for WNV DIII and E protein. A. ELISA of pHu-E16 binding to WNV DIII. Serial dilutions of pHu-E16 were incubated on plates coated with WNV DIII and detected with as HRP-conjugated anti-human kappa antibody. Dilutions of mHu-E16 were used in parallel as reference standards. A plant-produced humanized MAb against Ebola virus GP1 protein (pHu Ebola GP1) was used as a negative control. The OD450 (mean±SD) from three independent experiments are presented. B. Binding of pHu-E16 to DIII of WNV E displayed on yeast cell surface. DIII displaying or negative control yeast cells were stained with pHu-E16, mHu-E16, or a negative control MAb (pHu-Ebola GP1) and processed by flow cytometry. Representative data from several Independent experiments are shown. C. SPR analysis of binding affinity and kinetics of pHu-E16 and mHu-E16 for WNV DIII and E protein. WNV DIII fragment or E ectodomain protein was injected over pHu-E16 or mHu-E16 immobilized to the CM-5 biosensor chip. Binding responses were normalized to the same level of immobilized antibody and analyzed by Langmuir 1:1 interaction fit (black dashed lines). A representative set of SPR binding curves of pHu-E16 for WNV E protein is shown. The results are one of several independent experiments performed in duplicate.

To begin to establish a similarity of structural, biochemical and functional properties between plant- and mammalian cell-derived Hu-E16, we compared their recognition and binding kinetics for WNV E proteins or domains in three assays: (1) The binding of pHu-E16 to WNV E DIII was determined by ELISA in which DIII was immobilized (27). pHu-E16 and mHu-E16 bound in a similar manner to DIII (FIG. 3A). (2) Recognition of pHu-E16 for DIII was examined in a binding assay with yeast that display DIII on their surface. Flow cytometric analysis showed that the percentage of positive yeast and the mean fluorescence intensity of binding by pHu-E16 and mHu-E16 were virtually identical (FIG. 3B). (3) To assess the binding of pHu-E16 more quantitatively, a surface plasmon resonance (SPR) assay was utilized with purified pHu-E16 or mHu-E16 immobilized on a BiAcore chip. Monomeric WNV E protein and E domain III were generated, and flowed across the solid-phase Hu-E16 mAbs at six different concentrations. pHu-E16 had almost identical binding affinity and kinetics for WNV E protein and DIII compared to its mHu-E16 counterpart (FIG. 3C).

Example 5

Neutralizing Activity of pHu-E16

Figure 4:
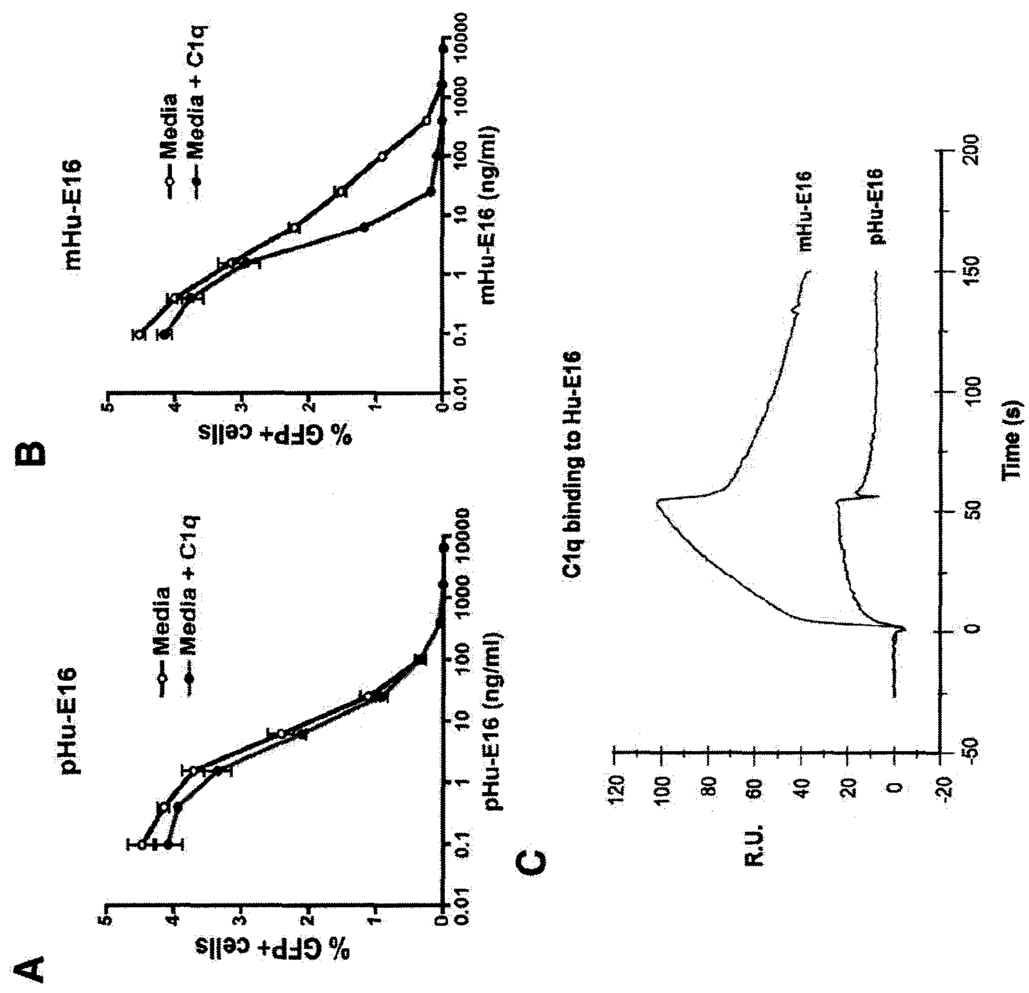
FIGS. 4A-4C. The neutralizing activity of mHu-E16 and pHu-E16 and effect of C1q. Serial dilutions (A) mHu-E16 or (B) pHu-E16 were incubated with WNV RVP in the presence of media or 50 μg/ml of purified human C1q prior to infection of Raji-CD SIGN-R cells. Forty hours later, cells were fixed and analyzed by flow cytometry for GFP expression. Data are representative of at least three independent experiments performed in triplicate and bars represent the standard error of the mean. C. SPR analysis of C1q binding to mHu-E16 and pHu-E16. C1q (24 nM) was injected over captured antibody on immobilized DIII fragment. Data are representative of several independent experiments.

To evaluate the neutralization potential of pHu-E16, we used a validated and quantitative flow cytometry-based neutralization assay (28) that measures antibody inhibition of infection with WNV reporter virus particles (RVP). WNV RVP were mixed with varying concentrations of pHu-E16 or MHu-E16 MAbs, and then incubated with permissive Raji-DC-SIGN-R cells. Neutralization was monitored as a function of GFP fluorescence by flow cytometry at 40 hours after infection. pHu-E16 neutralized WNV infection equivalently compared to mHu-E16 (FIGS. 4A and B). Recent studies have suggested that the complement component Clq augments the neutralizing potency of mHu-E16 (29). In the presence of purified Clq, the neutralization curve of mHu-E16 but not pHu-E16 showed a shift to the left, indicating greater inhibition at lower antibody concentrations. This suggests that slightly different carbohydrate modifications on the plant-derived MAb impaired an interaction with Clq as compared to mHu-E16. This was confirmed by an SPR assay as pHu-E16 showed lower binding to Clq (FIG. 4C). Overall, the binding and neutralization studies in vitro suggest that pHu-E16 and mHu-E16 had similar but not identical functional properties.

Example 6 pHu-E16 Protects Against Lethal WNV Infection

Figure 5:
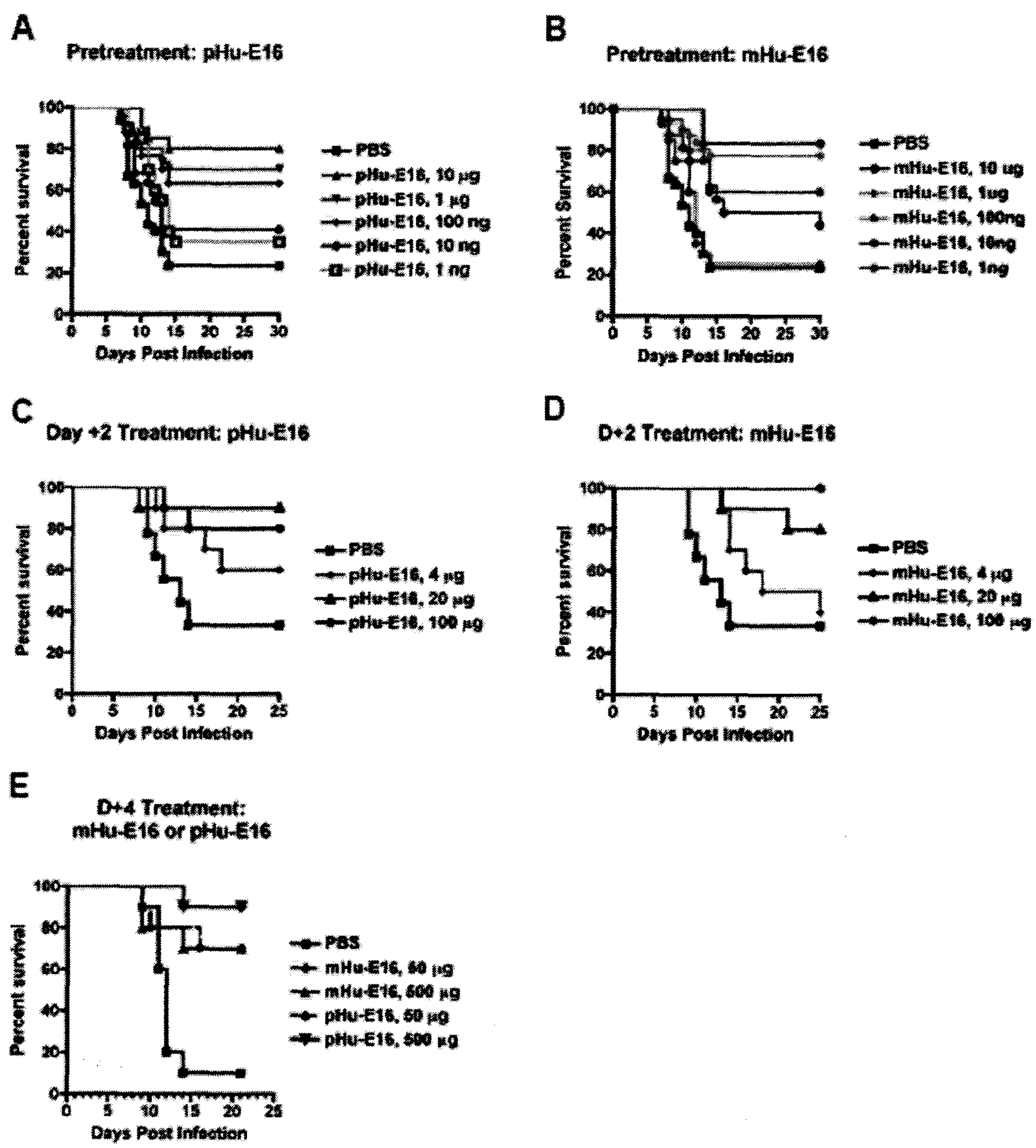
FIGS. 5A-5E. pHu-E16 and mHu-E16 mediated protection in mice. A-B. Five week-old C57BL/6 mice were passively transferred saline or serial 10-fold increases in dose (ranging from 0.001 to 10 μg, N>20 per dose) of pHu-E16 (A) or mHu-E16 (B) via an intraperitoneal route on the same day as subcutaneous infection with 102 PFU of WNV. Survival data from at least two independent experiments were analyzed by log rank test, and IC50s were calculated by non-linear regression of survival percentage at each MAb dose. As indicated in the text, both pHu-E16 and mHu-E16 were highly protective, there was no significant difference in IC50 values (P>0.6). C-E. Wild type C57BL/6 mice were infected with 102 PFU of WNV and then given a single dose of the indicated doses of pHu-E16 or mHu-E16 via an intraperitoneal route at (C and D) day +2 or (E) day +4 after infection. Survival data from at least two independent experiments (N=20 per dose) were analyzed by the log-rank test.

Prophylaxis studies. Although the functional studies suggested similar activity of the pHu-E16, it was essential to confirm this in vivo. Pre-treatment studies were performed in 5 week-old wild type C57BL/6 mice (N>20, per group) to compare the concentrations of pHu-E16 and mHu-E16 that prevent severe WNV infection. Mice were infected with $10^2$ PFU of WNV, which causes a baseline mortality of 80 to 90% (30). Increasing amounts (0.001 to 10 μg) of pHu-E16 or mHu-E16 were administered as a single dose on the day of infection. Mice were significantly protected when administered as little as 0.1 μg of pHu-E16 (FIG. 5A, P<0.001). Greater than 80% of mice were protected from lethal infection when 10 μg of pHu-E16 was administered (P<0.0001). Protection against WNV lethality achieved by pHu-E16 was similar in magnitude as that observed with mHu-E16 (pHu-E16, IC50=0.19 μg, mHu-E16, IC50=0.15 μg, P>0.6) (FIGS. 5A and B).

Therapeutic studies. Post-exposure treatment studies were performed to confirm the therapeutic activity of pHu-E16 when administered at a specific time point after infection in mice. Mice were passively administered a single dose (4 to 00 μg) of pHu-E16 or mHu-E16 by intraperitoneal injection at day 2 after subcutaneous inoculation of $10^2$ PFU of WNV (FIGS. 5C and D). Notably, 20 μg of pHu-E16 protected most mice from lethal infection when given 2 days after WNV inoculation and a single injection of as low as 4 μg also prevented mortality; these results were similar M that observed in experiments with mHu-E16 performed in parallel, Since WNV spreads to the brain in mice by day 4 after infection (12), we also investigated the therapeutic efficacy of pHu-E16 at this later time point (FIG. 5E). A single administration of 50 μg of pHu-E16 protected up to 70% of mice from lethal infection and a 90% survival rate was achieved with a single 500 μg dose, results that were equivalent in protection to mHu-E16. Overall, pHu-E16 appeared as potent as mHu-E16 in mice.

Example 7

Construction of Bifunctional Monoclonal Antibody using Hu-E16

A. Vector engineering for E16 fusion protein. The above examples show that MagnICON™ expression technology is an optimal platform for rapid, high-level MAb and MAb fusion proteins expression in plants. E16 fusion protein genes were cloned into these vectors for expression in plants.

Figure 7B:
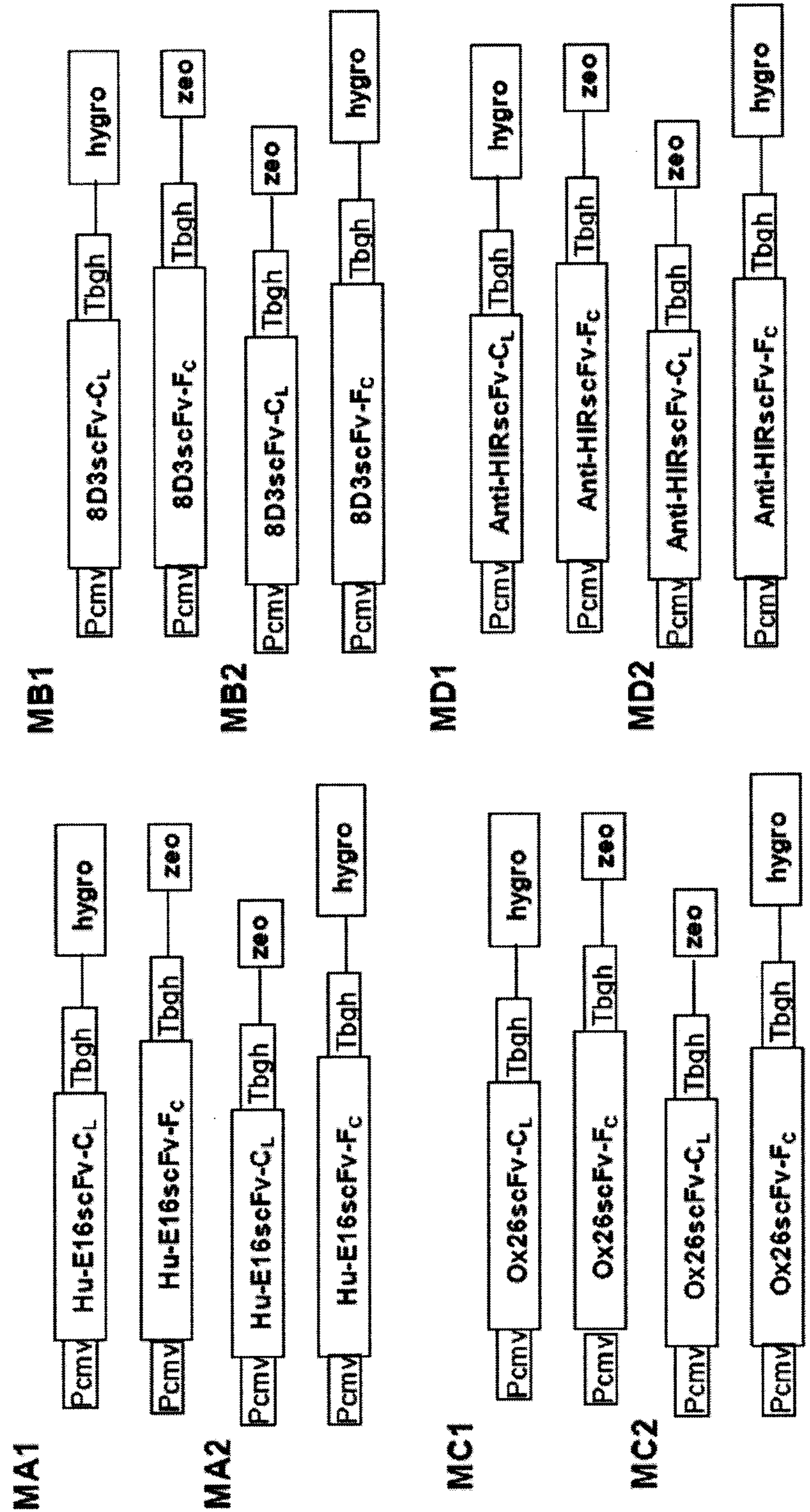
Figure 8:
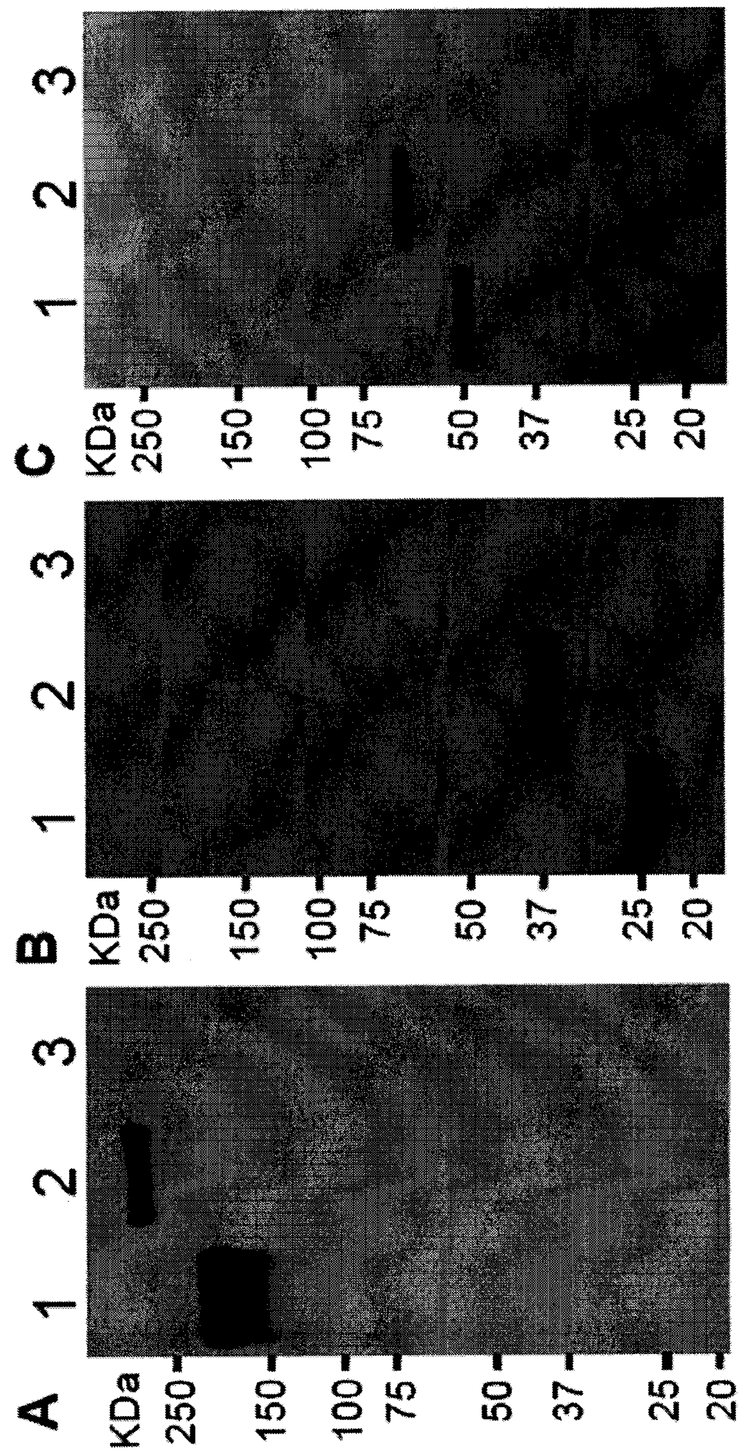
FIGS. 8A-8C. Western blot analysis of a plant-derived Bif-MAb. Proteins were separated on 4-20% SDS-PAGE gradient gels under a nonreducing (A) or reducing; (B anc C) condition and blotted onto PVDF membranes. The membranes were incubated with as goat anti-human-kappa chain antibody or goat anti-human-gamma-chain antibody to detect LC (A and B) or HC (C). Lane 1, E16 IgG standard; lane 2, Bif-MAb sample; lane 3. Plant negative control.
Figure 9:
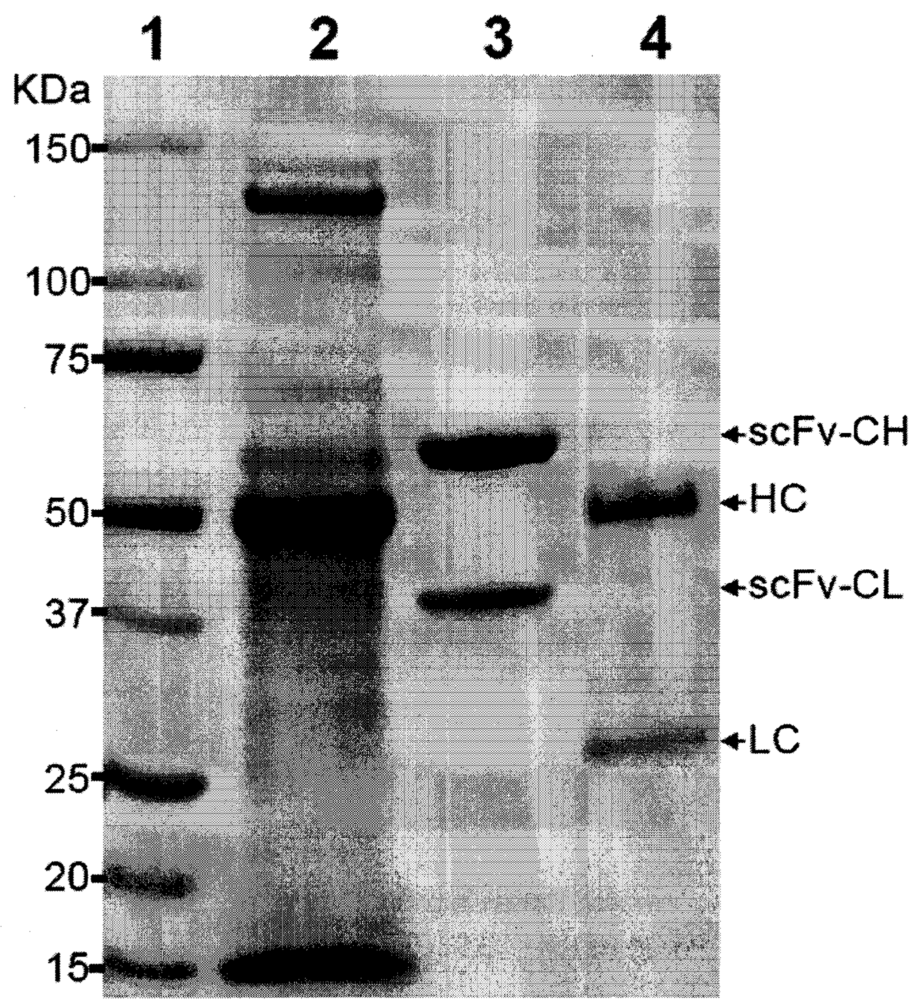
FIG. 9. Coomassie stained reducing SDS-PAGE gel of plant-derived Bif-MAb purification samples. Lane 1: MW marker, Lane 2: Crude plant extract, Lane 3: Purified Bif-MAb, Lane 4: E16 as reference standard.

For construction of a Bif-MAb that binds to WNV and the mouse TfR as a proof-of-principle for the in vivo studies, a fusion of E16 scFv and 8D3 scFv was created by genetic engineering (FIGS. 7A and B. PA-PB and MA-MB). The coding sequences of scFv 8D3 and E16 were linked to the constant region CH and CL of Human IgG1 respectively at its N-terminus. When scFv-CR and scFv-CL were co-expressed, they assembled into a tetravalent bifunctional MAb with divalent binding for both WNV E protein and mouse TM (FIG. 6*a*), as demonstrated in our feasibility studies (FIG. 8-9). Our results on the parent E16 MAb demonstrated that codon optimization (using plain-preferred codons, removal of spurious polyadenylation signals, and cryptic intron mRNA splicing signals) greatly increased expression levels in plants. To ensure high-level expression of Bif-MAb, we used a similar approach to optimized DNA sequences for plant expression. For expression in CHO cells, there is no need to do codon optimization; therefore, the original DNA sequences were used.

For construction of a Bif-MAb that binds to WNV and the rat TfR as a proof-of-principle for the in vivo studies, a fusion of E16 scFv and OX26 scFv was created by genetic engineering (FIGS. 7A and B. PC and MC). The strategy of vector construction for the 12 molecular constructs for both plant and CHO cell expression was similar to that discussed above except the sequence of 8D3 scFv was replaced by the sequence of OX26 scFv.

For construction of a Bif-MAb that binds to WNV and the human HIR for future studies in rhesus monkey and humans, a fusion of E16 scFv and anti-HIR scFv were created by genetic engineering (FIGS. 7A and B. PD and MD). The strategy of vector construction for the 12 molecular constructs for both plant and CHO cell expression was similar to that discussed in Example 1 above ("Recombinant protein expression and yeast surface display") except the sequence of 8D3 scFv was replaced by the sequence of anti-HIR scFv.

For plant expression, two sets of 4 vectors for each scFv component (hu-E16, ox26, 8D3, and anti HIR) (total 32) were constructed. with each set equivalent to the vectors shown in FIG. 7A. In each set, 4 constructs were in the IMP module and the other 4 in the PVX module. The major difference between the two sets was the linker used for connecting the variable regions of HC (VH) and LC (VL) in E16 scFv and 8D3 scFv.

For CHO cell expression, two sets of two vectors were constructed (FIG. 7B), In one set, the coding sequence of E16scFv was fused to that of HC, and the coding sequence of 8D3scFv was fused to that of LC. The opposite combination (8D3scFv-CH, E16scFv-CL) was designed in the other set.

Expression of Bif-E16. We evaluated optimized vectors for transient expression of Bif-E16 in both CHO cells and in *N. benthamiana* leaves. We predicted that some Bif-MAbs will express at high-levels and sufficient quantities of Bif-E16 can be obtained for characterization. For plant expression, using the combination of TMV module-Fc fusion and PVX module-CL fusion gives the highest expression level and assembly. For expression in CHO cells, the combination of E16scFv-CL and 8D3 scFv-CH gives the highest expression and assembly.

For plant expression of Bif-E16 MagnICON technology was used. The inventors used *Agrobacterium tumefaciens*, a bacterium that naturally transfers its DNA to plant cells, to deliver the DNA modules into leaves. *N benthamiana*, a relative of the common tobacco plant, was the plant of choice for high-level of MAb expression. *Agrobacteria* transformed with expression vectors were cultured to inoculate whole 4-week old plants by vacuum infiltration for transient expression of Bif-E16. To achieve the maximal percentage of fully-assembled Bif-MAbs, *Agrobacteria* cultures containing the E16 scFv-CH and 8D3 scFv-CL constructs (or 8D3 scFv-CH and E16scFv-CL) were mixed in various ratios and co-infiltrated into the plant leaf. At various intervals, leaves were harvested and gene expression analyzed. Our previous results indicate that the maximal MAb accumulation occurred 7 days post vector delivery (~0.8 to 1 mg MAb/g LFW) 1. Initially, E16 expression were analyzed with specific antibodies (rat anti-hu-E16 idiotype or anti-HC/LC). Levels of protein accumulation were followed by more detailed analysis of leaf extracts by Western analysis to determine if Bif-E16 accumulates at predicted sizes. Our results showed that Bif-E16 also reached the maximal accumulation seven days post vector delivery and assembled into the expected sizes (FIG. 8).

CHO cell expression of Bif-E16. Plasmids for E16 bif-mAbs production were transfected into CHO cell lines to generated stable transgenic cell lines with lipofectamine according to the published procedures. Cell lines were selected initially screened by resistance to both hygromycine and zeocine, then by expression of bif-mAbs. initially, E16 expression in the media was analyzed with specific antibodies (rat anti-hu-E16 idiotype or anti-HC/LC). Levels of protein accumulation was followed by more detailed analysis of cell culture media by Western analysis to determine if Bif-E16 accumulates at predicted sizes. The present results indicated that they accumulate at the expected size with the same pattern as the plant-derived Bif-D16 (FIG. 8).

Preliminary data (FIG. 8-9) demonstrates that these molecules can be expressed successfully in both CHO cells and plants. Nonetheless, some of the planned constructs were less efficient than others in expression level or assembly. As we generated 16 different vectors, we covered all possible combinations among E16 scFv, 8D3 ScFv, CH, and CL, and between TMV and PVX models known to the MagnICON technology to have the greatest chance fur success. The linker between HV and VL of the scFvs may determine the stability of the fusion molecule in plants. To address this, we have designed several linkers including ones with demonstrated stability and functionality in a similarly designed plant Bif-MAb (FIG. 8-9). If inefficient Bif-E16 assembly or aggregation occurred, we can use molecular and environmental optimization strategies to improve yield. For example, we can co-express chaperones known to be involved in antibody folding/assembly in plants. This strategy enhanced assembly and reduced aggregation of MAbs and MAb fusion proteins previously. The present results indicate that no aggregation occurred for any of the constructs. The combination of TMV module-Fc fusion and PVX module-CL fusion gave the highest expression level and assembly for plant expression. For expression in CHO cells, the combination of E16scFv-CL and 8D3 scFv-CH gave the highest expression and assembly. We also optimized experimental conditions for Bif-E16 accumulation by testing a range of plant age, *Agrobacteria* concentration, and LC/HC culture ratio and adapting from conditions for expressing a similar Bif-MAb in FIG. 8-9, Based on our preliminary studies, it is likely that Bif-E16 can be expressed (with bench mark of 0.3-0.5 mg/Leaf fresh weight (LFW)) in plants, and with some vectors attain even higher levels of accumulation. Our results indicated that 6-week greenhouse grown *N. benthamiana* plants, total *Agrobacteria* infiltration 0D600 of 0.8, and LC/HC culture ratio of 0.25 gave the best expression for Bif-E16.

Figure 10:
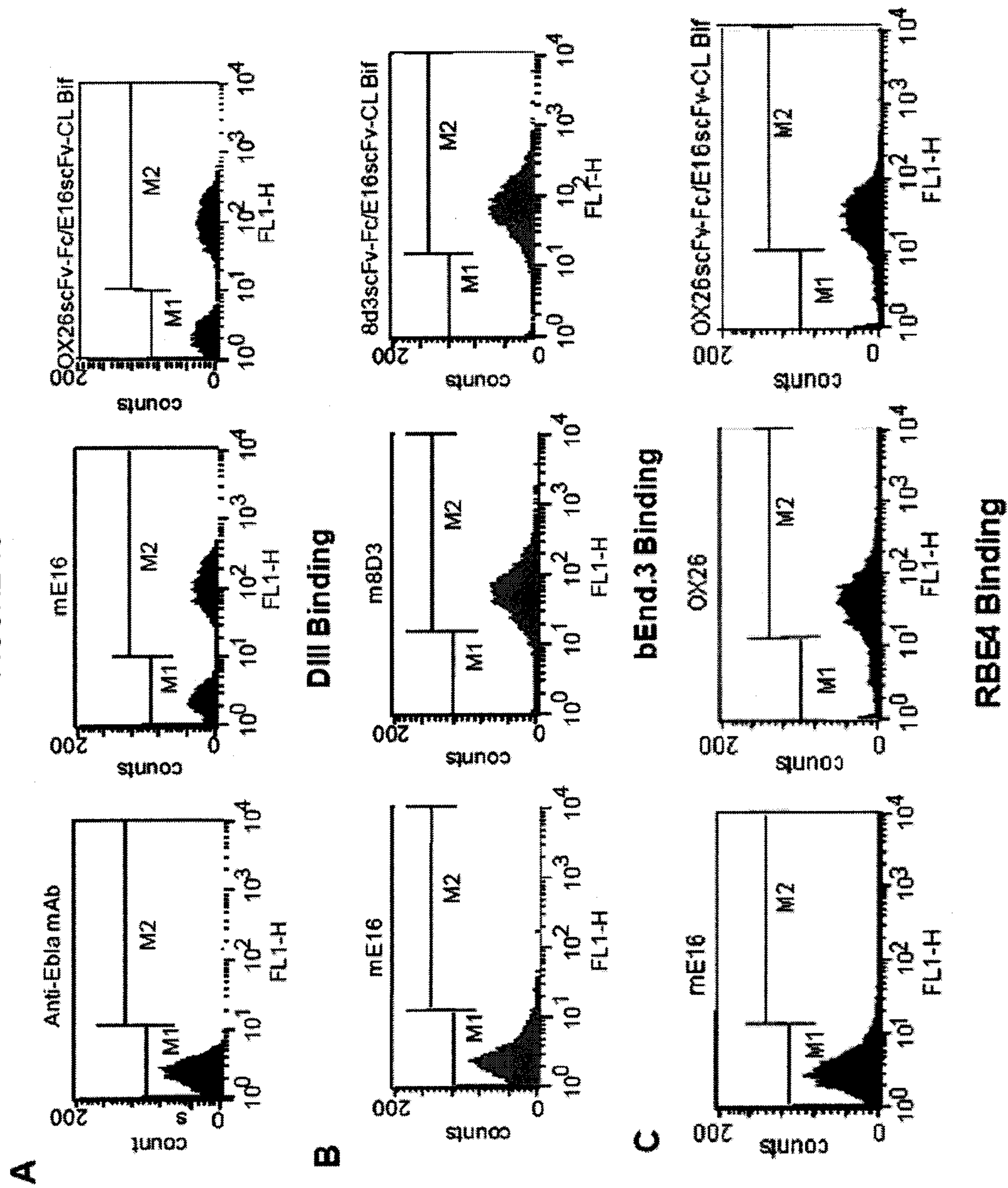
FIG. 10A-10C. Bispecific binding of E16 bifunctional mAbs to WNV antigen (DIII) and to BBB endothelial cell receptors. (A) Binding of bif-mAb to DIII of WNV E displayed on yeast cell surface. DIII-displaying yeast cells were stained with bif-mAb, or a negative control mAb an antibody against Ebola GP1), or a positive control mE16 and processed by flow cytometry. (B) 8D3/E16 Bif-MAb binding to mouse TfR expressing brain endothelial cells. bEnd.3 cells, a well characterized mouse brain endothelial cell line for mouse BBB TfR expression was stained with Bif-mAb of 8d3scFv-Fc/E16scFv-CL, or a positive control m8D3, or a negative control mE16 parental mAb and processed by flow cytometry. (C) Ox26/E16 Bif-MAb binding to mouse TfR expressing brain endothelial cells. bEnd.3 cells, a well characterized rat brain endothelial cell line for rat BBB TfR expression and in vitro BBB permeability study was stained with Bif-mAb of Ox26scFv-Fc/E16scFv-CL, or a positive control ox26, or a negative control mE16 parental mAb and processed by flow cytometry. Results show that bif mAbs retain E DIII binding while gain the ability to bind TfR on mouse or rat brain. These results were obtained for both plant and CHO cellderived bif-mAbs, and also for bif-MAbs with the opposite Fc and CL combination with 8D3 or OX26 (E16scFv-Fc/8D3scFv-CL, E16scFv-Fc/Ox26scFv-CL). Representative data from several experiments are shown.

Purification and characterization of Bif-E protein. To develop a robust production system, an efficient extraction and purification process must be developed. We have experience in purifying MAb and MAb fusion proteins from plants, which can be directly applied to Bif-E16 Protein extraction and purification followed our published procedures, which include homogenization, extraction, ammonium sulfate precipitation, and protein A affinity and ion exchange chromatographies. Bif-E16 produced in CHO cells was purified from culture media with protein A affinity chromatography, which have been demonstrated successfully with the purification of many mAb and mAb-derivatives including bifunctional mAbs. The optimized purification protocol will be scalable for future cGMP production. Material was evaluated for purity, integrity, and assembly by SDS-PAGE (reducing and non-reducing) and western blot analysis with anti-LC or anti-HC, or anti-8D3 sera. The present results showed that this protocol can purify the Bif-E16 efficiently with purity >95% and the purified product has the expected LC and HC fusion and assembly (FIG. 9). Our previous results showed that E16 MAb produced, in plants had similar structural and biochemical properties as those produced in mammalian cells. We analyzed the size, assembly, antigen recognition, and post-translational modification of Bif-E16 and directly compare the parent E16 and Bif-E16 for recognition of WNV E protein using, several independent assays. Both parent and Bif-MAbs was tested for binding to yeast displaying Dill of WNV on their surface by flow cytometry (results in FIG. 10). WNV F binding affinity and kinetics also were measured by surface plasmon resonance (SPR) (results in FIG. 12). Glycosylation of Bif-E16 was determined by liquid chromatography-electrospray ionization-mass spectrometry (LC-ESI-MS) of tryptic glycopeptides. The present results show that they all had the expected glycosylation pattern. Specifically, CHO cell-produced Bif-E16s had the typical mammalian glycoforms, and plant-produced Bif-E16s had the mammalian GnGn, G0-G2 galactose, GnGn fucosylated and G0-G2 galactose patterns depending on the specific “humanized” plant lines used for the expression of Bif-E16. To evaluate the “bispecificity” of Bif-E16, the recognition and binding affinity of Bif-E16 to mouse TfR was tested by flow cytometry with brain endothelial (b.END3) cells as described. The present results showed that Bif-E16 recognized both WNV F and mouse TfR in their native configurations, confirming the biospecificity of the Bif-E16 (FIG. 10).

Figure 14:
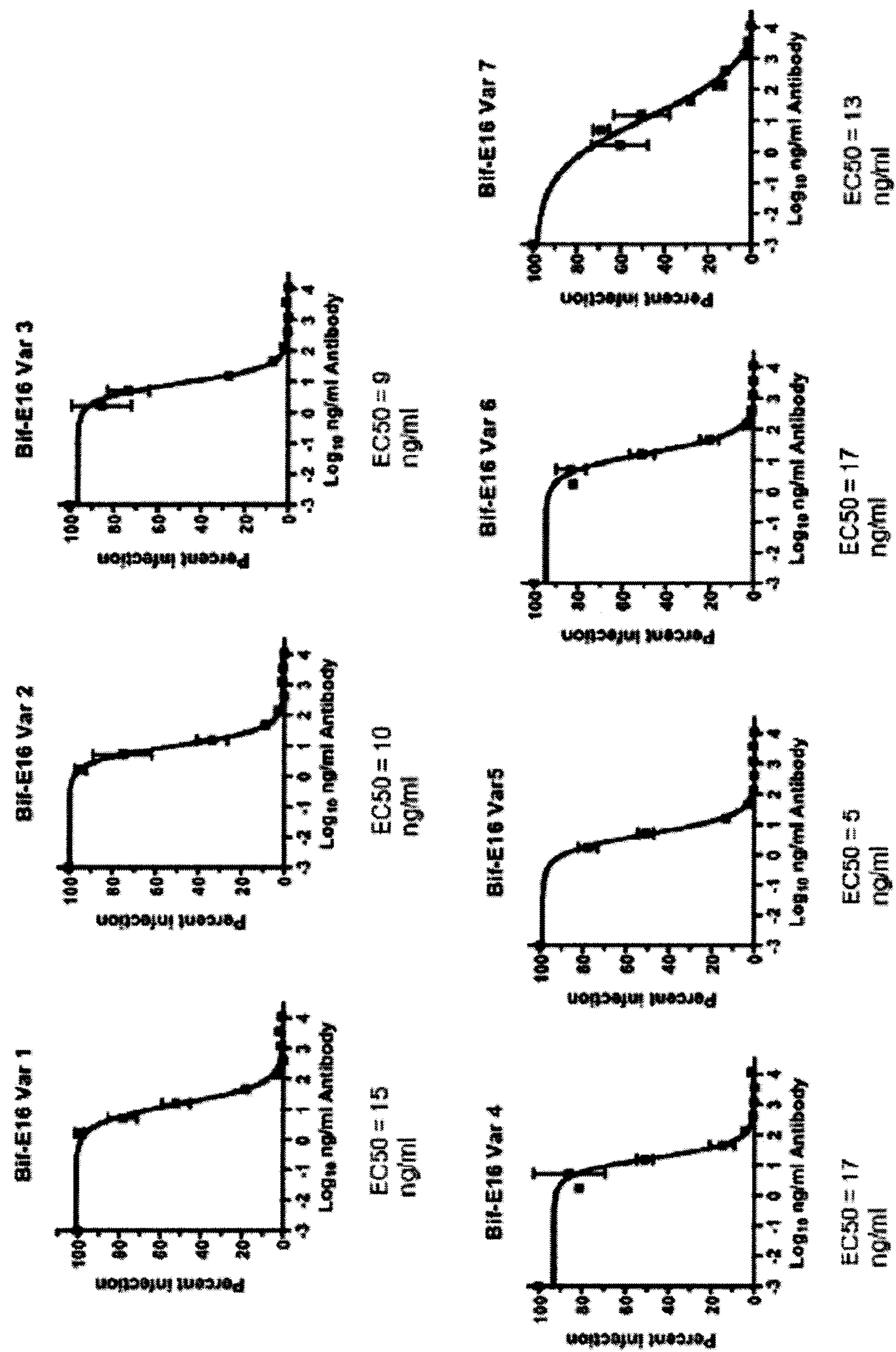
FIG. 14. Neutralization of WNV by plant and mammalian cell derived E16 bifunctional mAbs. WNV (strain New York 1999) was incubated with serial dilutions of parental hE16 (positive control) or E16 bifunctional mAb variants and used to infect Vero cells. Cells were then fixed, permeabilized, analyzed by focus reduction assay and quantitated by Biospot analysis. Mean±SD is shown from one of two independent experiments. Overall, these bifunctional variants show similar neutralization activity as the parental hu-E16mAb.

To test the hypotheses that (1) Bif-E16 crosses the BBB through the mechanism of receptor-dependent transcytosis and retains its ability to bind and neutralize WNV and (2) glycosylation pattern affects Bif-E16 effector function, we have generated Bif-E16 with different glycoforms and tested their in vitro protection characteristics including binding avidity, neutralization, and will test antibody effector function, as well as their ability to cross a monolayer of brain microvascular endothelial cells. Our results show that Bif-E16 binds and neutralizes WNV equivalently as the parent E16 (FIGS. 12 and 14), but will be more efficiently cross an endothelial cell barrier by TfR-binding dependent transcytosis. Moreover, Bif-E16 glycoform(s) required for antibody effector function will be identified for designing safer and more effective WNV therapeutics.

The overall goal of these experiments is develop more effective E16-based therapeutics with an extended window of treatment, through both BBB targeting and glycosylation selection.

Bif-E16 expression vectors generated were transfected into CHO cells or infiltrated into a collection of plant lines that have demonstrated ability to produce uniform MAbs with defined mammalian glycosylation pattern including. high mannose, GnGn, G0-G2 galactose, bisected GlcNAc, fucosylated and nonfucosylated, and full complex form with terminal sialic acid. Analysis of these Bif-MAbs will allow elucidation of the contribution of individual glycans (mannose, galactose, fucose, bisected GlcNAc, sialic acid) or their combination to various FcγR and Clq binding and in modulating effector functions. With the exception of fucose, the function of other glycans in binding to these immune molecules is unclear. Bif-E16 proteins produced from these transgenic plant lines and CHO cells were purified. Glycosylation pattern of these Bif-MAbs were determined by LC-ESIMS of Cryptic glycopeptides. The present results show that plant-produced Bif-E16s had the expected mammalian GnGn, G0-G2 galactose, GnGn fucosylated and G0-G2 galactose patterns depending on the specific “humanized” plant lines used for the expression of Bif-E16. The functional characteristics of these Bif-E16s will be examined with the methods described below. Glycoforms with distinct characteristics (viral neutralization, FcγR binding, ADCC and CDC) will be selected for further th vivo studies.

In vitro functional assays with plant Bif-E16 fusion protein. A series of functional assays were or will be performed to characterize the neutralizing activity and effector function of the newly generated CHO cell and plant. Bif-E16 protein. In each case, the Bif-E16 was or will be compared directly to the parent plant and mammalian E16 antibody and a non-binding isotype control.

(a) Virus neutralization. The ability to neutralize WNV infection in cell culture was determined initially using a plaque reduction neutralization assay with BHK21 cells. This is a gold-standard assay, which we have used previously but is somewhat subjective in terms of quantitation (visual scoring of plaques). To gain more quantitative and objective data, we will use a flow cytometry based neutralization assay that measures antibody inhibition of infection with pseudo-infectious WNV reporter virus particles (RVPs). In this assay, WNV RVPs will be incubated with varying concentrations of Bif-E16, and then used to infect permissive (Raji-DC-SIGN R) cells in a 96-well plate, Neutralization will be monitored as a function of GFP fluorescence by flow cytometry at 40 hours after infection. The present results (FIG. 14) indicated plant-derived Bif-E16 with different specific mammalian glyforms neutralized WNV as efficiently as the parental E16 positive control.

(b) Complement-mediated cytolysis. The ability of Bif-E16 with various defined glycoforms to trigger complement-mediated lysis of WNV-infected cells will be assessed by a standard target cell lysis assay. MC57GL-E cells, which transgenically express the WNV E protein on. their surface., will be labeled with 51Cr. Washed cells will be incubated with Bif-E16 (or negative controls) and human serum complement (1 h at 37° C.). Supernatants will be harvested and antibody-dependent complement-mediated cell lysis will be measured by scintillation counting.

(c) Antibody-dependent Clq binding on virus. We recently have shown that the ability of E16 to fix Clq can greatly augment (~20-fold) the neutralizing activity of WNV. To evaluate whether the Bif-E16 glycoforms will bind Clq similarly, WNV RVPs will be mixed with MAbs in the presence or absence of purified human Clq (50 μg/ml) prior to infection. After 40 hours, flow cytometry assays will be performed to assess Clq augmented neutralization. In parallel, a solid phase three-step ELISA with purified WNV E protein, Bif-E16 (or controls) and Clq will be performed, or direct SPR with Bif-MAb and purified Clq will be performed (see below).

(d) Antibody-dependent phagocytosis and ADCC. The ability of MAbs to promote antibody-dependent phagocytosis of WNV-infected cells will be evaluated according to previously described assays. Human Raji-DC-SIGN-R will be infected with WNV for 24 hrs, labeled with CSFE, incubated with Bif-E16 with various glycoforms, and mixed with different concentrations of IFN-γ stimulated monocyte-derived macrophages. After incubation (2 to 4 h at 37° C.), phagocytosis will be measured by flow cytometry or confocal microscopy as described.

Alternatively, for ADCC assays, WNV-infected cells Raji-DC-SIGN-R cells will be labeled with $^{51}$Cr, incubated with Bif-E16 or controls, and added to CD56+CD16+ Natural killer (NK) cells (purified by negative selection with magnetic beads from donors) in 96-well plates at 37° C. as described. Five hours later, supernatants will be harvested and ADCC will be measured by scintillation counting.

Figure 12:
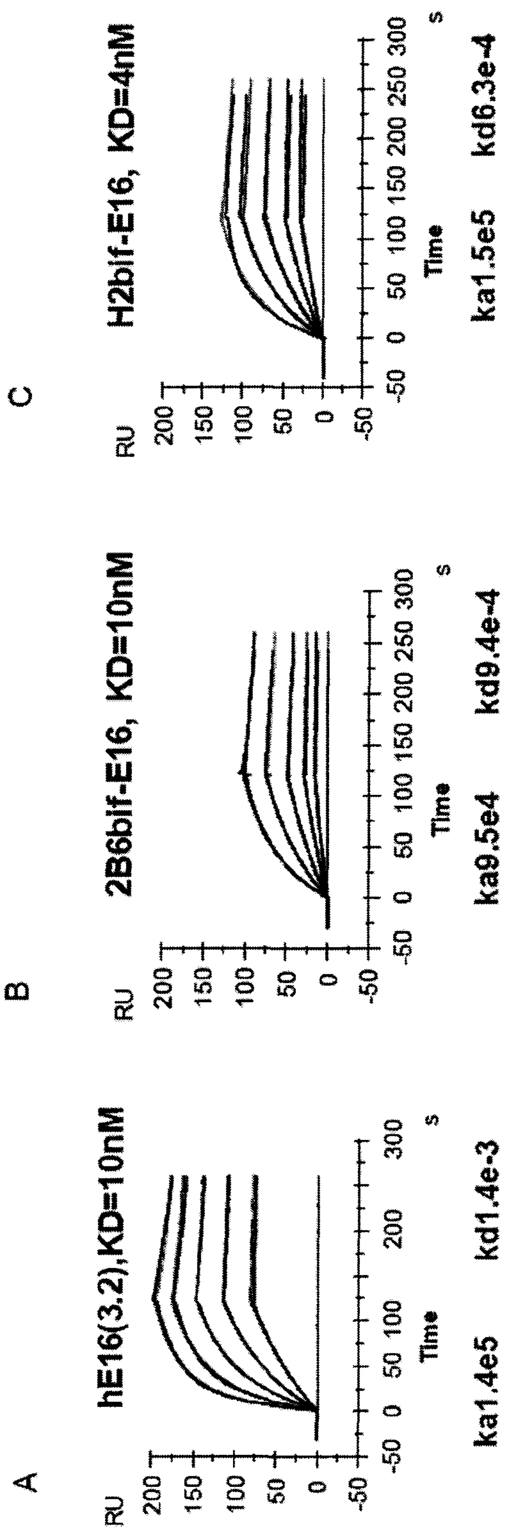
FIGS. 12A-12C. Surface plasma resonance (SPR) analysis of binding affinity and kinetics of E16 bifunctional mAbs to WNV antigen DIII. WNV DIII fragment was injected overmHu-E16 (positive control, Panel A), E16 Bif 2B6 (Panel B), or E16 bif H2 (Panel C) immobilized to the CM-5 biosensor chip. Binding responses were normalized to the same level of immobilized antibody and analyzed by Langmuir 1:1 interaction fit. A representative set of SPR binding curves of several independent experiments performed in duplicate is shown. Overall, E16 bifunctional mAbs show similar binding kinetics and similar (B) or better (C) binding affinity than the parental hu-E16mAb (A).
Figure 13:
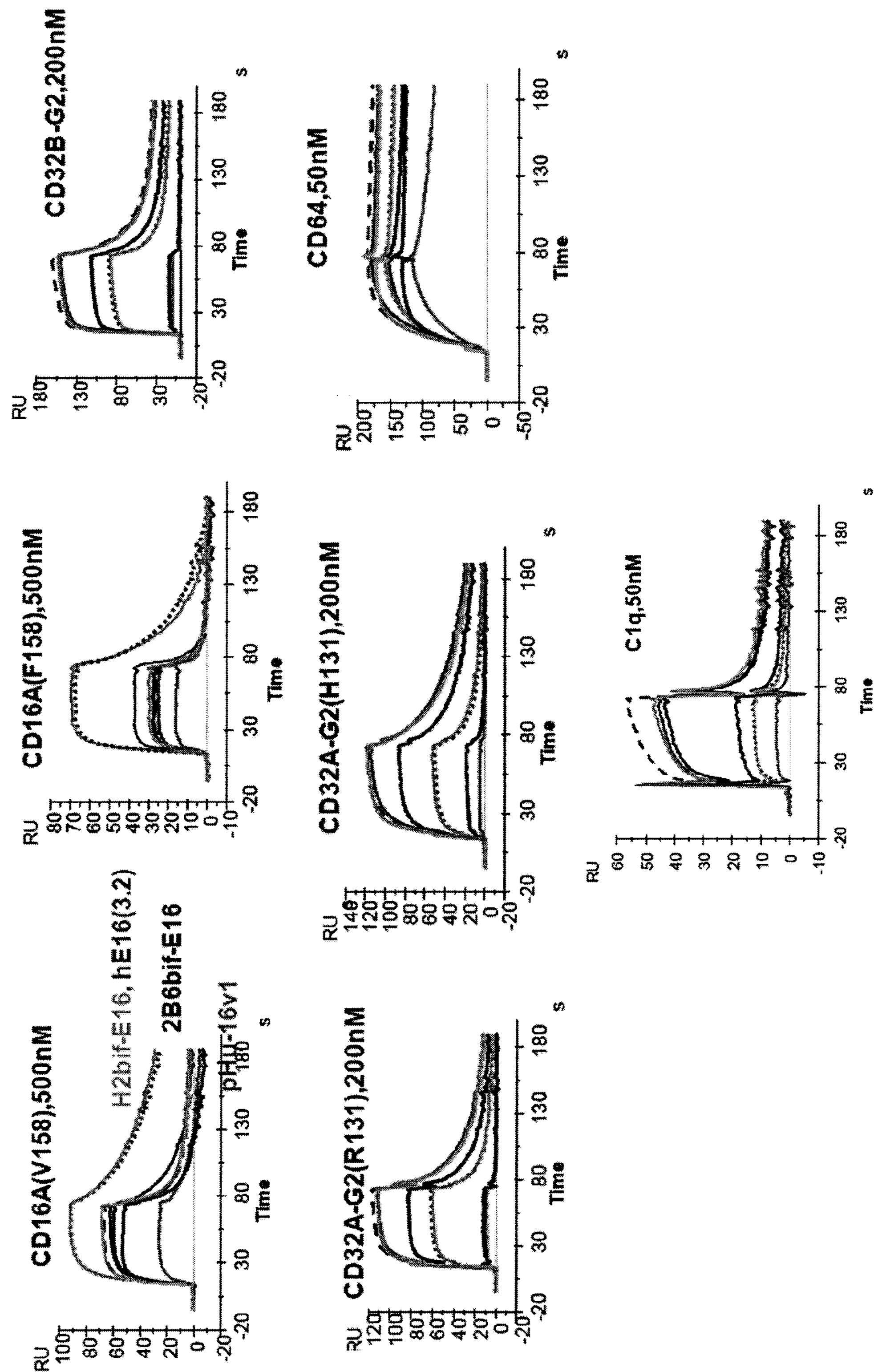
FIG. 13. Surface plasma resonance (SPR) analysis of binding affinity and kinetics of FcgRs and C1q to parental E16 (red line), or E16 Bif 2B6 (black line), or E16 bif H2 (orange line) captured on WNV E protein immobilized to the CM-5 biosensor chip. Data are representative of several independent experiments. Overall, The two different configuration of E16 bifunctional mAbs show different binding kinetics and affinity to FcrRs and Clq: with H2 similar to that of the parental hu-E16 mAb and 2B6 showing lower affinity than hu-E16.

Antibody binding affinity and kinetics. To quantitatively characterize the binding of Bif-E16 with different glycoform to WNV E, Clq and FcγRs. a SPR assay was utilized. We previously used this assay to compare plant and CHO cell-derived versions of E16 for binding to purified WNV DIII or E proteins. SPR provides accurate affinity measurements and kinetic parameters associated with complex formation and dissociation. We used a BIAcore optical biosensor to test the direct binding capacity of Bif-E16, E16 (positive control) and various Bif-E16s were immobilized onto the BIAcore chip WNV DIII fragments will be injected into the flow cells at several concentrations and their dissociation monitored as changes in SPR. The binding data from the injection of at least six different concentrations will be fitted. Independent trials, measuring the same series of concentrations, will be repeated at least three times. The present results indicate that Bif-E16 show similar DIII binding kinetics and similar (B) or better (C) binding affinity than the parental E16 mAb (FIG. 12). These studies provide insight into the characteristics of Bif-E16 binding that correlate with in vitro and in vivo neutralization activity. For testing of binding to FcγR, we immobilized the Bif-E16 and now across soluble human and/or mouse Fcγk (CD16, CD32, and CD64) that are commercially available. The present results demonstrated different configurations and glycoforms of Bif-E16 exhibited different binding to el q and different FcγRs (FIG. 13). The binding of different Bif-E16 glycoforms to various stimulating and inhibitory FcγRs will be compared and correlated to their activity in modulating Fc effector functions. In case of difficulty in identifying as clear correlation, in vivo or ex vivo experiments using transgenic mice and/or cells with humanized FcγRs will be use to address such issue.

Figure 6:
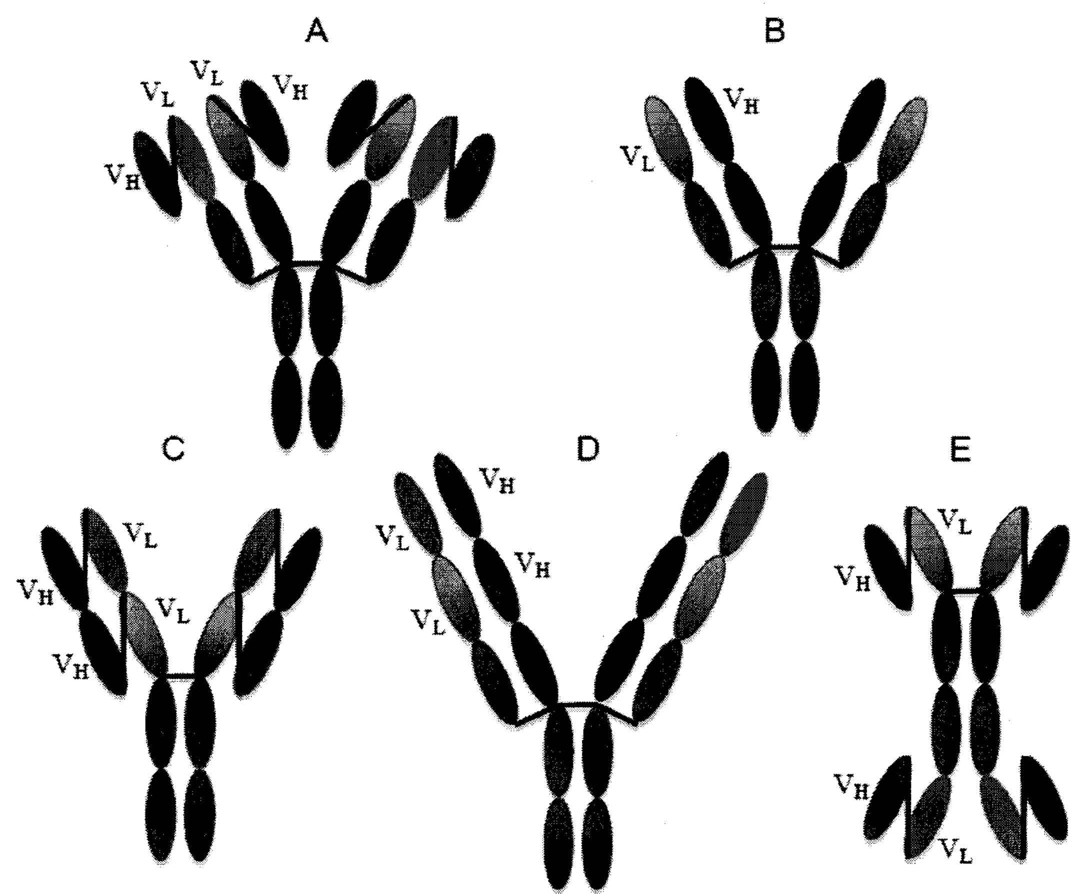
FIGS. 6A-6E, Bif-E16 designs. (A) Primary Bif-E16 design (B) Parent E16 (IgG) (C) Tandem ScFv alternative (D) Two VL and VH alternative (E) Two scFv-Fc-ScFv fusion alternative.

Drug delivery across the BBB for CNS diseases remains a challenge. The only pathway for nonlipid molecules to cross the BBB is carrier-mediated or receptor-mediated transport. Recent studies show that MAbs to the insulin and transferrin receptors on the brain microvasculature (such as 8D3) can be used to deliver MAb fragments and large proteins across the BBB. Our feasibility studies demonstrated that (i) A Bif-MAb expressed in CHO cells and plants can bind and trigger endocytosis in cultured b.END3 cells (FIG. 6); (ii) a scFv-Fc fusion of 8D3 expressed in CHO cells and plants shows strong TfR binding specificity (FIG. 10); and (iii); an E16 scFv-Fc expressed in plants retains WNV E protein binding and neutralization activity (FIG. 10-12,14). These results predict that Bif-E16 will have bispecific binding to both WNV E and mouse TfR and pass the BBS through TfR dependent transcytosis.

The inventors have demonstrated the bispecificity of Bif-E16 by a flow cytometry assay using yeast cells displaying WNV E and cultured b.END3 cells displaying TfR, showing that Bif-E16 recognized both ligands (WNV E and mouse TfR) in their native configurations (FIG. 10). The affinity for the mouse TfR of Bif-E16 and the parent 8D3 MAb will be evaluated with a radio-receptor assay using mouse fibroblasts as the source of the mouse TfR and [$^{125}$I]-Bif-E16 and 8D3 MAb as the receptor ligand.

Figure 11:
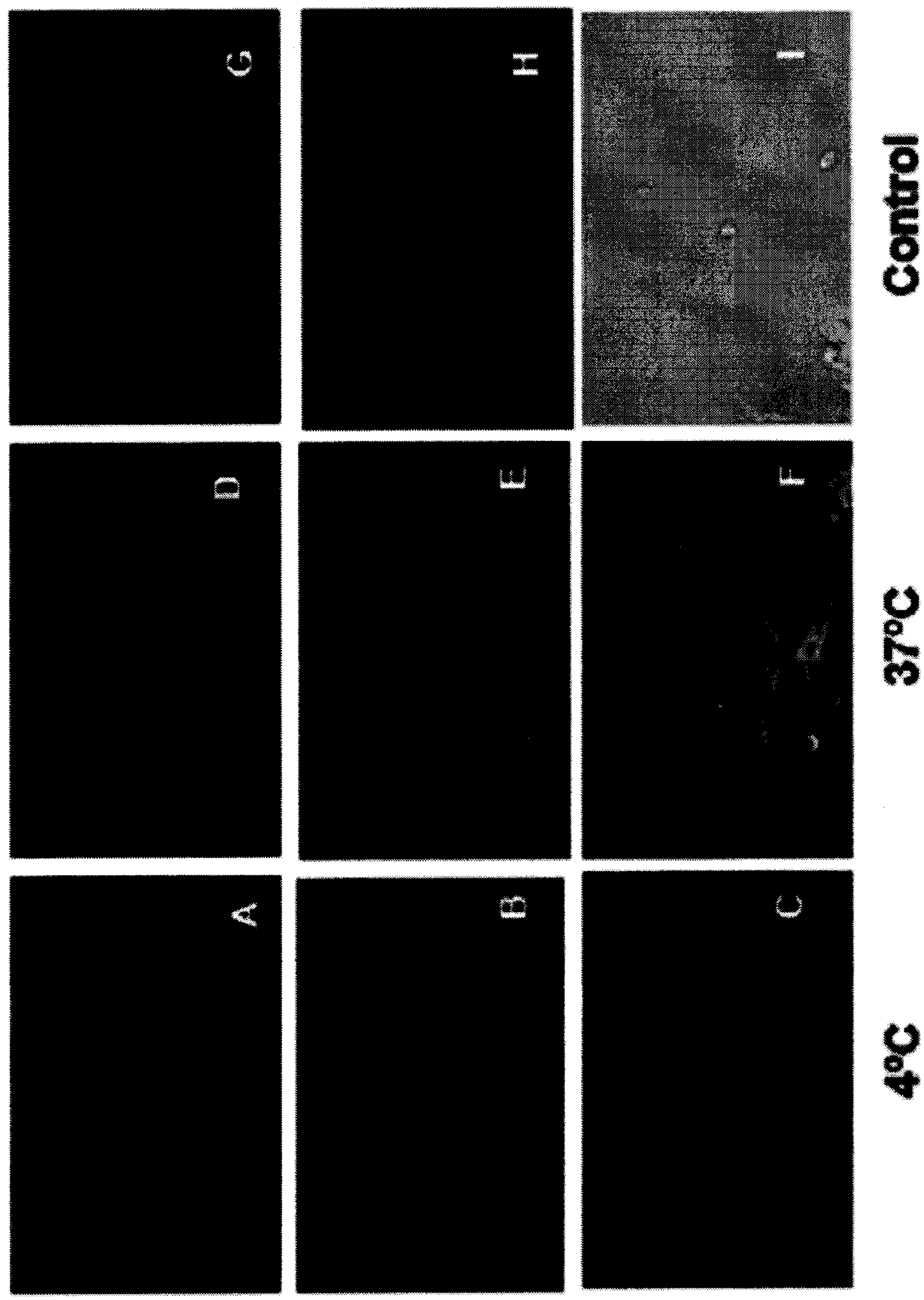
FIG. 11A-11I. Binding and endocytosis of a plant-derived Bif-MAb into brain endothelial cells. Cells were labeled by the Bif-MAb (A-F) or negative control MAb (G-H) at 4° C. followed by AlexaFluor 555 conjugated secondary antibody (red). The cells were then fixed and imaged (4° C. samples, A-C), or incubated at 37° C. for 30 min to allow internalization, and then labeled with AlexaFluor 555 conjugated secondary antibody (red) at 4° C. followed by AlexaFluor 488 conjugated secondary antibody (green) with cell permeabilization by saponin prior to fixation and imaging (37° C. samples, D-F). Merged images of the AlexaFluor-labeled images are shown in C and F.

To begin to demonstrate that Bif-E16 will have binding activity that facilitates accumulation in the brain, we confirmed that the 8D3 scFv moiety in Bif-E16 bound TfR and triggered TfR dependent endocytosis and transport into mouse brain capillary endothelial cells (MBCEC) (FIG. 11). To ensure the 8D3 scFv moiety in Bif-E16 can also induce transcytosis, a transwell assay will be performed.

First, MBCEC and glial cells will be isolated for primary culture. MBCEC monolayers will be grown on Transwell microporous membranes with glial cells at the bottom of the well. TMBCEC monolayers will be washed and purified Bif-E16 will be added to the apical side of the chamber, and incubated at 37° C. At 0-48 h, samples will be taken from the lower (basolateral) chamber, and the accumulation of Bif-E16 will be assayed by ELISA. The integrity of the barrier will be monitored by measuring transendothelial electrical resistance (TEER) and glucose permeability. A CHO cell derived 8D3 MAb with demonstrated BBB transcytosis activity will be used a positive control, and E16 parent MAb as a negative control.

If this particular Bif-E16 design were not optimal, as a backup strategy we would fuse the E16 and 8D3 in two other configurations as shown in FIGS. 6*c* and *d*. Both designs have been exploited in creating bispecific antibodies with success. If 8D3 does not efficiently target E16, we have available additional anti-TfR MAb candidates such as R17. Alternatively, a mouse anti-rat TfR scFv could be used as a carrier for E16 into the brain for the rat WNV pathogenesis model, as its function has already been demonstrated.

The Bif-E16 will also be used to test the hypothesis that a CHO cells and plant-made Bif-E16 with increased BBB permeability will enhance its therapeutic efficacy and extend the window for WNV treatment in a mouse model. To have the desired enhanced efficacy, Bif-E16 must show "bi-functionality" in targeting E16 across the BBB in vivo and ultimately demonstrate efficacy against lethal WNV challenge with an extended treatment window. We will evaluate the CHO cells and plant-derived Bif-E16 for its ability to cross the BBB in uninfected and infected mice and for its therapeutic efficacy at 5 days post infection and beyond against lethal WNV challenge. We predict that Bif-hu-E16 will achieve higher levels in the brain and protect mice beyond 5 days of infection.

In Vivo Testing:

Animals: For animal testing, Wild type C257BL/6 mice will be bred and housed in a BSL-3 animal facility at WUSM that has been approved by the USDA. Groups of mice will be inoculated for each condition and equal numbers of negative and positive controls will be included. In compliance with the Animal Studies Committee at Washington University, mice that manifest significant morbidity (inability to eat, lethargy, and paraplegia) will be regarded as moribund and euthanized, and considered to have a lethal infection.

Virus Stocks. Most cell culture and in vivo infection experiments will be performed with the virulent North American WNV strain 3000.0259 47 that has been passaged only once in C6/36 *Aedes albopictus* cells. For confirmation, a subset of experiments will be performed with the WNW strain 3301.0257 or a prototype African (Egypt 101) strain.

(a) Clinical Observation: For four weeks after inoculation, mice will be monitored daily for morbidity and mortality. Specific signs of disease such as fur ruffling, weight loss, hunched-back posture, lethargy, and paraplegia will be used as the basis for a morbidity index.

(b) Virologic Analysis: To confirm the antiviral effect of Bif-E16 tissue samples from key organs (e.g., brain, spleen, and spinal cord) will be collected from animals at necropsy. In some experiments, mice will he sacrificed, at specific times after infection to assess the kinetics of virus replication after treatment with Bif-E16. Organs will be evaluated for viral infection, tissue injury, and immune system response by histopathologic, immunohistochemical, and flow cytometric analyses. Priority will be placed on the examination of CNS tissue (brain and spinal cord). Immunohistochemistry will be performed with biotinylated anti-WNV MAbs that has been generated in the laboratory according to established protocols. Blood samples will be obtained by phlebotomy from the dorsal tail vein. Tissue samples will be snap-frozen in liquid nitrogen immediately after dissection. Quantitation of WNV viral RNA in serum and tissues will be performed by real-time fluorogenic RT-PCR using 18S ribosomal RNA to normalize for input tissue. Levels of infectious WNV in serum and tissues after homogenization will be measured by viral plaque assays in BHK21 cells.

(c) Passive Transfer of Antibodies: To assess the activity of human or plant MAbs in the protection against WNV, mice will be passively transferred each form of E16. Purified MAbs will be administered according to algorithms described below. For each experiment, saline injections and isotype control negative antibodies also will be included.

Characterization of BBB Crossing for Bif-E16 Fusion Protein In Vivo.

The studies above should establish that 8D3 scFv moiety in plant-derived Bif-E16 can trigger TfR dependent transcytosis to cross the brain microvascular endothelial cells in vitro. To confirm the BBB crossing and brain delivery of Bif-E16, several in vivo assays including brain immunohistochemistry and measurement of Bif-E16 distribution in mouse brain will be performed. Adult uninfected female C57BL/6 mice will be anesthetized and injected with Bif-E16 or with parent 8D3 and E16 MAbs as positive and negative controls respectively (1.5 to 150 μg/mouse). Mice will be sacrificed 4 h after extensive intravascular perfusion. The brain and other organs will be removed and tissue will be homogenized: the levels of Bif-E16 will be measured by ELISA with E16 anti-idiotypic antibodies. For brain immunohistochemistry mice will be injected with a (higher) dose of 300 μg/mouse of bif-E16 or control MAbs. At 60 min after i.v. injection, the brain plasma volume will be cleared with extensive intravascular perfusion with PBS. This will be followed by a 20-min perfusion of paraformaldehyde fixative. Brains will he removed and divided into four coronal slabs and further fixed, frozen sectioned, stained with Alexa-647-conjugated anti-E16 idiotype or antihuman IgG1 specific antibodies, and imaged using confocal microscopy. Depending on the results, dosage for both assays will be adjusted to achieve optimal results. If necessary, both assays can also be performed with [$^{125}$I]-labeled Bif-E16 as described previously, Pharmacokinetics of Bif-E16 in mice. To understand m greater detail the amount of Bif-E16 that is required for protection, pharmacokinetic (PK) studies are planned. These include measurement of serum and cerebrospinal fluid (CSF) levels of Bif-E16, and the correlation of these levels with clinical outcome. As variant glycoforms of Bif-E16 are generated, the PK studies will be repeated with these new reagents.

CSF concentrations of Bif-E16 in wild type and WNV-infected mice. Studies have shown that the permeability of the BBB is altered following WNV infection, due to an immune response against the virus in peripheral lymphoid tissues and the ensuing release of in cytokines.

The cytokine-mediated BBB insult results in increased permeability to the virus and the potential for neurological disease. The increased permeability, however, also allows the passage of therapeutic antibodies that can limit the neurological involvement. The goal of these studies is to assess the relative concentration of Bif-E16 (along with parent E16 MAb) in the serum and CSF of mice infected with WNV at various times after administration of the antibody and to compare these levels to those achieved in uninfected animals. The PK experiments in mice can be summarized as follows: (a) Uninfected. Uninfected 5-week-old mice will receive 1 to of Bif-E16 at day 1. On days 3, 5, 7, and 9, subsets of the mice from this group will be euthanized and Bif-E16 levels (measured. as human IgG levels) will be assessed in serum and CSF (the latter obtained, by stereotactic-directed sampling of the lateral ventricle), (b) WNV-infected. Mice will be infected with $10^2$ PFU of WNV on day 0, treated on day 1 with 1 mg and analyzed as on days 3, 5, 7, and 9 as described above. In a separate experiment, mice will be infected on day 0, the antibody treatment delayed until day 2, 4, or 6 after infection, and serum and CSF levels of human IgG determined one day after treatment.

Therapeutic Studies with Bif-E16 Protein in Mice:

Prophylaxis studies. Pre-treatment studies will be performed in wild type C57BL/6 mice to compare the concentrations of plant Bif-E16, plant E16 and mammalian E16 that prevent severe WNV infection. These experiments will be done to eliminate candidates the have poor efficacy in vivo, as a cost saving and animal sparing measure, Bif-E16 will be administered as a single dose one day prior to infection of 5 week-old wild type with $10^2$ PFU of WNV, which causes a baseline mortality of 90%.

Several doses (e.g., 0.1 to 100 μg) will be tested to determine the inhibitory concentrations that prevent 50% ($IC_{50}$) and 90% ($IC_{90}$) of lethal infections. In some limited experiments, serum and tissue samples will be obtained at defined intervals so that viremia and tissue viral burden, and antibody responses can be measured. By testing for the development of anti-NS1 antibodies 54, which only occurs with active infection in wild type mice, the minimum dose of Bif-E16 that confers sterile immunity can be identified. and. compared with parental E16. Virologic analysis will define the dose of Bif-E16 that prevents spread to the CNS and pathologic studies should assess protection against neuronal injury, Some of the dosing experiments will be repeated with a closely related WNV strain from New York (strain 3301.0257) and a distantly related strain (lineage II, Egypt 101) to insure protection against genetically diverse strains of WNV.

Figure 15:
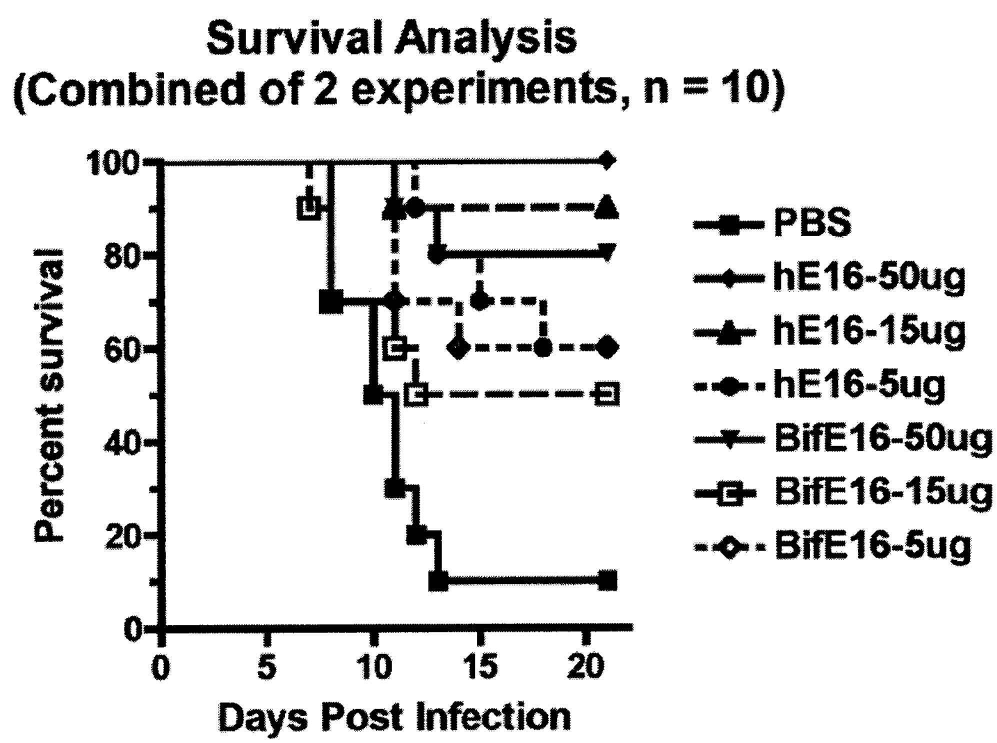
FIG. 15. E16 mediated protection against lethal WNV infection in mice. Wild type C57BL/6 mice were infected with $10^2$ PFU of WNV and then given a single dose of the indicated doses of mHu-E16 (parental E16 mAb control) or E16 bifunctional mAb via an intraperitoneal route day +4 after infection. Survival data from two independent experiments (N=10 per dose) were analyzed by the log-rank test.

Therapeutic studies. Post-exposure therapeutic studies will define the minimum single dose of plant Bif-E16 that provides virtually complete protection when administered at a specific point after infection in wild type mice. In our published studies with the parent E16 MAb, dose escalation studies were performed at days 2, 4, or 6 after WNV infection, and not beyond this as wild type mice begin to succumb to WNV infection by day 8. However, the newly constructed Bif-E16 fusion proteins should have increased BBB penetration, resulting in higher levels in the CNS and a prolonged therapeutic window for WNV treatment. Therefore, dose escalation studies will be performed at days 2, 4, 6, 7 and beyond (if applicable) after WNV infection. Post-exposure therapeutic studies for Bif-E16 variants (glycoforms) will be conducted in parallel with the parent E16 MAb as a control. Five week-old wild type mice will be passively administered a single dose of Bif-E16 (e.g., 0.3, 1, 3, 10, 30, 300, 1000, and 3000 μg) fusion protein by intraperitoneal injection at a defined point (days 2, 4, 6, 7, 8) after footpad inoculation with $10^2$ PFU of WNV, As additional controls, separate arms will be performed with saline, or a non-binding MAb of the same isotype. Administration of MAbs after day 4 corresponds to a stage when WNV has already disseminated into the CNS; thus, these trials will directly compare the efficacy of various forms of Bif-E16 and E16 in treating CNS infection and WNV encephalitis in mice. We used one of the Bif-E16 variants in this test. Our preliminary results showed that this Bif-E16 can protect mice from a lethal challenge of WNV infection 4 days post infection (FIG. 15). We did not intend to compare the efficacy of Bif-E16 with E16 in this experiment, since the glycoform and dosage of Bif-E16 used in this experiment were not optimal for brain delivery. Instead, we demonstrated that our bifunctional antibody design did not impede the therapeutic activity of the E16 moiety in this complex molecule, Mortality, average survival time over a month of observation, and virologic and histologic studies will be performed to confirm the efficacy of the intervention. In addition, inflammation and hemorrhage in the brain and will he examined with published methods to evaluate and compare the safety of these variants.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated. herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Hubalek Z., Halouzka (1999) West Nile fever—a reemerging mosquito-borne viral disease in Europe. *Emerg Inf Dis.* 5: 643-650.

2. Petersen S V, Thiel S. Jensenius JC (2001) The mannan-binding lectin pathway of complement activation: biology and disease association. *Mol Immunol.* 38: 133-149.

3. Bode A V, et al, (2006) West Nile virus disease: a descriptive study of 228 patients hospitalized in a 4-county region of Colorado in 2003. *Clin infect Dis.* 42: 1234-1240.

4. Glass W G, et al, (2006) CCR5 deficiency increases risk of symptomatic West Nile virus infection. *J Exp Med.* 203: 35-40.

5. Diamond M S, Klein R S (2006) A genetic basis for human susceptibility to West Nile virus. *Trends Microbiol.* 14: 287-289.

6. Lim J K, et al. (2009) Genetic variation in OAS1 is a risk lacior for initial infection with West Nile virus in man. *PLoS Pathog.* 5: e1000321.

7. Lim J K, et al. (2008) Genetic deficiency of chemokine receptor CCR5 is a strong risk factor for symptomatic West Nile virus infection: a meta-analysis of 4 cohorts in the US epidemic. *J Infect Dis.* 197: 262-265.

8. Diamond M S (2009) Progress on the development of therapeutics against West Nile virus. *Antiviral Res.* 83: 214-227.

9. Furuta Y, et. al. (2009) T-705 (favipiravir) and related compounds: Novel broad spectrum inhibitors of RNA viral infections. *Antiviral Res.* 82: 95-102.

10. Money J D, et al, (2008) Efficacy of orally administered T-705 pyrazine analog on lethal West Nile virus infection in rodents. *Antiviral Res.* 80: 377-379.

11. Diamond M S (2009) Mechanisms of Evasion of the Type I Interferon Antiviral Response by *Flaviviruses. Interferon Cytokine Res.* 29: 521-530.

12. Oliphant T, et al, (2005) Development of a humanized monoclonal antibody with therapeutic potential against West Nile virus. *Nat Med.* 11: 522-530.

13. Pierson T C, et al. (2007) The stoichiometry of antibody-mediated neutralization and enhancement of West Nile virus infection. *Cell Host Microbe.* 1: 135-145.

14. Thompson B S, et al. (2009) A therapeutic antibody against west nile virus neutralizes infection by blocking fusion within endosomes. *PLoS Pathog.* 5: e1000453.

15. Morrey J D, et al. (2006) Humanized monoclonal antibody against West Nile virus envelope protein administered after neuronal infection protects anainst lethal encephalitis in hamsters. *J Infect Dis.* 194: 1300-1308.

16. Morrey J D, et al. (2007) Defining limits of it eatment with humanized neutralizing monoclonal antibody for West Nile virus neurological infection in a hamster model. *Antimicrob Agents Chemother.* 51: 2396-2402.

17. Morrey J D, et al. (2008) West Nile virus-induced acute flaccid paralysis is prevented by monoclonal antibody treatment when administered after infection of spinal cord neurons *J Neurovirol.* 14: 152-163.

18. Samuel M A, et al, (2.007) Axonal transport mediates West Nile virus entry into the central nervous system and induces acute flaccid paralysis. *Proc Natl Acad Sci U S A.* 104: 17140-17145.

19. Chen Q (2008) Expression and purification of pharmaceutical proteins in plants *Biol Eng.* 1: 291-321.

20. Vitale A, Pedrazzini E (2005) Recombinant pharmaceuticals from plants: the plant endomembrane system as bioreactor. *Mol Interv.* 5: 216-225.

21. Gomord V, et al. (2004) Production and glycosylation of plant-made pharmaceuticals: the antibodies as a challenge. *Plant Biotechnol J.* 2: 83-100.

22. Giritch A, et al. (2006) Rapid high-yield expression of full-size IgG antibodies in plants coinfected with noncompeting viral vectors. *Proc Natl Acad Sci U S A.* 103: 14701-14706.

23. McLean M D, et al. (2007) A Human Anti-Pseudomonas aeruginosa Serotype O6ad Immunoglobulin G1 Expressed in Transgenic Tobacco Is Capable of Recruiting Immune System Effector Function In vitro. Antimicrob. *Agents Chemother.* 51: 3322-3328.

24. McCormick A A, et al. (2008) Plant-produced idiotype vaccines for the treatment of non-Hodgkin's lymphoma: Safety and immunogenicity in a phase I clinical study. *Proc Natl Acad Sci U S A.* 105: 10131-10136.

25. Weintraub J A, et al. (2005) Clinical trial of a plant-derived antibody on recolonization of mutans streptococci. *Caries Res.* 39: 241-250.

26. Villalobos A, et al. (2006) Gene Designer: a synthetic biology tool for constructing artificial DNA segments. *BMC Bioinformatics.* 7: 285.

27. Oliphant T, et al. (2007) Induction of epitope-specific neutralizing antibodies against West Nile virus. *J Virol.* 81: 11828-11839.

28. Pierson T C, et al, (2006) A rapid and quantitative assay for measuring antibody mediated neutralization of West Nile virus infection. *Virology.* 346: 53-65.

29. Mehlhop F, et al. (2009) Complement protein Clq reduces the stoichiometric threshold for antibody-mediated neutralization of West Nile virus. *Cell Host Microbe.* 6: 381-391.

30. Engle M, Diamond M S (2003) Antibody prophylaxis and therapy against West Nile Virus infection in wild type and immunodeficient mice. *J Virol.* 77: 12941-12949.

31. Ko K, et al, (2003) Function and glycosylation of plant-derived antiviral monoclonal antibody. *Proc Natl Acad Sci U S A.* 100: 8013-8018.

32. Ko K, Koprowski H (2005) Plant biopharming of monoclonal antibodies. *Virus Research.* 111: 93-100.

33. Diamond M S, et al, (2003) B cells and antibody play critical roles in the immediate defense of disseminated infection by West Nile encephalitis virus. *J Virol.* 77: 2578-2586.

34. Raju T S (2008) Terminal sugars of Fc glycans influence antibody effector functions of IgGs. *Curr Opin Immunol.* 20: 471-478.

35. Wang F, et al. (2006) Structural and functional characterization of glycosylation in an immunoglobulin G1 to Cryptococcus neoformans glucuronoxylomannan, *Mol Immunol.* 43: 987-998.

36. Quo Z, et al. (2008) Development of a simple and rapid method for producing non-fucosylated oligomannose containing antibodies with increased effector function. *Biotechnol Bioeng.* 99: 652-665.

37. Chargelegue D, et al. (2000) A routine monoclonal antibody produced in transgenic plants with plant-specific glycans is not immunogenic in mice. *Transgenic Res.* 9: 187-194.

38. Jin C, et al. (2008) A plant derived human monoclonal antibody induces an anticarbohydrate immune response in rabbits. *Glycoblotogy.*

39. Zeitlin L, et al. (1998) A humanized monoclonal antibody produced in transgenic plants for immunopiotection of the vagina against genital herpes. *Nat Biotech.* 16: 1361-1364.

40. Ma J K, et al. (1998) Characterization of a recombinant plant monoclonal secretory antibody and preventive immunotherapy in humans. *Nat Med.* 4: 601-606.

41. Schahs M, et al. (2007) Production of a monoclonal antibody in plants with a humanized N-glycosylation pattern. *Plant Biotechnol J.* 5: 657-663.

42. Strasser R, et al. (2008) Generation of glyco-engineered *Nicotiana benthamiana* for the production of monoclonal antibodies with a homogeneous human-like N glycan structure. *Plant Biotechnol J.* 6: 392-402.

43. Cox K M, et al. (2006) Glycan optimization of a human monoclonal antibody in the aquatic plant Lemna minor. *Nat Biotechnol.* 24: 1591-1597.

44. Shields R L, et al. 12002) Lack of fucose on human IgG1 N-linked oligosaccharide improves binding to human Fcgamma RIII and antibody-dependent cellular toxicity. *J Biol Chem.* 277: 26733-26740.

45. Huang Z, et al. (2009) A DNA replicon system for rapid high-level production of virus-like particles in plants. *Biotechnol Bioeng.* 103: 706-714.

46. Santi L, et al. (2008) An efficient plant viral expression system generating orally immunogenic Norwalk virus-like particles. *Vaccine.* 26: 1846-1854.

47. Pierson T C, et al. (2005) An infectious West Nile Virus that expresses a GFP reporter gene. *Virology.* 334: 28-40.

The invention claimed is:

1. A bifunctional antibody comprising:

(a) a first scFV specific for West Nile Virus, wherein the first scFV comprises CDR1, CDR2 and CDR3 sequences from the heavy chain variable domain sequence encoded by SEQ ID NO: 1 and CDR1, CDR2 and CDR3 sequences from the light chain variable domain sequence encoded by SEQ ID NO: 6, (b) a second scFV specific for a second antigen that is distinct from the first antigen, (c) a heavy chain constant domain (CH) and (d) a light chain constant domain (CL), wherein: the first scFV is linked to either the CH or the CL to produce a first scFV linked to constant domain; and the second scFV is linked to the CH when the first scFV is linked to CL or the second scFV is linked to CL when the first scFV is linked to CH to produce a second scFV-linked to a constant domain.

2. The bifunctional antibody of claim 1, wherein the first scFV linked to a constant domain is produced separately from the second scFV linked to a constant domain and the two linked scFVs are admixed together to form a bifunctional antibody.

3. The bifunctional antibody of claim 1, wherein the first scFV linked to a constant domain and the second scFV linked to a constant domain are prepared by co-expression of a nucleic acid that encodes each of the linked scFVs in a host cell produces a tetravalent molecule with divalent binding to two different epitopes and an intact Fc domain.

4. The bifunctional antibody of claim 1, wherein the first scFV specifically binds to an antigen or epitope from an antigen selected from the group consisting of the Domain III or any other parts of the Envelope protein of the West Nile Virus.

5. The bifunctional antibody of claim 4, wherein the second scFV specifically binds to an antigen or epitope from an antigen selected from the group consisting of transferrin receptors and insulin receptors of mouse, rat, rhesus monkey, and human cells, wherein the antigen or epitope is different from the antigen or epitope to which the first scFV binds.

6. The bifunctional antibody of claim 1, wherein the antibody is a humanized E16 antibody comprising a heavy chain variable domain sequence of SEQ ID NO: 3.

7. The bifunctional antibody of claim 1, wherein the second scFV binds to an entity expressed on the blood-brain barrier to uptake of the bifunctional antibody through the blood brain barrier.

8. The bifunctional antibody of claim 7, wherein the scFV that binds to the blood brain barrier entity binds to a receptor expressed on the blood brain barrier.

9. The bifunctional antibody of claim 8, wherein the receptor is a trasferrin receptor or insulin receptor.

10. A pharmaceutical composition comprising an antibody of claim 1.

11. An isolated humanized E16 antibody that is specific for West Nile Virus wherein the antibody is a bifunctional antibody comprising two scFVs wherein one of the scFVs is from humanized E16 and the second scFV specifically binds to a receptor or other blood-brain barrier targeting sequence, wherein the first scFV is linked to either a CH or the CL domain to produce a first scFV linked to constant domain; and the second scFV is linked to a CH domain when the first scFV is linked to a CL domain or the second scFV is linked to a CL when the first scFV is linked to a CH domain to produce a second scFV-linked to a constant domain, wherein the first scFV specifically binds to West Nile Virus, and wherein the first scFV comprises CDR1, CDR2 and CDR3 sequences from the heavy chain variable domain sequence encoded by SEQ ID NO: 1 and CDR1, CDR2 and CDR3 sequences from the light chain variable domain sequence encoded by SEQ ID NO: 6.

12. The isolated humanized E16 antibody of claim 11, wherein the antibody has an increased in vivo efficacy as compared to humanized E16 antibody that is not bifunctional.

13. The bifunctional antibody of claim 11, wherein the antibody is a humanized E16 antibody comprising a heavy chain variable domain sequence of SEQ ID NO: 3.

14. The bifunctional antibody of claim 11, wherein the second scFV binds to an entity expressed on the blood-brain barrier to uptake of the bifunctional antibody through the blood brain barrier.

15. A pharmaceutical composition comprising an antibody of claim 11.

16. A method of treating a West Nile Virus infection comprising administering to a subject infected with West Nile Virus with a composition comprising an antibody of claim 11.

* * * * *